US008268314B2

(12) United States Patent
Baehner et al.

(10) Patent No.: US 8,268,314 B2
(45) Date of Patent: Sep. 18, 2012

(54) BISPECIFIC ANTI-VEGF/ANTI-ANG-2 ANTIBODIES

(75) Inventors: Monika Baehner, Munich (DE); Ulrich Brinkmann, Weilheim (DE); Guy Georges, Habach (DE); Remko Albert Griep, Slemmestad (NO); Sabine Imhof-Jung, Planegg (DE); Anita Kavlie, Oslo (NO); Hubert Kettenberger, Munich (DE); Christian Klein, Iffeldorf (DE); Joerg Thomas Regula, Munich (DE); Wolfgang Schaefer, Mannheim (DE); Juergen Michael Schanzer, Muensing (DE); Werner Scheuer, Penzberg (DE); Stefan Seeber, Penzberg (DE); Markus Thomas, Penzberg (DE)

(73) Assignee: Hoffmann-La Roche Inc., Nutley, NJ (US)

(*) Notice: Subject to any disclaimer, the term of this patent is extended or adjusted under 35 U.S.C. 154(b) by 110 days.

(21) Appl. No.: 12/572,289

(22) Filed: Oct. 2, 2009

(65) Prior Publication Data

US 2010/0111967 A1 May 6, 2010

(30) Foreign Application Priority Data

Oct. 8, 2008 (EP) .................................. 08017607
Dec. 16, 2008 (EP) .................................. 08021834

(51) Int. Cl.
*A61K 39/00* (2006.01)
*A61K 39/395* (2006.01)
(52) U.S. Cl. ................... 424/136.1; 530/388.24
(58) Field of Classification Search ................. None
See application file for complete search history.

(56) References Cited

U.S. PATENT DOCUMENTS

| | | | |
|---|---|---|---|
| 5,202,238 | A | 4/1993 | Fell, Jr. et al. |
| 5,204,244 | A | 4/1993 | Fell et al. |
| 6,166,185 | A | 12/2000 | Davis et al. |
| 6,897,044 | B1 | 5/2005 | Braslawsky et al. |
| 7,129,330 | B1 | 10/2006 | Little et al. |
| 7,919,257 | B2 | 4/2011 | Hoogenboom et al. |
| 2003/0064053 | A1 | 4/2003 | Liu et al. |
| 2003/0124129 | A1 | 7/2003 | Oliner |
| 2005/0079170 | A1 | 4/2005 | Le Gall et al. |
| 2006/0122370 | A1 | 6/2006 | Oliner et al. |
| 2006/0280747 | A1 | 12/2006 | Fuh et al. |
| 2007/0141065 | A1 | 6/2007 | Fuh et al. |

FOREIGN PATENT DOCUMENTS

| | | |
|---|---|---|
| EP | 1870459 | 3/2006 |
| WO | 93/06217 | 4/1993 |
| WO | WO 94/10202 | 5/1994 |
| WO | WO 95/09917 | 4/1995 |
| WO | 96/27011 | 9/1996 |
| WO | WO 96/27011 | 9/1996 |
| WO | WO 97/01580 | 1/1997 |
| WO | WO 98/45331 | 10/1998 |
| WO | WO 98/45332 | 10/1998 |
| WO | 99/37791 | 7/1999 |
| WO | WO 00/35956 | 6/2000 |
| WO | WO 01/77342 | 10/2001 |
| WO | 03/020906 | 3/2003 |
| WO | WO 03/030833 | 4/2003 |
| WO | WO03/030833 | * 4/2003 |
| WO | WO 03/057134 | 7/2003 |
| WO | WO 03/106501 | 12/2003 |
| WO | WO 2005/000900 | 1/2005 |
| WO | 2005/044853 | 5/2005 |
| WO | WO 2006/020258 | 2/2006 |
| WO | 2006/031370 | 3/2006 |
| WO | 2006/031370 A2 | 3/2006 |
| WO | 2006/044908 | 4/2006 |
| WO | WO 2006/045049 | 4/2006 |
| WO | WO 2006/068953 | 6/2006 |
| WO | 2006/093794 | 9/2006 |
| WO | WO 2007/024715 | 3/2007 |
| WO | 2007/044887 | 4/2007 |
| WO | WO 2007/068895 | 6/2007 |
| WO | WO/2007/068895 | * 7/2007 |
| WO | 2007/089445 | 8/2007 |
| WO | WO 2007/089445 | 8/2007 |
| WO | 2008/077077 | 6/2008 |
| WO | WO 2008/132568 | 11/2008 |
| WO | 2009/032782 | 3/2009 |
| WO | WO 2009/080251 | 7/2009 |
| WO | WO 2009/080252 | 7/2009 |
| WO | WO 2009/080253 | 7/2009 |

OTHER PUBLICATIONS

Fischer et al. (Pathobiology vol. 74, 2007, p. 3-14). Cited on IDS.*
Coloma et al., Nature Biotech., 15, pp. 159-163 (1997).
Xie et al., Journal of Immunological Methods, 296, pp. 95-101 (2005).
Schoonjans, et al. Fab chains as an efficient heterodimerization scaffold for the production of recombinant bispecific and trispecific antibody derivatives. Journal of Immunology, 2000. vol. 165, pp. 7050-7057.
Simon et al., The EMBO Journal, 9, pp. 1051-1056 (1990).
Chan, L.A., et al., Variable Region Domain Exchange in Human IgGs Promotes Antibody Complex Formation with Accompanying Structural Changes and Altered Effector Functions; Molecular Immunology, 41 (2004) 527-538 XP002519713.
Miller, K., et al., Design, Construction, and in Vitro Analyses of Multivalent Antibodies; Journal of Immunology, 170 (2003) 4854-4861 XP002508787.
Morrison, S.L., et al., Variable Region Domain Exchange Influences the Functional Properties of IgG; Journal of Immunology 160 (1998) 2802-2808 XP003001892.
Rossi, E.A., et al., Multivalent Anti-CD20/Anti-CD22 Bispecific Antibody Fusion Proteins Made by the DNL Method Show Potent Lymphoma Cytotoxicity; Blood (ASH Annual Meeting Abstracts) 2006 108: Abstract 2495.

(Continued)

*Primary Examiner* — Laura B Goddard
*Assistant Examiner* — Meera Natarajan
(74) *Attorney, Agent, or Firm* — George W. Johnston; Patricia S. Rocha-Tramaloni; Gene J. Yao

(57) ABSTRACT

The present invention relates to bispecific antibodies against human VEGF and against human ANG-2, methods for their production, pharmaceutical compositions containing said antibodies, and uses thereof.

18 Claims, 26 Drawing Sheets

OTHER PUBLICATIONS

Coxon Angela et al, Combined treatment of angiopoietin and VEGF pathway antagonists enhances antitumor activity in preclinical models of colon carcinoma, Proceedings Fo the American Assocation for Cancer Research Annual Meeting, A49: (2008) 262-263 XP002517789 and 99th Annual Meetin gof the American Association for Cancer Research (2008).
Jendreyko N et al, "Simultaneous, phenotypic knockout of VEGF-F2 and Tie-2 with an intradiabody enhances antiangiogenic effects in vivo." Klinische Padiatrie (2006) 143-151 XP008102910.
Kim et al., Nature vol. 362 (1993) pp. 841-844.
Warren et al., J. Clin. Invest. vol. 95 (1995) pp. 1789-1797.
Borgstrom et al., Cancer Res. Vo. 56 (1996) pp. 4032-4039.
Melnyk et al., Cancer Res. vol. 56 (1996) pp. 921-924.
Morrison, PNAS, vol. 81 pp. 6851-6855.
Ridgway, Protein Eng. vol. 9 (1996) pp. 617-621.
Merchant et al., Nature Biotech. Vo. 16 (1998) pp. 677-681.
Atwell et al., J. Mol. Biol. 270 (1997) pp. 26-35.
Oliner et al., Cancer Cell (2004) vol. 6, pp. 507-516.
Liang et al., J. Biol. Chem. (2006) vol. 281 pp. 951-961.
Coloma et al., Nature Biotech. vol. 15 (1997) pp. 159-163.
Morrison S. L., Nature Biotech vol. 25 (2007) pp. 1233-1234.
Holliger et al., Nature Biotech vol. 23 (2005) pp. 1126-1136.
Fischer et al., Pathobiology (2007) pp. 3-14.
Shen et al., J. of Immunological Methods vol. 318 (2007) pp. 65-74.
Wu et al., Nature Biotech vol. 25 (2007) pp. 1290-1297.
Jendreyko, N. et al., PNAS 102(23):8293-8298 (Jun. 7, 2005).
Fischer et al., Pathobiology 74:3-14 (2007).

* cited by examiner

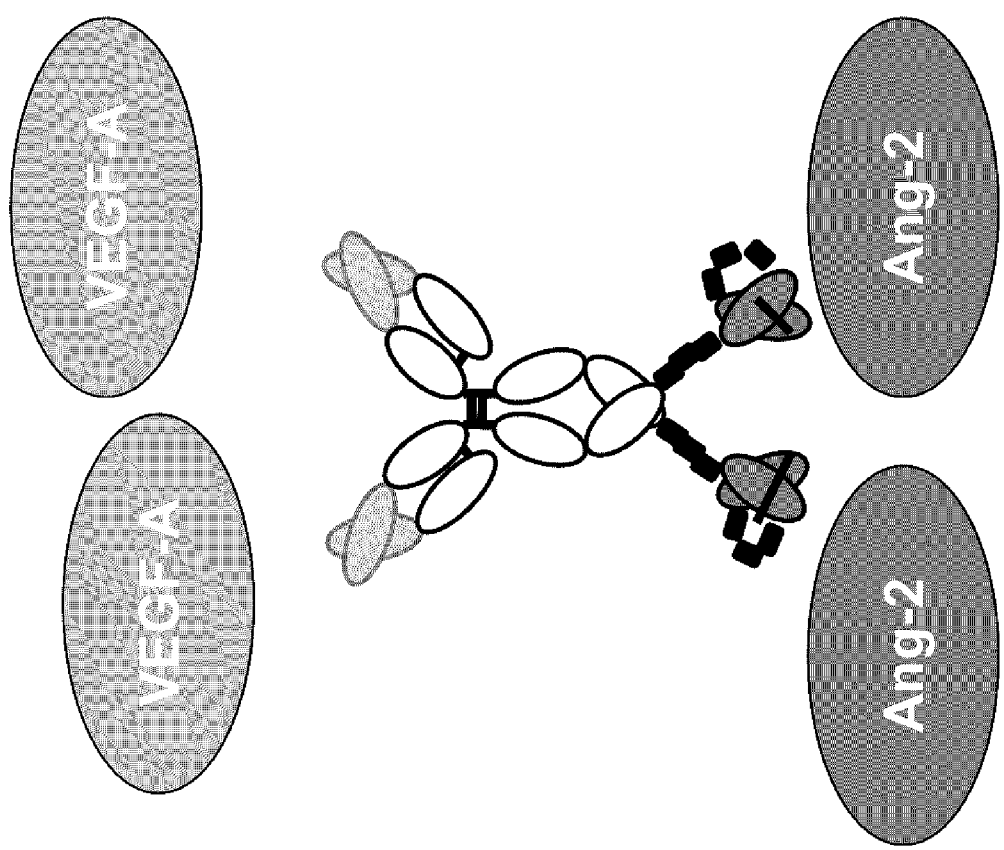

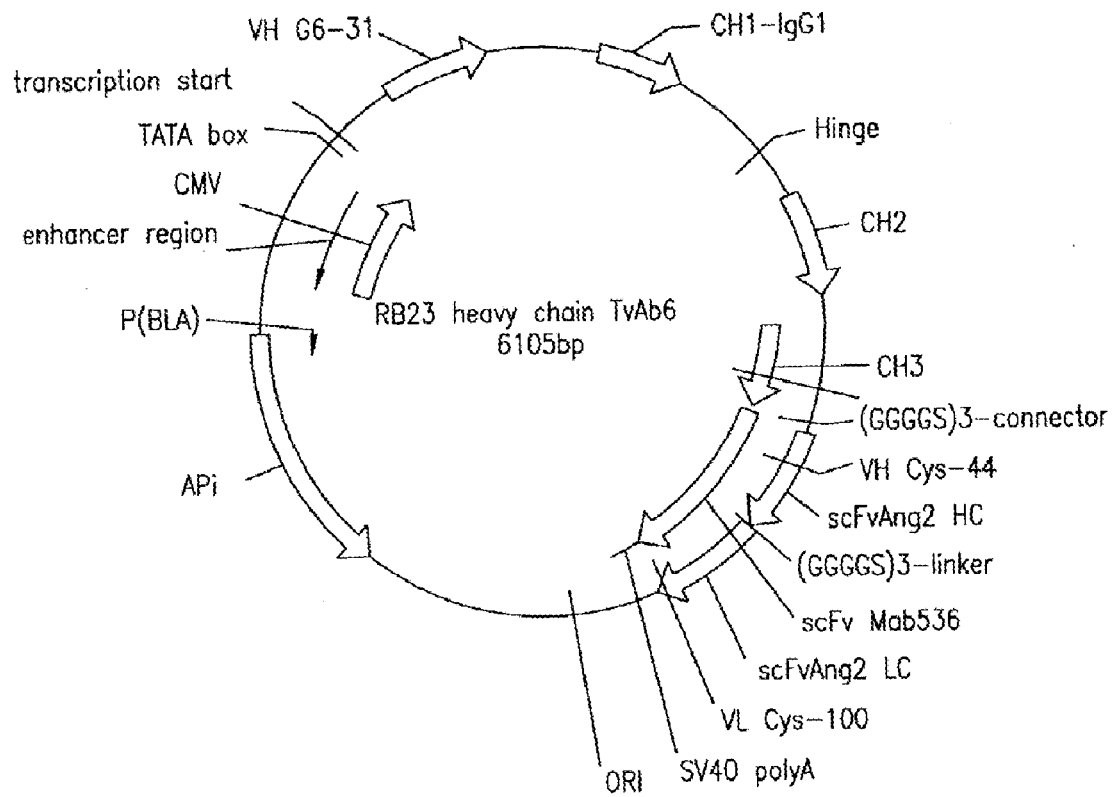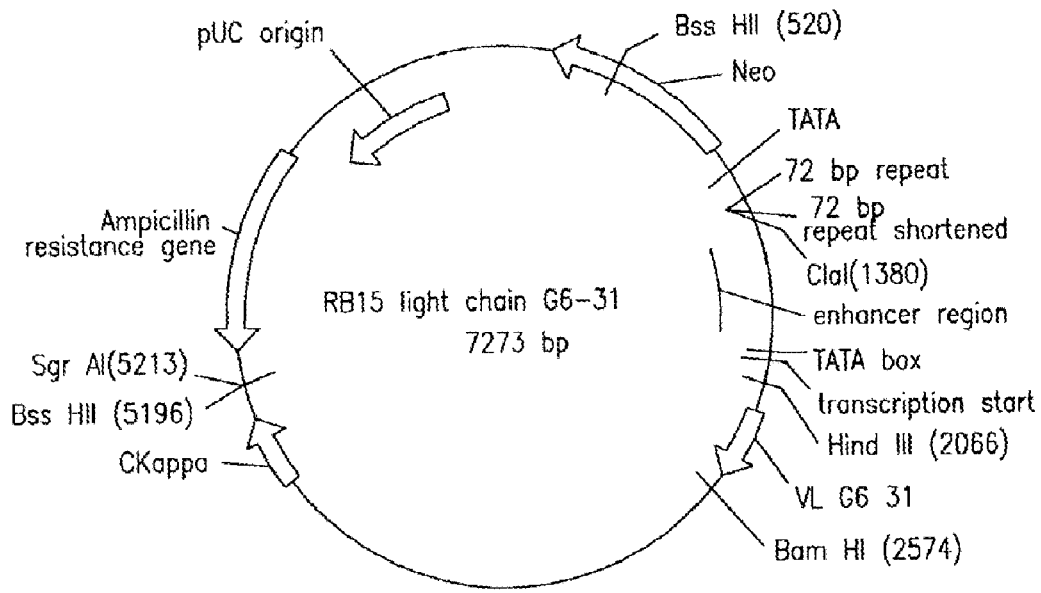
FIG. 2B

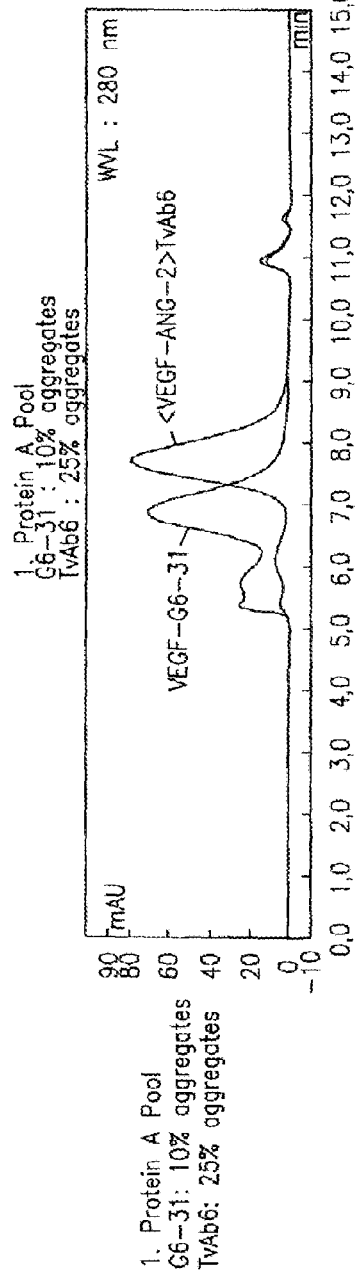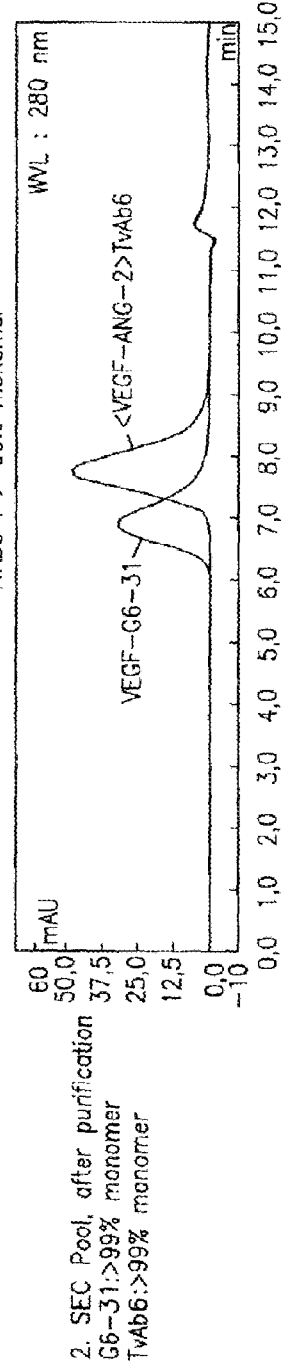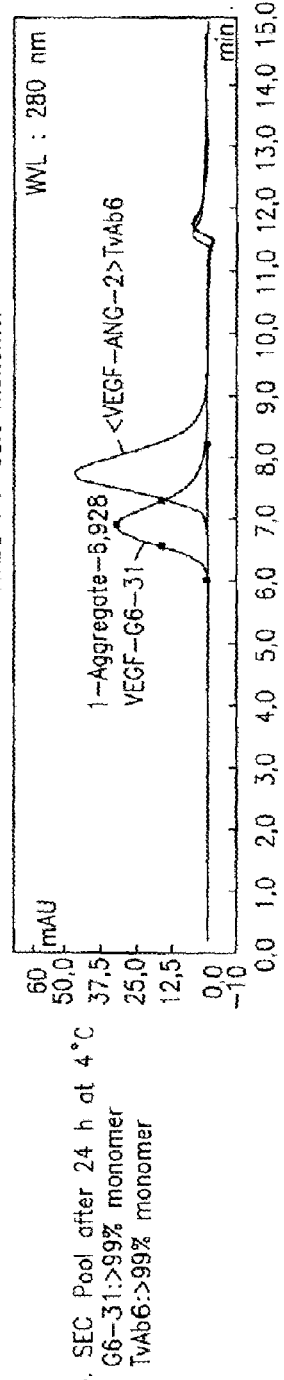
FIG. 4A
FIG. 4B
FIG. 4C

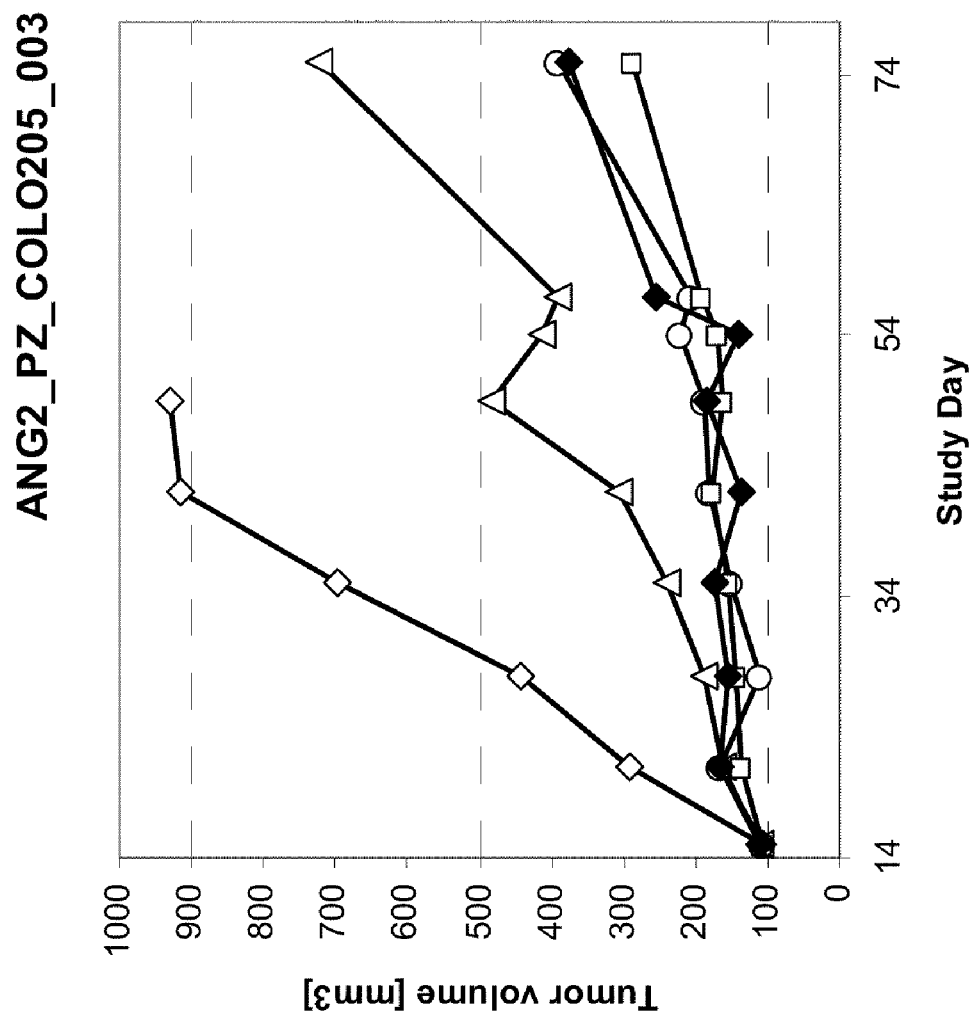

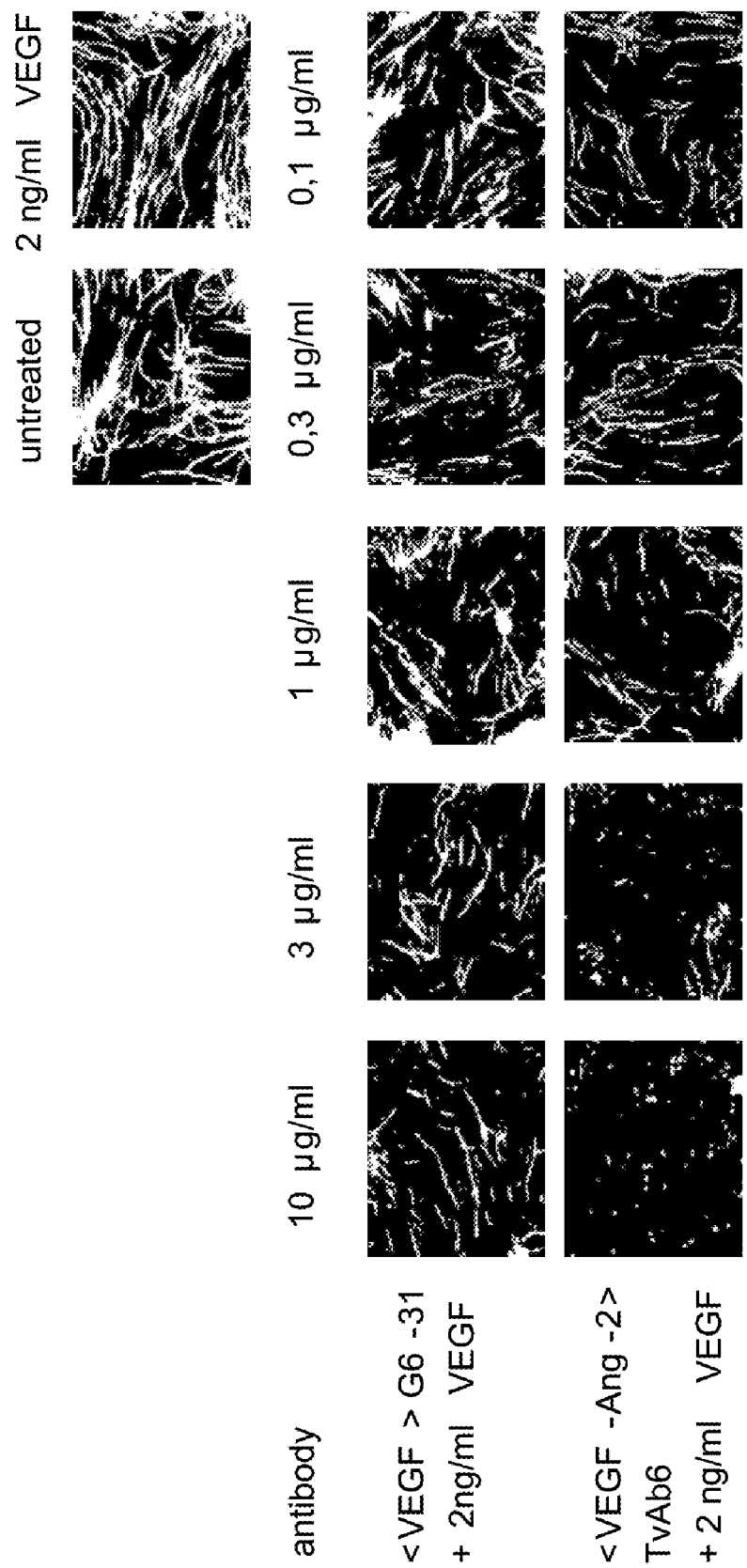

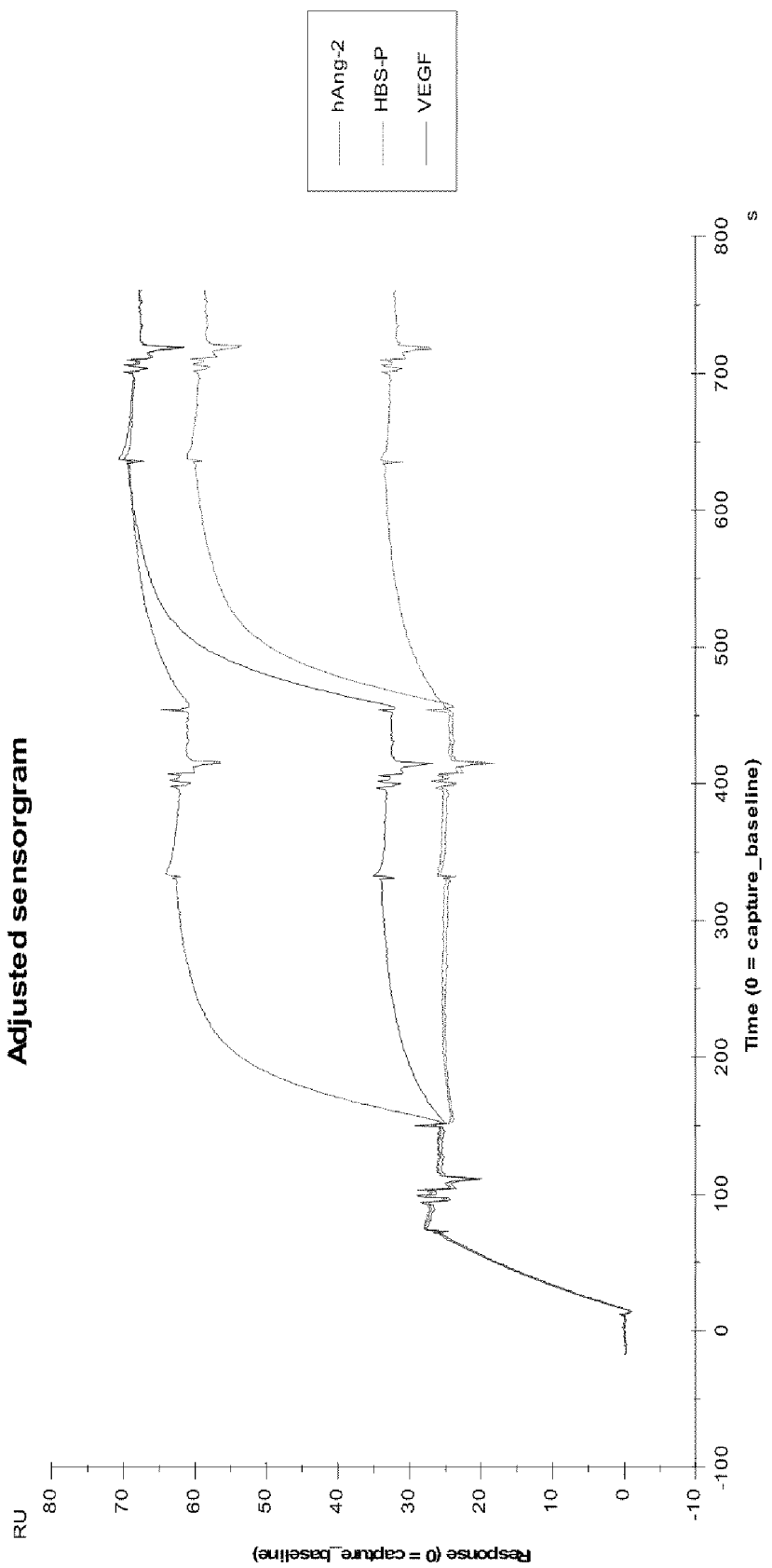

BISPECIFIC ANTI-VEGF/ANTI-ANG-2 ANTIBODIES

PRIORITY TO RELATED APPLICATION(S)

This application claims the benefit of European Patent Application No. 08017607.6, filed Oct. 8, 2008, and European Patent Application No. 08021834.0, filed Dec. 16, 2008, each of which is hereby incorporated by reference in its entirety.

BACKGROUND OF THE INVENTION

The present invention relates to bispecific antibodies against human vascular endothelial growth factor (VEGF/VEGF-A) and human angiopoietin-2 (ANG-2), methods for their production, pharmaceutical compositions containing said antibodies, and uses thereof.

Angiogenesis is implicated in the pathogenesis of a variety of disorders which include solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al., Annu Rev. Physiol. 53 (1991) 217-239; and Garner, A., Vascular diseases, in: Pathobiology of ocular disease, A dynamic approach, Garner, A., and Klintworth, G. K. (eds.), 2nd edition, Marcel Dekker, N.Y. (1994), pp 1625-1710). In the case of solid tumors, the neovascularization allows the tumor cells to acquire a growth advantage and proliferative autonomy compared to the normal cells. Accordingly, a correlation has been observed between density of microvessels in tumor sections and patient survival in breast cancer as well as in several other tumors (Weidner, N., et al., N Engl J Med. 324 (1991) 1-8; Horak, E. R., et al., Lancet 340 (1992) 1120-1124; and Macchiarini, P., et al., Lancet 340 (1992) 145-146).

VEGF and Anti-VEGF Antibodies

Human vascular endothelial growth factor (VEGF/VEGF-A) (SEQ ID No: 105) is described in e.g. Leung, D. W., et al., Science 246 (1989) 1306-9; Keck, P. J., et al., Science 246 (1989) 1309-12 and Connolly, D. T., et al., J. Biol. Chem. 264 (1989) 20017-24. VEGF is involved in the regulation of normal and abnormal angiogenesis and neovascularization associated with tumors and intraocular disorders (Ferrara, N., et al., Endocr. Rev. 18 (1997) 4-25; Berkman, R. A., et al., J. Clin. Invest. 91 (1993) 153-159; Brown, L. F., et al., Human Pathol. 26 (1995) 86-91; Brown, L. F., et al., Cancer Res. 53 (1993) 4727-4735; Mattern, J., et al., Brit. J. Cancer. 73 (1996) 931-934; and Dvorak, H., et al., Am. J. Pathol. 146 (1995) 1029-1039). VEGF is a homodimeric glycoprotein that has been isolated from several sources. VEGF shows highly specific mitogenic activity for endothelial cells. VEGF has important regulatory functions in the formation of new blood vessels during embryonic vasculogenesis and in angiogenesis during adult life (Carmeliet, P., et al., Nature, 380 (1996) 435-439; Ferrara, N., et al., Nature, 380 (1996) 439-442; reviewed in Ferrara and Davis-Smyth, Endocrine Rev., 18 (1997) 4-25. The significance of the role played by VEGF has been demonstrated in studies showing that inactivation of a single VEGF allele results in embryonic lethality due to failed development of the vasculature (Carmeliet, P., et al., Nature, 380 (1996) 435-439; Ferrara, N., et al., Nature, 380 (1996) 439-442. In addition VEGF has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). The isolation and properties of VEGF have been reviewed; see Ferrara, N., et al., J. Cellular Biochem., 47 (1991) 211-218 and Connolly, J. Cellular Biochem., 47 (1991) 219-223. Alternative mRNA splicing of a single VEGF gene gives rise to five isoforms of VEGF.

Anti-VEGF neutralizing antibodies suppress the growth of a variety of human tumor cell lines in mice (Kim, I., et al., Nature 362 (1993) 841-844; Warren, S. R., et al., J. Clin. Invest. 95 (1995) 1789-1797; Borgstrom, P., et al., Cancer Res. 56 (1996) 4032-4039; and Melnyk, O., et al., Cancer Res. 56 (1996) 921-924). WO 94/10202, WO 98/45332, WO 2005/00900 and WO 00/35956 refer to antibodies against VEGF. Humanized monoclonal antibody bevacizumab (sold under the trade name Avastin®) is an anti-VEGF antibody used in tumor therapy WO 98/45331).

Ranibizumab (trade name Lucentis®) is a monoclonal antibody fragment derived from the same parent murine antibody as bevacizumab. It is much smaller than the parent molecule and has been affinity matured to provide stronger binding to VEGF-A (WO 98/45331). It is an anti-angiogenic that has been approved to treat the "wet" type of age-related macular degeneration (ARMD), a common form of age-related vision loss. Another anti-VEGF antibody is e.g. HuMab G6-31 described e.g. in US 2007/0141065.

ANG-2 and Anti-ANG-2 Antibodies

Human angiopoietin-2 (ANG-2) (alternatively abbreviated with ANGPT2 or ANG2) (SEQ ID No: 106) is described in Maisonpierre, P. C., et al, Science 277 (1997) 55-60 and Cheung, A. H., et al., Genomics 48 (1998) 389-91. The angiopoietins-1 and -2 (ANG-1 (SEQ ID No: 107) and ANG-2 (SEQ ID No: 106)) were discovered as ligands for Ties, a family of tyrosine kinases that is selectively expressed within the vascular endothelium. Yancopoulos, G. D., et al., Nature 407 (2000) 242-48. There are now four definitive members of the angiopoietin family. Angiopoietin-3 and -4 (ANG-3 and ANG-4) may represent widely diverged counterparts of the same gene locus in mouse and man. Kim, I., et al., FEBS Let, 443 (1999) 353-56; Kim, I., et al., J Biol Chem 274 (1999) 26523-28. ANG-1 and ANG-2 were originally identified in tissue culture experiments as agonist and antagonist, respectively (see for ANG-1: Davis, S., et al., Cell 87 (1996) 1161-69; and for ANG-2: Maisonpierre, P. C., et al., Science 277 (1997) 55-60). All of the known angiopoietins bind primarily to Tie2, and both ANG-1 and -2 bind to Tie2 with an affinity of 3 nM ($K_D$). Maisonpierre, P. C., et al., Science 277 (1997) 55-60. ANG-1 was shown to support EC survival and to promote endothelium integrity, Davis, S., et al., Cell 87 (1996) 1161-69; Kwak, H. J., et al., FEBS Lett 448 (1999) 249-53; Suri, C., et al., Science 282 (1998) 468-71; Thurston, G., et al., Science 286 (1999) 251 1-14; Thurston, G., et al., Nat. Med. 6 (2000) 460-63, whereas ANG-2 had the opposite effect and promoted blood vessel destabilization and regression in the absence of the survival factors VEGF or basic fibroblast growth factor. Maisonpierre, P. C., et al., Science 277 (1997) 55-60. However, many studies of ANG-2 function have suggested a more complex situation. ANG-2 might be a complex regulator of vascular remodeling that plays a role in both vessel sprouting and vessel regression. Supporting such roles for ANG-2, expression analysis reveals that ANG-2 is rapidly induced, together with VEGF, in adult settings of angiogenic sprouting, whereas ANG-2 is induced in the absence of VEGF in settings of vascular regression. Holash, J., et al., Science 284 (1999) 1994-98; Holash, J., et al., Oncogene 18 (1999) 5356-62. Consistent with a context-dependent role, ANG-2 specifically binds to the same endothelial-specific receptor, Tie-2, which is activated by ANG-1, but has context-dependent effects on its activation. Maisonpierre, P. C., et al., Science 277 (1997) 55-60.

Corneal angiogenesis assays have shown that both ANG-1 and ANG-2 had similar effects, acting synergistically with VEGF to promote growth of new blood vessels. Asahara, T., et al., Circ. Res. 83 (1998) 233-40. The possibility that there was a dose-dependent endothelial response was raised by the observation that, in vitro at high concentration, ANG-2 can also be pro-angiogenic. Kim, I., et al., Oncogene 19 (2000) 4549-52. At high concentration, ANG-2 acts as an apoptosis survival factor for endothelial cells during serum deprivation apoptosis through activation of Tie2 via PI-3 Kinase and Akt pathway. Kim, I., et al., Oncogene 19 (2000) 4549-52.

Other in vitro experiments suggested that, during sustained exposure, the effects of ANG-2 may progressively shift from that of an antagonist to an agonist of Tie2, and, at later time points, it may contribute directly to vascular tube formation and neovessel stabilization. Teichert-Kuliszewska, K., et al., Cardiovasc. Res. 49 (2001) 659-70. Furthermore, if ECs were cultivated on fibrin gel, activation of Tie2 with ANG-2 was also observed, perhaps suggesting that the action of ANG-2 could depend on EC differentiation state. Teichert-Kuliszewska, K., et al., Cardiovasc. Res. 49 (2001) 659-70. In microvascular EC cultured in a three-dimensional collagen gel, ANG-2 can also induce Tie2 activation and promote formation of capillary-like structures. Mochizuki, Y., et al., J. Cell. Sci. 115 (2002) 175-83. Use of a 3-D spheroidal coculture as an in-vitro model of vessel maturation demonstrated that direct contact between ECs and mesenchymal cells abrogates responsiveness to VEGF, whereas the presence of VEGF and ANG-2 induced sprouting. Korff, T., et al., Faseb J. 15 (2001) 447-57. Etoh, T. H. et al. demonstrated that ECs that constitutively express Tie2, the expression of MMP-1,-9 and u-PA were strongly upregulated by ANG-2 in the presence of VEGF. Etoh, T., et al., Cancer Res. 61 (2001) 2145-53. With an in vivo pupillary membrane model, Lobov, I. B. et al. showed that ANG-2 in the presence of endogenous VEGF promotes a rapid increase in capillary diameter, remodeling of the basal lamina, proliferation and migration of endothelial cells, and stimulates sprouting of new blood vessels. Lobov, I. B., et al., Proc. Natl. Acad. Sci. USA 99 (2002) 11205-10. By contrast, ANG-2 promotes endothelial cell death and vessel regression without endogenous VEGF. Lobov, I. B., et al., Proc. Natl. Acad. Sci. USA 99 (2002) 11205-10. Similarly, with an in vivo tumor model, Vajkoczy, P., et al. demonstrated that multicellular aggregates initiate vascular growth by angiogenic sprouting via the simultaneous expression of VEGFR-2 and ANG-2 by host and tumor endothelium. Vajkoczy, P., et al., J. Clin. Invest. 109 (2002) 777-85. This model illustrated that the established microvasculature of growing tumors is characterized by a continuous remodeling, putatively mediated by the expression of VEGF and ANG-2. Vajkoczy, P., et al., J Clin. Invest. 09 (2002) 777-85.

Knock-out mouse studies of Tie-2 and Angiopoietin-1 show similar phenotypes and suggest that Angiopoietin-1 stimulated Tie-2 phosphorylation mediates remodeling and stabilization of developing vessel, promoting blood vessel maturation during angiogenesis and maintenance of endothelial cell-support cell adhesion (Dumont, J., et al., Genes & Development, 8 (1994) 1897-1909; Sato, T. N., Nature, 376 (1995) 70-74; (Thurston, G., et al., Nature Medicine: 6 (2000) 460-463). The role of Angiopoietin-1 is thought to be conserved in the adult, where it is expressed widely and constitutively (Hanahan, D., Science, 277 (1997) 48-50; Zagzag, D., et al., Exp Neurology, 159:391-400 (1999)). In contrast, Angiopoietin-2 expression is primarily limited to sites of vascular remodeling where it is thought to block the constitutive stabilizing or maturing function of Angiopoietin-1, allowing vessels to revert to, and remain in, a plastic state which may be more responsive to sprouting signals (Hanahan, D., 1997; Holash, J., et al., Orzcogerze 18 (199) 5356-62; Maisonpierre, P. C., 1997). Studies of Angiopoietin-2 expression in pathological angiogenesis have found many tumor types to show vascular Angiopoietin-2 expression (Maisonpierre, P. C., et al., Science 277 (1997) 55-60). Functional studies suggest Angiopoietin-2 is involved in tumor angiogenesis and associate Angiopoietin-2 overexpression with increased tumor growth in a mouse xenograft model (Ahmad, S. A., et al., Cancer Res., 61 (2001) 1255-1259). Other studies have associated Angiopoietin-2 overexpression with tumor hypervascularity (Etoh, T., et al., Cancer Res. 61 (2001) 2145-53; Tanaka, F., et al., Cancer Res. 62 (2002) 124-29).

In recent years Angiopoietin-1, Angiopoietin-2 and/or Tie-2 have been proposed as possible anti-cancer therapeutic targets. For example U.S. Pat. Nos. 6,166,185, 5,650,490 and 5,814,464 each disclose anti-Tie-2 ligand and receptor antibodies. Studies using soluble Tie-2 were reported to decrease the number and size of tumors in rodents (Lin, 1997; Lin 1998). Siemester, G., et al. Siemeister, G., et al., Cancer Res. 59 (1999) 3185-91 generated human melanoma cell lines expressing the extracellular domain of Tie-2, injected these into nude mice and reported soluble Tie-2 to result in significant inhibition of tumor growth and tumor angiogenesis. Given that both Angiopoietin-1 and Angiopoietin-2 bind to Tie-2, it is unclear from these studies whether Angiopoietin-1, Angiopoietin-2 or Tie-2 would be an attractive target for anti-cancer therapy. However, effective anti-Angiopoietin-2 therapy is thought to be of benefit in treating diseases such as cancer, in which progression is dependant on aberrant angiogenesis where blocking the process can lead to prevention of disease advancement (Follunan, J., Nature Medicine. 1 (1995) 27-31).

In addition some groups have reported the use of antibodies and peptides that bind to Angiopoietin-2. See, for example, U.S. Pat. No. 6,166,185 and US 2003/10124129. WO 03/030833, WO 2006/068953, WO 03/057134 or US 2006/0122370.

Study of the effect of focal expression of Angiopoietin-2 has shown that antagonizing the Angiopoietin-1/Tie-2 signal loosens the tight vascular structure thereby exposing ECs to activating signals from angiogenesis inducers, e.g. VEGF (Hanahan, D., Science, 277 (1997) 48-50). This pro-angiogenic effect resulting from inhibition of Angiopoietin-1 indicates that anti-Angiopoietin-1 therapy would not be an effective anti-cancer treatment.

ANG-2 is expressed during development at sites where blood vessel remodeling is occurring. Maisonpierre, P. C., et al., Science 277 (1997) 55-60. In adult individuals, ANG-2 expression is restricted to sites of vascular remodeling as well as in highly vascularized tumors, including glioma, Osada, H., et al., Int. J. Oncol. 18 (2001) 305-09); Koga, K., et al., Cancer Res. 61 (2001) 6248-54, hepatocellular carcinoma, Tanaka, S., et al., J. Clin. Invest. 103 (1999) 341-45, gastric carcinoma, Etoh, T., et al., Cancer Res. 61 (2001) 2145-53; Lee, J. H., et al., Int. J. Oncol. 18 (2001) 355-61, thyroid tumor, Bunone, G., et al., Am J Pathol 155 (1999) 1967-76 non-small cell lung cancer, Wong, M. P., et al., Lung Cancer 29 (2000) 11-22, and cancer of colon, Ahmad, S. A., et al., Cancer 92 (2001) 1138-43, and prostate Wurmbach, J. H., et al., Anticancer Res. 20 (2000) 5217-20. Some tumor cells are found to express ANG-2. For example, Tanaka, S., et al., J. Clin. Invest. 103 (1999) 341-45 detected ANG-2 mRNA in 10 out of 12 specimens of human hepatocellular carcinoma (HCC). Ellis' group reported that ANG-2 is expressed ubiquitously in tumor epithelium. Ahmad, S. A., et al., Cancer 92 (2001) 1138-43. Other investigators reported similar findings. Chen, L., et al., J. Tongji Med. Univ. 21 (2001) 228-35. By detecting ANG-2 mRNA levels in archived human breast cancer specimens, Sfiligoi, C., et al., Int. J. Cancer 103 (2003) 466-74 reported that ANG-2 mRNA is significantly associated with auxiliary lymph node invasion, short disease-free time and poor overall survival. Tanaka, F., et al., Cancer Res. 62 (2002) 7124-29 reviewed a total of 236 patients of non-small cell lung cancer (NSCLC) with pathological stage-I to -IIIA, respectively. Using immunohistochemistry, they found that 16.9% of the NSCLC patients were ANG-2 positive. The microvessel density for ANG-2 positive tumor is significantly higher than that of ANG-2 negative. Such an angiogenic effect of ANG-2 was seen only when VEGF expression was high. Moreover, positive expression of ANG-2 was a significant factor to predict a poor postoperative survival. Tanaka, F., et al., Cancer Res. 62 (2002) 7124-29. However, they found no significant correlation between Ang-1 expression and the microvessel density. Tanaka, F., et al., Cancer Res. 62 (2002) 7124-29. These results suggest that ANG-2 is an indicator of poor prognosis patients with several types of cancer.

Recently, using an ANG-2 knockout mouse model, Yancopoulos' group reported that ANG-2 is required for postnatal angiogenesis. Gale, N. W., et al., Dev. Cell 3 (2002) 411-23. They showed that the developmentally programmed regression of the hyaloid vasculature in the eye does not occur in the ANG-2 knockout mice and their retinal blood vessels fail to sprout out from the central retinal artery. Gale, N. W., et al., Dev. Cell 3 (2002) 411-23. They also found that deletion of ANG-2 results in profound defects in the patterning and function of the lymphatic vasculature. Gale, N. W., et al., Dev. Cell 3 (200) 411-23. Genetic rescue with Ang-1 corrects the lymphatic, but not the angiogenesis defects. Gale, N. W., et al., Dev. Cell 3 (2002) 411-23.

Peters and his colleagues reported that soluble Tie2, when delivered either as recombinant protein or in a viral expression vector, inhibited in vivo growth of murine mammary carcinoma and melanoma in mouse models. Lin, P., et al., Proc. Natl. Acad. Sci. USA 95 (1998) 8829-34; Lin, P., et al., J. Clin. Invest. 100 (1997) 2072-78. Vascular densities in the tumor tissues so treated were greatly reduced. In addition, soluble Tie2 blocked angiogenesis in the rat corneal stimulated by tumor cell conditioned media. Lin, P., et al., J. Clin. Invest. 100 (1997) 2072-78. Furthermore, Isner and his team demonstrated that addition of ANG-2 to VEGF promoted significantly longer and more circumferential neovascularity than VEGF alone. Asahara, T., et al., Circ. Res. 83 (1998) 233-40. Excess soluble Tie2 receptor precluded modulation of VEGF-induced neovascularization by ANG-2. Asahara, T., et al., Circ. Res. 83 (1998) 233-40. Siemeister, G., et al., Cancer Res. 59 (1999) 3185-91 showed with nude mouse xenografts that overexpression of the extracellular ligand-binding domains of either Flt-1 or Tie2 in the xenografts results in significant inhibition of pathway could not be compensated by the other one, suggesting that the VEGF receptor pathway and the Tie2 pathway should be considered as two independent mediators essential for the process of in vivo angiogenesis. Siemeister, G., et al., Cancer Res. 59:3 (1999) 3185-91. This is proven by a more recent publication by White, R., R., et al., Proc. Natl. Acad. Sci. USA 100 (2003) 5028-33. In their study, it was demonstrated that a nuclease-resistant RNA aptamer that specifically binds and inhibits ANG-2 significantly inhibited neovascularization induced by bFGF in the rat corneal micropocket angiogenesis model.

Bispecific Antibodies

A wide variety of recombinant antibody formats have been developed in the recent past, e.g. tetravalent bispecific antibodies by fusion of, e.g., an IgG antibody format and single chain domains (see e.g. Coloma, M. J., et al., Nature Biotech 15 (1997) 159-163; WO 2001/077342; and Morrison, S. L., Nature Biotech 25 (2007) 1233-1234).

Also several other new formats wherein the antibody core structure (IgA, IgD, IgE, IgG or IgM) is no longer retained such as dia-, tria- or tetrabodies, minibodies, several single chain formats (scFv, Bis-scFv), which are capable of binding two or more antigens, have been developed (Holliger, P., et al., Nature Biotech 23 (2005) 1126-1136; Fischer, N., Léger, O., Pathobiology 74 (2007) 3-14; Shen, J., et al., Journal of Immunological Methods 318 (2007) 65-74; Wu, C., et al., Nature Biotech. 25 (2007) 1290-1297).

All such formats use linkers either to fuse the antibody core (IgA, IgD, IgE, IgG or IgM) to a further binding protein (e.g. scFv) or to fuse e.g. two Fab fragments or scFvs (Fischer, N., Léger, O., Pathobiology 74 (2007) 3-14). It has to be kept in mind that one may want to retain effector functions, such as e.g. complement-dependent cytotoxicity (CDC) or antibody dependent cellular cytotoxicity (ADCC), which are mediated through the Fc receptor binding, by maintaining a high degree of similarity to naturally occurring antibodies.

In WO 2007/024715 are reported dual variable domain immunoglobulins as engineered multivalent and multispecific binding proteins. A process for the preparation of biologically active antibody dimers is reported in U.S. Pat. No. 6,897,044. Multivalent $F_v$ antibody construct having at least four variable domains which are linked with each over via peptide linkers are reported in U.S. Pat. No. 7,129,330. Dimeric and multimeric antigen binding structures are reported in US 2005/0079170. Tri- or tetra-valent monospecific antigen-binding protein comprising three or four Fab fragments bound to each other covalently by a connecting structure, which protein is not a natural immunoglobulin are reported in U.S. Pat. No. 6,511,663. In WO 2006/020258 tetravalent bispecific antibodies are reported that can be efficiently expressed in prokaryotic and eukaryotic cells, and are useful in therapeutic and diagnostic methods. A method of separating or preferentially synthesizing dimers which are linked via at least one interchain disulfide linkage from dimers which are not linked via at least one interchain disulfide linkage from a mixture comprising the two types of polypeptide dimers is reported in US 2005/0163782. Bispecific tetravalent receptors are reported in U.S. Pat. No. 5,959,083. Engineered antibodies with three or more functional antigen binding sites are reported in WO 2001/077342.

Multispecific and multivalent antigen-binding polypeptides are reported in WO 1997/001580. WO 1992/004053 reports homoconjugates, typically prepared from monoclonal antibodies of the IgG class which bind to the same antigenic determinant are covalently linked by synthetic cross-linking Oligomeric monoclonal antibodies with high avidity for antigen are reported in WO 1991/06305 whereby the oligomers, typically of the IgG class, are secreted having two or more immunoglobulin monomers associated together to form tetravalent or hexavalent IgG molecules. Sheep-derived antibodies and engineered antibody constructs are reported in U.S. Pat. No. 6,350,860, which can be used to treat diseases wherein interferon gamma activity is pathogenic. In US 2005/0100543 are reported targetable constructs that are multivalent carriers of bi-specific antibodies, i.e., each molecule of a targetable construct can serve as a carrier of two or more bi-specific antibodies. Genetically engineered bispecific tetravalent antibodies are reported in WO 1995/009917. In WO 2007/109254 stabilized binding molecules that consist of or comprise a stabilized scFv are reported.

Combination of VEGF and ANG-2 Inhibitors

WO 2007/068895 refers to a combination of an ANG-2 antagonist and a VEGF, KDR and/or FLTL antagonists. WO 2007/089445 refers to ANG-2 and VEGF inhibitor combinations.

WO 2003/106501 refers to fusion proteins binding to Angiopoetin and conataining a multimerization domain. WO 2008/132568 fusion proteins binding to Angiopoetin and VEGF.

SUMMARY OF THE INVENTION

A first aspect of the current invention is a bispecific antibody that binds specifically to human vascular endothelial growth factor (VEGF) and human angiopoietin-2 (ANG-2), said antibody comprising a first antigen-binding site that specifically binds to human VEGF and a second antigen-binding site that specifically binds to human ANG-2.

Said bispecific antibodies are at least bivalent and may be trivalent, tetravalent or multivalent. Preferably the bispecific antibody according to the invention is bivalent, trivalent or tetravalent.

A further aspect of the invention is a nucleic acid molecule encoding said bispecific antibody.

The invention further provides an expression vector which comprises said nucleic acid according to the invention and which is capable of expressing said nucleic acid in a prokaryotic or eukaryotic host cell.

Also provided is are host cells containing such vectors for the recombinant production of an antibody according to the invention.

The invention further comprises a prokaryotic or eukaryotic host cell comprising a vector according to the invention.

The invention further comprises a method for the production of a bispecific antibody according to the invention, comprising expressing a nucleic acid according to the invention in a prokaryotic or eukaryotic host cell and recovering said bispecific antibody from said cell or the cell culture supernatant. The invention further comprises the antibody obtained by such a recombinant method.

Still further aspects of the invention are a pharmaceutical composition comprising said bispecific antibody, said composition for the treatment of cancer, the use of said bispecific antibody for the manufacture of a medicament for the treatment of cancer, a method of treatment of patient suffering from cancer by administering said bispecific antibody, to a patient in the need of such treatment.

The bispecific antibodies according to the invention show benefits for human patients in need of a VEGF and ANG-2 targeting therapy. The antibodies according to the invention have new and inventive properties causing a benefit for a patient suffering from such a disease, especially suffering from cancer. Surprisingly it has found out that the bispecific antibodies according to the invention are more effective in tumor growth and/or inhibition of tumor angiogenesis compared to combination of the respective monospecific parent antibodies.

| Description of the Amino acid Sequences | | |
|---|---|---|
| SEQ ID NO: | 1 | heavy chain CDR3, <VEGF>bevacizumab |
| SEQ ID NO: | 2 | heavy chain CDR2, <VEGF>bevacizumab |
| SEQ ID NO: | 3 | heavy chain CDR1, <VEGF>bevacizumab |
| SEQ ID NO: | 4 | light chain CDR3, <VEGF>bevacizumab |
| SEQ ID NO: | 5 | light chain CDR2, <VEGF>bevacizumab |
| SEQ ID NO: | 6 | light chain CDR1, <VEGF>bevacizumab |
| SEQ ID NO: | 7 | heavy chain variable domain, <VEGF>bevacizumab |
| SEQ ID NO: | 8 | light chain variable domain, <VEGF>bevacizumab |
| SEQ ID NO: | 9 | heavy chain CDR3, <VEGF>ranibizumab |
| SEQ ID NO: | 10 | heavy chain CDR2, <VEGF>ranibizumab |
| SEQ ID NO: | 11 | heavy chain CDR1, <VEGF>ranibizumab |
| SEQ ID NO: | 12 | light chain CDR3, <VEGF>ranibizumab |
| SEQ ID NO: | 13 | light chain CDR2, <VEGF>ranibizumab |
| SEQ ID NO: | 14 | light chain CDR1, <VEGF>ranibizumab |
| SEQ ID NO: | 15 | heavy chain variable domain, <VEGF>ranibizumab |
| SEQ ID NO: | 16 | light chain variable domain, <VEGF>ranibizumab |
| SEQ ID NO: | 17 | heavy chain CDR3, <VEGF>HuMab G6-31 |
| SEQ ID NO: | 18 | heavy chain CDR2, <VEGF> HuMab G6-31 |
| SEQ ID NO: | 19 | heavy chain CDR1, <VEGF> HuMab G6-31 |
| SEQ ID NO: | 20 | light chain CDR3, <VEGF> HuMab G6-31 |
| SEQ ID NO: | 21 | light chain CDR2, <VEGF> HuMab G6-31 |
| SEQ ID NO: | 22 | light chain CDR1, <VEGF> HuMab G6-31 |
| SEQ ID NO: | 23 | heavy chain variable domain, <VEGF> HuMab G6-31 |
| SEQ ID NO: | 24 | light chain variable domain, <VEGF> HuMab G6-31 |
| SEQ ID NO: | 25 | heavy chain CDR3, <ANG-2> Mab 536 |
| SEQ ID NO: | 26 | heavy chain CDR2, <ANG-2> Mab 536 |
| SEQ ID NO: | 27 | heavy chain CDR1, <ANG-2> Mab 536 |
| SEQ ID NO: | 28 | light chain CDR3, <ANG-2> Mab 536 |
| SEQ ID NO: | 29 | light chain CDR2, <ANG-2> Mab 536 |
| SEQ ID NO: | 30 | light chain CDR1, <ANG-2> Mab 536 |
| SEQ ID NO: | 31 | heavy chain variable domain, <ANG-2> Mab 536 |
| SEQ ID NO: | 32 | light chain variable domain, <ANG-2> Mab 536 |
| SEQ ID NO: | 33 | (G4S)4 linker |
| SEQ ID NO: | 34 | lambda light chain constant region |
| SEQ ID NO: | 35 | human heavy chain constant region derived from IgG1 |
| SEQ ID NO: | 36 | human heavy chain constant region derived from IgG4 |
| SEQ ID NO: | 37 | kappa light chain constant region |
| SEQ ID NO: | 38 | heavy chain CDR3, <ANG-2> Ang2s_R3_LC03 |
| SEQ ID NO: | 39 | heavy chain CDR2, <ANG-2> Ang2s_R3_LC03 |
| SEQ ID NO: | 40 | heavy chain CDR1, <ANG-2> Ang2s_R3_LC03 |
| SEQ ID NO: | 41 | light chain CDR3, <ANG-2> Ang2s_R3_LC03 |
| SEQ ID NO: | 42 | light chain CDR2, <ANG-2> Ang2s_R3_LC03 |
| SEQ ID NO: | 43 | light chain CDR1, <ANG-2> Ang2s_R3_LC03 |
| SEQ ID NO: | 44 | heavy chain variable domain, <ANG-2> Ang2s_R3_LC03 |
| SEQ ID NO: | 45 | light chain variable domain, <ANG-2> Ang2s_R3_LC03 |
| SEQ ID NO: | 46 | heavy chain CDR3, <ANG-2>Ang2i_LC06 |
| SEQ ID NO: | 47 | heavy chain CDR2, <ANG-2>Ang2i_LC06 |
| SEQ ID NO: | 48 | heavy chain CDR1, <ANG-2>Ang2i_LC06 |
| SEQ ID NO: | 49 | light chain CDR3, <ANG-2>Ang2i_LC06 |
| SEQ ID NO: | 50 | light chain CDR2, <ANG-2>Ang2i_LC06 |
| SEQ ID NO: | 51 | light chain CDR1, <ANG-2>Ang2i_LC06 |
| SEQ ID NO: | 52 | heavy chain variable domain, <ANG-2>Ang2i_LC06 |
| SEQ ID NO: | 53 | light chain variable domain, <ANG-2>Ang2i_LC06 |
| SEQ ID NO: | 54 | heavy chain CDR3, <ANG-2>Ang2i_LC07 |
| SEQ ID NO: | 55 | heavy chain CDR2, <ANG-2>Ang2i_LC07 |
| SEQ ID NO: | 56 | heavy chain CDR1, <ANG-2>Ang2i_LC07 |
| SEQ ID NO: | 57 | light chain CDR3, <ANG-2>Ang2i_LC07 |
| SEQ ID NO: | 58 | light chain CDR2, <ANG-2>Ang2i_LC07 |
| SEQ ID NO: | 59 | light chain CDR1, <ANG-2>Ang2i_LC07 |
| SEQ ID NO: | 60 | heavy chain variable domain, <ANG-2>Ang2i_LC07 |
| SEQ ID NO: | 61 | light chain variable domain, <ANG-2>Ang2i_LC07 |
| SEQ ID NO: | 62 | heavy chain CDR3, <ANG-2>Ang2k_LC08 |
| SEQ ID NO: | 63 | heavy chain CDR2, <ANG-2> Ang2k_LC08 |
| SEQ ID NO: | 64 | heavy chain CDR1, <ANG-2> Ang2k_LC08 |
| SEQ ID NO: | 65 | light chain CDR3, <ANG-2> Ang2k_LC08 |
| SEQ ID NO: | 66 | light chain CDR2, <ANG-2> Ang2k_LC08 |
| SEQ ID NO: | 67 | light chain CDR1, <ANG-2> Ang2k_LC08 |
| SEQ ID NO: | 68 | heavy chain variable domain, <ANG-2> Ang2k_LC08 |
| SEQ ID NO: | 69 | light chain variable domain, <ANG-2> Ang2k_LC08 |
| SEQ ID NO: | 70 | heavy chain CDR3, <ANG-2> Ang2s_LC09 |
| SEQ ID NO: | 71 | heavy chain CDR2, <ANG-2> Ang2s_LC09 |

-continued

| | | Description of the Amino acid Sequences |
|---|---|---|
| SEQ ID NO: | 72 | heavy chain CDR1, <ANG-2> Ang2s_LC09 |
| SEQ ID NO: | 73 | light chain CDR3, <ANG-2> Ang2s_LC09 |
| SEQ ID NO: | 74 | light chain CDR2, <ANG-2> Ang2s_LC09 |
| SEQ ID NO: | 75 | light chain CDR1, <ANG-2> Ang2s_LC09 |
| SEQ ID NO: | 76 | heavy chain variable domain, <ANG-2> Ang2s_LC09 |
| SEQ ID NO: | 77 | light chain variable domain, <ANG-2> Ang2s_LC09 |
| SEQ ID NO: | 78 | heavy chain CDR3, <ANG-2> Ang2i_LC10 |
| SEQ ID NO: | 79 | heavy chain CDR2, <ANG-2> Ang2i_LC10 |
| SEQ ID NO: | 80 | heavy chain CDR1, <ANG-2> Ang2i_LC10 |
| SEQ ID NO: | 81 | light chain CDR3, <ANG-2> Ang2i_LC10 |
| SEQ ID NO: | 82 | light chain CDR2, <ANG-2> Ang2i_LC10 |
| SEQ ID NO: | 83 | light chain CDR1, <ANG-2> Ang2i_LC10 |
| SEQ ID NO: | 84 | heavy chain variable domain, <ANG-2> Ang2i_LC10 |
| SEQ ID NO: | 85 | light chain variable domain, <ANG-2> Ang2i_LC10 |
| SEQ ID NO: | 86 | heavy chain CDR3, <ANG-2> Ang2k_LC11 |
| SEQ ID NO: | 87 | heavy chain CDR2, <ANG-2> Ang2k_LC11 |
| SEQ ID NO: | 88 | heavy chain CDR1, <ANG-2> Ang2k_LC11 |
| SEQ ID NO: | 89 | light chain CDR3, <ANG-2> Ang2k_LC11 |
| SEQ ID NO: | 90 | light chain CDR2, <ANG-2> Ang2k_LC11 |
| SEQ ID NO: | 91 | light chain CDR1, <ANG-2> Ang2k_LC11 |
| SEQ ID NO: | 92 | heavy chain variable domain, <ANG-2> Ang2k_LC11 |
| SEQ ID NO: | 93 | light chain variable domain, <ANG-2> Ang2k_LC11 |
| SEQ ID NO: | 94 | heavy chain CDR3, <VEGF>B20-4.1 |
| SEQ ID NO: | 95 | heavy chain CDR2, <VEGF>B20-4.1 |
| SEQ ID NO: | 96 | heavy chain CDR1, <VEGF>B20-4.1 |
| SEQ ID NO: | 97 | light chain CDR3, <VEGF>B20-4.1 |
| SEQ ID NO: | 98 | light chain CDR2, <VEGF>B20-4.1 |
| SEQ ID NO: | 99 | light chain CDR1, <VEGF>B20-4.1 |
| SEQ ID NO: | 100 | heavy chain variable domain, <VEGF>B20-4.1 |
| SEQ ID NO: | 101 | light chain variable domain, <VEGF>B20-4.1 |
| SEQ ID NO: | 102 | bevacizumab heavy chain Ang2i_LC06 scFv fusion peptide of <VEGF-ANG-2> TvAb-2441-bevacizumab-LC06 |
| SEQ ID NO: | 103 | bevacizumab heavy chain Ang2i_LC08 scFv fusion peptide of <VEGF-ANG-2> TvAb-2441-bevacizumab-LC08 |
| SEQ ID NO: | 104 | light chain of bevacizumab |
| SEQ ID NO: | 105 | Human vascular endothelial growth factor (VEGF) |
| SEQ ID NO: | 106 | Human angiopoietin-2 (ANG-2) |
| SEQ ID NO: | 107 | Human angiopoietin-1 (ANG-1) |
| SEQ ID NO: | 108 | Human Tie-2 receptor |
| SEQ ID NO: | 109 | Heavy chain 1 of bispecific, tetravalent single chain Fab <VEGF-ANG-2> antibody molecule scFAb-Bevacizumab-LC06-2620 |
| SEQ ID NO: | 110 | Light chain of bispecific, tetravalent single chain Fab <VEGF-ANG-2> antibody molecule scFAb-Bevacizumab-LC06-2620 |
| SEQ ID NO: | 111 | Heavy chain 1 of bispecific, tetravalent single chain Fab <VEGF-ANG-2> antibody molecule scFab-Bevacizumab-Ang2i-LC06-2640 |
| SEQ ID NO: | 112 | Light chain of bispecific, tetravalent single chain Fab <VEGF-ANG-2> antibody molecule scFab-Bevacizumab-Ang2i-LC06-2640 |
| SEQ ID NO: | 113 | Heavy chain 1 of bispecific, tetravalent single chain Fab <VEGF-ANG-2> antibody molecule scFab-Bevacizumab-Ang2i-LC06-2641 |
| SEQ ID NO: | 114 | Light chain of bispecific, tetravalent single chain Fab <VEGF-ANG-2> antibody molecule scFab-Bevacizumab-Ang2i-LC06-2641 |
| SEQ ID NO: | 115 | Heavy chain 1 of bispecific, trivalent single chain Fab <VEGF-ANG-2> antibody molecule Bevacizumab-LC06-KiH-C-scFab |
| SEQ ID NO: | 116 | Heavy chain 2 of bispecific, trivalent single chain Fab <VEGF-ANG-2> antibody molecule Bevacizumab-LC06-KiH-C-scFab |
| SEQ ID NO: | 117 | Light chain of bispecific, trivalent single chain Fab <VEGF-ANG-2> antibody molecule Bevacizumab-LC06-KiH-C-scFab |
| SEQ ID NO: | 118 | Heavy chain 1 of bispecific, trivalent <VEGF-ANG-2> antibody molecule Bevacizumab-LC06-C-Fab-6CSS |
| SEQ ID NO: | 119 | Heavy chain 2 of bispecific, trivalent <VEGF-ANG-2> antibody molecule Bevacizumab-LC06-C-Fab-6CSS |
| SEQ ID NO: | 120 | Light chain of bispecific, trivalent <VEGF-ANG-2> antibody molecule Bevacizumab-LC06-C-Fab-6CSS |
| SEQ ID NO: | 121 | Heavy chain 1 of bispecific, bivalent domain exchanged <VEGF-ANG-2> antibody molecule Bevacizumab-LC06-CH1-CL |
| SEQ ID NO: | 122 | Heavy chain 2 of bispecific, bivalent domain exchanged <VEGF-ANG-2> antibody molecule Bevacizumab-LC06-CH1-CL |
| SEQ ID NO: | 123 | Light chain 1 of bispecific, bivalent domain exchanged <VEGF-ANG-2> antibody molecule Bevacizumab-LC06-CH1-CL |
| SEQ ID NO: | 124 | Light chain 2 of bispecific, bivalent domain exchanged <VEGF-ANG-2> antibody molecule Bevacizumab-LC06-CH1-CL |
| SEQ ID NO: | 125 | Heavy chain 1 of bispecific, bivalent domain exchanged <VEGF-ANG-2> antibody molecule Bevacizumab-LC06-VH-VL |
| SEQ ID NO: | 126 | Heavy chain 2 of bispecific, bivalent domain exchanged <VEGF-ANG-2> antibody molecule Bevacizumab-LC06-VH-VL |
| SEQ ID NO: | 127 | Light chain 1 of bispecific, bivalent domain exchanged <VEGF-ANG-2> antibody molecule Bevacizumab-LC06-VH-VL |
| SEQ ID NO: | 128 | Light chain 2 of bispecific, bivalent domain exchanged <VEGF-ANG-2> antibody molecule Bevacizumab-LC06-VH-VL |
| SEQ ID NO: | 129 | Heavy chain 1 of bispecific, bivalent domain exchanged <VEGF-ANG-2> antibody molecule Bevacizumab-LC06-VH-VL-SS |
| SEQ ID NO: | 130 | Heavy chain 2 of bispecific, bivalent domain exchanged <VEGF-ANG-2> antibody molecule Bevacizumab-LC06-VH-VL-SS |
| SEQ ID NO: | 131 | Light chain 1 of bispecific, bivalent domain exchanged <VEGF-ANG-2> antibody molecule Bevacizumab-LC06-VH-VL-SS |
| SEQ ID NO: | 132 | Light chain 2 of bispecific, bivalent domain exchanged <VEGF-ANG-2> antibody molecule Bevacizumab-LC06-VH-VL-SS |
| SEQ ID NO: | 133 | Heavy chain 1 of bispecific, bivalent ScFab-Fc fusion <VEGF-ANG-2> antibody molecule Bevacizumab-LC06-N-scFab |
| SEQ ID NO: | 134 | Heavy chain 2 of bispecific, bivalent ScFab-Fc fusion <VEGF-ANG-2> antibody molecule Bevacizumab-LC06-N-scFab |
| SEQ ID NO: | 135 | Heavy chain 1 of bispecific, bivalent ScFab-Fc fusion <VEGF-ANG-2> antibody molecule Bevacizumab-LC06-N-scFabSS |
| SEQ ID NO: | 136 | Heavy chain 2 of bispecific, bivalent ScFab-Fc fusion <VEGF-ANG-2> antibody molecule Bevacizumab-LC06-N-scFabSS |

DESCRIPTION OF THE FIGURES

FIG. 2B Plasmid maps of the modified heavy chain and the light vectors used for the expression of disulfide-stabilized <VEGF-ANG-2> TvAb6

FIG. 8a Efficacy of disulfide-stabilized <VEGF-ANG-2> TvAb6 in comparison to <ANG-2> Mab536, <VEGF> G6-31 and the combination of Mab536 and G6-31 in the staged subcutaneous Colo205 xenograft model in Scid beige mice (study ANG2_Pz_Colo205_003)

FIG. 9 Blocking of VEGF-induced tube formation by the bispecific tetravalent antibody <VEGF-ANG-2> TvAb6—Results FIG. 10A+B Blocking of VEGF-induced tube formation by the disulfide-stabilized <VEGF-ANG-2> TvAb6—Quantitative analysis FIG. 11 Schematic view of VEGF binding analysis by surface plasmon resonance (Biacore).

DETAILED DESCRIPTION OF THE INVENTION

Figure 1A:
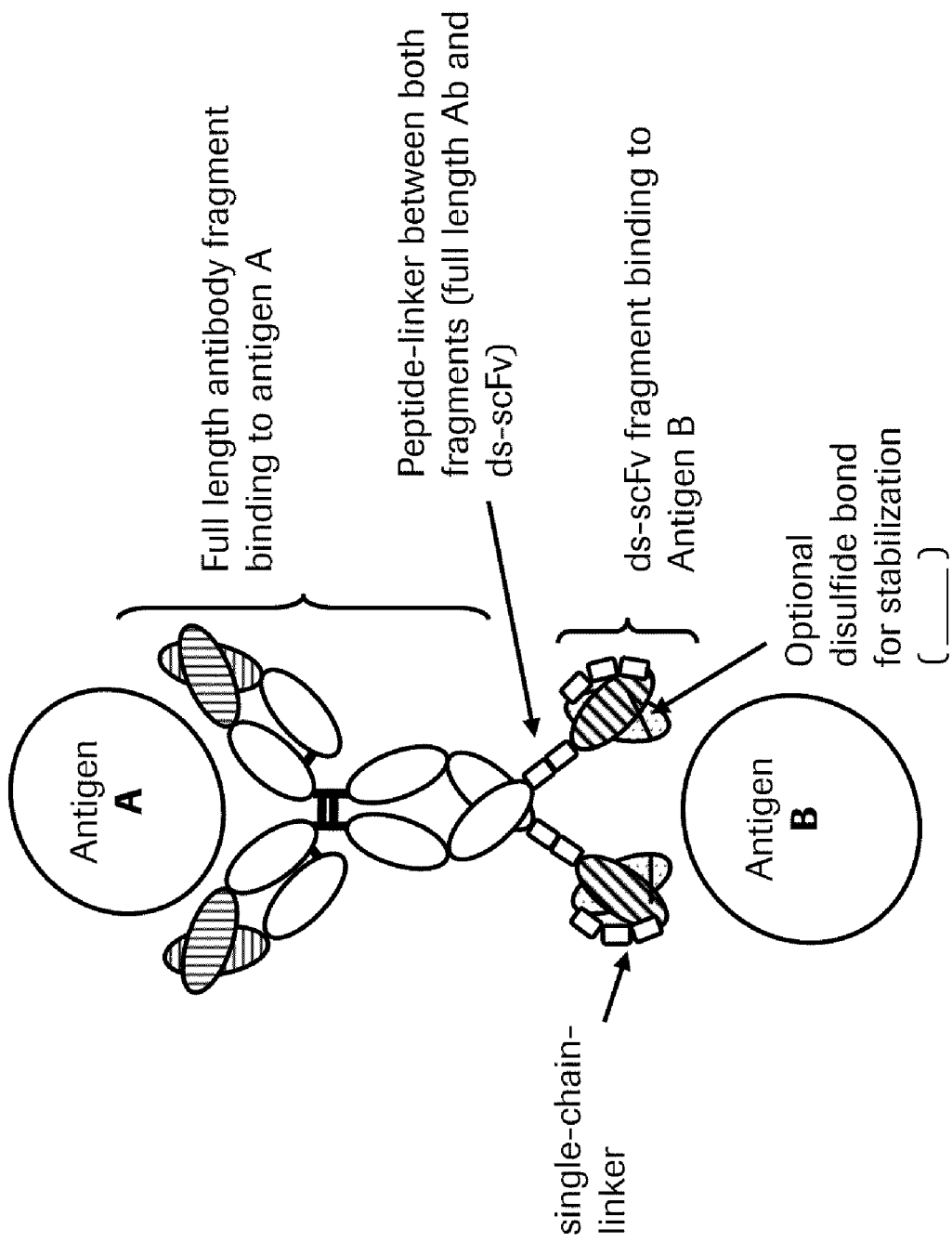
FIG. 1A Schematic structure of one tetravalent embodiment of a bispecific antibody according to the invention which binds to VEGF and ANG-2, wherein one of the Antigens A or B is VEGF, while the other is ANG-2. The structure is based on a full length antibody binding to Antigen A, to which two (optionally disulfide-stabilized) single chain Fv's binding to Antigen B, are linked via the a peptide-linker.

The present invention relates to a bispecific antibody that binds specifically to human vascular endothelial growth factor (VEGF) and human angiopoietin-2 (ANG-2), said antibody comprising a first antigen-binding site that specifically binds to human VEGF and a second antigen-binding site that specifically binds to human ANG-2.

In an embodiment of the present invention, the bispecific antibody is characterized in that
i) the antibody comprises a first antigen-binding site that specifically binds to human VEGF and a second antigen-binding site that specifically binds to human ANG-2, and each antigen-binding site comprises an antibody heavy chain variable domain and an antibody light chain variable domain;
ii) said first antigen-binding site comprises in the heavy chain variable domain:
a CDR3 region having an amino acid sequence selected from the group consisting of: SEQ ID NO: 1, SEQ ID NO: 9, SEQ ID NO: 17, and SEQ ID NO: 94;
a CDR2 region having an amino acid sequence selected from the group consisting of: SEQ ID NO: 2, SEQ ID NO: 10, SEQ ID NO: 18, and SEQ ID NO: 95;
and a CDR1 region having an amino acid sequence selected from the group consisting of: SEQ ID NO:3, SEQ ID NO: 11, SEQ ID NO: 19, and SEQ ID NO: 96, and in the light chain variable domain:
a CDR3 region having an amino acid sequence selected from the group consisting of: SEQ ID NO: 4, SEQ ID NO: 12, SEQ ID NO: 20, and SEQ ID NO: 97,
a CDR2 region having an amino acid sequence selected from the group consisting of: SEQ ID NO:5, SEQ ID NO: 13, SEQ ID NO: 21, and SEQ ID NO: 98; and
a CDR1 region having an amino acid sequence selected from the group consisting of:SEQ ID NO:6, SEQ ID NO: 14, SEQ ID NO: 22, and SEQ ID NO: 99; and
iii) said second antigen-binding site comprises
in the heavy chain variable domain:
a CDR3 region having an amino acid sequence selected from the group consisting of: SEQ ID NO: 25, SEQ ID NO: 38, SEQ ID NO: 46, SEQ ID NO: 54, SEQ ID NO: 62, SEQ ID NO: 70, SEQ ID NO: 78, and SEQ ID NO: 86;
a CDR2 region having an amino acid sequence selected from the group consisting of: SEQ ID NO: 26, SEQ ID NO: 39, SEQ ID NO: 47, SEQ ID NO: 55, SEQ ID NO: 63, SEQ ID NO: 71, SEQ ID NO: 79, and SEQ ID NO: 87; and
a CDR1 region having an amino acid sequence selected from the group consisting of: SEQ ID NO:27, SEQ ID NO: 40, SEQ ID NO: 48, SEQ ID NO: 56, SEQ ID NO: 64, SEQ ID NO: 72, SEQ ID NO: 80, and SEQ ID NO: 88; and in the light chain variable domain:
a CDR3 region having an amino acid sequence selected from the group consisting of: SEQ ID NO: 28, SEQ ID NO: 28 with the mutations T92L, H93Q and W94T, SEQ ID NO: 41, SEQ ID NO: 49, SEQ ID NO: 57, SEQ ID NO: 65, SEQ ID NO: 73, SEQ ID NO: 81, and SEQ ID NO: 89;
a CDR2 region having an amino acid sequence selected from the group consisting of: SEQ ID NO:29, SEQ ID NO: 42, SEQ ID NO: 50, SEQ ID NO: 58, SEQ ID NO: 66, SEQ ID NO: 74, SEQ ID NO: 82 and SEQ ID NO: 90; and
a CDR1 region having an amino acid sequence selected from the group consisting of: SEQ ID NO:30, SEQ ID NO: 43, SEQ ID NO: 51, SEQ ID NO: 59, SEQ ID NO: 67, SEQ ID NO: 75, SEQ ID NO: 83, and SEQ ID NO: 91.

In one embodiment of the invention the bispecific antibody according to the invention is characterized in that
i) said antigen-binding sites each comprise an antibody heavy chain variable domain and an antibody light chain variable domain;
ii) said first antigen-binding site comprises, in the heavy chain variable domain, a CDR3 region of SEQ ID NO: 1, a CDR2 region of SEQ ID NO: 2, and a CDR1 region of SEQ ID NO:3, and, in the light chain variable domain, a CDR3 region of SEQ ID NO: 4, a CDR2 region of SEQ ID NO:5, and a CDR1 region of SEQ ID NO:6;
or said first antigen-binding site comprises, in the heavy chain variable domain, a CDR3 region of SEQ ID NO: 9, a CDR2 region of SEQ ID NO: 10, and a CDR1 region of SEQ ID NO:11, and, in the light chain variable domain, a CDR3 region of SEQ ID NO: 12, a CDR2 region of SEQ ID NO:13, and a CDR1 region of SEQ ID NO:14;
or said first antigen-binding site comprises, in the heavy chain variable domain, a CDR3 region of SEQ ID NO: 17, a CDR2 region of SEQ ID NO: 18, and a CDR1 region of SEQ ID NO:19, and, in the light chain variable domain, a CDR3 region of SEQ ID NO: 20, a CDR2 region of SEQ ID NO:21, and a CDR1 region of SEQ ID NO:22; and
iii) said second antigen-binding site comprises, in the heavy chain variable domain, a CDR3 region of SEQ ID NO: 25, a CDR2 region of SEQ ID NO: 26, and a CDR1 region of SEQ ID NO:27, and, in the light chain variable domain, a CDR3 region of SEQ ID NO: 28 or SEQ ID NO: 28 with the mutations T92L, H93Q and W94T, a CDR2 region of SEQ ID NO:29, and a CDR1 region of SEQ ID NO:30.

In one embodiment of the invention the bispecific antibody according to the invention is characterized in that
i) said antigen-binding sites are each a pair of an antibody heavy chain variable domain and an antibody light chain variable domain;
ii) said first antigen-binding site comprises, as the heavy chain variable domain, SEQ ID NO: 7, SEQ ID NO: 15, SEQ ID NO: 23, or SEQ ID NO: 100, and, as the light chain variable domain, SEQ ID NO: 8, SEQ ID NO: 16, SEQ ID NO: 24, or SEQ ID NO: 101, and
iii) said second antigen-binding site comprises, as the heavy chain variable domain, SEQ ID NO: 31, SEQ ID NO: 44, SEQ ID NO: 52, SEQ ID NO: 60, SEQ ID NO: 68, SEQ ID NO: 76, SEQ ID NO: 84 or SEQ ID NO: 92, and, as the light chain variable domain, SEQ ID NO: 32, SEQ ID NO: 32 with the mutations T92L, H93Q and W94T SEQ ID NO: 45, SEQ ID NO: 53, SEQ ID NO: 61, SEQ ID NO: 69, SEQ ID NO: 77, SEQ ID NO: 85 or SEQ ID NO: 93.

In one embodiment of the invention the bispecific antibody according to the invention is characterized in that said first antigen-binding site comprises, in the heavy chain variable domain, a CDR3 region of SEQ ID NO: 1, or SEQ ID NO: 94, a CDR2 region of SEQ ID NO: 2, or SEQ ID NO: 95, and a CDR1 region of SEQ ID NO:3, or SEQ ID NO: 96, and, in the light chain variable domain, a CDR3 region of SEQ ID NO: 4, or SEQ ID NO: 97, a CDR2 region of SEQ ID NO:5, or SEQ ID NO: 98, and a CDR1 region of SEQ ID NO:6, or SEQ ID NO: 99; said second antigen-binding site comprises, in the heavy chain variable domain, a CDR3 region of SEQ ID NO: 38, SEQ ID NO: 46, SEQ ID NO: 54, SEQ ID NO: 62, SEQ ID NO: 70, SEQ ID NO: 78, or SEQ ID NO: 86, a CDR2 region of SEQ ID NO: 39, SEQ ID NO: 47, SEQ ID NO: 55, SEQ ID NO: 63, SEQ ID NO: 71, SEQ ID NO: 79, or SEQ ID NO: 87, and a CDR1 region of SEQ ID NO: 40, SEQ ID NO: 48, SEQ ID NO: 56, SEQ ID NO: 64, SEQ ID NO: 72, SEQ ID NO: 80, or SEQ ID NO: 88, and, in the light chain variable domain, a CDR3 region of SEQ ID NO: 41, SEQ ID NO: 49, SEQ ID NO: 57, SEQ ID NO: 65, SEQ ID NO: 73, SEQ ID NO: 81, or SEQ ID NO: 89, a CDR2 region of SEQ ID NO: 42, SEQ ID NO: 50, SEQ ID NO: 58, SEQ ID NO: 66, SEQ ID NO: 74, SEQ ID NO: 82 or SEQ ID NO: 90, and a CDR1 region of SEQ ID NO: 43, SEQ ID NO: 51, SEQ ID NO: 59, SEQ ID NO: 67, SEQ ID NO: 75, SEQ ID NO: 83, or SEQ ID NO: 91.

In one embodiment of the invention the bispecific antibody according to the invention is characterized in that said first antigen-binding site comprises, as the heavy chain variable domain, SEQ ID NO: 7, or SEQ ID NO: 100, and, as the light chain variable domain, SEQ ID NO: 8 or SEQ ID NO: 101, and said second antigen-binding site specifically binding to ANG-2 comprises, as the heavy chain variable domain, SEQ ID NO: 44, SEQ ID NO: 52, SEQ ID NO: 60, SEQ ID NO: 68, SEQ ID NO: 76, SEQ ID NO: 84 or SEQ ID NO: 92, and, as the light chain variable domain, SEQ ID NO: 45, SEQ ID NO: 53, SEQ ID NO: 61, SEQ ID NO: 69, SEQ ID NO: 77, SEQ ID NO: 85 or SEQ ID NO: 93.

In one embodiment of the invention the bispecific antibody according to the invention is characterized in that said second antigen-binding site comprises, in the heavy chain variable domain, a CDR3 region of SEQ ID NO: 38, SEQ ID NO: 46, SEQ ID NO: 54, SEQ ID NO: 62, SEQ ID NO: 70, SEQ ID NO: 78, or SEQ ID NO: 86, a CDR2 region of SEQ ID NO: 39, SEQ ID NO: 47, SEQ ID NO: 55, SEQ ID NO: 63, SEQ ID NO: 71, SEQ ID NO: 79, or SEQ ID NO: 87, and a CDR1 region of SEQ ID NO: 40, SEQ ID NO: 48, SEQ ID NO: 56, SEQ ID NO: 64, SEQ ID NO: 72, SEQ ID NO: 80, or SEQ ID NO: 88, and, in the light chain variable domain, a CDR3 region of SEQ ID NO: 41, SEQ ID NO: 49, SEQ ID NO: 57, SEQ ID NO: 65, SEQ ID NO: 73, SEQ ID NO: 81, or SEQ ID NO: 89, a CDR2 region of SEQ ID NO: 42, SEQ ID NO: 50, SEQ ID NO: 58, SEQ ID NO: 66, SEQ ID NO: 74, SEQ ID NO: 82 or SEQ ID NO: 90, and a CDR1 region of SEQ ID NO: 43, SEQ ID NO: 51, SEQ ID NO: 59, SEQ ID NO: 67, SEQ ID NO: 75, SEQ ID NO: 83, or SEQ ID NO: 91.

In one embodiment of the invention the bispecific antibody according to the invention is characterized in that said second antigen-binding site comprises, as the heavy chain variable domain, SEQ ID NO: 44, SEQ ID NO: 52, SEQ ID NO: 60, SEQ ID NO: 68, SEQ ID NO: 76, SEQ ID NO: 84 or SEQ ID NO: 92, and, as the light chain variable domain, SEQ ID NO:

45, SEQ ID NO: 53, SEQ ID NO: 61, SEQ ID NO: 69, SEQ ID NO: 77, SEQ ID NO: 85 or SEQ ID NO: 93.

In one embodiment of the invention the bispecific antibody according to the invention is characterized in that said first antigen-binding site comprises, in the heavy chain variable domain, a CDR3 region of SEQ ID NO: 1, a CDR2 region of SEQ ID NO: 2, and a CDR1 region of SEQ ID NO:3, and, in the light chain variable domain, a CDR3 region of SEQ ID NO: 4, a CDR2 region of SEQ ID NO:5, and a CDR1 region of SEQ ID NO:6; and said second antigen-binding site comprises, in the heavy chain variable domain, a CDR3 region of SEQ ID NO: 46, a CDR2 region of SEQ ID NO: 47, and a CDR1 region of SEQ ID NO: 48, and, in the light chain variable domain, a CDR3 region of SEQ ID NO: 49, a CDR2 region of SEQ ID NO: 50, and a CDR1 region of SEQ ID NO: 51.

In one embodiment of the invention the bispecific antibody according to the invention is characterized in that said first antigen-binding site comprises, as the heavy chain variable domain, SEQ ID NO: 7, and, as the light chain variable domain, SEQ ID NO: 8, and said second antigen-binding site comprises, as the heavy chain variable domain, SEQ ID NO: 52, and, as the light chain variable domain, SEQ ID NO: 53.

In one embodiment of the invention the bispecific antibody according to the invention is characterized in that said first antigen-binding site comprises, in the heavy chain variable domain, a CDR3 region of SEQ ID NO: 1, or SEQ ID NO: 94, a CDR2 region of SEQ ID NO: 2, or SEQ ID NO: 95, and a CDR1 region of SEQ ID NO:3, or SEQ ID NO: 96, and, in the light chain variable domain, a CDR3 region of SEQ ID NO: 4, or SEQ ID NO: 97, a CDR2 region of SEQ ID NO:5, or SEQ ID NO: 98, and a CDR1 region of SEQ ID NO:6, or SEQ ID NO: 99; said second antigen-binding site comprises, in the heavy chain variable domain, a CDR3 region of SEQ ID NO: 62, or SEQ ID NO: 86, a CDR2 region of SEQ ID NO: 63, or SEQ ID NO: 87, and a CDR1 region of SEQ ID NO: 64, or SEQ ID NO: 88, and, in the light chain variable domain, a CDR3 region of SEQ ID NO: 65, or SEQ ID NO: 89, a CDR2 region of SEQ ID NO: 66, or SEQ ID NO: 90, and a CDR1 region of SEQ ID NO: 67, or SEQ ID NO: 91.

In one embodiment of the invention the bispecific antibody according to the invention is characterized in that said first antigen-binding site comprises, as the heavy chain variable domain, SEQ ID NO: 7, or SEQ ID NO: 100, and as light chain variable domain SEQ ID NO: 8 or SEQ ID NO: 101, and said second antigen-binding site comprises, as the heavy chain variable domain, SEQ ID NO: 68 or SEQ ID NO: 92, and, as the light chain variable domain, SEQ ID NO: 69 or SEQ ID NO: 93.

In one embodiment of the invention the bispecific antibody according to the invention is characterized in that said first antigen-binding site comprises, in the heavy chain variable domain, a CDR3 region of SEQ ID NO: 1, a CDR2 region of SEQ ID NO: 2, and a CDR1 region of SEQ ID NO:3, and, in the light chain variable domain, a CDR3 region of SEQ ID NO: 4, a CDR2 region of SEQ ID NO:5, and a CDR1 region of SEQ ID NO:6; said second antigen-binding site comprises, in the heavy chain variable domain, a CDR3 region of SEQ ID NO: 62, a CDR2 region of SEQ ID NO: 63, and a CDR1 region of SEQ ID NO: 64, and, in the light chain variable domain, a CDR3 region of SEQ ID NO: 65, a CDR2 region of SEQ ID NO: 66, and a CDR1 region of SEQ ID NO: 67.

In one embodiment of the invention the bispecific antibody according to the invention is characterized in that said first antigen-binding site comprises, as the heavy chain variable domain, SEQ ID NO: 7, and, as the light chain variable domain, SEQ ID NO: 8; and said second antigen-binding site comprises, as the heavy chain variable domain, SEQ ID NO: 68, and, as the light chain variable domain, SEQ ID NO: 69.

In one embodiment of the invention the bispecific antibody according to the invention is characterized in that said first antigen-binding site s comprises, in the heavy chain variable domain, a CDR3 region of SEQ ID NO: 1, a CDR2 region of SEQ ID NO: 2, and a CDR1 region of SEQ ID NO:3, and, in the light chain variable domain, a CDR3 region of SEQ ID NO: 4, a CDR2 region of SEQ ID NO:5, and a CDR1 region of SEQ ID NO:6; and said second antigen-binding site comprises, in the heavy chain variable domain, a CDR3 region of SEQ ID NO: 78, a CDR2 region of SEQ ID NO: 79, and a CDR1 region of SEQ ID NO: 80, and, in the light chain variable domain a CDR3 region of SEQ ID NO: 81, a CDR2 region of SEQ ID NO: 82, and a CDR1 region of SEQ ID NO: 83.

In one embodiment of the invention the bispecific antibody according to the invention is characterized in that said first antigen-binding site comprises, as the heavy chain variable domain, SEQ ID NO: 7, and, as the light chain variable domain, SEQ ID NO: 8; and said second antigen-binding site comprises, as the heavy chain variable domain, SEQ ID NO: 84, and, as the light chain variable domain, SEQ ID NO: 85.

Another embodiment of the invention is a bispecific antibody that specifically binds to human vascular endothelial growth factor (VEGF) and human angiopoietin-2 (ANG-2) characterized in that the parent anti-ANG-2 antibody does not specifically bind to human Angiopoietin 1 (ANG-1). Typical parent antibodies which specifically bind to human ANG-2, but not to human ANG-1 are e.g. Ang2s_R3_LC03, Ang2s_LC09, Ang2i_LC06, Ang2i_LC07, and preferably Ang2i_LC10 or antibodies binding to the same epitope as Ang2s_R3_LC03, Ang2s_LC09, Ang2i_LC06, Ang2i_LC07, Ang2i_LC10, preferably antibodies binding to the same epitope as Ang2i_LC06, or Ang2i_LC10. Therefore in one embodiment of the invention the bispecific antibody that specifically binds to human vascular endothelial growth factor (VEGF) and human angiopoietin-2 (ANG-2) but not to human ANG-1 (or wherein the parent anti-ANG-2 antibody does not specifically bind to human Angiopoietin 1 (ANG-1)) binds to the same epitope as Ang2s_R3_LC03, Ang2s_LC09, Ang2i_LC06, Ang2i_LC07, Ang2i_LC10, preferably to the same epitope as Ang2i_LC06 or Ang2i_LC10. Such bispecific antibodies that bind specifically to human vascular endothelial growth factor (VEGF) and human angiopoietin-2 (ANG-2) but not to human ANG-1 (or wherein the parent anti-ANG-2 antibody does not specifically bind to human Angiopoetin 1 (ANG-1)) can have improved properties such as e.g. biological or pharmacological activity, less toxicity, or pharmacokinetic profile, compared to bispecific antibodies that specifically bind to human vascular endothelial growth factor (VEGF) and human angiopoietin-2 (ANG-2) as well as to human ANG-1.

Thus a preferred embodiment is a bispecific antibody that specifically binds to human VEGF and human ANG-2 which comprises a first antigen-binding site that specifically binds to human VEGF and a second antigen-binding site that specifically binds to human ANG-2, characterized in that the second antigen-binding site does not specifically bind to human Angiopoetin 1 (ANG-1).

One embodiment of the invention is a bispecific antibody that specifically binds to human vascular endothelial growth factor (VEGF) and human angiopoietin-2 (ANG-2) which comprises a first antigen-binding site that specifically binds to human VEGF and a second antigen-binding site that specifically binds to human ANG-2, characterized in that the ratio of the binding affinities $K_D$ (antigen-binding site specific for VEGF)/$K_D$ (antigen-binding site specific for ANG-2) is 1.0-10.0, preferably 1.5-8.0 (In one embodiment 5.0-8.0) and preferably the absolute $K_D$ value is in the range of $10^{-8}$-$10^{-13}$ mol/l. $K_D$ values are determined in a ANG-2/VEGF binding BIACORE (see Example 2, and FIG. 15A). As both proteins human VEGF and human ANG-2 are present as soluble receptor ligands in human serum at approximately the same concentrations, blocking of both receptor ligands by a bispecific antibody characterized as described above can lead to improved properties with respect to the anti-angiogenic effects, tumor growth inhibition or resistance mechanism during the treatment of cancer or vascular diseases with such a bispecific antibody. Preferably said bispecific antibody comprises a first antigen-binding site that specifically binds to VEGF and has a heavy chain variable domain of SEQ ID NO: 7 and a light chain variable domain of SEQ ID NO: 8 and a second antigen-binding site that binds specifically to ANG-2 and has: a) either a heavy chain variable domain of SEQ ID NO: 52 and a light chain variable domain of SEQ ID NO: 53 or b) a heavy chain variable domain of SEQ ID NO: 84 and a light chain variable domain of SEQ ID NO: 85.

As used herein, "antibody" refers to a binding protein that comprises antigen-binding sites. The terms "binding site" or "antigen-binding site" as used herein denote the region(s) of an antibody molecule to which a ligand actually binds. The term "antigen-binding site" includes antibody heavy chain variable domains (VH) and/or an antibody light chain variable domains (VL), or pairs of VH/VL, and can be derived from whole antibodies or antibody fragments such as single chain Fv, a VH domain and/or a VL domain, Fab, or (Fab)2. In one embodiment of the current invention, each of the antigen-binding sites comprises an antibody heavy chain variable domain (VH) and/or an antibody light chain variable domain (VL), and preferably is formed by a pair consisting of an antibody light chain variable domain (VL) and an antibody heavy chain variable domain (VH).

The antigen-binding site, and especially heavy chain variable domains (VH) and/or antibody light chain variable domains (VL), that specifically bind to human vascular endothelial growth factor (VEGF) can be derived a) from known anti-VEGF antibodies such as Kim et al., Nature 362 (1993) 841-844; Warren, R. S., et al., J. Clin. Invest. 95 (1995) 1789-1797; Borgstrom, P., et al., Cancer Res. 56 (1996) 4032-4039; Melnyk, O., et al., Cancer Res. 56 (1996) 921-924). WO 94/10202, WO 98/45332, WO 2005/00900, WO 00/35956 and US 2007/0141065 or b) from new anti-VEGF antibodies obtained by de novo immunization methods using inter alia either the human VEGF protein or nucleic acid or fragments thereof or by phage display.

The antigen-binding site, and especially heavy chain variable domains (VH) and/or antibody light chain variable domains (VL), that specifically bind to human angiopoietin-2 (ANG-2) can be derived a) from known anti-ANG-2 antibodies such as WO 03/030833, WO 2006/068953, WO 2006/045049 or U.S. Pat. No. 6,166,185; or b) from new anti-ANG-2 antibodies obtained e.g. by de novo immunization methods using inter alia either the human ANG-2 protein or nucleic acid or fragments thereof or by phage display.

Antibody specificity refers to selective recognition of the antibody for a particular epitope of an antigen. Natural antibodies, for example, are monospecific.

"Bispecific antibodies" according to the invention are antibodies which have two different antigen-binding specificities. Where an antibody has more than one specificity, the recognized epitopes may be associated with a single antigen or with more than one antigen. Antibodies of the present invention are specific for two different antigens, i.e. VEGF as first antigen and ANG-2 as second antigen.

The term "monospecific" antibody as used herein denotes an antibody that has one or more binding sites, each of which bind to the same epitope of the same antigen.

The term "valent" as used within the current application denotes the presence of a specified number of binding sites in an antibody molecule. As such, the terms "bivalent", "tetravalent", and "hexavalent" denote the presence of two binding sites, four binding sitess, and six binding sites, respectively, in an antibody molecule. The bispecific antibodies according to the invention are at least "bivalent" and may be "trivalent" or "multivalent" (e.g.("tetravalent" or "hexavalent"). Preferably the bispecific antibody according to the invention is bivalent, trivalent or tetravalent. In one embodiment said bispecific antibody is bivalent. In one embodiment said bispecific antibody is trivalent. In one embodiment said bispecific antibody is tetravalent.

Antibodies of the present invention have two or more binding sites and are bispecific. That is, the antibodies may be bispecific even in cases where there are more than two binding sites (i.e. that the antibody is trivalent or multivalent). Bispecific antibodies of the invention include, for example, multivalent single chain antibodies, diabodies and triabodies, as well as antibodies having the constant domain structure of full length antibodies to which further antigen-binding sites (e.g., single chain Fv, a VH domain and/or a VL domain, Fab, or (Fab)2,) are linked via one or more peptide-linkers. The antibodies can be full length from a single species, or be chimerized or humanized. For an antibody with more than two antigen binding sites, some binding sites may be identical, so long as the protein has binding sites for two different antigens. That is, whereas a first binding site is specific for a VEGF, a second binding site is specific for ANG-2, and vice versa.

Human vascular endothelial growth factor (VEGF/VEGF-A) (SEQ ID No: 105) is described in e.g. Leung, D. W., et al., Science 246 (1989) 1306-9; Keck, P. J., et al., Science 246 (1989) 1309-12 and Connolly, D. T., et al., J. Biol. Chem. 264 (1989) 20017-24. VEGF is involved in the regulation of normal and abnormal angiogenesis and neovascularization associated with tumors and intraocular disorders (Ferrara, N., et al., Endocr. Rev. 18 (1997) 4-25; Berkman, R. A., et al., J. Clin. Invest. 91 (1993) 153-159; Brown, L. F., et al., Human Pathol. 26 (1995) 86-91; Brown, L. F., et al., Cancer Res. 53 (1993) 4727-4735; Mattern, J., et al., Brit. J. Cancer. 73 (1996) 931-934; and Dvorak, H., et al., Am. J. Pathol. 146 (1995) 1029-1039). VEGF is a homodimeric glycoprotein that has been isolated from several sources. VEGF shows highly specific mitogenic activity for endothelial cells.

Human angiopoietin-2 (ANG-2) (alternatively abbreviated with ANGPT2 or ANG2) (SEQ ID No: 106) is described in Maisonpierre, P. C., et al, Science 277 (1997) 55-60 and Cheung, A. H., et al., Genomics 48 (1998) 389-91. The angiopoietins-1 and -2 (ANG-1(SEQ ID No: 107) and ANG-2(SEQ ID No: 106)) were discovered as ligands for the Ties, a family of tyrosine kinases that is selectively expressed within the vascular endothelium. Yancopoulos, G. D., et al., Nature 407 (2000) 242-48. There are now four definitive members of the angiopoietin family. Angiopoietin-3 and -4 (Ang-3 and Ang-4) may represent widely diverged counterparts of the same gene locus in mouse and man. Kim, I., et al., FEBS Let, 443 (1999) 353-56; Kim, I., et al., J Biol Chem 274 (1999) 26523-28. ANG-1 and ANG-2 were originally identified in tissue culture experiments as agonist and antagonist, respectively (see for ANG-1: Davis, S., et al., Cell 87 (1996) 1161-69; and for ANG-2: Maisonpierre, P. C., et al., Science 277 (1997) 55-60) All of the known angiopoietins bind primarily to Tie2, and both Ang-1 and -2 bind to Tie2 with an affinity of 3 nM ($K_D$). Maisonpierre, P. C., et al., Science 277 (1997) 55-60.

An antigen-binding site of an antibody of the invention can contain six complementarity determining regions (CDRs) which contribute in varying degrees to the affinity of the binding site for antigen. There are three heavy chain variable domain CDRs (CDRH1, CDRH2 and CDRH3) and three light chain variable domain CDRs (CDRL1, CDRL2 and CDRL3). The extent of CDR and framework regions (FRs) is determined by comparison to a compiled database of amino acid sequences in which those regions have been defined according to variability among the sequences. Also included within the scope of the invention are functional antigen binding sites comprised of fewer CDRs (i.e., where binding specificity is determined by three, four or five CDRs). For example, less than a complete set of 6 CDRs may be sufficient for binding. In some cases, a VH or a VL domain will be sufficient.

In certain embodiments, antibodies of the invention further comprise immunoglobulin constant regions of one or more immunoglobulin classes. Immunoglobulin classes include IgG, IgM, IgA, IgD, and IgE isotypes and, in the case of IgG and IgA, their subtypes. In a preferred embodiment, an antibody of the invention has a constant domain structure of an IgG type antibody, but has four antigen binding sites. This is accomplished e.g. by linking two complete antigen binding sites (e.g., a single chain Fv) specifically binding to VEGF to either to N- or C-terminus heavy or light chain of a full antibody specifically binding to ANG-2. Alternatively this is accomplished by fusing two complete binding peptides specifically binding to ANG-2 to either to C-terminus heavy chain of a full antibody specifically binding to VEGF. The four antigen-binding sites preferably comprise two antigen-binding sites for each of two different binding specificities.

The terms "monoclonal antibody" or "monoclonal antibody composition" as used herein refer to a preparation of antibody molecules of a single amino acid composition.

The term "chimeric antibody" refers to an antibody comprising a variable region, i.e., binding region, from one source or species and at least a portion of a constant region derived from a different source or species, usually prepared by recombinant DNA techniques. Chimeric antibodies comprising a murine variable region and a human constant region are preferred. Other preferred forms of "chimeric antibodies" encompassed by the present invention are those in which the constant region has been modified or changed from that of the original antibody to generate the properties according to the invention, especially in regard to C1q binding and/or Fc receptor (FcR) binding. Such chimeric antibodies are also referred to as "class-switched antibodies.". Chimeric antibodies are the product of expressed immunoglobulin genes comprising DNA segments encoding immunoglobulin variable regions and DNA segments encoding immunoglobulin constant regions. Methods for producing chimeric antibodies involve conventional recombinant DNA and gene transfection techniques are well known in the art. See, e.g., Morrison, S. L., et al., Proc. Natl. Acad. Sci. USA 81 (1984) 6851-6855; U.S. Pat. No. 5,202,238 and U.S. Pat. No. 5,204,244.

The term "humanized antibody" refers to antibodies in which the framework or "complementarity determining regions" (CDR) have been modified to comprise the CDR of an immunoglobulin of different specificity as compared to that of the parent immunoglobulin. In a preferred embodiment, a murine CDR is grafted into the framework region of a human antibody to prepare the "humanized antibody." See, e.g., Riechmann, L., et al., Nature 332 (1988) 323-327; and Neuberger, M. S., et al., Nature 314 (1985) 268-270. Particularly preferred CDRs correspond to those representing sequences recognizing the antigens noted above for chimeric antibodies. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

The term "human antibody", as used herein, is intended to include antibodies having variable and constant regions derived from human germ line immunoglobulin sequences. Human antibodies are well-known in the state of the art (van Dijk, M. A., and van de Winkel, J. G., Curr. Opin. Chem. Biol. 5 (2001) 368-374). Human antibodies can also be produced in transgenic animals (e.g., mice) that are capable, upon immunization, of producing a full repertoire or a selection of human antibodies in the absence of endogenous immunoglobulin production. Transfer of the human germ-line immunoglobulin gene array in such germ-line mutant mice will result in the production of human antibodies upon antigen challenge (see, e.g., Jakobovits, A., et al., Proc. Natl. Acad. Sci. USA 90 (1993) 2551-2555; Jakobovits, A., et al., Nature 362 (1993) 255-258; Bruggemann, M., et al., Year Immunol. 7 (1993) 33-40). Human antibodies can also be produced in phage display libraries (Hoogenboom, H. R., and Winter, G., J. Mol. Biol. 227 (1992) 381-388; Marks, J. D., et al., J. Mol. Biol. 222 (1991) 581-597). The techniques of Cole, A., et al. and Boerner, P., et al. are also available for the preparation of human monoclonal antibodies (Cole, A., et al., Monoclonal Antibodies and Cancer Therapy, Liss, A. L., p. 77 (1985); and Boerner, P., et al., J. Immunol. 147 (1991) 86-95). As already mentioned for chimeric and humanized antibodies according to the invention the term "human antibody" as used herein also comprises such antibodies which are modified in the constant region to generate the properties according to the invention, especially in regard to C1q binding and/or FcR binding, e.g. by "class switching" i.e. change or mutation of Fc parts (e.g. from IgG1 to IgG4 and/or IgG1/IgG4 mutation).

The term "recombinant human antibody", as used herein, is intended to include all human antibodies that are prepared, expressed, created or isolated by recombinant means, such as antibodies isolated from a host cell such as a NS0 or CHO cell or from an animal (e.g. a mouse) that is transgenic for human immunoglobulin genes or antibodies expressed using a recombinant expression vector transfected into a host cell. Such recombinant human antibodies have variable and constant regions in a rearranged form. The recombinant human antibodies according to the invention have been subjected to in vivo somatic hypermutation. Thus, the amino acid sequences of the VH and VL regions of the recombinant antibodies are sequences that, while derived from and related to human germ line VH and VL sequences, may not naturally exist within the human antibody germ line repertoire in vivo.

The term "variable domain", when used in reference to a domain of a heavy chain or a light chain, refer respectively to the portion of a heavy chain or a light chain which is involved directly in binding the antibody to the antigen. The variable domains of human light and heavy chains have the same general structure and each domain comprises four framework (FR) regions whose sequences are widely conserved, connected by three "hypervariable regions" (or complementarity determining regions, CDRs). The framework regions adopt a β-sheet conformation and the CDRs may form loops connecting the β-sheet structure. The CDRs in each chain are held in their three-dimensional structure by the framework regions and form together with the CDRs from the other chain the antigen binding site. The antibody heavy and light chain CDR3 regions play a particularly important role in the binding specificity/affinity of the antibodies according to the invention and therefore provide a further object of the invention.

The terms "hypervariable region" or "antigen-binding portion of an antibody", when used herein, refer to the amino acid residues of an antibody which are responsible for antigen-binding. The hypervariable region comprises amino acid residues from the "complementarity determining regions" or "CDRs". "Framework" or "FR" regions are those variable domain regions other than the hypervariable region residues as herein defined. Therefore, the light and heavy chains of an antibody comprise from N- to C-terminus the domains FR1, CDR1, FR2, CDR2, FR3, CDR3, and FR4. CDRs on each chain are separated by such framework amino acids. Especially, CDR3 of the heavy chain is the region which contributes most to antigen binding. CDR and FR regions are determined according to the standard definition of Kabat et al., Sequences of Proteins of Immunological Interest, 5th ed., Public Health Service, National Institutes of Health, Bethesda, Md. (1991).

The bispecific antibodies according to the invention include, in addition, such antibodies having "conservative sequence modifications" (which is meant by "variants" of the bispecific antibodies). This means nucleotide and amino acid sequence modifications which do not affect or alter the above-mentioned characteristics of the antibody according to the invention. Modifications can be introduced by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine, tryptophan), nonpolar side chains (e.g. alanine, valine, leucine, isoleucine, proline, phenylalanine, methionine), beta-branched side chains (e.g. threonine, valine, isoleucine) and aromatic side chains (e.g. tyrosine, phenylalanine, tryptophan, histidine). Thus, a predicted nonessential amino acid residue in a bispecific <VEGF-ANG-2> antibody can be preferably replaced with another amino acid residue from the same side chain family. A "variant" bispecific <VEGF-ANG-2> antibody, refers therefore herein to a molecule which differs in amino acid sequence from a "parent" bispecific <VEGF-ANG-2> antibody amino acid sequence by up to ten, preferably from about two to about five, additions, deletions and/or substitutions in one or more variable region or constant region of the parent antibody. Amino acid substitutions can be performed by mutagenesis based upon molecular modeling as described by Riechmann, L., et al., Nature 332 (1988) 323-327 and Queen, C., et al., Proc. Natl. Acad. Sci. USA 86 (1989) 10029-10033. A "variant" bispecific <VEGF-ANG-2> antibody according to the invention includes also bispecific antibodies formats in which the linker (if existing) was modified, or replaced by another linker.

As used herein, the term "binding" or "specifically binding" refers to the binding of the antibody to an epitope of the antigen(either human VEGF or human ANG-2) in an in vitro assay, preferably in an plasmon resonance assay (BIAcore, GE-Healthcare Uppsala, Sweden) (Example 2) with purified wild-type antigen. The affinity of the binding is defined by the terms $K_A$ (rate constant for the association of the antibody from the antibody/antigen complex), $K_D$ (dissociation constant), and $K_D$ ($K_D/K_A$). Binding or specifically binding means a binding affinity ($K_D$) of $10^{-8}$ mol/l or less, preferably $10^{-9}$ M to $10^{-13}$ mol/l.

Binding of the antibody to the FcγRIII can be investigated by a BIAcore assay (GE-Healthcare Uppsala, Sweden). The affinity of the binding is defined by the terms $K_A$ (rate constant for the association of the antibody from the antibody/antigen complex), $K_D$ (dissociation constant), and $K_D$ ($K_D/K_A$).

As used herein, the term "not binding to ANG-1" or "not specifically binding to ANG-1" denotes that the antibody has an EC50-value above 8000 ng/ml in an in-vitro ANG-1 binding ELISA assay (according to Example 9).

The term "epitope" includes any polypeptide determinant capable of specific binding to an antibody. In certain embodiments, epitope determinants include chemically active surface groupings of molecules such as amino acids, sugar side chains, phosphoryl, or sulfonyl, and, in certain embodiments, may have specific three dimensional structural characteristics, and or specific charge characteristics. An epitope is a region of an antigen that is bound by an antibody.

In certain embodiments, an antibody is said to specifically bind an antigen when it preferentially recognizes its target antigen in a complex mixture of proteins and/or macromolecules.

In one embodiment of the invention the bispecific antibody comprises a full length parent antibody as scaffold.

The term "full length antibody" denotes an antibody consisting of two "full length antibody heavy chains" and two "full length antibody light chains" A "full length antibody heavy chain" is a polypeptide consisting in N-terminal to C-terminal direction of an antibody heavy chain variable domain (VH), an antibody constant heavy chain domain 1 (CH1), an antibody hinge region (HR), an antibody heavy chain constant domain 2 (CH2), and an antibody heavy chain constant domain 3 (CH3), abbreviated as VH—CH1-HR—CH2-CH3; and optionally an antibody heavy chain constant domain 4 (CH4) in the case of an antibody of the subclass IgE. Preferably the "full length antibody heavy chain" is a polypeptide consisting in N-terminal to C-terminal direction of VH, CH1, HR, CH2 and CH3. A "full length antibody light chain" is a polypeptide consisting in N-terminal to C-terminal direction of an antibody light chain variable domain (VL), and an antibody light chain constant domain (CL), abbreviated as VL-CL. The antibody light chain constant domain (CL) can be κ (kappa) or λ (lambda). The two full length antibody chains are linked together via inter-polypeptide disulfide bonds between the CL domain and the CH1 domain and between the hinge regions of the full length antibody heavy chains. Examples of typical full length antibodies are natural antibodies like IgG (e.g. IgG 1 and IgG2), IgM, IgA, IgD, and IgE. The full length antibodies according to the invention can be from a single species e.g. human, or they can be chimerized or humanized antibodies. The full length antibodies according to the invention comprise two antigen binding sites each formed by a pair of VH and VL, which both specifically bind to the same antigen. Thus a monospecific bivalent (=full length) antibody comprising a first antigen-binding site and consisting of two antibody light chains and two antibody heavy chains is a full length antibody. The C-terminus of the heavy or light chain of said full length antibody denotes the last amino acid at the C-terminus of said heavy or light chain. The N-terminus of the heavy or light chain of said full length antibody denotes the last amino acid at the N-terminus of said heavy or light chain.

A preferred embodiment for bispecific antibody formats for the bispecific antibody that specifically binds to human vascular endothelial growth factor (VEGF) and human angiopoietin-2 (ANG-2) according to the invention are bivalent antibodies with two different specifities as e.g. a) described in WO 2009/080251, WO 2009/080252 or WO 2009/080253 (domain exchanged antibodies- see Example 13) or b) based on a scFab-Fc fusion antibody wherein one single chain Fab fragment (eventually disulfide stabilized) is specific for VEGF and the other single chain Fab fragment (eventually disulfide stabilized) for ANG-2 (see Example 14) or c) described in Ridgway, J. B., Protein Eng. 9 (1996) 617-621; WO 96/027011; Merchant, A. M., et al., Nature Biotech 16 (1998) 677-681; Atwell, S., et al., J. Mol. Biol. 270 (1997) 26-35 and EP 1 870 459A1.

In one embodiment the bispecific antibody according to the invention comprises the amino acid sequences of SEQ ID NO: 121, SEQ ID NO: 122, SEQ ID NO: 123 and SEQ ID NO: 124 or variants thereof In one embodiment the bispecific antibody according to the invention comprises the amino acid sequences of SEQ ID NO: 125, SEQ ID NO: 126, SEQ ID NO: 127 and SEQ ID NO: 128 or variants thereof In one embodiment the bispecific antibody according to the invention comprises the amino acid sequences of SEQ ID NO: 129, SEQ ID NO: 130, SEQ ID NO: 131 and SEQ ID NO: 132 or variants thereof In one embodiment the bispecific antibody according to the invention comprises the amino acid sequences of SEQ ID NO: 133, and SEQ ID NO: 134 or variants thereof.

In one embodiment the bispecific antibody according to the invention comprises the amino acid sequences of SEQ ID NO: 135 and SEQ ID NO: 136 or variants thereof These amino acid sequences are based on the heavy chain variable domains of SEQ ID NO: 7, and the light chain variable domains of SEQ ID NO: 8 (derived from bevacizumab) as the binding site for VEGF, and on the heavy chain variable domains of SEQ ID NO: 52, and the light chain variable domains of SEQ ID NO: 53 (derived from Ang2i_LC06)) as the binding site for ANG-2.

In one embodiment said bispecific antibody is trivalent using, for example, formats based on a full length antibody specifically binding to one of the two antigens VEGF or ANG-2, to which only at one C-terminus of one heavy chain a scFab fragment is fused which specifically binds to the other of the two antigens VEGF or ANG-2, including knobs—into holes technology, as described e.g. in EP Appl. No 09004909.9 (see Example 11) or, for example, formats based on a full length antibody specifically binding to one of the two antigens VEGF or ANG-2, to which at one C-terminus of one heavy chain a VH or VH—CH1 fragment and at the other C-terminus of the second heavy chain a VL or VL-CL fragment is fused which specifically binds to the other of the two antigens VEGF or ANG-2, including knobs—into holes technology, as described e.g. in EP Appl. No 09005108.7 (see Example 12).

In one embodiment the bispecific antibody according to the invention is comprises the amino acid sequences of SEQ ID NO: 115, SEQ ID NO: 116, and SEQ ID NO: 117 or variants thereof.

In one embodiment the bispecific antibody according to the invention comprises the amino acid sequences of SEQ ID NO: 118, SEQ ID NO: 119, and SEQ ID NO: 120 or variants thereof.

These amino acid sequences are based on the heavy chain variable domains of SEQ ID NO: 7, and the light chain variable domains of SEQ ID NO: 8 (derived from bevacizumab) as the binding site for VEGF, and on the heavy chain variable domains of SEQ ID NO: 52, and the light chain variable domains of SEQ ID NO: 53 (derived from Ang2i_LC06)) as the binding site for ANG-2.

Preferred bispecific antibody formats for the bispecific antibody that specifically binds to human vascular endothelial growth factor (VEGF) and human angiopoietin-2 (ANG-2) according to the invention are tetravalent antibodies (TvAb) with two different specifities as described e.g. in WO 2007/024715, or WO 2007/109254 or EP Appl. No 09004909.9. Thus in one embodiment said bispecific antibody is tetravalent using formats as described e.g. in WO 2007/024715, or WO 2007/109254 or EP Appl. No 09004909.9 (see Examples 1 or 10).

In one embodiment of the invention the bispecific tetravalent antibody TvAb-2441-bevacizumab-LC06 comprises a peptide of SEQ ID No: 102 and the light chain of SEQ ID No: 62 or variants thereof.

In one embodiment the bispecific antibody according to the invention comprises the amino acid sequences of SEQ ID NO: 109 and SEQ ID NO: 110 or variants thereof In one embodiment the bispecific antibody according to the invention comprises the amino acid sequences of SEQ ID NO: 111 and SEQ ID NO: 112 or variants thereof In one embodiment the bispecific antibody according to the invention comprises the amino acid sequences of SEQ ID NO: 113 and SEQ ID NO: 114 or variants thereof These amino acid sequences are based on the heavy chain variable domains of SEQ ID NO: 7, and the light chain variable domains of SEQ ID NO: 8 (derived from bevacizumab) as to the binding site for VEGF, and on the heavy chain variable domains of SEQ ID NO: 52, and the light chain variable domains of SEQ ID NO: 53 (derived from Ang2i_LC06)) as to the binding site for ANG-2.

In one embodiment of the invention the bispecific tetravalent antibody TvAb-2441-bevacizumab-LC08comprises a peptide of SEQ ID No: 103 and the light chain of SEQ ID No: 62 or variants thereof.

The binding sites in an antibody according to the invention may be each formed by a pair of two variable domains, i.e. of one heavy chain variable domain and one light chain variable domain. The minimal binding site determinant in an antibody is the heavy chain CDR3 region.

In one embodiment the bispecific antibody according to the invention is tetravalent. In a further embodiment said tetravalent bispecific antibody consists of:
  a) a monospecific bivalent parent antibody consisting of two full length antibody heavy chains and two full length antibody light chains whereby each chain comprises only one variable domain,
  b) two peptide-linkers, and
  c) two monospecific monovalent single chain antibodies each consisting of an antibody heavy chain variable domain, an antibody light chain variable domain, and a single-chain-linker between said antibody heavy chain variable domain and said antibody light chain variable domain.

Preferably said single chain antibodies are linked to the same terminus (C- and N-terminus) of the monospecific bivalent antibody heavy chains or, alternatively to the same terminus (preferably the C-terminus) of the monospecific bivalent antibody light chains, and more preferably to the same terminus (C- and N-terminus) of the monospecific bivalent antibody heavy chains.

In another embodiment said bispecific antibody is tetravalent and consists of:

a) a full length antibody comprising said antigen-binding site and consisting of two antibody heavy chains and two antibody light chains; and
b) two identical single chain Fab fragments comprising said second antigen-binding site, wherein said single chain Fab fragments are fused to said full length antibody via a peptide connector at the C- or N-terminus of the heavy or light chain of said full length antibody.

In another embodiment said bispecific antibody is tetravalent, and consists of
a) a full length antibody comprising said second antigen-binding site and consisting of two antibody heavy chains and two antibody light chains; and
b) two identical single chain Fab fragments comprising said first antigen-binding site, wherein said single chain Fab fragments are fused to said full length antibody via a peptide connector at the C- or N-terminus of the heavy or light chain of said full length antibody.

Preferably said single chain Fab fragments under b) are fused to said full length antibody under a) via a peptide connector at the C-terminus of the heavy or light chain of said full length antibody.

In one embodiment the two identical single chain Fab fragments which bind to a second antigen are fused to the full length antibody via a peptide connector at the C-terminus of each heavy or light chain of said full length antibody.

In one embodiment the two identical single chain Fab fragments which bind to a second antigen are fused to the full length antibody via a peptide connector at the C-terminus of each heavy chain of said full length antibody.

In one embodiment the two identical single chain Fab fragments which bind to a second antigen are fused to the full length antibody via a peptide connector at the C-terminus of each light chain of said full length antibody.

Such embodiments which include single chain Fab fragments are described in more detail in e.g. EP Appl. No 09004909.9 which is incorporated by reference.

The term "peptide-linker" as used within the invention denotes a peptide with amino acid sequences, which is preferably of synthetic origin. These peptide-linkers according to invention are used to link the different antigen-binding sites and/or antibody fragments eventually comprising the different antigen-binding sites (e.g. single chain Fv, full length antibodies, a VH domain and/or a VL domain, Fab, (Fab)2, Fc part) together to form a bispecific antibody according to the invention. The peptide-linkers can comprise one or more of the following amino acid sequences listed in Table 1 as well as further arbitrarily selected amino acids. Said peptide-linkers are peptides with an amino acid sequence with a length of at least 5 amino acids, preferably of at least 10 amino acids, more preferably with a length between 10 and 50 amino acids. Preferably said peptide-linkers under b) are peptides with an amino acid sequence with a length of at least 10 amino acids. In one embodiment said peptide-linker is (GxS)n with G=glycine, S=serine, (x=3 and n=3, 4, 5 or 6) or (x=4 and n=2, 3, 4 or 5), preferably and n=2 or 3, more preferably with x=4, n=2 ($(G_4S)_2$). To said (GxS)n peptide-linker also additional G=glycines can be added, e.g. GG, or GGG.

The term "single-chain-linker" as used within the invention denotes a peptide with amino acid sequences, which is preferably of synthetic origin. These single-chain-linkers according to invention are used to link a VH and a VL domain to form a single chain Fv. Preferably the single-chain-linker is a peptide with an amino acid sequence with a length of at least 15 amino acids, more preferably with a length of at least 20 amino acids. In one embodiment said single-chain-linker is (GxS)n with G=glycine, S=serine, (x=3 and n=4, 5 or 6) or (x=4 and n=3, 4 or 5), preferably with x=4, n=4 or 5, more preferably with x=4, n=4.

Furthermore said single chain (single chain Fv) antibodies are preferably disulfide stabilized. Such further disulfide stabilization of single chain antibodies is achieved by the introduction of a disulfide bond between the variable domains of the single chain antibodies and is described e.g in WO 94/029350, Rajagopal, V., et al., Prot. Engin. 10 (12) (1997) 1453-59; Kobayashi, H., et al., Nuclear Medicine & Biology 25 (1998) 387-393; or Schmidt, M., et al., Oncogene 18 (1999) 1711-1721.

In one embodiment of the disulfide stabilized single chain antibodies, the disulfide bond is independently for each single chain antibody selected from:
i) a bond between position 44 of the heavy chain variable domain to position 100 of the light chain variable domain,
ii) a bond between position 105 of the heavy chain variable domain to position 43 of the light chain variable domain, and
iii) a bond between position 101 of the heavy chain variable domain to position 100 of the light chain variable domain.

In one embodiment the disulfide bond is a bond between position 44 of the heavy chain variable domain to position 100 of the light chain variable domain.

In one embodiment the disulfide bond a bond between position 105 of the heavy chain variable domain to position 43 of the light chain variable domain.

In one embodiment of the present invention, the antibody is tetravalent and has a structure based on a full length antibody that specifically binds to Antigen A to which two (optionally disulfide-stabilized) single chain Fvs specifically binding to Antigen B are linked via a peptide-linker One of Antigens A or B is VEGF and the other is ANG-2. The single chain Fvs are linked via a peptide linker to the full-length antibody. This embodiment is exemplified in the schemes of FIGS. 1 and 2.

In one embodiment, single chain (single chain Fv) antibodies without said optional disulfide stabilization between the variable domains VH and VL of the single chain antibody (single chain Fv) are preferred.

In a further embodiment said tetravalent bispecific antibody is characterized in that the full-length antibody specifically binds to VEGF and the two monovalent monospecific single chain antibodies bind to ANG-2.

In a further embodiment said tetravalent bispecific antibody is characterized in that the full-length antibody specifically binds to ANG-2 and the two monovalent monospecific single chain antibodies bind to VEGF A "single chain Fab fragment" (see FIG. 11) is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction:
a) VH—CH1-linker-VL-CL, b) VL-CL-linker-VH—CH1, c) VH—CL-linker-VL-CH1 or d) VL-CH1-linker-VH—CL; and wherein said linker is a polypeptide of at least 30 amino acids, preferably between 32 and 50 amino acids. Said single chain Fab fragments a) VH—CH1-linker-VL-CL, b) VL-CL-linker-VH—CH1, c) VH—CL-linker-VL-CH1 and d) VL-CH1-linker-VH—CL, are stabilized via the natural disulfide bond between the CL domain and the CH1 domain. The term "N-terminus" denotes the last amino acid of the N-terminus. The term "C-terminus" denotes the last amino acid of the C-terminus.

In a preferred embodiment said antibody domains and said linker in said single chain Fab fragment have one of the following orders in N-terminal to C-terminal direction:
a) VH—CH1-linker-VL-CL, or b) VL-CL-linker-VH—CH1, more preferably VL-CL-linker-VH—CH 1.

In another preferred embodiment said antibody domains and said linker in said single chain Fab fragment have one of the following orders in N-terminal to C-terminal direction:
a) VH—CL-linker-VL-CH1 or b) VL-CH1-linker-VH—CL.

The term "peptide connector" as used within the invention denotes a peptide with amino acid sequences, which is preferably of synthetic origin. These peptide connectors according to invention are used to fuse the single chain Fab fragments to the C- or N-terminus of the full length antibody to form a multispecific antibody according to the invention. Preferably said peptide connectors are peptides with an amino acid sequence with a length of at least 5 amino acids, preferably with a length of 5 to 100, more preferably of 10 to 50 amino acids. In one embodiment said peptide connector is (GxS)n or (GxS)nGm with G=glycine, S=serine, and (x=3, n=3, 4, 5 or 6, and m=0, 1, 2 or 3) or (x=4, n=2, 3, 4 or 5 and m=0, 1, 2 or 3), preferably x=4 and n=2 or 3, more preferably with x=4, n=2. In one embodiment said peptide connector is $(G_4S)_2$.

The term "linker" as used within the invention denotes a peptide with amino acid sequences which is preferably of synthetic origin. These peptides according to invention are used to link a) VH—CH1 to VL-CL, b) VL-CL to VH—CH1, c) VH—CL to VL-CH1 or d) VL-CH1 to VH—CL to form the following single chain Fab fragments according to the invention a) VH—CH1-linker-VL-CL, b) VL-CL-linker-VH—CH1, c) VH—CL-linker-VL-CH1 or d) VL-CH1-linker-VH—CL. Said linker within the single chain Fab fragments is a peptide with an amino acid sequence with a length of at least 30 amino acids, preferably with a length of 32 to 50 amino acids. In one embodiment said linker is (GxS)n with G=glycine, S=serine, (x=3, n=8, 9 or 10 and m=0, 1, 2 or 3) or (x=4 and n=6, 7 or 8 and m=0, 1, 2 or 3), preferably with x=4, n=6 or 7 and m=0, 1, 2 or 3, more preferably with x=4, n=7 and m=2. In one embodiment said linker is $(G_4S)_6G_2$.

Optionally in said single chain Fab fragment, in addition to the natural disulfide bond between the CL-domain and the CH1 domain, the antibody heavy chain variable domain (VH) and the antibody light chain variable domain (VL) are disulfide stabilized by the introduction of a disulfide bond between the following positions:
i) heavy chain variable domain position 44 and light chain variable domain position 100,
ii) heavy chain variable domain position 105 and light chain variable domain position 43, or
iii) heavy chain variable domain position 101 and light chain variable domain position 100 (numbering always according to EU index of Kabat).

Such further disulfide stabilization of single chain Fab fragments is achieved by the introduction of a disulfide bond between the variable domains VH and VL of the single chain Fab fragments. Techniques to introduce unnatural disulfide bridges for stabilization for a single chain Fv are described e.g. in WO 94/029350, Rajagopal, V., et al, Prot. Engin. (1997) 1453-59; Kobayashi, H., et al; Nuclear Medicine & Biology, Vol. 25, (1998) 387-393; or Schmidt, M., et al , Oncogene (1999) 18, 1711-1721. In one embodiment the optional disulfide bond between the variable domains of the single chain Fab fragments comprised in the antibody according to the invention is between heavy chain variable domain position 44 and light chain variable domain position 100. In one embodiment the optional disulfide bond between the variable domains of the single chain Fab fragments comprised in the antibody according to the invention is between heavy chain variable domain position 105 and light chain variable domain position 43 (numbering always according to EU index of Kabat).

In an embodiment of the present invention, single chain Fab fragments without said optional disulfide stabilization between the variable domains VH and VL of the single chain Fab fragments are preferred.

In a preferred embodiment of an tetravalent bispecific antibody according to the invention, the antibody comprises two identical single chain Fab fragments (preferably VL-CL-linker-VH—CH1) which are both fused to the two C-termini of the two heavy chains or to the two C-termini of the two light chains of a full length antibody under. Such fusion results in two identical fusion peptides (either i) heavy chain and single chain Fab fragment or ii) light chain and single chain Fab fragment) which are coexpressed with either i) the light chain or the heavy chain of the full length antibody to give the bispecific antibody according to the invention.

In a further embodiment said bispecific antibody is characterized in that the constant region is of human origin.

In a further embodiment said bispecific antibody is characterized in that the constant region of the bispecific antibody according to the invention is of the human IgG1 subclass or of the human IgG1 subclass with the mutations L234A and L235A.

In a further embodiment said bispecific antibody is characterized in that the constant region of the bispecific antibody according to the invention antibody is of the human IgG2 subclass.

In a further embodiment said bispecific antibody is characterized in that the constant region of the bispecific antibody according to the invention antibody is of the human IgG3 subclass.

In a further embodiment said bispecific antibody is characterized in that the constant region of the bispecific antibody according to the invention is of the human IgG4 subclass or of the human IgG4 subclass with the additional mutation S228P.

It has now been found that the bispecific antibodies against human VEGF and human ANG-2 according to the current invention have improved characteristics such as biological or pharmacological activity, pharmacokinetic properties or toxicity. They show increased in vivo tumor growth inhibition and/or inhibition of tumor angiogenesis when compared to the monospecific parent antibodies against VEGF and ANG-2 (see Examples 16, 17 and 18: comparison of different bispecific <VEGF-ANG-2> antibodies bevacizumab-ANG2i-LC06 with the monospecific antibodies bevacicumab alone, ANG2i-LC06 alone, or both in combination).

Furthermore less toxic side effects (which is reflected in the improved body weight of the test animals as well as less deaths of test animals during the in vivo application) compared to the application of two corresponding individual monospecific antibodies against VEGF and ANG-2 in combination also represent an advantage of the bispecific antibodies according to the invention.

Furthermore the bispecific antibodies according to the current invention may provide benefits such as reduced dose and/or frequency of administration and concomitantly cost savings.

The term "constant region" as used within the current applications denotes the sum of the domains of an antibody other than the variable region. The constant region is not involved directly in binding of an antigen, but exhibits various effector functions. Depending on the amino acid sequence of the constant region of their heavy chains, antibodies are divided in the classes: IgA, IgD, IgE, IgG and IgM, and several of these may be further divided into subclasses, such as IgG1, IgG2, IgG3, and IgG4, IgA1 and IgA2. The heavy chain constant regions that correspond to the different classes of antibodies are called α, δ, ε, γ, and μ, respectively. The light chain constant regions which can be found in all five antibody classes are called κ (kappa) and λ (lambda).

The term "constant region derived from human origin" as used in the current application denotes a constant heavy chain region of a human antibody of the subclass IgG1, IgG2, IgG3, or IgG4 and/or a constant light chain kappa or lambda region. Such constant regions are well known in the state of the art and e.g. described by Kabat, E. A., (see e.g. Johnson, G., and Wu, T. T., Nucleic Acids Res. 28 (2000) 214-218; Kabat, E. A., et al., Proc. Natl. Acad. Sci. USA 72 (1975) 2785-2788).

While antibodies of the IgG4 subclass show reduced Fc receptor (FcγRIIIa) binding, antibodies of other IgG subclasses show strong binding. However Pro238, Asp265, Asp270, Asn297 (loss of Fc carbohydrate), Pro329, Leu234, Leu235, Gly236, Gly237, Ile253, Ser254, Lys288, Thr307, Gln311, Asn434, and His435 are residues which, if altered, provide also reduced Fc receptor binding (Shields, R. L., et al., J. Biol. Chem. 276 (2001) 6591-6604; Lund, J., et al., FASEB J. 9 (1995) 115-119; Morgan, A., et al., Immunology 86 (1995) 319-324; EP 0 307 434).

In one embodiment an antibody according to the invention has a reduced FcR binding compared to an IgG1 antibody and the monospecific bivalent (full length) parent antibody is in regard to FcR binding of IgG4 subclass or of IgG1 or IgG2 subclass with a mutation in S228, L234, L235 and/or D265, and/or contains the PVA236 mutation. In one embodiment the mutations in the monospecific bivalent (full length) parent antibody are S228P, L234A, L235A, L235E and/or PVA236. In another embodiment the mutations in the monospecific bivalent (full length) parent antibody are in IgG4 S228P and in IgG1 L234A and L235A. Constant heavy chain regions are shown in SEQ ID NO: 35 and 36. In one embodiment the constant heavy chain region of the monospecific bivalent (full length) parent antibody is of SEQ ID NO: 35 with mutations L234A and L235A. In another embodiment the constant heavy chain region of the monospecific bivalent (full length) parent antibody is of SEQ ID NO: 36 with mutation S228P. In another embodiment the constant light chain region of the monospecific bivalent (full length) parent antibody is a kappa light chain region of SEQ ID NO: 37 or lambda light chain region of SEQ ID NO: 34. Preferably the constant heavy chain region of the monospecific bivalent (full length) parent antibody is of SEQ ID NO: 35 or of SEQ ID NO: 36 with mutation S228P.

The constant region of an antibody is directly involved in ADCC (antibody-dependent cell-mediated cytotoxicity) and CDC (complement-dependent cytotoxicity). Complement activation (CDC) is initiated by binding of complement factor C1q to the constant region of most IgG antibody subclasses. Binding of C1q to an antibody is caused by defined protein-protein interactions at the so called binding site. Such constant region binding sites are known in the state of the art and described e.g. by Lukas, T. J., et al., J. Immunol. 127 (1981) 2555-2560; Brunhouse, R. and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such constant region binding sites are, e.g., characterized by the amino acids L234, L235, D270, N297, E318, K320, K322, P331, and P329 (numbering according to EU index of Kabat).

The term "antibody-dependent cellular cytotoxicity (ADCC)" refers to lysis of human target cells by an antibody according to the invention in the presence of effector cells. ADCC is measured preferably by the treatment of a preparation of CCR5 expressing cells with an antibody according to the invention in the presence of effector cells such as freshly isolated PBMC or purified effector cells from buffy coats, like monocytes or natural killer (NK) cells or a permanently growing NK cell line.

The term "complement-dependent cytotoxicity (CDC)" denotes a process initiated by binding of complement factor C1q to the Fc part of most IgG antibody subclasses. Binding of C1q to an antibody is caused by defined protein-protein interactions at the so called binding site. Such Fc part binding sites are known in the state of the art (see above). Such Fc part binding sites are, e.g., characterized by the amino acids L234, L235, D270, N297, E318, K320, K322, P331, and P329 (numbering according to EU index of Kabat). Antibodies of subclass IgG1, IgG2, and IgG3 usually show complement activation including C1q and C3 binding, whereas IgG4 does not activate the complement system and does not bind C1q and/or C3.

The antibody according to the invention is produced by recombinant means. Thus, one aspect of the current invention is a nucleic acid encoding the antibody according to the invention and a further aspect is a cell comprising said nucleic acid encoding an antibody according to the invention. Methods for recombinant production are widely known in the state of the art and comprise protein expression in prokaryotic and eukaryotic cells with subsequent isolation of the antibody and usually purification to a pharmaceutically acceptable purity. For the expression of the antibodies as aforementioned in a host cell, nucleic acids encoding the respective modified light and heavy chains are inserted into expression vectors by standard methods. Expression is performed in appropriate prokaryotic or eukaryotic host cells like CHO cells, NS0 cells, SP2/0 cells, HEK293 cells, COS cells, PER.C6 cells, yeast, or *E.coli* cells, and the antibody is recovered from the cells (supernatant or cells after lysis). General methods for recombinant production of antibodies are well-known in the state of the art and described, for example, in the review articles of Makrides, S. C., Protein Expr. Purif. 17 (1999) 183-202; Geisse, S., et al., Protein Expr. Purif. 8 (1996) 271-282; Kaufman, R. J., Mol. Biotechnol. 16 (2000) 151-161; Werner, R. G., Drug Res. 48 (1998) 870-880.

The bispecific antibodies are suitably separated from the culture medium by conventional immunoglobulin purification procedures such as, for example, protein A-Sepharose, hydroxylapatite chromatography, gel electrophoresis, dialysis, or affinity chromatography. DNA and RNA encoding the monoclonal antibodies is readily isolated and sequenced using conventional procedures. The hybridoma cells can serve as a source of such DNA and RNA. Once isolated, the DNA may be inserted into expression vectors, which are then transfected into host cells such as HEK 293 cells, CHO cells, or myeloma cells that do not otherwise produce immunoglobulin protein, to obtain the synthesis of recombinant monoclonal antibodies in the host cells.

Amino acid sequence variants (or mutants) of the bispecific antibody are prepared by introducing appropriate nucleotide changes into the antibody DNA, or by nucleotide synthesis. Such modifications can be performed, however, only in a very limited range, e.g. as described above. For example, the modifications do not alter the above mentioned antibody characteristics such as the IgG isotype and antigen binding, but may improve the yield of the recombinant production, protein stability or facilitate the purification.

The term "host cell" as used in the current application denotes any kind of cellular system which can be engineered to generate the antibodies according to the current invention. In one embodiment HEK293 cells and CHO cells are used as host cells. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included.

Expression in NSO cells is described by, e.g., Barnes, L. M., et al., Cytotechnology 32 (2000) 109-123; Barnes, L. M., et al., Biotech. Bioeng. 73 (2001) 261-270. Transient expression is described by, e.g., Durocher, Y., et al., Nucl. Acids. Res. 30 (2002) E9. Cloning of variable domains is described by Orlandi, R., et al., Proc. Natl. Acad. Sci. USA 86 (1989) 3833-3837; Carter, P., et al., Proc. Natl. Acad. Sci. USA 89 (1992) 4285-4289; and Norderhaug, L., et al., J. Immunol. Methods 204 (1997) 77-87. A preferred transient expression system (HEK 293) is described by Schlaeger, E.-J., and Christensen, K., in Cytotechnology 30 (1999) 71-83 and by Schlaeger, E.-J., in J. Immunol. Methods 194 (1996) 191-199.

The control sequences that are suitable for prokaryotes, for example, include a promoter, optionally an operator sequence, and a ribosome binding site. Eukaryotic cells are known to utilize promoters, enhancers and polyadenylation signals.

A nucleic acid is "operably linked" when it is placed in a functional relationship with another nucleic acid sequence. For example, DNA for a pre-sequence or secretory leader is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice.

Purification of antibodies is performed in order to eliminate cellular components or other contaminants, e.g. other cellular nucleic acids or proteins, by standard techniques, including alkaline/SDS treatment, CsCl banding, column chromatography, agarose gel electrophoresis, and others well known in the art. See Ausubel, F., et al., ed. Current Protocols in Molecular Biology, Greene Publishing and Wiley Interscience, New York (1987). Different methods are well established and widely used for protein purification, such as affinity chromatography with microbial proteins (e.g. protein A or protein G affinity chromatography), ion exchange chromatography (e.g. cation exchange (carboxymethyl resins), anion exchange (amino ethyl resins) and mixed-mode exchange), thiophilic adsorption (e.g. with beta-mercaptoethanol and other SH ligands), hydrophobic interaction or aromatic adsorption chromatography (e.g. with phenyl-sepharose, aza-arenophilic resins, or m-aminophenylboronic acid), metal chelate affinity chromatography (e.g. with Ni(II)- and Cu(II)-affinity material), size exclusion chromatography, and electrophoretical methods (such as gel electrophoresis, capillary electrophoresis) (Vijayalakshmi, M. A., Appl. Biochem. Biotech. 75 (1998) 93-102).

One aspect of the invention is a pharmaceutical composition comprising an antibody according to the invention. Another aspect of the invention is the use of an antibody according to the invention for the manufacture of a pharmaceutical composition. A further aspect of the invention is a method for the manufacture of a pharmaceutical composition comprising an antibody according to the invention. In another aspect, the present invention provides a composition, e.g. a pharmaceutical composition, containing an antibody according to the present invention, formulated together with a pharmaceutical carrier.

One embodiment of the invention is the bispecific antibody according to the invention for the treatment of cancer.

Another aspect of the invention is said pharmaceutical composition for the treatment of cancer.

Another aspect of the invention is the use of an antibody according to the invention for the manufacture of a medicament for the treatment of cancer.

Another aspect of the invention is method of treatment of a patient suffering from cancer comprising the step of administering an antibody according to the invention to a patient in the need of such treatment.

As used herein, "pharmaceutical carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g. by injection or infusion).

A composition of the present invention can be administered by a variety of methods known in the art. As will be appreciated by the skilled artisan, the route and/or mode of administration will vary depending upon the desired results. To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Pharmaceutical carriers include sterile aqueous solutions or dispersions and sterile powders for the extemporaneous preparation of sterile injectable solutions or dispersion. The use of such media and agents for pharmaceutically active substances is known in the art.

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intra-articular, subcapsular, subarachnoid, intraspinal, epidural and intrasternal injection and infusion.

The term cancer as used herein refers to proliferative diseases, such as lymphomas, lymphocytic leukemias, lung cancer, non small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

Another aspect of the invention is the bispecific antibody according to the invention or said pharmaceutical composition as anti-angiogenic agent. Such anti-angiogenic agent can be used for the treatment of cancer, especially solid tumors, and other vascular diseases.

One embodiment of the invention is the bispecific antibody according to the invention for the treatment of vascular diseases.

Another aspect of the invention is said pharmaceutical composition for the treatment of vascular diseases.

Another aspect of the invention is the use of an antibody according to the invention for the manufacture of a medicament for the treatment of vascular diseases.

Another aspect of the invention is method of treatment of a patient suffering from a vascular disease comprising the step of administering an antibody according to the invention to a patient in the need of such treatment.

The term "vascular disease" includes Cancer, Inflammatory diseases, Atherosclerosis, Ischemia, Trauma, Sepsis, COPD, Asthma, Diabetes, AMD, Retinopathy, Stroke, Adipositas, Acute lung injury, Hemorrhage, Vascular leak e.g. Cytokine induced, Allergy, Graves' Disease, Hashimoto's Autoimmune Thyroiditis, Idiopathic Thrombocytopenic Purpura, Giant Cell Arteritis, Rheumatoid Arthritis, Systemic Lupus Erythematosus (SLE), Lupus Nephritis, Crohn's Disease, Multiple Sclerosis, Ulcerative Colitis, especially to solid tumors, intraocular neovascular syndromes such as proliferative retinopathies or age-related macular degeneration (AMD), rheumatoid arthritis, and psoriasis (Folkman, J., et al., J. Biol. Chem. 267 (1992) 10931-10934; Klagsbrun, M., et al., Annu. Rev. Physiol. 53 (1991) 217-239; and Garner, A., Vascular diseases, In: Pathobiology of ocular disease, A dynamic approach, Garner, A., and Klintworth, G. K., (eds.), 2nd edition, Marcel Dekker, New York (1994), pp 1625-1710).

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The composition must be sterile and fluid to the extent that the composition is deliverable by syringe. In addition to water, the carrier preferably is an isotonic buffered saline solution.

Proper fluidity can be maintained, for example, by use of a coating such as lecithin, by maintenance of required particle size in the case of dispersion, or by use of surfactants. In many cases, it is preferable to include isotonic agents, for example, sugars, polyalcohols such as mannitol or sorbitol, and sodium chloride in the composition.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Variant progeny that have the same function or biological activity as screened for in the originally transformed cell are included. Where distinct designations are intended, it will be clear from the context.

The term "transformation" as used herein refers to process of transfer of a vectors/nucleic acid into a host cell. If cells without formidable cell wall barriers are used as host cells, transfection is carried out e.g. by the calcium phosphate precipitation method as described by Graham, F. L., van der Eb, A. J., Virology 52 (1978) 546ff. However, other methods for introducing DNA into cells such as by nuclear injection or by protoplast fusion may also be used. If prokaryotic cells or cells which contain substantial cell wall constructions are used, e.g. one method of transfection is calcium treatment using calcium chloride as described by Cohen, S. N., et al., PNAS. 69 (1972) 2110-2114.

As used herein, "expression" refers to the process by which a nucleic acid is transcribed into mRNA and/or to the process by which the transcribed mRNA (also referred to as transcript) is subsequently being translated into peptides, polypeptides, or proteins. The transcripts and the encoded polypeptides are collectively referred to as gene product. If the polynucleotide is derived from genomic DNA, expression in a eukaryotic cell may include splicing of the mRNA.

A "vector" is a nucleic acid molecule, in particular self-replicating, which transfers an inserted nucleic acid molecule into and/or between host cells. The term includes vectors that function primarily for insertion of DNA or RNA into a cell (e.g., chromosomal integration), replication of vectors that function primarily for the replication of DNA or RNA, and expression vectors that function for transcription and/or translation of the DNA or RNA. Also included are vectors that provide more than one of the functions as described.

An "expression vector" is a polynucleotide which, when introduced into an appropriate host cell, can be transcribed and translated into a polypeptide. An "expression system" usually refers to a suitable host cell comprised of an expression vector that can function to yield a desired expression product.

EXAMPLES

The following examples, and aforementioned sequence listing and figures are provided to aid the understanding of the present invention, the true scope of which is set forth in the appended claims. It is understood that modifications can be made in the procedures set forth without departing from the spirit of the invention.

Materials & General Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to EU numbering (Edelman, G. M., et al., Proc. Natl. Acad. Sci. USA 63 (1969) 78-85; Kabat, E. A., et al., Sequences of Proteins of Immunological Interest, 5th ed., Public Health Service, National Institutes of Health, Bethesda, Md., (1991)).

Recombinant DNA Techniques

Standard methods were used to manipulate DNA as described in Sambrook, J. et al., Molecular cloning: A laboratory manual; Cold Spring Harbor Laboratory Press, Cold Spring Harbor, N.Y., 1989. The molecular biological reagents were used according to the manufacturer's instructions.

Gene Synthesis

Desired gene segments were prepared from oligonucleotides made by chemical synthesis. The gene segments, which are flanked by singular restriction endonuclease cleavage sites, were assembled by annealing and ligation of oligonucleotides including PCR amplification and subsequently cloned via the indicated restriction sites e.g. KpnI/SacI or AscI/PacI into a pPCRScript (Stratagene) based pGA4 cloning vector. The DNA sequences of the subcloned gene fragments were confirmed by DNA sequencing. Gene synthesis fragments were ordered according to given specifications at Geneart (Regensburg, Germany). All gene segments encoding light and heavy chains of Ang-2/VEGF bispecific antibodies were synthesized with a 5'-end DNA sequence coding for a leader peptide (MGWSCIILFLVATATGVHS), which targets proteins for secretion in eukaryotic cells, and 5'-BamHI and 3'-XbaI restriction sites. DNA sequences carrying disulfide stabilized "knobs-into-hole" modified heavy chains were designed with S354C and T366W mutations in the "knobs" heavy chain and Y349C, T366S, L368A and Y407V mutations in the "hole" heavy chain.

DNA Sequence Determination

DNA sequences were determined by double strand sequencing performed at MediGenomix GmbH (Martinsried, Germany) or Sequiserve GmbH (Vaterstetten, Germany).

DNA and Protein Sequence Analysis and Sequence Data Management

The GCG's (Genetics Computer Group, Madison, Wis.) software package version 10.2 and Infomax's Vector NT1 Advance suite version 8.0 was used for sequence creation, mapping, analysis, annotation and illustration.

Expression Vectors (for Example 1)

For the expression of the described antibodies, variants of expression plasmids for transient expression (e.g. in HEK293 EBNA or HEK293-F) cells or for stable expression (e.g. in CHO cells) based either on a cDNA organization with a CMV-Intron A promoter or on a genomic organization with a CMV promoter (e.g. FIG. 2B) were applied.

Beside the antibody expression cassette the vectors contained:
an origin of replication which allows replication of this plasmid in E. coli, and
a β-lactamase gene which confers ampicillin resistance in E. coli.

The transcription unit of the antibody gene is composed of the following elements:
unique restriction site(s) at the 5' end
the immediate early enhancer and promoter from the human cytomegalovirus,
followed by the Intron A sequence in the case of the cDNA organization,
a 5'-untranslated region of a human antibody gene,
a immunoglobulin heavy chain signal sequence,
the human antibody chain (heavy chain, modified heavy chain or light chain) either as cDNA or as genomic organization with an the immunoglobulin exon-intron organization
a 3' untranslated region with a polyadenylation signal sequence, and
unique restriction site(s) at the 3' end.

The fusion genes comprising the heavy chain sequences of the selected antibody and the C-terminal scFv fusion as described below were generated by PCR and/or gene synthesis and assembled with known recombinant methods and techniques by connection of the nucleic acid segments, for example, using unique NsiI and EcoRI sites in the genomic heavy chain vectors. The subcloned nucleic acid sequences were verified by DNA sequencing. For transient and stable transfections larger quantities of the plasmids were prepared by plasmid preparation from transformed E. coli cultures (Nucleobond AX, Macherey-Nagel).

Expression Vectors (for Example 10-14)

An expression vector was used which composed of the following elements:
a hygromycin resistance gene as a selection marker,
an origin of replication, oriP, of Epstein-Barr virus (EBV),
an origin of replication from the vector pUC18 which allows replication of this plasmid in E. coli
a beta-lactamase gene which confers ampicillin resistance in E. coli,
the immediate early enhancer and promoter from the human cytomegalovirus (HCMV),
the human 1-immunoglobulin polyadenylation ("poly A") signal sequence, and
unique BamHI and XbaI restriction sites.

The immunoglobulin fusion genes comprising the heavy or light chain constructs as well as "knobs-into-hole" constructs with C-terminal VH and VL domains were prepared by gene synthesis and cloned into pGA18 (ampR) plasmids as described. The pG18 (ampR) plasmids carrying the synthesized DNA segments and the Roche expression vector were digested with BamHI and XbaI restriction enzymes (Roche Molecular Biochemicals) and subjected to agarose gel electrophoresis. Purified heavy and light chain coding DNA segments were then ligated to the isolated Roche expression vector BamHI/XbaI fragment resulting in the final expression vectors. The final expression vectors were transformed into E. coli cells, expression plasmid DNA was isolated (Miniprep)

and subjected to restriction enzyme analysis and DNA sequencing. Correct clones were grown in 150 ml LB-Amp medium, again plasmid DNA was isolated (Maxiprep) and sequence integrity confirmed by DNA sequencing.

Cell Culture Techniques

Standard cell culture techniques were used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

Transient Transfections in HEK293-F System (for Example 1)

Antibodies were generated by transient transfection of the two plasmids encoding the heavy or modified heavy chain, respectively and the corresponding light chain using the HEK293-F system (Invitrogen) according to the manufacturer's instruction. Briefly, HEK293-F cells (Invitrogen) growing in suspension either in a shake flask or in a stirred fermenter in serumfree FreeStyle 293 expression medium (Invitrogen) were transfected with a mix of the two respective expression plasmids and 293fectin or fectin (Invitrogen). For e.g. 2 L shake flask (Corning) HEK293-F cells were seeded at a density of $1.0E*6$ cells/mL in 600 mL and incubated at 120 rpm, 8% $CO_2$. The day after the cells were transfected at a cell density of ca. $1.5E*6$ cells/mL with ca. 42 mL mix of A) 20 mL Opti-MEM (Invitrogen) with 600 µg total plasmid DNA (1 µg/mL) encoding the heavy or modified heavy chain, respectively and the corresponding light chain in an equimolar ratio and B) 20 ml Opti-MEM+1.2 mL 293 fectin or fectin (2 µl/mL). According to the glucose consumption glucose solution was added during the course of the fermentation. The supernatant containing the secreted antibody was harvested after 5-10 days and antibodies were either directly purified from the supernatant or the supernatant was frozen and stored.

Transient Transfections in HEK293-F System (for Example 10-14)

Recombinant immunoglobulin variants were expressed by transient transfection of human embryonic kidney 293-F cells using the FreeStyle™ 293 Expression System according to the manufacturer's instruction (Invitrogen, USA). Briefly, suspension FreeStyle™ 293-F cells were cultivated in FreeStyle™ 293 Expression medium at 37° C./8% $CO_2$ and the cells were seeded in fresh medium at a density of $1-2 \times 10^6$ viable cells/ml on the day of transfection. DNA-293fectin™ complexes were prepared in Opti-MEM® I medium (Invitrogen, USA) using 325 µl of 293fectin™ (Invitrogen, Germany) and 250 µg of heavy and light chain plasmid DNA in a 1:1 molar ratio for a 250 ml final transfection volume. "Knobs-into-hole" DNA-293fectin complexes with two heavy chains and one light chain were prepared in Opti-MEM® I medium (Invitrogen, USA) using 325 µl of 293fectin™ (Invitrogen, Germany) and 250 µg of "Knobs-into-hole" heavy chain 1 and 2 and light chain plasmid DNA in a 1:1:2 molar ratio for a 250 ml final transfection volume. "Knobs-into-hole" DNA-293fectin complexes with two heavy chains were prepared in Opti-MEM® I medium (Invitrogen, USA) using 325 µl of 293fectin™ (Invitrogen, Germany) and 250 µg of "Knobs-into-hole" heavy chain 1 and 2 DNA in a 1:1 molar ratio for a 250 ml final transfection volume. CrossMab DNA-293fectin complexes were prepared in Opti-MEM® I medium (Invitrogen, USA) using 325 µl of 293fectin™ (Invitrogen, Germany) and 250 µg of "Knobs-into-hole" heavy chain 1 and 2 and light chain plasmid DNA in a 1:1:1:1 molar ratio for a 250 ml final transfection volume. Antibody containing cell culture supernatants were harvested 7 days after transfection by centrifugation at 14000 g for 30 minutes and filtered through a sterile filter (0.22 µm). Supernatants were stored at −20° C. until purification.

Protein Determination

The protein concentration of purified antibodies and derivatives was determined by determining the optical density (OD) at 280 nm, using the molar extinction coefficient calculated on the basis of the amino acid sequence according to Pace et. al., Protein Science, 1995, 4, 2411-1423.

Antibody Concentration Determination in Supernatants

The concentration of antibodies and derivatives in cell culture supernatants was estimated by immunoprecipitation with Protein A Agarose-beads (Roche). 60 µL Protein A Agarose beads are washed three times in TBS-NP40 (50 mM Tris, pH 7.5, 150 mM NaCl, 1% Nonidet-P40). Subsequently, 1-15 mL cell culture supernatant are applied to the Protein A Agarose beads pre-equilibrated in TBS-NP40. After incubation for at 1 h at room temperature the beads are washed on an Ultrafree-MC-filter column (Amicon] once with 0.5 mL TBS-NP40, twice with 0.5 mL 2× phosphate buffered saline (2× PBS, Roche) and briefly four times with 0.5 mL 100 mM Na-citrate pH 5.0. Bound antibody is eluted by addition of 35 µl NuPAGE® LDS Sample Buffer (Invitrogen). Half of the sample is combined with NuPAGE® Sample Reducing Agent or left unreduced, respectively, and heated for 10 min at 70° C. Consequently, 20 µl are applied to an 4-12% NuPAGE® Bis-Tris SDS-PAGE (Invitrogen) (with MOPS buffer for non-reduced SDS-PAGE and MES buffer with NuPAGE® Antioxidant running buffer additive (Invitrogen) for reduced SDS-PAGE) and stained with Coomassie Blue.

The concentration of antibodies and derivatives in cell culture supernatants was measured by Protein A-HPLC chromatography. Briefly, cell culture supernatants containing antibodies and derivatives that bind to Protein A were applied to a HiTrap Protein A column (GE Healthcare) in 50 mM $K_2HPO_4$, 300 mM NaCl, pH 7.3 and eluted from the matrix with 550 mM acetic acid, pH 2.5 on a Dionex HPLC-System. The eluted protein was quantified by UV absorbance and integration of peak areas. A purified standard IgG1 antibody served as a standard.

Alternatively, the concentration of antibodies and derivatives in cell culture supernatants was measured by Sandwich-IgG-ELISA. Briefly, StreptaWell High Bind Strepatavidin A-96 well microtiter plates (Roche) were coated with 100 µL/well biotinylated anti-human IgG capture molecule F(ab')2<h-Fcgamma> BI (Dianova) at 0.1 µg/mL for 1 h at room temperature or alternatively over night at 4° C. and subsequently washed three times with 200 µL/well PBS, 0.05% Tween (PBST, Sigma). 100 µL/well of a dilution series in PBS (Sigma) of the respective antibody containing cell culture supernatants was added to the wells and incubated for 1-2 h on a microtiterplate shaker at room temperature. The wells were washed three times with 200 µL/well PBST and bound antibody was detected with 100 µl F(ab')2<hFcgamma>POD (Dianova) at 0.1 µg/mL as detection antibody for 1-2 h on a microtiterplate shaker at room temperature. Unbound detection antibody was washed away three times with 200 µL/well PBST and the bound detection antibody was detected by addition of 100 µL ABTS/well. Determination of absorbance was performed on a Tecan Fluor Spectrometer at a measurement wavelength of 405 nm (reference wavelength 492 nm).

Protein Purification

Figure 3:
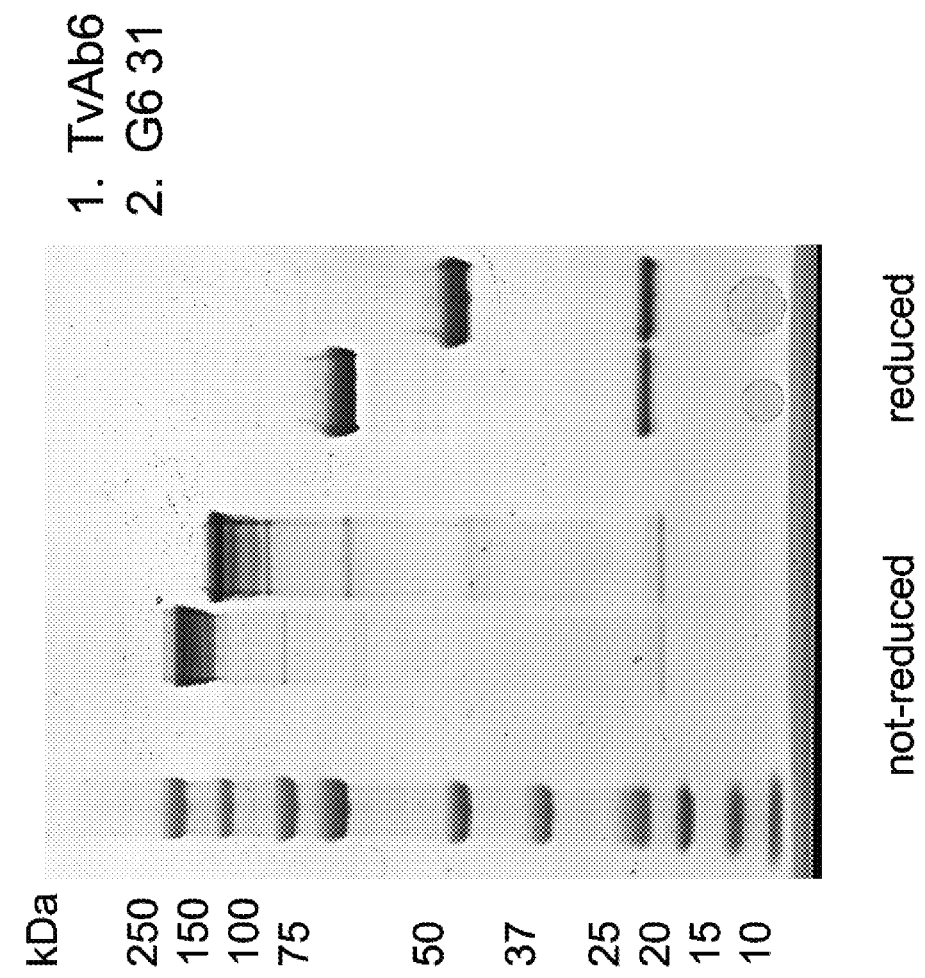
FIG. 3 SDS-PAGE of purified disulfide-stabilized <VEGF-ANG-2> TvAb6 in comparison to the "standard" human IgG1 antibody G6-31 (<VEGF> HuMab G6-31) under reducing and non-reducing conditions FIG. 4 Size exclusion chromatography of purified disulfide-stabilized <VEGF-ANG-2> TvAb6 in comparison to the "standard" human IgG1 antibody G6-31 shows that disulfide-stabilized TvAb6 does not form again aggregates upon purification FIG. 5 Schematic view and results from VEGF binding ELISA. Disulfide-stabilized <VEGF-ANG-2> TvAb6 binds to VEGF comparably to <VEGF> G6-31. <ANG-2> Mab536 does not bind to VEGF FIG. 6A Schematic view and results from ANG-2 binding ELISA, disulfide-stabilized <VEGF-ANG-2>. TvAb6 binds to ANG-2 comparably to <ANG-2> Mab536. <VEGF> G6-31 does not bind to ANG-2.

Proteins were purified from filtered cell culture supernatants referring to standard protocols. In brief, antibodies were applied to a Protein A Sepharose column (GE Healthcare) and washed with PBS. Elution of antibodies was achieved at acidic pH followed by immediate neutralization of the sample. Aggregated protein was separated from monomeric antibodies by size exclusion chromatography (Superdex 200, GE Healthcare) in 20 mM Histidine, 140 mM NaCl pH 6.0. Monomeric antibody fractions were pooled, concentrated if required using e.g. a MILLIPORE Amicon Ultra (30 MWCO) centrifugal concentrator and stored at −80° C. Part of the samples were provided for subsequent protein analytics and analytical characterization e.g. by SDS-PAGE, size exclusion chromatography, mass spectrometry and Endotoxin determination (see FIGS. 3 and 4).

SDS-PAGE

The NuPAGE® Pre-Cast gel system (Invitrogen) was used according to the manufacturer's instruction. In particular, 4-20% NuPAGE® Novex® TRIS-Glycine Pre-Cast gels and a Novex® TRIS-Glycine SDS running buffer were used. (see e.g. FIG. 3). Reducing of samples was achieved by adding NuPAGE® sample reducing agent prior to running the gel.

Analytical Size Exclusion Chromatography

Size exclusion chromatography for the determination of the aggregation and oligomeric state of antibodies was performed by HPLC chromatography. Briefly, Protein A purified antibodies were applied to a Tosoh TSKgel G3000SW column in 300 mM NaCl, 50 mM KH2PO4/K2HPO4, pH 7.5 on an Agilent HPLC 1100 system or to a Superdex 200 column (GE Healthcare) in 2× PBS on a Dionex HPLC-System. The eluted protein was quantified by UV absorbance and integration of peak areas. BioRad Gel Filtration Standard 151-1901 served as a standard. (see e.g. FIG. 4).

Mass Spectrometry

The total deglycosylated mass of crossover antibodies was determined and confirmed via electrospray ionization mass spectrometry (ESI-MS). Briefly, 100 µg purified antibodies were deglycosylated with 50 mU N-Glycosidase F (PN-GaseF, ProZyme) in 100 mM KH2PO4/K2HPO4, pH 7 at 37° C. for 12-24 h at a protein concentration of up to 2 mg/ml and subsequently desalted via HPLC on a Sephadex G25 column (GE Healthcare). The mass of the respective heavy and light chains was determined by ESI-MS after deglycosylation and reduction. In brief, 50 µg antibody in 115 µl were incubated with 60 µl 1M TCEP and 50 µl 8 M Guanidine-hydrochloride subsequently desalted. The total mass and the mass of the reduced heavy and light chains was determined via ESI-MS on a Q-Star Elite MS system equipped with a NanoMate source.

VEGF Binding ELISA

Figure 5:
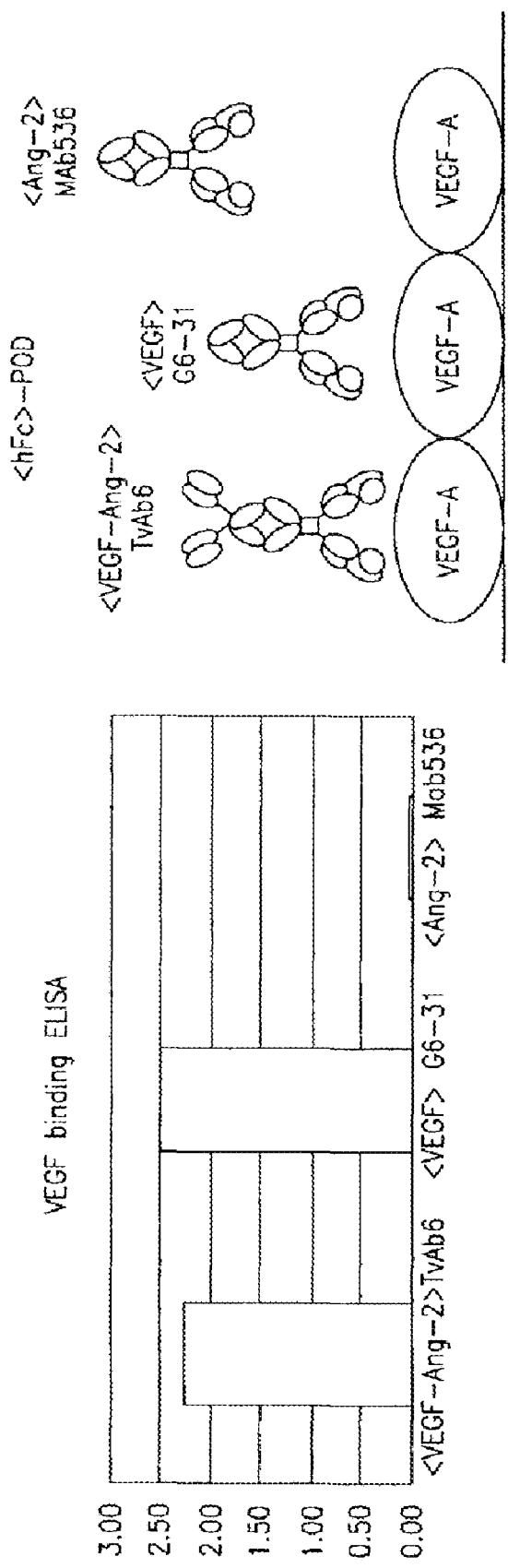

The binding properties of the tetravalent antibodies (TvAb) was evaluated in an ELISA assay with full-length VEGF165-His protein (R&D Systems) (FIG. 5). For this sake Falcon polystyrene clear enhanced microtiter plates were coated with 100 µl 2 µg/mL recombinant human VEGF165 (R&D Systems) in PBS for 2 h at room temperature or over night at 4° C. The wells were washed three times with 300 µl PBST (0.2% Tween 20) and blocked with 200 µl 2% BSA 0.1% Tween 20 for 30 min at room temperature and subsequently washed three times with 300 µl PBST. 100 µL/well of a dilution series (40pM-0.01 pM) of purified <VEGF-ANG-2> TvAb and as a reference the human anti-ANG-2 antibody <ANG-2> antibody Mab536 (Oliner et al., Cancer Cell. 2004 November; 6(5):507-16, US 2006/0122370) and the anti VEGF antibody <VEGF> antibody G6-31 (Liang et al., J Biol Chem. 2006 Jan. 13; 281(2):951-61; US 2007/0141065) in PBS (Sigma) was added to the wells and incubated for 1 h on a microtiterplate shaker at room temperature. The wells were washed three times with 300 µl PBST (0.2% Tween 20) and bound antibody was detected with 100 µL/well 0.1 µg/ml F(ab') <hFcgamma>POD (Immuno research) in 2% BSA 0.1% Tween 20 as detection antibody for 1 h on a microtiterplate shaker at room temperature. Unbound detection antibody was washed away three times with 300 µL/well PBST and the bound detection antibody was detected by addition of 100 µL ABTS/well. Determination of absorbance was performed on a Tecan Fluor Spectrometer at a measurement wavelength of 405 nm (reference wavelength 492 nm).

VEGF Binding: Kinetic Characterization of VEGF Binding at 37° C. by Surface Plasmon Resonance (Biacore)

Figure 11:
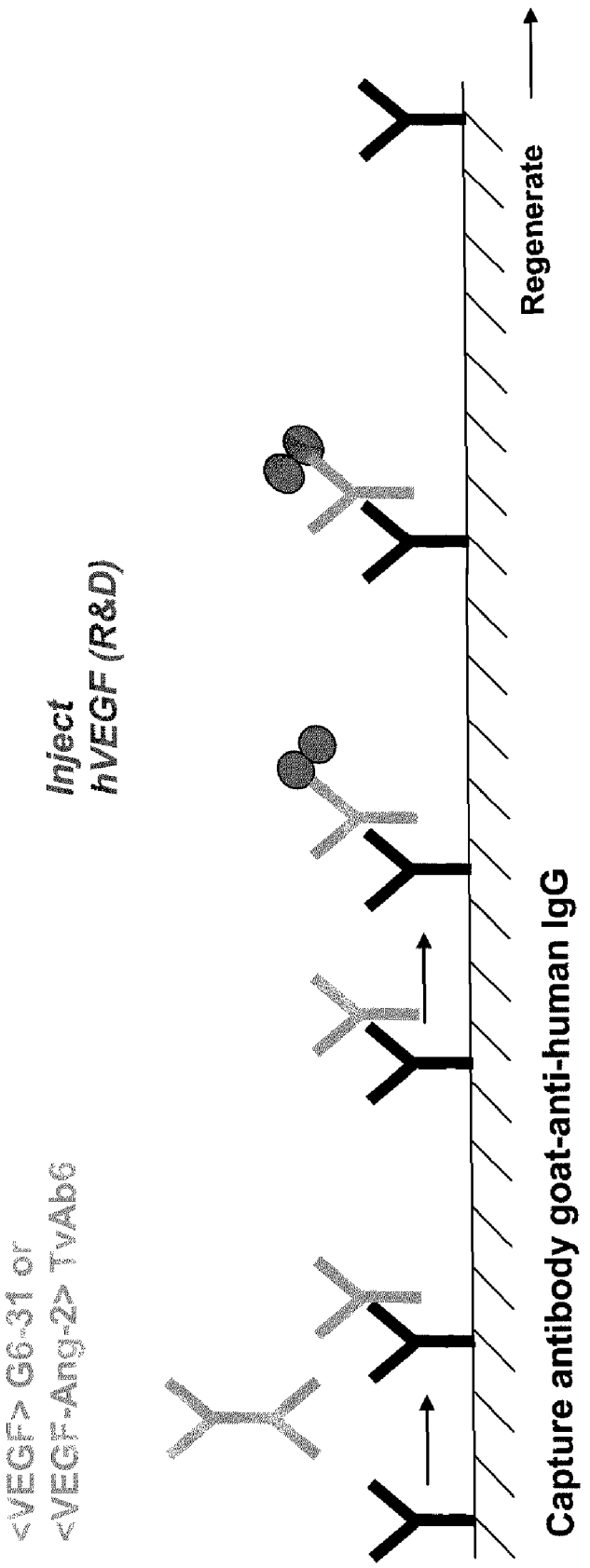

In order to further corroborate the ELISA findings the binding of <VEGF> antibodies G6-31 or bevacizumab and <VEGF-Ang-2> TvAb6 or TvAb-2441-bevacizumab-LC06 or TvAb-2441-bevacizumab-LC08 to VEGF was quantitatively analyzed using surface plasmon resonance technology on a Biacore T100 instrument according to the following protocol and analyzed using the T100 software package: Briefly <VEGF> antibodies were captured on a CM5-Chip via binding to a Goat Anti Human IgG (JIR 109-005-098). The capture antibody was immobilized by amino coupling using standard amino coupling as follows: HBS-N buffer served as running buffer, activation was done by mixture of EDC/NHS with the aim for a ligand density of 700 RU. The Capture-Antibody was diluted in coupling buffer NaAc, pH 5.0, c=2 µg/mL, finally still activated carboxyl groups were blocked by injection of 1 M Ethanolamine. Capturing of Mabs <VEGF> antibodies was done at a flow of 5 µL/min and c(Mabs<VEGF>)=10 nM, diluted with running buffer+1 mg/mL BSA; a capture level of approx. 30 RU should be reached. rhVEGF (rhVEGF, R&D-Systems Cat.-No, 293-VE) was used as analyte. The kinetic characterization of VEGF binding to <VEGF> antibodies was performed at 37° C. in PBS+0.005% (v/v) Tween20 as running buffer. The sample was injected with a flow of 50 µL/min and an association of time 80 sec. and a dissociation time of 1200 sec with a concentration series of rhVEGF from 300-0.29 nM. Regeneration of free capture antibody surface was performed with 10 mM Glycin pH 1.5 and a contact time of 60 sec after each analyte cycle. Kinetic constants were calculated by using the usual double referencing method (control reference: binding of rhVEGF to capture molecule Goat Anti Human IgG, blanks on the measuring flow cell, rhVEGF concentration "0", Model: Langmuir binding 1:1, (Rmax set to local because of capture molecule binding). FIG. 11 shows a schematic view of the Biacore assay.

ANG-2 Binding ELISA

Figure 6A:
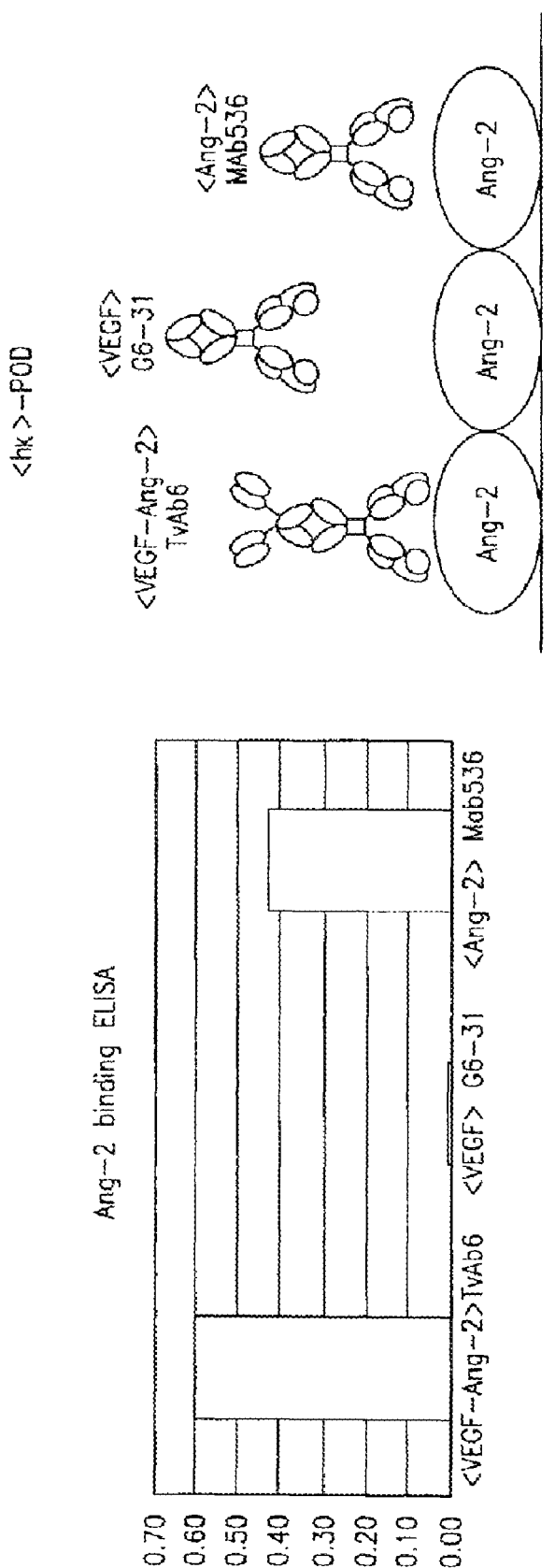
FIG. 6B Schematic view and results from ANG-2 binding analysis by surface plasmon resonance (Biacore). Disulfide-stabilized <VEGF-ANG-2> TvAb6 binds to ANG-2 with comparable affinity as <ANG-2> Mab536.

The binding properties of the tetravalent antibodies (TvAb) was evaluated in an ELISA assay with full-length Angiopoietin-2-His protein (R&D Systems) (FIG. 6a). For this sake Falcon polystyrene clear enhanced microtiter plates were coated with 100 µl 1 µg/mL recombinant human Angiopoietin-2 (R&D Systems, carrier-free) in PBS for 2 h at room temperature or over night at 4° C. The wells were washed three times with 300 µl PBST (0.2% Tween 20) and blocked with 200 µl 2% BSA 0.1% Tween 20 for 30 min at room temperature and subsequently washed three times with 300 µl PBST. 100 µL/well of a dilution series (40pM-0.01 pM) of purified <VEGF-ANG-2> TvAb and as a reference <ANG-2> antibody Mab536 and VEGF> antibody G6-31 in PBS (Sigma) was added to the wells and incubated for 1 h on a microtiterplate shaker at room temperature. The wells were washed three times with 300 µl PBST (0.2% Tween 20) and bound antibody was detected with 100 µL/well 0.1 µg/ml F(ab') <hk>POD (Biozol Cat. No. 206005) in 2% BSA 0.1% Tween 20 as detection antibody for 1 h on a microtiterplate shaker at room temperature. Unbound detection antibody was washed away three times with 300 µL/well PBST and the bound detection antibody was detected by addition of 100 µL ABTS/well. Determination of absorbance was performed on a Tecan Fluor Spectrometer at a measurement wavelength of 405 nm (reference wavelength 492 nm).

Comparative Binding to ANG-1 and ANG-2 (ANG-1 and ANG-2 Binding ELISA)

The binding properties of antibodies were evaluated in an ELISA assay with full-length Angiopoietin-2-His protein (R&D Systems #623-AN/CF or in house produced material) or Angiopoietin-1-His (R&D systems #923-AN). Therefore 96 well plates (Falcon polystyrene clear enhanced microtiter plates or Nunc Maxisorb) were coated with 100 µl 1 µg/mL recombinant human Angiopoietin-1 or Angiopoietin-2 (carrier-free) in PBS (Sigma) for 2 h at room temperature or over night at 4° C. The wells were washed three times with 300 µl PBST (0.2% Tween 20) and blocked with 200 µl 2% BSA 0.1% Tween 20 for 30 min at room temperature and subsequently washed three times with 300 µl PBST. 100 µL/well of a dilution series (40pM-0.01 pM) of purified test antibody in PBS was added to the wells and incubated for 1 h on a microtiterplate shaker at room temperature. The wells were washed three times with 300 µl PBST (0.2% Tween 20) and bound antibody was detected with 100 µL/well 0.1 µg/ml F(ab') <hk>POD (Biozol Cat. No. 206005) in 2% BSA 0.1% Tween 20 as detection antibody for 1 h on a microtiterplate shaker at room temperature. Unbound detection antibody was washed away three times with 300 µL/well PBST and the bound detection antibody was detected by addition of 100 µL ABTS/well. Determination of absorbance was performed on a Tecan Fluor Spectrometer at a measurement wavelength of 405 nm (reference wavelength 492 nm).

ANG-2 Binding BIACORE

Figure 6B:
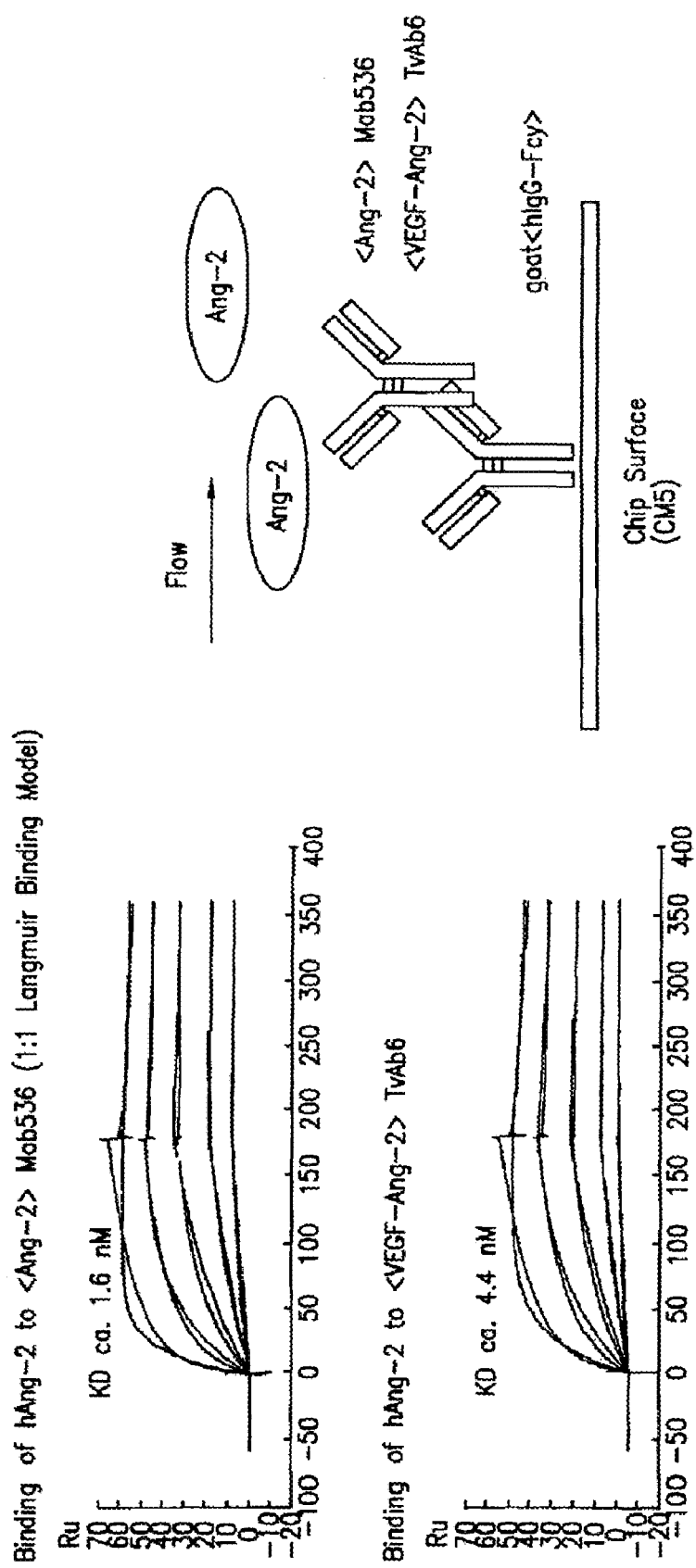

Binding of the antibodies to the antigen e.g. human ANG-2 were investigated by surface plasmon resonance using a BIACORE T100 instrument (GE Healthcare Biosciences AB, Uppsala, Sweden). Briefly, for affinity measurements goat<hIgG-Fcgamma> polyclonal antibodies were immobilized on a CM5 chip via amine coupling for presentation of the antibodies against human ANG-2 (FIG. 6B). Binding was measured in HBS buffer (HBS-P (10 mM HEPES, 150 mM NaCl, 0.005% Tween 20, ph 7.4), 25° C. Purified ANG-2-His (R&D systems or in house purified) was added in various concentrations between 6.25 nM and 200 nM in solution. Association was measured by an ANG-2-injection of 3 minutes; dissociation was measured by washing the chip surface with HBS buffer for 3 minutes and a $K_D$ value was estimated using a 1:1 Langmuir binding model. Due to heterogenity of the ANG-2 preparation no 1:1 binding could be observed; $K_D$ values are thus only relative estimations. Negative control data (e.g. buffer curves) were subtracted from sample curves for correction of system intrinsic baseline drift and for noise signal reduction. Biacore T100 Evaluation Software version 1.1.1 was used for analysis of sensorgrams and for calculation of affinity data. Alternatively, Ang-2 could be captured with a capture level of 2000-1700 RU via a PentaHisAntibody (PentaHis-Ab BSA-free, Qiagen No. 34660) that was immobilized on a CM5 chip via amine coupling (BSA-free) (see below).

Inhibition of huANG-2 Binding to Tie-2 (ELISA)

The interaction ELISA was performed on 384 well microtiter plates (MicroCoat, DE, Cat. No. 464718) at RT. After each incubation step plates were washed 3 times with PBST. ELISA plates were coated with 0.5 µg/ml Tie-2 protein (R&D Systems, UK, Cat. No. 313-TI) for at least 2 hours (h). Thereafter the wells were blocked with PBS supplemented with 0.2% Tween-20 and 2% BSA (Roche Diagnostics GmbH, DE) for 1 h. Dilutions of purified antibodies in PBS were incubated together with 0.2 µg/ml huAngiopoietin-2 (R&D Systems, UK, Cat. No. 623-AN) for 1 h at RT. After washing a mixture of 0.5 µg/ml biotinylated anti-Angiopoietin-2 clone BAM0981 (R&D Systems, UK) and 1:3000 diluted streptavidin HRP (Roche Diagnostics GmbH, DE, Cat. No. 11089153001) was added for 1 h. Thereafter the plates were washed 6 times with PBST. Plates were developed with freshly prepared ABTS reagent (Roche Diagnostics GmbH, DE, buffer #204 530 001, tablets #11 112 422 001) for 30 minutes at RT. Absorbance was measured at 405 nm.

ANG-2-VEGF Bridging ELISA

Figure 7:
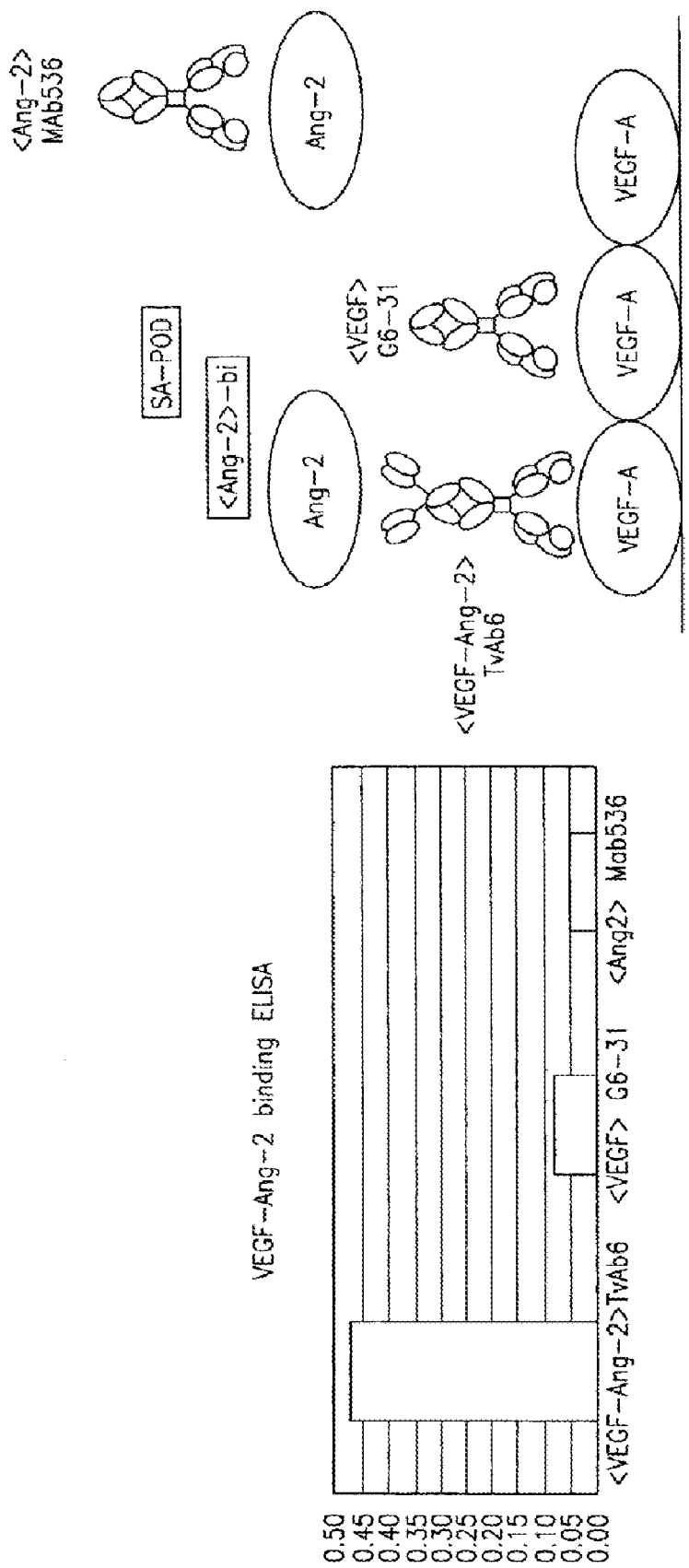
FIG. 7 Schematic view and results from VEGF-ANG-2 bridging ELISA. Disulfide-stabilized <VEGF-ANG-2> TvAb6 binds simultaneously to VEGF and ANG-2 whereas <VEGF> G6-31 and <ANG-2> Mab536 are not capable of binding simultaneously to VEGF and ANG-2.

The binding properties of the tetravalent antibodies (TvAb) was evaluated in an ELISA assay with immobilized full-length VEGF165-His protein (R&D Systems) and human ANG-2-His protein (R&D Systems) for detection of bound bispecific antibody (FIG. 7). Only a bispecific <VEGF-ANG-2> TvAb is able to bind simultaneously to VEGF and ANG-2 and thus bridge the two antigens whereas monospecific "standard" IgG1 antibodies should not be capable of simultaneously binding to VEGF and ANG-2 (FIG. 7).

For this sake Falcon polystyrene clear enhanced microtiter plates were coated with 100 µl 2 µg/mL recombinant human VEGF165 (R&D Systems) in PBS for 2 h at room temperature or over night at 4° C. The wells were washed three times with 300 µl PBST (0.2% Tween 20) and blocked with 200 µl 2% BSA 0.1% Tween 20 for 30 min at room temperature and subsequently washed three times with 300 µl PBST. 100 gL/well of a dilution series (40pM-0.01 pM) of purified <VEGF-ANG-2> TvAb and as a reference <ANG-2> antibody Mab536 and VEGF> antibody G6-31 in PBS (Sigma) was added to the wells and incubated for 1 h on a microtiterplate shaker at room temperature. The wells were washed three times with 300 µl PBST (0.2% Tween 20) and bound antibody was detected by addition of 100 µl 0.5 µg/ml human ANG-2-His (R&D Systems) in PBS. The wells were washed three times with 300 µl PBST (0.2% Tween 20) and bound ANG-2 was detected with 100 µl 0.5 µg/mL <ANG-2> mIgG1-Biotin antibody (BAM0981, R&D Systems) for 1 h at room temperature. Unbound detection antibody was washed away with three times 300 µl PBST (0.2% Tween 20) and bound antibody was detected by addition of 100 µl 1:2000 Streptavidin-POD conjugate (Roche Diagnostics GmbH, Cat. No. 11089153) 1:4 diluted in blocking buffer for 1 h at room temperature. Unbound Streptavidin-POD conjugate was washed away with three-six times 300 µl PBST (0.2% Tween 20) and bound Strepatavidin-POD conjugate was detected by addition of 100 µL ABTS/well. Determination of absorbance was performed on a Tecan Fluor Spectrometer at a measurement wavelength of 405 nm (reference wavelength 492 nm).

Figure 13:
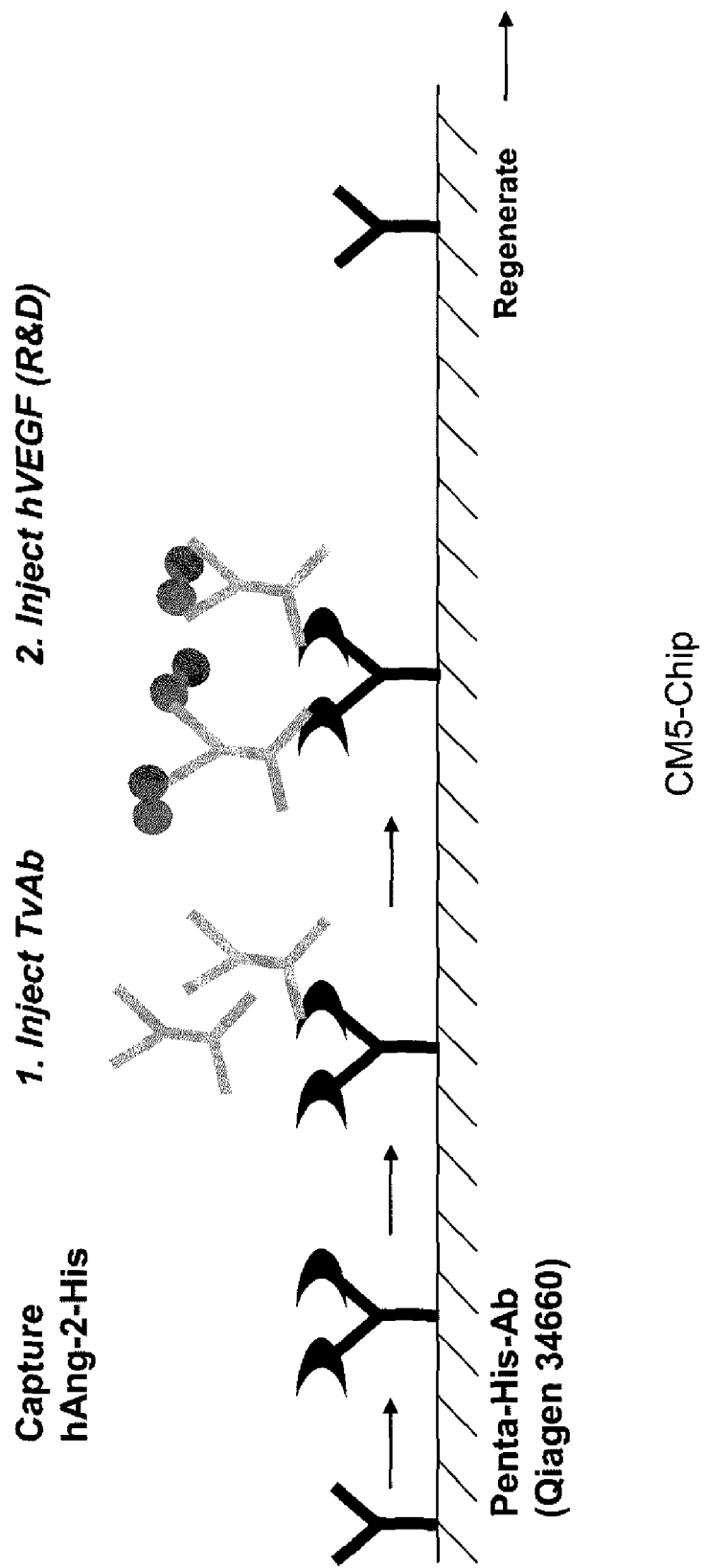
FIG. 13 Schematic view of surface plasmon resonance (Biacore) assay to detect simultaneous binding of ANGPT2 and VEGF to bispecific antibodies FIG. 14 Results from surface plasmon resonance (Biacore) experiments showing that TvAb6 binds simultaneously to ANGPT2 and VEGF.

Demonstration of Simultaneous Binding of Bispecific Tetravalent Antibody <VEGF-Ang-2> TvAb6 to VEGF-A and Ang-2 by Biacore In order to further corroborate the data from the bridging ELISA an additional assay was established to confirm simultaneous binding to VEGF and Ang-2 using surface plasmon resonance technology on a Biacore T100 instrument according to the following protocol and analyzed using the T100 software package (T100 Control, Version 2.01, T100 Evaluation, Version 2.01, T100 Kinetics Summary, Version 1.01): Ang-2 was captured with a capture level of 2000-1700 RU in PBS, 0.005% (v/v) Tween20 running buffer via a PentaHisAntibody (PentaHis-Ab BSA-free, Qiagen No. 34660) that was immobilized on a CM5 chip via amine coupling (BSA-free). HBS-N buffer served as running buffer during coupling, activation was done by mixture of EDC/NHS. The PentaHis-Ab BSA-free Capture-Antibody was diluted in coupling buffer NaAc, pH 4.5, c=30 µg/mL, finally still activated carboxyl groups were blocked by injection of 1 M Ethanolamine; ligand densities of 5000 and 17000 RU were tested. Ang-2 with a concentration of 500 nM was captured by the PentaHis-Ab at a flow of 5 μL/min diluted with running buffer+1 mg/mL BSA. Subsequently, <Ang-2, VEGF> bispecific antibody binding to Ang-2 and to VEGF was demonstrated by incubation with rhVEGF and formation of a sandwich complex. For this sake, bispecific <VEGF-Ang-2> TvAb6 was bound to Ang-2 at a flow of 50 μL/min and a concentration of 100 nM, diluted with running buffer+1 mg/mL BSA and simultaneous binding was detected by incubation with VEGF (rhVEGF, R&D-Systems Cat.-No, 293-VE) in PBS+0.005% (v/v) Tween20 running buffer at a flow of 50 μL/min and a VEGF concentration of 150 nM. Association time 120 sec, dissociation time 1200 sec. Regeneration was done after each cycle at a flow of 50 μL/min with 2×10 mM Glycin pH 2.0 and a contact time of 60 sec. Sensorgrams were corrected using the usual double referencing (control reference: binding of bispecific antibody and rhVEGF to capture molecule PentaHisAb). Blanks for each Ab were measured with rhVEGF concentration "0". A scheme of the Biacore assay is shown in FIG. 13. An alternative Biacore assay format is shown in FIG. 15.

Generation of HEK293-Tie2 Cell Line

In order to determine the interference of Angiopoietin-2 antibodies with ANGPT2 stimulated Tie2 phosphorylation and binding of ANGPT2 to Tie2 on cells a recombinant HEK293-Tie cell line was generated. Briefly, a pcDNA3 based plasmid (RB22-pcDNA3 Topo hTie2) coding for full-length human Tie2 (SEQ ID 108) under control of a CMV promoter and a Neomycin resistance marker was transfected using Fugene (Roche Applied Science) as transfection reagent into HEK293 cells (ATCC) and resistant cells were selected in DMEM 10% FCS, 500 μg/ml G418. Individual clones were isolated via a cloning cylinder, and subsequently analyzed for Tie2 expression by FACS. Clone 22 was identified as clone with high and stable Tie2 expression even in the absence of G418 (HEK293-Tie2 clone22). HEK293-Tie2 clone22 was subsequently used for cellular assays: ANGPT2 induced Tie2 phosphorylation and ANGPT2 cellular ligand binding assay.

ANGPT2 Induced Tie2 Phosphorylation Assay

Inhibition of ANGPT2 induced Tie2 phosphorylation by ANGPT2 antibodies was measured according to the following assay principle. HEK293-Tie2 clone22 was stimulated with ANGPT2 for 5 minutes in the absence or presence of ANGPT2 antibody and P-Tie2 was quantified by a sandwich ELISA. Briefly, 2×105 HEK293-Tie2 clone 22 cells per well were grown over night on a Poly-D-Lysine coated 96 well-microtiter plate in 100 μl DMEM, 10% FCS, 500 μg/ml Geneticin. The next day a titration row of ANGPT2 antibodies was prepared in a microtiter plate (4-fold concentrated, 75 μl final volume/well, duplicates) and mixed with 75 μl of an ANGPT2 (R&D systems #623-AN] dilution (3.2 μg/ml as 4-fold concentrated solution). Antibodies and ANGPT2 were pre-incubated for 15 min at room temperature. 100 μl of the mix were added to the HEK293-Tie2 clone 22 cells (pre-incubated for 5 min with 1 mM NaV3O4, Sigma #S6508) and incubated for 5 min at 37° C. Subsequently, cells were washed with 200 μl ice-cold PBS+1 mM NaV3O4 per well and lysed by addition of 120 μl lysis buffer (20 mM Tris, pH 8.0, 137 mM NaCl, 1% NP-40, 10% glycerol, 2 mM EDTA, 1 mM NaV3O4, 1 mM PMSF and 10 μg/ml Aprotinin) per well on ice. Cells were lysed for 30 min at 4° C. on a microtiter plate shaker and 100 μl lysate were transferred directly into a p-Tie2 ELISA microtiter plate (R&D Systems, R&D #DY990) without previous centrifugation and without total protein determination. P-Tie2 amounts were quantified according to the manufacturer's instructions and IC50 values for inhibition were determined using XLfit4 analysis plug-in for Excel (Dose-response one site, model 205). IC50 values can be compared within on experiment but might vary from experiment to experiment.

VEGF Induced HUVEC Proliferation Assay

VEGF induced HUVEC (Human Umbilical Vein Endothelial Cells, Promocell #C-12200) proliferation was chosen to measure the cellular function of VEGF antibodies. Briefly, 5000 HUVEC cells (low passage number, <5 passages) per 96 well were incubated in 100 μl starvation medium (EBM-2 Endothelial basal medium 2, Promocell #C-22211, 0.5% FCS, Penicilline/Streptomycine) in a collagen I-coated BD Biocoat Collagen I 96-well microtiter plate (BD #354407/35640 over night. Varying concentrations of antibody were mixed with rhVEGF (30 ng 1/ml final concentration, BD #354107) and pre-incubated for 15 minutes at room temperature. Subsequently, the mix was added to the HUVEC cells and they were incubated for 72 h at 37° C., 5% CO2. On the day of analysis the plate was equilibrated to room temperature for 30 min and cell viability/proliferation was determined using the CellTiter-Glo™ Luminescent Cell Viability Assay kit according to the manual (Promega, #G7571/2/3). Luminescence was determined in a spectrophotometer.

Design of Tetravalent Bispecific and Tetravalent Monospecific Antibodies

The bispecific antibodies binding to VEGF (VEGF-A) and ANG-2 (Angiopoietin-2) according to the invention comprise a first antigen-binding site that binds to VEGF and a second antigen-binding site that binds to ANG-2. As first antigen-binding site binding to VEGF, e.g. the heavy chain variable domain of SEQ ID NO: 23, and the light chain variable domains of SEQ ID NO: 24 which are both derived from the human phage display derived anti-VEGF antibody G6-31 which is described in detail in Liang, W. C., et al., J Biol Chem. 281(2) (2006) 951-61 and in US 2007/0141065, can be used. Alternatively e.g. the second antigen-binding site specifically binding to VEGF comprises the heavy chain variable domains of SEQ ID NO: 7, or SEQ ID NO: 100, and the light chain variable domains SEQ ID NO:8 or SEQ ID NO: 101 from the anti-VEGF antibodies <VEGF>bevacizumab and <VEGF>B20-4.1., preferably from <VEGF>bevacizumab.

As second antigen-binding site comprises the heavy chain variable domains SEQ ID NO: 31, and the light chain variable domains SEQ ID NO: 32 or SEQ ID NO: 32 with the mutations T92L, H93Q and W94T (Kabat numbering), which are both derived from the human anti-ANG-2 antibody <ANG-2> Mab536 which is described in detail in Oliner, J., et al., Cancer Cell. 6(5) (2004) 507-16, and in US 2006/0122370, can be used. Alternatively e.g. the second antigen-binding site specifically binding to ANG-2 comprises the heavy chain variable domains of SEQ ID NO: 44, SEQ ID NO: 52, SEQ ID NO: 60, SEQ ID NO: 68, SEQ ID NO: 76, SEQ ID NO: 84 or SEQ ID NO: 92, and the light chain variable domains SEQ ID NO: 45, SEQ ID NO: 53, SEQ ID NO: 61, SEQ ID NO: 69, SEQ ID NO: 77, SEQ ID NO: 85, SEQ ID NO: 93 from the anti-ANG-2 antibodies <ANG-2>Ang2s_R3_LC03, <ANG-2>Ang2i_LC06, <ANG-2>Ang2i_LC07, <ANG-2> Ang2k_LC08, <ANG-2> Ang2s_LC09, <ANG-2> Ang2i_LC10, or <ANG-2> Ang2k_LC11, preferably from <ANG-2>Ang2i_LC06, or <ANG-2> Ang2k_LC08.

To generate agents that combine features of both antibodies, novel tetravalent bispecific antibody-derived protein entities were constructed. In these molecules, recombinant single-chain binding molecules of one antibody are connected via recombinant protein fusion technologies to the other antibody which was retained in the format of a full-length IgG1. This second antibody carries the desired second binding specificity.

By gene synthesis and recombinant molecular biology techniques, the heavy chain variable domain (VH) and the light chain variable domain (VL) of the respective antibody were linked by a glycine serine (G4S)3 or (G4S)4 single-chain-linker to give a single chain Fv (scFv), which was attached to the C-terminus of the other antibody heavy chain using a (G)6- or (G4S)3-linker.

In addition, cysteine residues were introduced in the VH (including Kabat position 44,) and VL (including Kabat position 100) domain of the scFv binding to ANG-2 or VEGF as described earlier (e.g. WO 94/029350; Reiter, Y., et al., Nature biotechnology (1996) 1239-1245; Young, N. M., et al, FEBS Letters (1995) 135-139; or Rajagopal, V., et al., Protein Engineering (1997) 1453-59).

All these molecules were recombinantly produced, purified and characterized and protein expression, stability and biological activity was evaluated.

A summary of the bispecific antibody designs that were applied to generate tetravalent bispecific <VEGF-ANG-2>, <ANG-2-VEGF> antibodies and tetravalent monospecific <ANG-2> antibodies is given in Table 3. For this study, we use the term 'TvAb' to describe the various tetravalent protein entities.

Figure 1B:
FIG. 1B Schematic representation of the generated bispecific tetravalent antibodies using the TvAb nomenclature (see Examples)—either without or with disulfide stabilization of the scFv FIG. 2A Schematic representation of disulfide-stabilized <VEGF-ANG-2> bispecific tetravalent antibody (=<VEGF-ANG-2> TvAb6; No. 2331, see Table 3)

In order to obtain the bispecific tetravalent antibodies <VEGF-ANG-2> TvAb5 and TvAb6 the single chain Fv (scFv) binding to Angiopoietin-2 derived from the heavy chain variable domain (VH) of SEQ ID NO: 31, and the light chain variable domain (VL) of SEQ ID NO: 32 with the mutations T92L, H93Q and W94T derived from the human anti-ANG-2 antibody <ANG-2> Mab536 was fused to the sequence corresponding to the C-terminus of the heavy chain vector of the human anti-VEGF antibody <VEGF> G6-31 of SEQ ID NO: 23 and co-expressed with the respective light chain expression vector based on SEQ ID NO: 24. A representation of the designed formats is shown in FIG. 1B and listed in Table 3.

In order to obtain the bispecific tetravalent antibodies TvAb9 and TvAb15 the single chain Fv (scFv) binding to VEGF derived from the heavy chain variable domain (VH) of SEQ ID NO: 23, and the light chain variable domain (VL) of SEQ ID NO: 24 derived from the human anti-VEGF antibody <VEGF> G6-31 were fused to the sequence corresponding to the C-terminus of the heavy chain vector of the human anti-ANG-2 antibody <ANG-2> Mab536 of SEQ ID NO: 31 and co-expressed with the respective light chain expression vector based on SEQ ID NO: 32. A representation of the designed formats is shown in FIG. 1B and listed in Table 3.

TABLE 3

The different bispecific tetravalent antibody formats with C-terminal scFv attachments and the corresponding TvAb-nomenclature. An "—" in the table means "not present"

| Molecule Name (TvAb-nomenclature for bispecific antibodies) | Antibody backbone derived from | scFv derived from | Variable Domains VH and VL: SEQ ID NO: | Position of scFv | Single-chain-linker | Peptide-linker | scFv disulfied VH44/ VL100 stabilized |
|---|---|---|---|---|---|---|---|
| G6-31 (1000) | <VEGF> G6-31 | — | 23 + 24 | — | — | — | — |
| Mab536 (1000) | <ANG-2> Mab536 | — | 31 + 32 | — | — | — | — |
| bevacizumab | <VEGF>bevacizumab | — | 23 + 24 | — | — | — | — |
| Ang2i_LC06 (LC06) | <ANG-2>Ang2i_LC06 | — | 52 + 53 | — | — | — | — |
| Ang2k_LC06 (LC08) | <ANG-2>Ang2k_LC08 | — | 68 + 69 | — | — | — | — |
| TvAb5 (2310) | <VEGF> G6-31 | <ANG-2> Mab536 | 23 + 24, 31 + 32 with the mutations T92L, H93Q and W94T | C-term. HC | (G4S)3 | (G)6 | — |
| TvAb6 (2331) | <VEGF> G6-31 | <ANG-2> Mab536 | 23 + 24, 31 + 32 with the mutations T92L, H93Q and W94T | C-term. HC | (G4S)3 | (G4S)3 | scFv disulfide VH44/VL100 stabilized |
| TvAb9 (2330) | <ANG-2> Mab536 | <VEGF> G6-31 | 31 + 32, and 23 + 24 | C-term. HC | (G4S)3 | (G4S)3 | — |
| TvAb15 (2431) | <ANG-2> Mab536 | <VEGF> G6-31 | 31 + 32, and 23 + 24 | C-term. HC | (G4S)4 | (G4S)3 | scFv disulfide VH44/VL100 stabilized |
| TvAb-2441-bevacizumab-LC06 | bevacizumab | LC06 | 7 + 8 and 52 + 53 | C-term. HC | (G4S)4 | (G4S)4 | scFv disulfide VH44/VL100 stabilized |

TABLE 3-continued

The different bispecific tetravalent antibody formats with C-terminal scFv attachments and the corresponding TvAb-nomenclature.
An "—" in the table means "not present"

| Molecule Name (TvAb-nomenclature for bispecific antibodies) | Antibody backbone derived from | scFv derived from | Variable Domains VH and VL: SEQ ID NO: | Position of scFv | Single-chain-linker | Peptide-linker | scFv disulfied VH44/ VL100 stabilized |
|---|---|---|---|---|---|---|---|
| TvAb-2441-bevacizumab-LC08 | bevacizumab | LC08 | 7 + 8 and 68 + 69 | C-term. HC | (G4S)4 | (G4S)4 | scFv disulfide VH44/VL100 stabilized |
| TvAb-3421_bevacizumab_LC06 | bevacizumab | LC06 | 7 + 8 and 52 + 53 | N-term. HC | (G4S)4 | (G4S)2 | scFv disulfide VH44/VL100 stabilized |
| TvAb-4421_bevacizumab_LC06 | bevacizumab | LC06 | 7 + 8 and 52 + 53 | C-term LC | (G4S)4 | (G4S)2 | scFv disulfide VH44/VL100 stabilized |
| TvAb-4461_bevacizumab_LC06 | bevacizumab | LC06 | 7 + 8 and 52 + 53 | C-term LC | (G4S)4 | (G4S)6 | scFv disulfide VH44/VL100 stabilized |

The TvAb formats are based e.g. on a) aa) the human anti-VEGF antibody <VEGF> G6-31 and ab) two single chain Fv (scFv) binding to Angiopoietin-2 derived from the heavy chain variable domain (VH) of SEQ ID NO: 31, and the light chain variable domain (VL) of SEQ ID NO: 32 with the mutations T92L, H93Q and W94T, which are linked to the C-terminus of the heavy chain of the anti-VEGF antibody <VEGF> G6-31 (SEQ ID NO: 23); or b) ba) the human anti-ANG-2 antibody <ANG-2> Mab536 and bb) two single chain Fv (scFv) binding to VEGF derived from the heavy chain variable domain (VH) of SEQ ID NO: 23, and the light chain variable domain (VL) of SEQ ID NO: 24, which are linked to the C-terminus of the heavy chain of the anti-ANG-2 antibody <ANG-2> Mab536 (SEQ ID NO: 31); or c) ca) the human anti-VEGF antibody <VEGF> bevacizumab and cb) two single chain Fv (scFv) binding to Angiopoietin-2 derived from the heavy chain variable domain (VH) of SEQ ID NO: 52 or of SEQ ID NO: 68, and the light chain variable domain (VL) of SEQ ID NO: 53 or of SEQ ID NO: 69, which are linked to the C-terminus of the heavy chain of the anti-VEGF antibody <VEGF> bevacizumab (the Sequences of the resulting fusion peptide are SEQ ID NO: 102 or SEQ ID NO: 103, which are co-expressed with the light chain of bevacizumab SEQ ID NO: 104. (Alternatively two single chain Fv (scFv) binding to Angiopoietin-2 can also be linked to the C-terminus of the light chain or the N-terminus of the heavy chain).

d) Alternatively to the single two single chain Fv (scFv) also single chain Fab fragments can be used as described above (using peptide connectors for the fusion to C or N-termini), in EP Appl. No 09004909.9 and in Example 10.

Example 1

Expression of Bispecific Tetravalent Antibodies

<VEGF-ANG-2> TvAb5, TvAb6, TvAb-2441-bevacizumab-LC06 and TvAb-2441-bevacizumab-LC08

Light and heavy chains of the corresponding tetravalent bispecific antibodies TvAb5 and TvAb6 were constructed in genomic expression vectors as described above. The plasmids were amplified in E. coli, purified, and subsequently transfected for transient expression of recombinant proteins in HEK293-F cells (utilizing Invitrogen's FreeStyle 293 system). After 7 days, HEK 293-F cell supernatants were harvested, filtered and the bispecific antibodies were purified by protein A and size exclusion chromatography. Homogeneity of all bispecific antibody constructs was confirmed by SDS-PAGE under non reducing and reducing conditions and analytical size exclusion chromatography. Under reducing conditions (FIG. 3), polypeptide heavy chains of <VEGF-ANG-2> TvAb6 carrying the C-terminal scFv fusion showed upon SDS-PAGE apparent molecular sizes of ca. 75 kDa analogous to the calculated molecular weights. Mass spectrometry confirmed the identity of the purified antibody constructs. Expression levels of all constructs were analysed by Protein A HPLC and were similar to expression yields of 'standard' IgGs. Protein yields achieved up to 150 mg of TvAb6 <VEGF-ANG-2> per liter of cell-culture supernatant as determined by Protein A HPLC.

Size exclusion chromatography analysis of the purified non-disulfide stabilized construct TvAb5 with C-terminal fused scFv at the heavy chain showed that, compared to 'standard' IgGs, it had an increased tendency to aggregate again after purification of monomeric antibody via size exclusion chromatography (so-called "daisy chain" phenomenon). This finding has been supported by other examples (Rajagopal, V., et al., Prot. Engin. (1997) 1453-1459; Kobayashi, H., et al, Nucl Med Biol. (1998) 387-393 or Schmidt, M., et al, Oncogene (1999) 18, 1711-1721) showing that molecules that contained scFvs that were not stabilized by interchain disulfides between VH and VL exhibited an increased tendency to aggregate and reduced yields. To address the problems with aggregation of such bispecific antibodies, disulfide-stabilization of the scFv moieties was applied. For that we introduced single cysteine replacements within VH and VL of the scFv at defined positions (positions VH44/VL100 according to the Kabat numbering scheme). These mutations enable the formation of stable interchain disulfides between VH and VL, which in turn stabilize the resulting disulfide-stabilized scFv module. Introduction of the VH44/VL100 disulfides in the scFv at the C-terminus of the Fv in TvAb6 <VEGF-ANG-2> lead to a stable tetravalent antibody that showed no aggregation tendency any longer after purification and remained in a monomeric state (FIG. 4). In addition, TvAb6 <VEGF-ANG-2> showed no increase in aggregation tendency upon repeated freeze-thaw cycles e.g. at the concentration applied for in vitro and in vivo of 3 mg/kg.

All other TvAb molecules described in Table 3 (e.g. TvAb-2441-bevacizumab-LC06 and TvAb-2441-bevacizumab-LC08) were prepared and analytically characterized analogously to the procedure described.

Example 2

Simultaneous Binding of Bispecific Tetravalent Antibody <VEGF-ANG-2> TvAb6, TvAb-2441-Bevacizumab-LC06 and TvAb-2441-Bevacizumab-LC08 to VEGF-A and ANG-2

The binding of the scFv modules and of the Fvs retained in the IgG-module of the different bispecific antibody formats were compared to the binding of the 'wildtype' IgGs from which the binding modules and bispecific antibodies were derived. These analyses were carried out at equimolar concentrations by performing biochemical binding ELISAs and by applying Surface Plasmon Resonance (Biacore).

For <VEGF-ANG-2> TvAb6 is was shown by VEGF binding ELISA as described above that it binds to VEGF comparable to its parent antibody G6-31 at an equimolar concentration of 0.625 pM (FIG. 5). This finding could be expected as the Fv region of the TvAb is identical to that of G6-31. The slight difference between <VEGF-ANG-2> TvAb6 and <VEGF> G6-31 is due to small differences in protein concentration and a slight steric interference of the C-terminal scFv with binding of the <hFc>-POD detection antibody and can be overcome by application of a <hk> POD (Biozol Cat. No. 206005) detection antibody like used for the ANG-2 binding ELISA.

Figure 12:
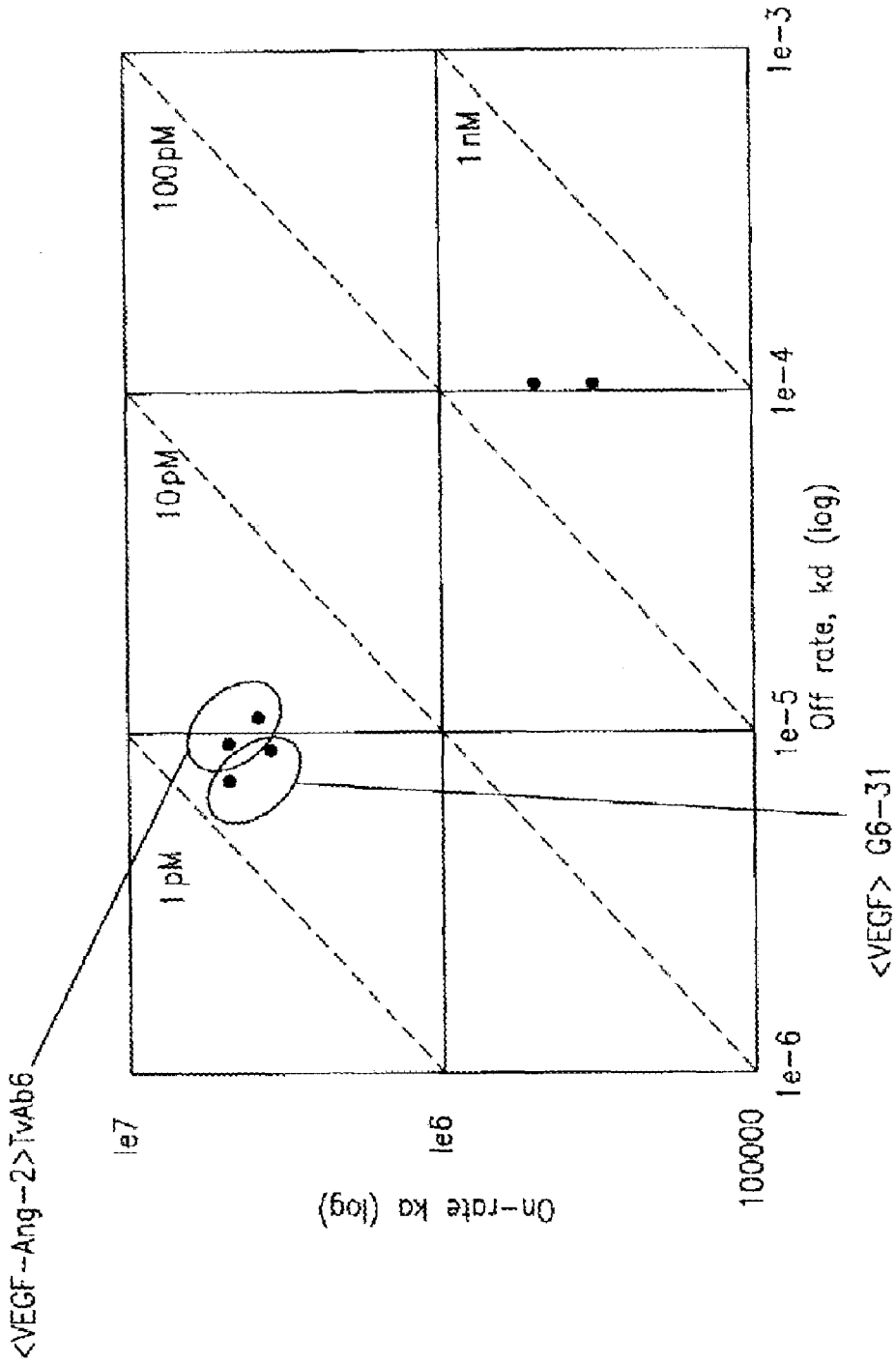
FIG. 12 Kinetic characteristics of the two <VEGF> antibodies <VEGF-Ang-2> TvAb6 and <VEGF> G6-31 in a $K_A$-$K_D$ plot.

Using Biacore these findings were confirmed using a classical concentration series at 37° C. (FIG. 11). These data showed fast Kon-rates k(a) of 4.7-4.8 E+6 l/(Ms), saturation was reached with the highest concentrations of VEGF. Koff-rates reached limits of technical specification.(i.e. 5×E-6 (s/s) probably due to still bivalent binding (avidity effect) under this conditions as a consequence of the dimeric analyte rhVEGF, although a very low ligand density was used resulting in final VEGF-response of 10-15 RU. Nevertheless, the kinetic constants of the different <VEGF> antibodies could be compared by this method and within the error of the method there was no significant difference in the kinetic constants of the tetravalent bispecific antibody <VEGF-Ang-2> TvAb6 and the original antibody <VEGF> G6-31 detectable. The kinetic constants for <VEGF-Ang-2> TvAb6 and <VEGF> G6-31 under these conditions were virtually identical by this method. Thus, it can be concluded that TvAb6 completely retained its VEGF binding properties. Tab. 4 shows the respective kinetic constants and FIG. 12 shows the kinetic characteristics of the two <VEGF> antibodies <VEGF-Ang-2> TvAb6 and <VEGF> G6-31 in a $K_A$-$K_D$ plot.

TABLE 14

Kinetic properties of <VEGF-Ang-2> TvAb6 and <VEGF> G6-31

| | Measured at 37° C. | | | |
|---|---|---|---|---|
| Antibodies | $K_A$ [1/(Ms)] | $K_D$ [1/s] | t½ [min] | $K_D$ [M] |
| <VEGF> G6-31 | 4.83E+06 | 9.33E−06 | 1237.8 | 1.93E−12 |
| <VEGF-Ang-2> TvAb6 | 4.72E+06 | 7.24E−06 | 1596.7 | 1.53E−12 |

In a further experiment it was shown by ANG-2 binding ELISA using a <hk>-POD detection antibody (Biozol Catalogue No. 206005) as described above that <VEGF-ANG-2> TvAb6 binds to ANG-2 in a manner comparable to that of Mab536 at an equimolar concentration of 0.039 pM (FIG. 6A). This showed that the scFv module of TvAb6 retained its binding properties in the TvAb construct.

In order to further corroborate this finding <ANG-2> Mab536 and <VEGF-ANG-2> TvAb6 were immobilized by a secondary antibody on a Biacore CM5 chip and binding kinetics to human ANG-2 were determined. Due to heterogeneity of the ANG-2 preparation no 1:1 binding can be observed; $K_D$ values are thus only relative estimations. The Biacore analysis showed that <VEGF-ANG-2> TvAb6 has an estimated $K_D$ value of 4.4 nM for ANG-2. In comparison, Mab536 has an estimated $K_D$ value of 1.6 nM. Within the error of the method no difference in binding mode and affinities between <ANG-2> Mab536 and <VEGF-ANG-2> TvAb6 could be observed (FIG. 6B). Thus, it can be concluded that the scFv module of TvAb6 completely retained its binding properties in the TvAb construct.

In order to prove that <VEGF-ANG-2> TvAb6 was able to bind simultaneously to VEGF and ANG-2 bridging ELISA assays and Biacore assays as described above were applied.

By applying the VEGF-ANG-2-bridging ELISA described above it was shown that only <VEGF-ANG-2> TvAb6 was able to bind simultaneously to VEGF and ANG-2 at an equimolar concentration of 0.625 pM whereas the monospecific "standard" IgG1 antibodies <ANG-2> Mab536 and <VEGF> G6-31 were not capable of simultaneously binding to VEGF and ANG-2 (FIG. 7).

Figure 14:
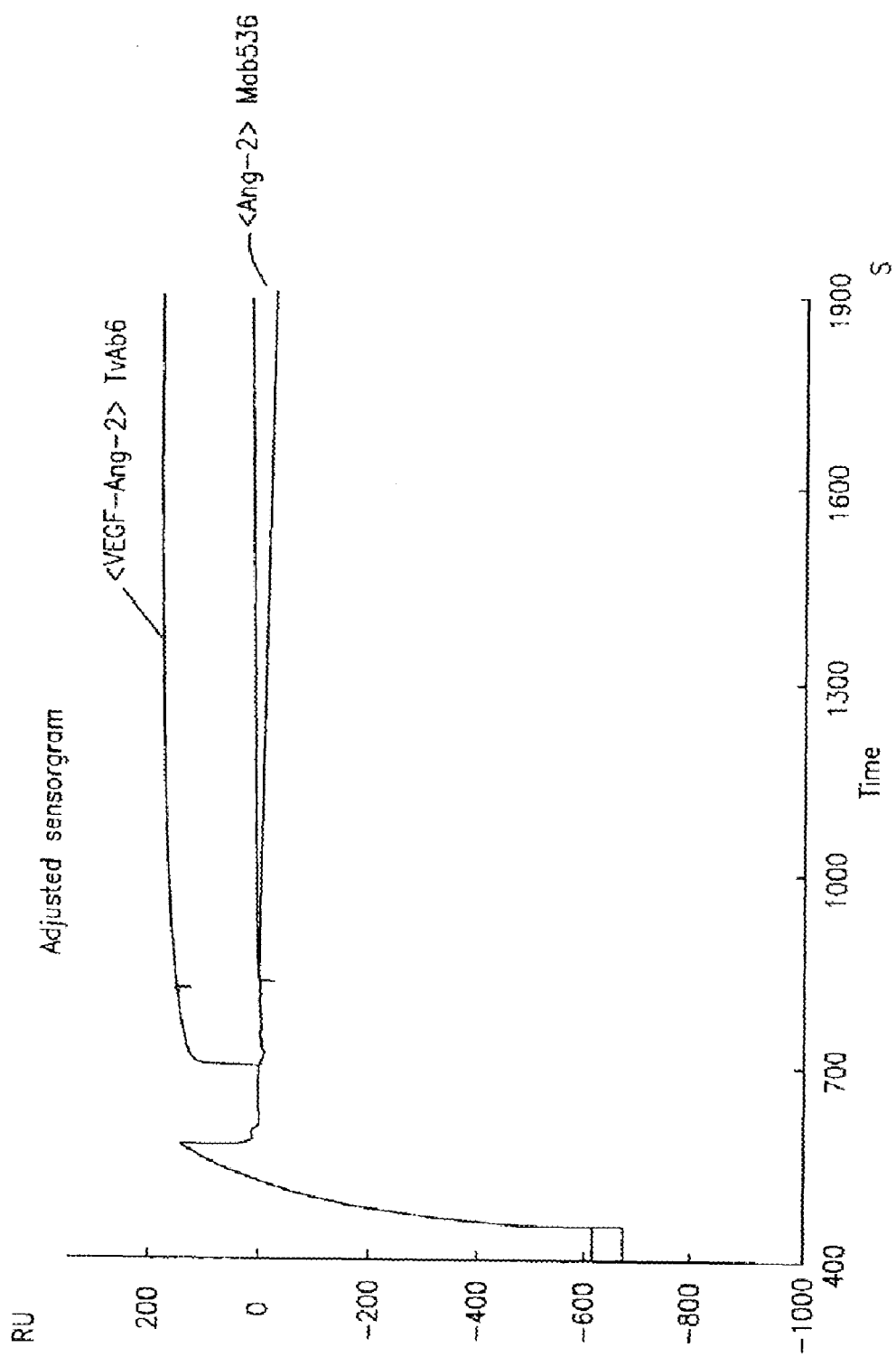

FIG. 14 shows the respective data from the Biacore assay. Simultaneous binding of both antigens Ang-2 and VEGF could be shown for the tetravalent bispecific antibody <VEGF-Ang-2>TvAb6. Negative controls were as expected: The monospecific antibody <Ang-2> Mab536 showed only binding to Ang-2, but no VEGF-binding. The monospecific antibody <VEGF> G6-31 showed binding to VEGF but no binding to Ang-2 at all (data not shown). From the relative response units of the tetravalent bispecific antibody <VEGF-Ang-2> TvAb6 binding to the Ang-2 coated surface, and subsequent binding to dimeric VEGF binding the stochiometry could be calculated to be in the range from 1:1 to 1:1.4. Taken together, by applying the described ELISA and Biacore assays it was shown that only <VEGF-Ang-2> TvAb6 was able to bind simultaneously to VEGF and Ang-2 whereas the monospecific "standard" IgG1 antibodies <Ang-2> Mab536 and <VEGFY G6-31 were not capable of simultaneously binding to VEGF and Ang-2 (FIG. 15).

Figure 15A:
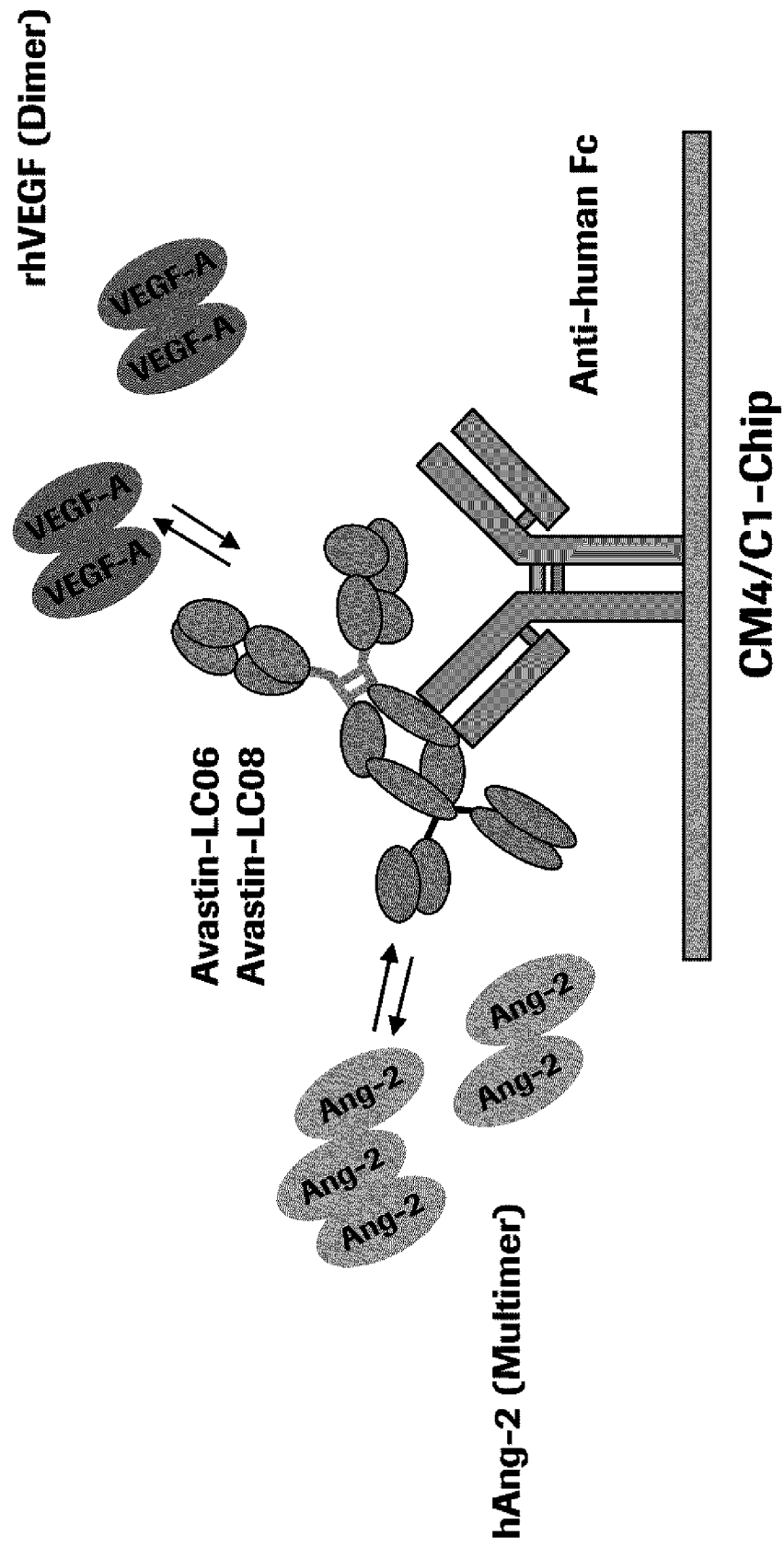
FIG. 15A+B A) Schematic representation of the bispecific and simultaneous Biacore binding assay of the <VEGF-ANG-2> bispecific antibodies. B) Biacore data demonstrating simultaneous binding of ANG-2 and VEGF to TvAb-2441-bevacicumab_LC06

Similar results were obtained with the constructs TvAb-2441-bevacizumab-LC06 and TvAb-2441-bevacizumab-LC08 in an analogous Biacore assay shown in FIG. 15A. Binding of the antibodies to the antigen e.g. human ANG-2 and VEGF were investigated by surface plasmon resonance using a BIACORE T100 instrument (GE Healthcare Biosciences AB, Uppsala, Sweden). Briefly, for affinity measurements goat<hIgG-Fcγ)> polyclonal antibodies were immobilized on a CM4 chip via amine coupling for presentation of the bispecific antibodies against human ANG-2 and VEGF. Binding was measured in HBS buffer (HBS-P (10 mM HEPES, 150 mM NaCl, 0.005% Tween 20, ph 7.4), 25° C. Purified ANG-2-His (R&D systems or in house purified) was added in various concentrations between 6.25 nM and 200 nM in solution. Association was measured by an ANG-2-injection of 3 minutes; dissociation was measured by washing the chip surface with HBS buffer for 3 minutes and a $K_D$ value was estimated using a 1:1 Langmuir binding model. Due to heterogenity of the ANG-2 preparation no 1:1 binding could be observed; $K_D$ values are thus only relative estimations.

VEGF (R&D systems) was added in various concentrations between 6.25 nM and 200 nM in solution. Association was measured by an VEGF-injection of 3 minutes; dissociation was measured by washing the chip surface with HBS buffer for 3 minutes and a $K_D$ value was estimated using a 1:1 Langmuir binding model.

The order of injection of the binding partners can switched, first VEGF and then Ang2 or vice versa.

Negative control data (e.g. buffer curves) were subtracted from sample curves for correction of system intrinsic baseline drift and for noise signal reduction. Biacore T100 Evaluation Software version 1.1.1 was used for analysis of sensorgrams and for calculation of affinity data.

| Antibody | Affinity hAng-2 | Affinity hVEGF |
|---|---|---|
| TvAb-2441-bevacizumab-LC06 | 2.3 nM | 0.35 nM |
| TvAb-2441-bevacizumab-LC08 | 0.7 nM | 0.34 nM |
| G6-31 | — | <0.1 nM |
| MAb536 | 3 nM | — |
| bevacizumab | — | 0.59 nM |

Finally, simultaneous binding of TvAb-2441-bevacizumab-LC06 and TvAb-2441-bevacizumab-LC08 could be shown by incubating with ANGPT2 and VEGF in a consecutive manner. As shown in FIG. 15B ANGPT2 and VEGF can bind simultaneously to the bispecific antibodies.

Example 3

In Vivo Efficacy of Disulfide-Stabilized Bispecific Tetravalent Antibody <VEGF-ANG-2> TvAb6 in Comparison to <ANG-2> Mab536, <VEGF> G6-31 and the Combination of Mab536 and G6-31 in the Staged Subcutaneous Colo205 Xenograft Model in Scid Beige Mice The purified disulfide-stabilized <VEGF-ANG-2> TvAb6 (n00.2331 see Table 3) was compared to the antibodies <ANG-2> Mab536, <VEGF> G6-31 and the combination of <ANG-2> Mab536 and <VEGF> G6-31 in two staged subcutaneous Colo205 xenograft model studies (Ang2_PZ_Colo205_003 and Ang2_PZ_Colo205_005) in female Scid beige mice at different doses.

Antibodies: <ANG-2> Mab536 was provided as frozen stock solution (c=4.5 mg/mL), <VEGF> G6-31 was provided as frozen solution (c=0.6 mg/mL) and <VEGF-ANG-2> TvAb6 was provided as frozen stock solution (c=0.5 mg/mL) in 20 mM Histidine, 140 mM NaCl, pH 6.0. Antibody solution was diluted appropriately in PBS from stock prior injections where required and PBS was applied as vehicle.

Cell lines and culture conditions: Colo205 human colorectal cancer cells were originally obtained from ATCC and after expansion deposited in the Roche Penzberg internal cell bank. Tumor cell line was routinely cultured in RPMI 1640 medium (PAA, Laboratories, Austria) supplemented with 10% fetal bovine serum (PAA Laboratories, Austria) and 2 mM L-glutamine, at 37° C. in a water-saturated atmosphere at 5% $CO_2$. Passage 2-5 was used for transplantation.

Animals: Female SCID beige mice; age 4-5 weeks at arrival (purchased from Charles River Germany) were maintained under specific-pathogen-free condition with daily cycles of 12 h light/12 h darkness according to committed guidelines (GV-Solas; Felasa; TierschG). Experimental study protocol was reviewed and approved by local government. After arrival animals were maintained in the quarantine part of the animal facility for one week to get accustomed to the new environment and for observation. Continuous health monitoring was carried out on regular basis. Diet food (Provimi Kliba 3337) and water (acidified pH 2.5-3) were provided ad libitum. Age of mice at start of the study was about 10 weeks.

Monitoring: Animals were controlled daily for clinical symptoms and detection of adverse effects. For monitoring throughout the experiment body weight of animals was documented and tumor volume was measured by caliper after staging.

Tumor cell injection: At day of injection Colo205 cells were centrifuged, washed once and resuspended in PBS. After an additional washing with PBS cell concentration and cell size were determined using a cell counter and analyzer system (Vi-CELL, Beckman Coulter). For injection of Colo205 cells, the final titer was adjusted to 5.0×10E7 cells/ml, viability ca. 90%. Subsequently 100 μl of this suspension corresponding to 2.5*106 cells per animal was injected s.c. into the right flank of the mice.

Treatment of animals started at day of randomisation, 16 days after cell transplantation (study Ang2_PZ_Colo205_003) and 14 days after cell transplantation (study Ang2_PZ_Colo205_005) at a mean tumor volume of 100 mm3 or 150 mm3, respectively.

Dose schedule until Day 74 (see FIG. 8A) of Study Ang2_PZ_Colo205_003:

| Group | No of animals | Compound | Dose (mg/kg) | Route/Mode of administration | No of treatments | Cumulative Dose mg/kg |
|---|---|---|---|---|---|---|
| 1 | 10 | Vehicle | | i.p. once weekly | 4 | |

-continued

| Group | No of animals | Compound | Dose (mg/kg) | Route/Mode of administration | No of treatments | Cumulative Dose mg/kg |
|---|---|---|---|---|---|---|
| 2 | 10 | <VEGF> G6-31 | 6 mg/kg | i.p. once weekly | 8 | 48 |
| 3 | 10 | <ANG-2> Mab536 | 6 mg/kg | i.p. once weekly | 8 | 48 |
| 4 | 10 | <VEGF> G6-31 + | 5 mg/kg + 6 mg/kg | i.p. once weekly | 8 | 40 |
|   |   | <ANG-2> Mab536 |   | i.p. once weekly | 8 | 48 |
| 5 | 10 | <VEGF-ANG-2> TvAb6 | 7 mg/kg | i.p. once weekly | 8 | 56 |

In the study Ang2_PZ_Colo205_003<VEGF-ANG-2> TvAb6 was by mistake underdosed with respect to an equimolar ratio. The dose of <VEGF-ANG-2> TvAb6 was adjusted in study Ang2_PZ_Colo205_005 so that the animals received an equimolar ratio of ANG-2 and VEGF binding sites by <VEGF-ANG-2> TvAb6 as well as the combination of <VEGF> G6-31 and <ANG-2> Mab536.

Tumor growth inhibition until Day 74 (see FIG. 8*a*) Ang2_PZ_Colo205_003 study: <VEGF-ANG-2> TvAb6 at a dose of 7 mg/kg exhibited efficacy comparable to that of the combination of <VEGF> G6-31 at 5 mg/kg and <ANG-2> Mab536 at 6 mg/kg and <VEGF> G6-31 as single agent at a dose of 6 mg/kg (FIG. 8A) and was superior to single agent <ANG-2> Mab536 at a dose of 6 mg/kg. As the subcutaneous Colo205 model is very responsive to the <VEGF> G6-31 antibody that blocks human as well as murine VEGF resulting in almost complete tumor growth inhibition <VEGF-ANG-2> TvAb6 could thus not be differentiated from G6-31 as single agent (6 mg/kg) under the chosen experimental conditions, while <VEGF-ANG-2> TvAb6 showed a comparable inhibition like the combination of <ANG-2> Mab536 and <VEGF> G6-31 at a clearly lower cumulative dose (<VEGF-ANG-2> TvAb6=56 mg/kg antibody compared to the combination of <ANG-2> Mab536 and <VEGF> G6-31=40+48=88 mg/kg antibody).

Figure 8B:
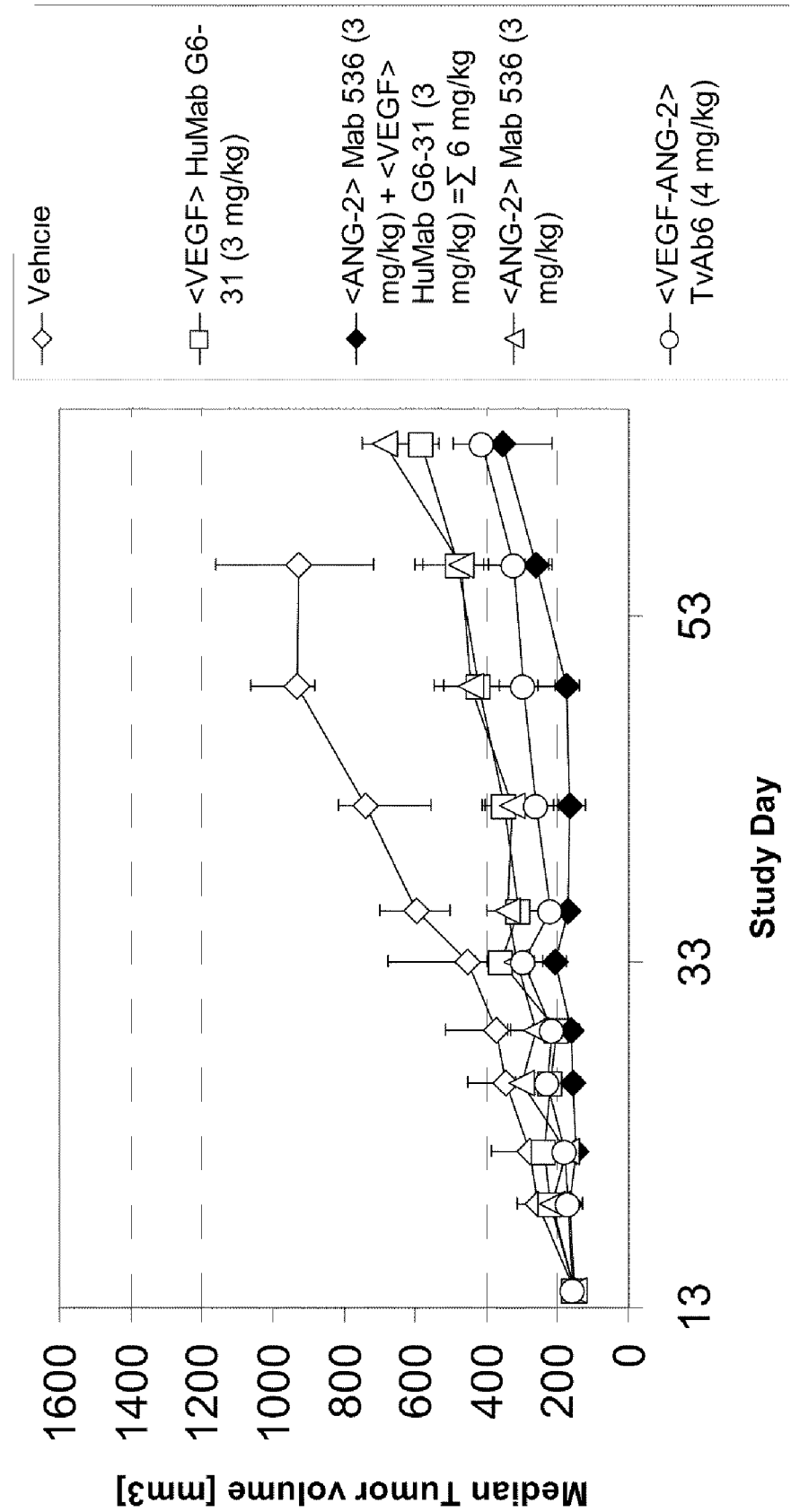
FIG. 8b Efficacy of disulfide-stabilized <VEGF-ANG-2> TvAb6 in comparison to <ANG-2> Mab536, <VEGF> G6-31 and the combination of Mab536 and G6-31 in the staged subcutaneous Colo205 xenograft model in Scid beige mice (study ANG2_Pz_Colo205_005)

Dose schedule of Study until Day 63 Ang2_PZ_Colo205_005:

Tumor growth inhibition until day 63 Ang2_PZ_Colo205_005 study:

<VEGF-ANG-2> TvAb6 at a dose of 4 mg/kg exhibited efficacy comparable to that of the combination of <VEGF> G6-31 and <ANG-2> Mab536 at 3 mg/kg each and was superior to either single agent <VEGF> G6-31 as well as <ANG-2> Mab536 at a dose of 3 mg/kg (FIG. 8B). This is the first example showing that at a lower dose (with respect to the summarized concentration of antibody—the cumulative dose of the combination is 21+21=42 m/kg versus 28 mg/kg of the bispecific antibody TvAb6) a bispecific antibody targeting VEGF and ANG-2 can result in strong anti-tumor efficacy comparable to the combination of the respective single agents blocking VEGF and ANG-2 and superior to either single agent.

Example 4

Blocking of VEGF-Induced Tube Formation

In order to confirm that the anti-VEGF related activities were retained in the bispecific tetravalent <VEGF-ANG-2> TvAb6 is was shown in a VEGF induced tube formation assay AngioKit TCS CellWorks (CellSystems) that <VEGF-ANG-2> TvAb6 mediated dose dependent inhibition of tube formation was comparable to inhibition of tube formulation when the monospecific antibody <VEGF> G6-31 was used. The AngioKit TCS CellWorks assay was performed according to the following procedure: Cells were stimulated each time with 2 ng/ml VEGF before treatment with antibodies on day 1, 4, 7 and 9. Vascular tubes were visualized by staining

Figure 10A:
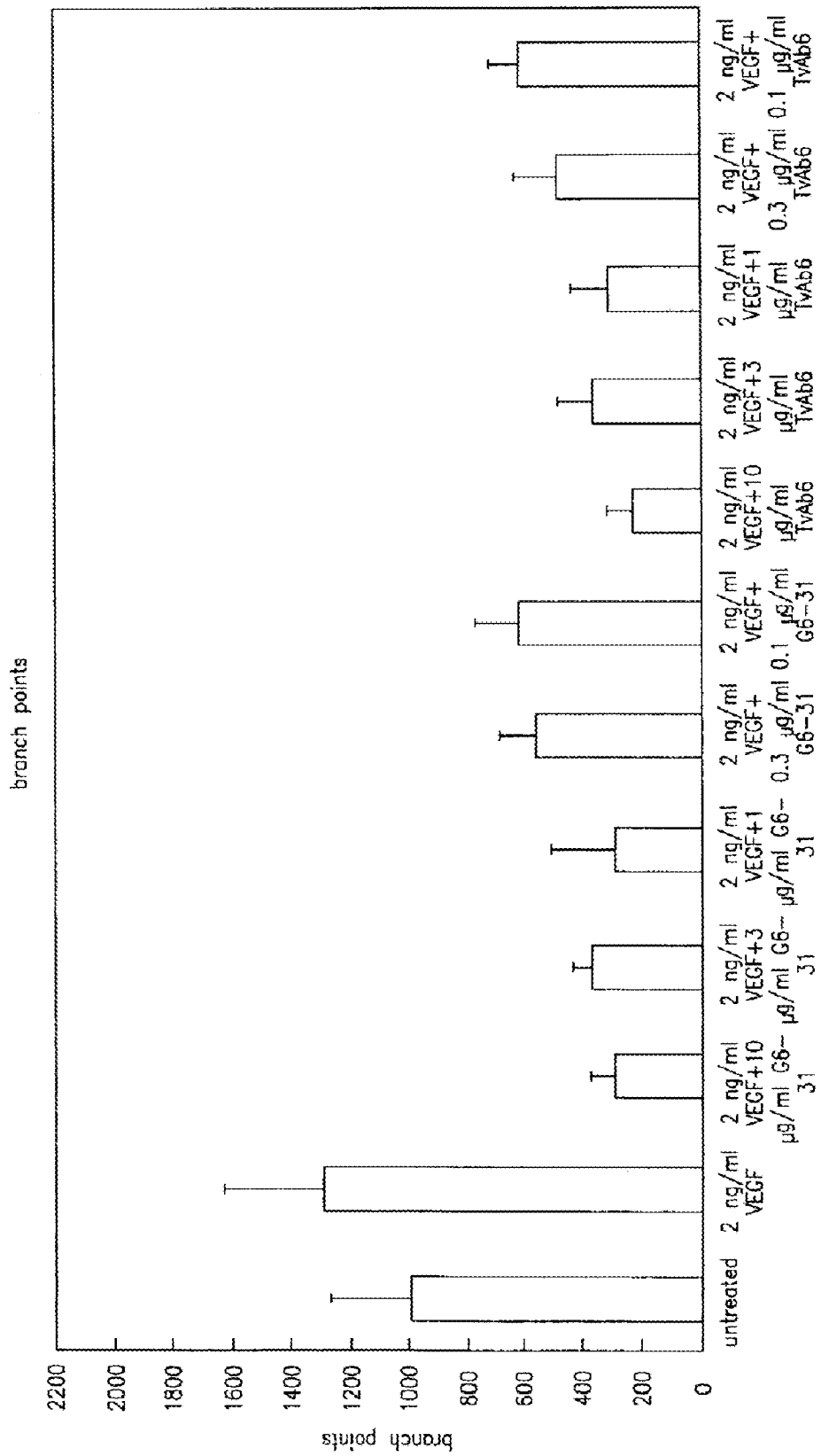
Figure 10B:
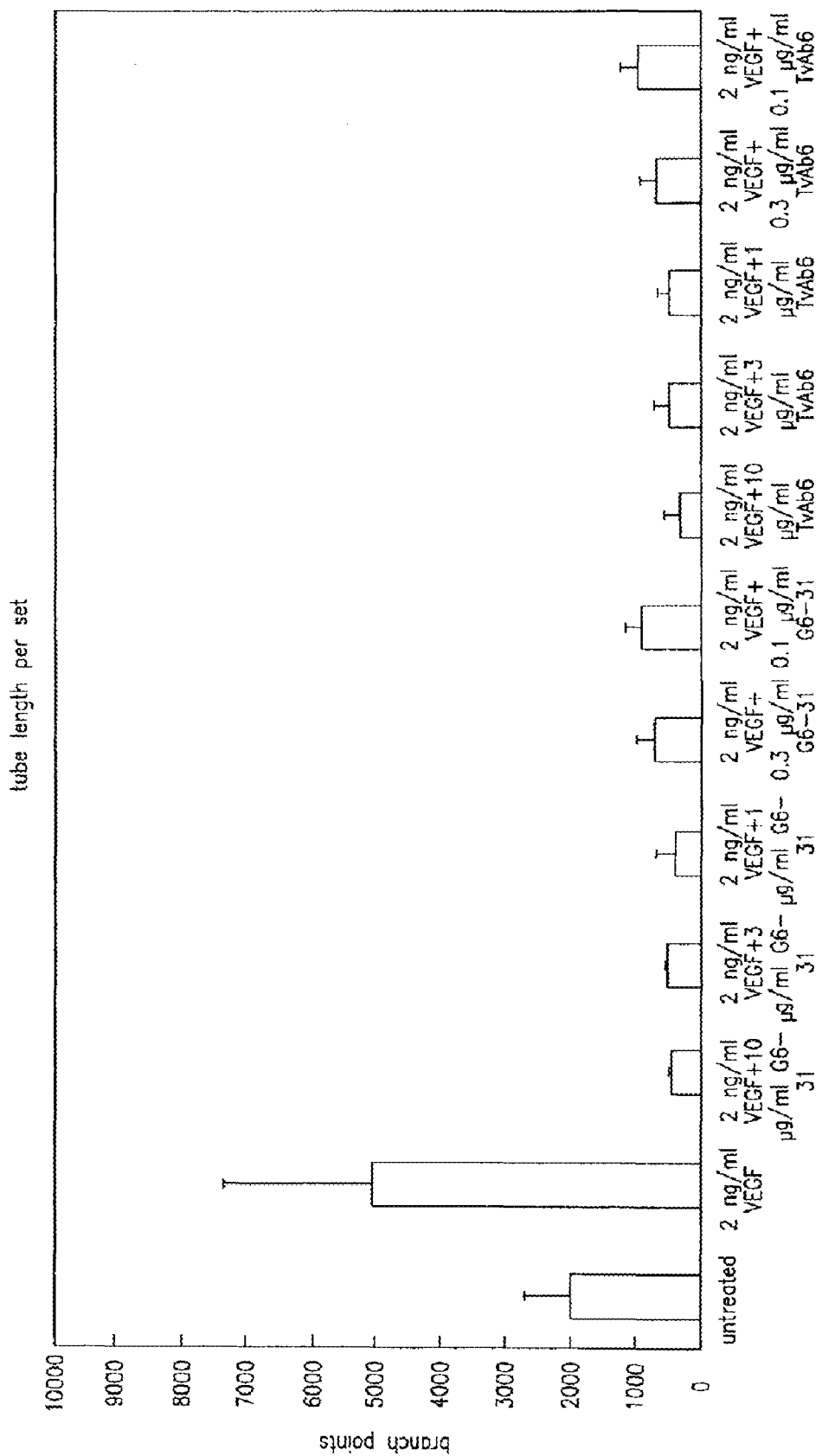

| Group | No of animals | Compound | Dose (mg/kg) | Route/Mode of administration | No of treatment | Cumulative Dose |
|---|---|---|---|---|---|---|
| 6 | 10 | Vehicle |   | i.p. once weekly | 6 |   |
| 7 | 10 | <VEGF> G6-31 | 3 | i.p. once weekly | 7 | 21 mg/kg |
| 8 | 10 | <VEGF> G6-31 + | 3 | i.p. once weekly | 7 | 21 mg/kg |
|   |   | <ANG-2> Mab536 | 3 | i.p. once weeklyI | 7 | 21 mg/kg |
| 9 | 10 | <ANG-2> Mab536 | 3 | i.p. once weekly | 7 | 21 mg/kg |
| 10 | 10 | <VEGF-ANG-2> TvAb6 | 4 | i.p. once weekly | 7 | 28 mg/kg | of endothelial cells using a CD31-PE antibody (BD Pharmingen #555446) on day 11. Pictures were taken at a magnification of 4× and values for tube length and number of branch points were quantitatively analysed using the Angiogenesis Tube Formation Application Module in MetaMorph (Molecular Devices). Values and standard deviation were calculated by duplicates and analysis of 4 pictures per specimen. FIG. 9 shows the respective results and FIGS. 10A and B the quantitative analysis. Angiopietin-2 has no influence on tube formation and thus inhibition of ANG-2 was not studied in this assay. The data show that the bispecific <VEGF-ANG-2> TvAb6 and the monospecific <VEGF> G6-31 antibodies are equally efficacious in inhibiting VEGF stimulated tube formation.

Example 5

Tie2 Phosphorylation

In order to confirm that the anti-ANGPT2 related activities were retained in the bispecific tetravalent <VEGF-ANGPT2> antibodies TvAb-2441-bevacizumab-LC06 and TvAb-2441-bevacizumab-LC08, it was shown that TvAb-2441-bevacizumab-LC06 and TvAb-2441-bevacizumab-LC08 interfere with ANGPT2 stimulated Tie2 phosphorylation in a comparable manner as their mother clones LC06 and LC08 in the ANGPT2 stimulated Tie2 phosphorylation assay as described above.

Figure 16A:
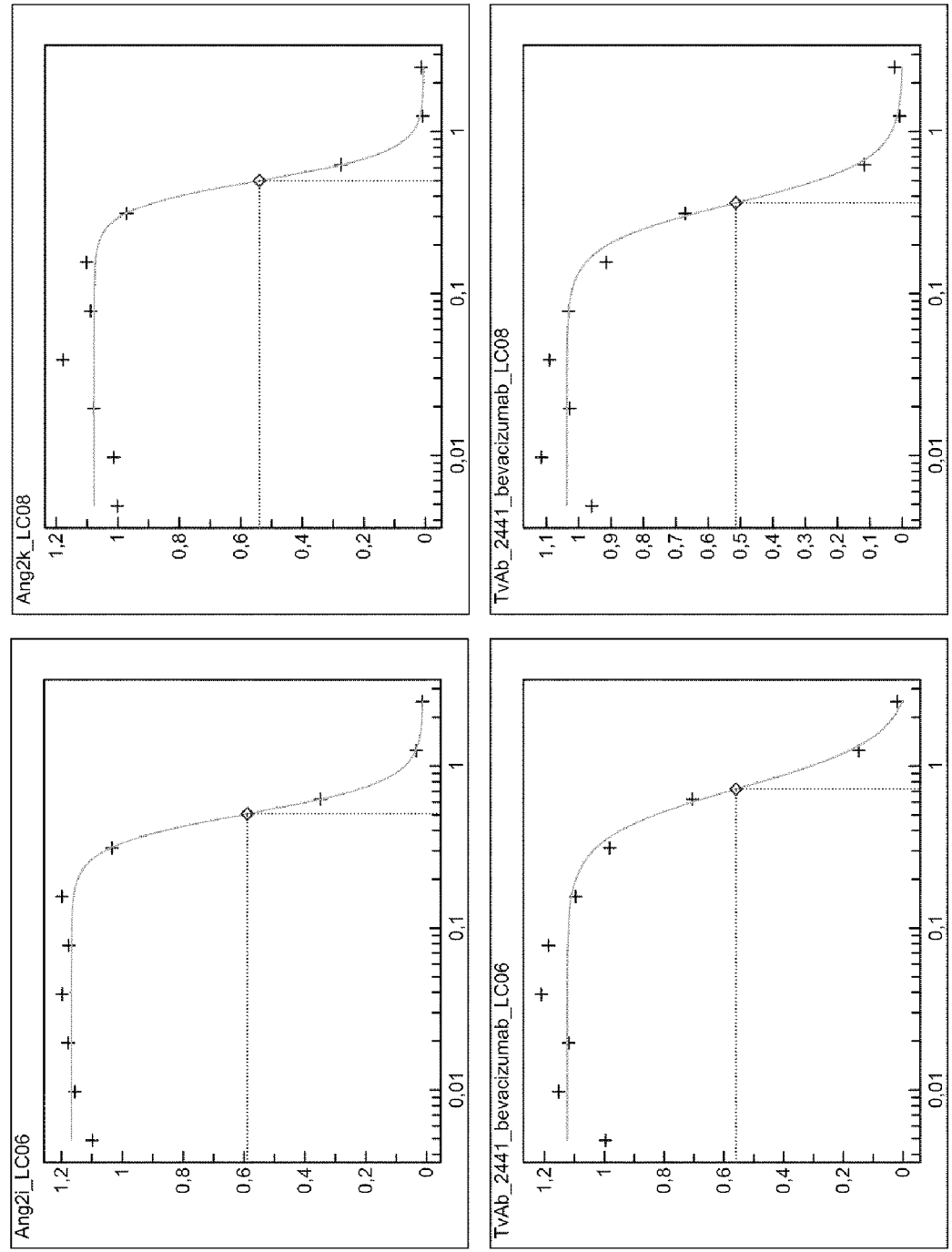
FIG. 16A+B Tie2 phosphorylation of the bispecific antibodies <VEGF-ANG-2>TvAb-2441-bevacizumab-LC06 and <VEGF-ANG-2>TvAb-2441, in comparison with the anti-Ang2 antibodies <ANG-2>Ang2i_LC06 and <ANG-2>Ang2k_LC08

In a first experiment both bispecific antibodies TvAb-2441-bevacizumab-LC06 and TvAb-2441-bevacizumab-LC08 showed a dose-dependent interference with ANGPT2 stimulated Tie2 phosphorylation with IC50 values comparable to those of the mother clones LC06 and LC08 as shown in FIG. 16A. TvAb-2441-bevacizumab-LC06 interfered with ANGPT2 stimulated Tie2 phosphorylation with a IC50 value of approx. 721 ng/ml, whereas LC06 interfered with ANGPT2 stimulated Tie2 phosphorylation with a IC50 value of approx. 508 ng/ml. TvAb-2441-bevacizumab-LC08 interfered with ANGPT2 stimulated Tie2 phosphorylation with a IC50 value of approx. 364 ng/ml, whereas LC08 interfered with ANGPT2 stimulated Tie2 phosphorylation with a IC50 value of approx. 499 ng/ml.

Figure 16B:
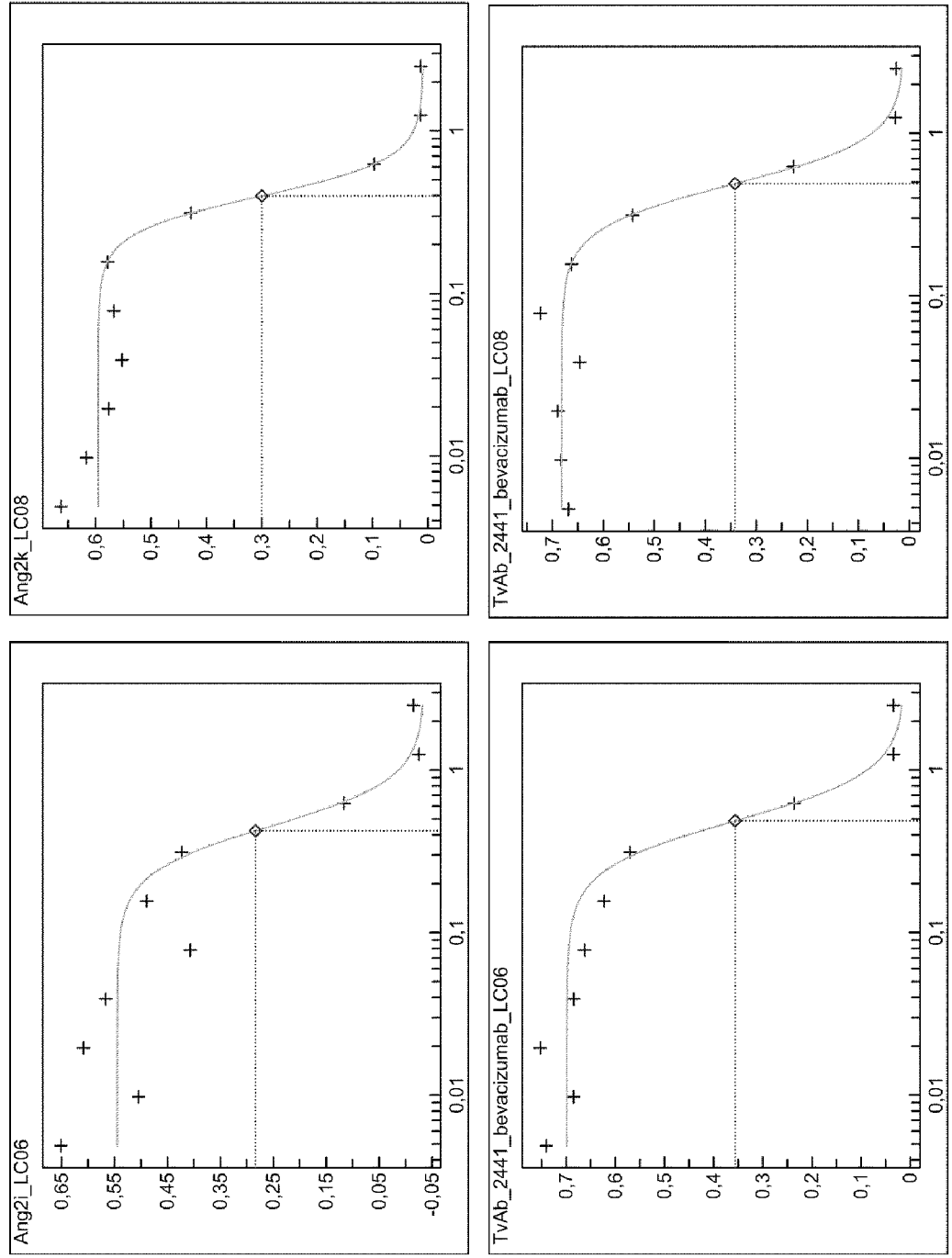
Figure 17:
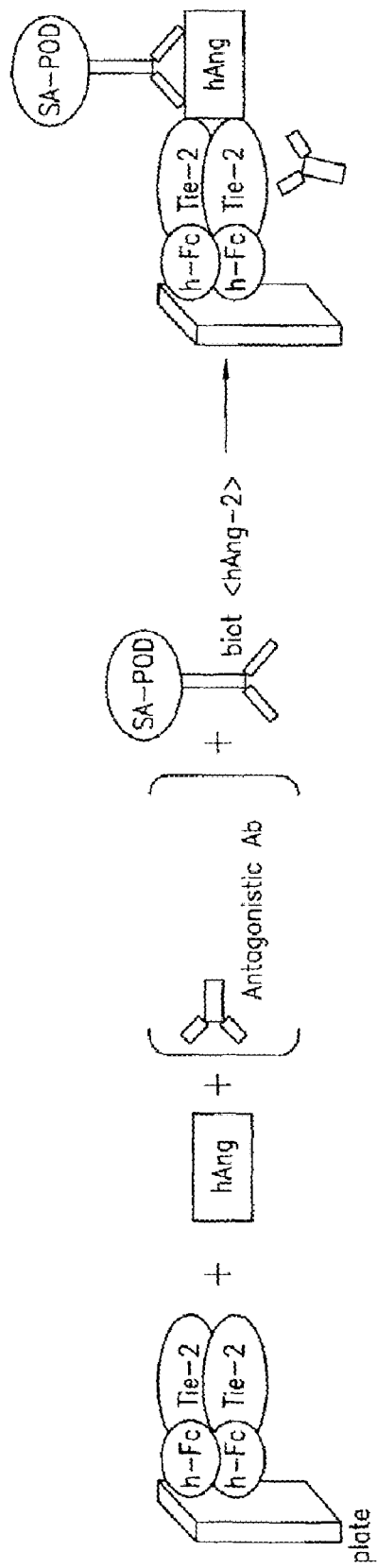
FIG. 17 Schematic representation of human Angiopoietin interaction ELISA

In a second experiment both bispecific antibodies TvAb-2441-bevacizumab-LC06 and TvAb-2441-bevacizumab-LC08 showed a dose-dependent interference with ANGPT2 stimulated Tie2 phosphorylation with IC50 values comparable to those of the mother clones LC06 and LC08 as shown in FIG. 16B. TvAb-2441-bevacizumab-LC06 interfered with ANGPT2 stimulated Tie2 phosphorylation with a IC50 value of approx. 488 ng/ml, whereas LC06 interfered with ANGPT2 stimulated Tie2 phosphorylation with a IC50 value of approx. 424 ng/ml. TvAb-2441-bevacizumab-LC08 interfered with ANGPT2 stimulated Tie2 phosphorylation with a IC50 value of approx. 490 ng/ml, whereas LC08 interfered with ANGPT2 stimulated Tie2 phosphorylation with a IC50 value of approx. 399 ng/ml.

Taken together these data show that the bispecific tetravalent <VEGF-ANGPT2> antibodies TvAb-2441-bevacizumab-LC06 and TvAb-2441-bevacizumab-LC08 interfere with ANGPT2 stimulated Tie2 phosphorylation in a manner comparable to their mother clones LC06 and LC08 within the error of this cellular assay.

Example 6

Inhibition of huANG-2 Binding to Tie-2 (ELISA)

The interaction ELISA was performed on 384 well microtiter plates (MicroCoat, DE, Cat. No. 464718) at RT. After each incubation step plates were washed 3 times with PBST. ELISA plates were coated with 0.5 μg/ml Tie-2 protein (R&D Systems, UK, Cat. No. 313-TI) for at least 2 hours (h). Thereafter the wells were blocked with PBS supplemented with 0.2% Tween-20 and 2% BSA (Roche Diagnostics GmbH, DE) for 1 h. Dilutions of purified antibodies in PBS were incubated together with 0.2 μg/ml huAngiopoietin-2 (R&D Systems, UK, Cat. No. 623-AN) for 1 h at RT. After washing a mixture of 0.5 μg/ml biotinylated anti-Angiopoietin-2 clone BAM0981 (R&D Systems, UK) and 1:3000 diluted streptavidin HRP (Roche Diagnostics GmbH, DE, Cat. No. 11089153001) was added for 1 h. Thereafter the plates were washed 6 times with PBST. Plates were developed with freshly prepared ABTS reagent (Roche Diagnostics GmbH, DE, buffer #204 530 001, tablets #11 112 422 001) for 30 minutes at RT. Absorbance was measured at 405 nm.

Summary Data for Ang2 Interaction ELISA

| <VEGF-ANG-2> bispecific antibody (or monospecific parent antibodies) | AVG IC50 (ng/ml) hANG2 | STDEV |
|---|---|---|
| <VEGF-ANG-2> G6_31 | >20000 | |
| TvAb-2441_G6_31_Ang2i_LC06 | 75 | 39 |
| TvAb-2441_G6_31_Ang2k_LC08 | 66 | 31 |
| TvAb-2441_bevacizumab_LC06 | 44 | 8 |
| TvAb-2441_bevacizumab_LC08 | 42 | 11 |
| <ANG-2>Mab 536 | 15 | 8 |
| <VEGF>Bevacizumab | >20000 | |
| TvAb-3421_bevacizumab_LC06 | 31 | 1 |
| TvAb-4421_bevacizumab_LC06 | 35 | 17 |
| TvAb-4461_bevacizumab_LC06 | 46 | 10 |

Example 7

Inhibition of hVEGF Binding to hVEGF Receptor (ELISA)

The test was performed on 384 well microtiter plates (MicroCoat, DE, Cat. No. 464718) at RT. After each incubation step plates were washed 3 times with PBST. At the beginning, plates were coated with 0.5 μg/ml hVEGF-R protein (R&D Systems, UK, Cat. No. 321-FL) for at least 2 hours (h). Thereafter the wells were blocked with PBS supplemented with 0.2% Tween-20 and 2% BSA (Roche Diagnostics GmbH, DE) for 1 h. Dilutions of purified antibodies in PBS were incubated together with 0.15 μg/ml huVEGF121 (R&D Systems, UK, Cat. No. 298-VS) for 1 h at RT. After washing a mixture of 0.5 μg/ml anti VEGF clone Mab923 (R&D Systems, UK) and 1:2000 horse radish peroxidase (HRP)-conjugated F(ab')2 anti mouse IgG (GE Healthcare, UK, Cat. No. NA9310V) was added for 1 h. Thereafter the plates were washed 6 times with PBST. Plates were developed with freshly prepared ABTS reagent (Roche Diagnostics GmbH, DE, buffer #204 530 001, tablets #11 112 422 001) for 30 minutes at RT. Absorbance was measured at 405 nm.

Summary Data for VEGF Interaction ELISA

| <VEGF-ANG-2> bispecific antibody | AVG IC50 (ng/ml) VEGF | STDEV |
|---|---|---|
| <VEGF-ANG-2> G6_31 | 1431 | 130 |
| TvAb-2441_G6_31_Ang2i_LC06 | 1654 | 213 |
| TvAb-2441_G6_31_Ang2k_LC08 | 1392 | 184 |
| TvAb-2441_bevacizumab_LC06 | 2831 | 503 |
| TvAb-2441_bevacizumab_LC08 | 2305 | 972 |
| TvAb-<ANG-2>Mab 536 | >20000 | |
| TvAb-<VEGF>Bevacizumab | 1584 | 357 |
| TvAb-3421_bevacizumab_LC06 | 2660 | 284 |
| TvAb-4421_bevacizumab_LC06 | 1980 | 1319 |
| TvAb-4461_bevacizumab_LC06 | 1677 | 394 |

Example 8

HUVEC Proliferation

In order to confirm that the anti-VEGF related activities were retained in the bispecific tetravalent <VEGF-ANG2> antibodies TvAb-2441-bevacizumab-LC06 and TvAb-2441-bevacizumab-LC08 it was shown that TvAb-2441-bevacizumab-LC06 and TvAb-2441-bevacizumab-LC08 interfere with VEGF-induced HUVEC proliferation in a comparable manner as their mother clones LC06 and LC08 in the VEGF-induced HUVEC proliferation assay as described above.

Figure 18:
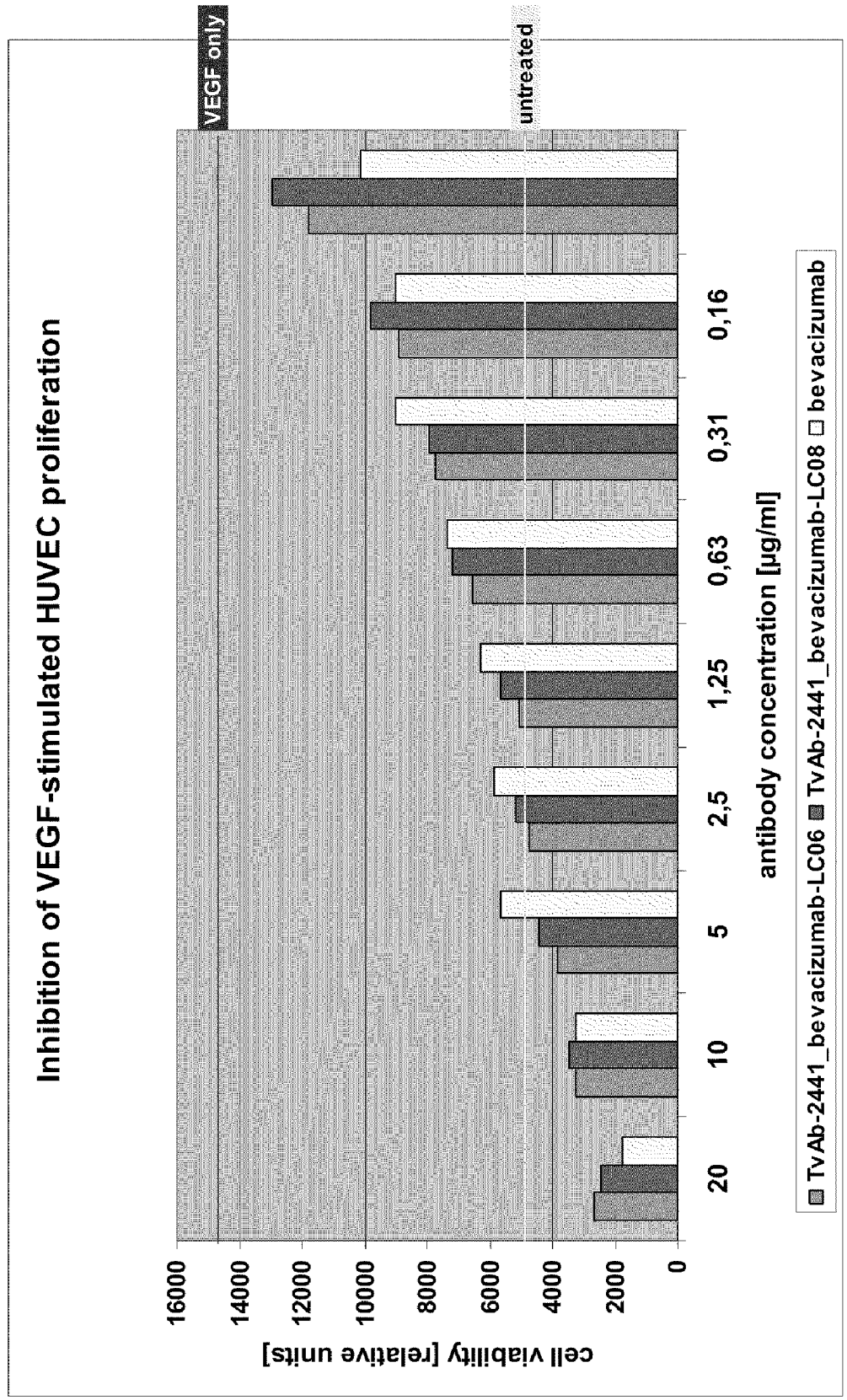
FIG. 18 VEGF-induced HUVEC proliferation of <VEGF-ANG-2>TvAb-2441-bevacizumab-LC06 and <VEGF-ANG-2>TvAb-2441-bevacizumab-LC08 and bevacizumab FIG. 19 In vivo anti-angiogenic efficacy of bispecific antibody <VEGF-ANG-2> bevacizumab-LC06 antibody in comparison to <ANG-2> ANG2i-LC06, and the combination of <ANG-2> ANG2i-LC06 and bevacizumab in Calu3 xenograft model monitored via labeled anti-CD31 antibody and the relative change of CD31 signal during therapy.

FIG. 18 shows that indeed TvAb-2441-bevacizumab-LC06 and TvAb-2441-bevacizumab-LC08 interfere in a concentration dependent manner with VEGF-induced HUVEC proliferation comparable to the parental antibody bevacizumab.

Example 9

ELISA Binding Assay to Human ANG-1 and to Human ANG-2

The binding of parent <ANG-2> antibodies Ang2i-LC06, Ang2i-LC07 and Ang2k-LC08 to human ANG-1 and human ANG-2 was determined in an ANG-1 or ANG-2 binding ELISA as described above (see Comparative binding to ANG-1 and ANG-2 (ANG-1 and ANG-2 binding ELISA)). Briefly, the ELISA-type assay is based on the immobilization of human wild-type Angiopoietin-1 or -2 in a microtiter plate. Binding of an antibody directed against the immobilized ANG-1 or ANG-2 is measured via an <human Fc> (anti-IgG) antibody with a POD conjugate. A dilution series of the <ANG-2>antibody allows to determine an $EC_{50}$ concentration. As a reference the human anti-ANG-2 antibody <ANG-2> antibody Mab536 (Oliner et al., Cancer Cell. 2004 November; 6(5):507-16, US 2006/0122370) was used.

The determined EC50 concentrations are summarized in the table below.

| Antibody | hANG-1 binding EC50 | hANG-2 binding EC50 |
|---|---|---|
| <ANG-2>MAb536 | 2538 ng/mL | 133 ng/mL |
| <ANG-2>Ang2i-LC06 | >8000 ng/mL | 84 ng/mL |
| <ANG-2>Ang2i-LC07 | >8000 ng/mL | 3006 ng/mL |
| <ANG-2>Ang2i-LC08 | 4044 ng/mL | 105 ng/mL |

All antibodies specifically bind to ANG-2. MAb536 and Ang2k-LC08 show also specific binding towards ANG-1, whereas Ang2i-LC06 and Ang2i-LC07 do not specifically bind to ANG-1 as they have an EC50-value of above 8000 ng/ml (detection limit).

Example 10

Expression & Purification of Bispecific, Tetravalent Single Chain Fab <VEGF-ANG-2> Antibody Molecules scFAb-Bevacizumab-LC06-2620, scFab-Bevacizumab-Ang2i-LC06-2640 and scFab-Bevacizumab-Ang2i-LC06-2641

Analogous to the procedures described in Example 1 and in the materials and methods above, the bispecific, tetravalent single chain Fab <VEGF-ANG-2> antibody molecules scFAb-bevacizumab-LC06-2620, scFab-bevacizumab-LC06-2640 and scFab-bevacizumab-LC06-2641, all three based on <VEGF> bevacizumab and <ANG-2> Ang2i-LC06, were expressed and purified. Binding affinities and other properties were determined as described in the the Examples above. The relevant (eventually modified) light and heavy chains amino acid sequences of these bispecific antibodies are given in SEQ ID NO: 109-110 (scFAb-bevacizumab-LC06-2620), in SEQ ID NO: 111-112 (scFAb-bevacizumab-LC06-2640) and in SEQ ID NO: 113-114 (scFAb-bevacizumab-LC06-2641).

|  | scFAb-Bevacizumab-LC06-2620 | scFAb-Bevacizumab-Ang2i-LC06-2640 | scFAb-Bevacizumab-LC06-Ang2i-2641 |
|---|---|---|---|
| Key data | | | |
| Expression (Yield) | 29 µg/mL | 27 µg/mL | 18 µg/mL |
| Purification (Yield, Prot. A. homog.) | 21 mg, 57% | 19 mg, 86% | 12 mg, 90% |
| Homogeneity after preparative SEC | 98% | 98% | 99% |
| Function | | | |
| hANG-2 affinity (Biacore) | 1.9E−9 M | 1.8E−9 M | 1.9E−9 M |
| hVEGF affinity (Biacore) | 1E−10 M | 1E−10 M | 1E−10 M |

Example 11

Expression & Purification of Bispecific, Trivalent Single Chain Fab <VEGF-ANG-2> Antibody Molecule Bevacizumab-LC06-KiH-C-scFab Analogous to the procedures described in Example 1 and in the materials and methods above, the bispecific, trivalent single chain Fab <VEGF-ANG-2> antibody molecule bevacizumab-LC06-KiH-C-scFab based on <VEGF> bevacizumab and <ANG-2> Ang2i-LC06 were expressed and purified. Binding affinities and other properties were determined as described in the the Examples above. The relevant (eventually modified) light and heavy chains amino acid sequences of this bispecific antibody are given in SEQ ID NO: 115-117 (bevacizumab-LC06-KiH-C-scFab).

|  | Bevacizumab-LC06-KiH-C-scFab |
| --- | --- |
| Key data | |
| Expression (Yield) | 15 µg/mL |
| Purification (Yield, Prot. A. homog.) | 4.8 mg, 91% |
| Homogeneity after preparative SEC | 97% |
| Function | |
| hANG-2 affinity (Biacore) | 4.4E−9 M |
| hVEGF affinity (Biacore) | 1E−10 M |

Example 12

Expression & Purification of Bispecific, Trivalent <VEGF-ANG-2> Antibody Molecule Bevacizumab-LC06-C-Fab-6CSS Analogous to the procedures described in Example 1 and in the materials and methods above (see also, the bispecific, trivalent <VEGF-ANG-2> antibody molecule bevacizumab-LC06-C-Fab-6CSS based on <VEGF> bevacizumab and <ANG-2> Ang2i-LC06 were expressed and purified. Binding affinities and other properties were determined as described in the the Examples above. Bispecific, trivalent antibody molecules of this format in general are described in EP Appl. No 09005108.7. The relevant (eventually modified) light and heavy chains amino acid sequences of this bispecific <VEGF-ANG-2> antibody are given in SEQ ID NO: 118-120 (bevacizumab-LC06-C-Fab-6CSS).

|  | scFAb-Bevacizumab-LC06-2620 | scFAb-Bevacizumab-LC06-2640 | scFAb-Bevacizumab-LC06-2641 |
| --- | --- | --- | --- |
| Key data | | | |
| Expression (Yield) | 29 µg/mL | 27 µg/mL | 18 µg/mL |
| Purification (Yield, Prot. A. homog.) | 21 mg, 57% | 19 mg, 86% | 12 mg, 90% |
| Homogeneity after preparative SEC | 98% | 98% | 99% |
| Function | | | |
| hANG-2 affinity (Biacore) | 1.9E−9 M | 1.8E−9 M | 1.9E−9 M |
| hVEGF affinity (Biacore) | 1E−10 M | 1E−10 M | 1E−10 M |

Example 13

Expression & Purification of Bispecific, Bivalent Domain Exchanged <VEGF-ANG-2> Antibody Molecules Bevacizumab-LC06-CH1-CL, Bevacizumab-LC06-VH-VL and Bevacizumab-LC06-VH-VL-SS Analogous to the procedures described in Example 1 and in the materials and methods above, the bispecific, bivalent domain exchanged <VEGF-ANG-2> antibody molecules bevacizumab-LC06-CH1-CL (CH-CL exchange as described in WO 2009/080253), bevacizumab-LC06-VH-VL (VH-VL exchange as described in WO 2009/080252) and bevacizumab-LC06-VH-VL-SS (VH-VL exchange as described in WO 2009/080252 and an additional introduced VH44 VL100 disulfide bridge) based on <VEGF> bevacizumab and <ANG-2> Ang2i-LC06 were expressed and purified. Binding affinities and other properties were determined as described in the the Examples above. The relevant (eventually modified) light and heavy chains amino acid sequences of these bispecific antibodies are given in SEQ ID NO: 121-124 (bevacizumab-LC06-CH1-CL), in SEQ ID NO: 125-128 (Bevacizumab-LC06-VH-VL) and in SEQ ID NO: 129-132 (bevacizumab-LC06-VH-VL-SS).

|  | Bevacizumab-LC06-CM-CH1-CL | Bevacizumab-LC06-CM-VH-VL | Bevacizumab-LC06-VH-VL-SS |
| --- | --- | --- | --- |
| Key data | | | |
| Expression (Yield) | 87 µg/mL | 44 µg/mL | 65 µg/mL |
| Purification (Yield, Prot. A. homog.) | 50 mg, 62% | 22 mg, 95% | 91 mg, 74% |
| Homogeneity after preparative SEC | 84% | >99% | 95% |
| Function | | | |
| hANG-2 affinity (Biacore) | 1.3E−9 M | 2.1E−9 M | 1.46E−9 M |
| hVEGF affinity (Biacore) | 1E−10 M | 1E−10 M | 1E−10 M |

Example 14

Expression & Purification of Bispecific, Bivalent ScFab-Fc Fusion <VEGF-ANG-2> Antibody Molecules Bevacizumab-LC06-N-scFab and Bevacizumab-LC06-N-scFabSS Analogous to the procedures described in Example 1 and in the materials and methods above, the bispecific, bivalent ScFab-Fc fusion <VEGF-ANG-2> antibody molecules bevacizumab-LC06-N-scFab and bevacizumab-LC06-N-scFabSS based on <VEGF> bevacizumab and <ANG-2> Ang2i-LC06 were expressed and purified. Binding affinities and other properties were determined as described in the the Examples above. The relevant modified heavy chains amino acid sequences of these bispecific antibodies are given in SEQ ID NO: 133-134 (bevacizumab-LC06-N-scFab), and in SEQ ID NO: 135-136 (bevacizumab-LC06-N-scFabSS).

|  | Bevacizumab-LC06-N-scFab | Bevacizumab-LC06-N-scFabSS |
| --- | --- | --- |
| Key data | | |
| Expression (Yield) | | 62 µg/mL |
| Purification (Yield, Prot. A. homog.) | | 43% |
| Function | | |
| hANG-2 affinity (Biacore) | | 1 nM |
| hVEGF affinity (Biacore) | | 1 nM |

Example 15

Inhibition of hVEGF Binding to hVEGF Receptor (ELISA), Blocking of VEGF-Induced Tube Formation, Inhibition of huANG-2 Binding to Tie-2 (ELISA), Tie2 Phosphorylation, and HUVEC Proliferation of the Bispecific, <VEGF-ANG-2> Antibody Molecules of Examples 10 to 14

Inhibition of hVEGF binding to hVEGF Receptor (ELISA), blocking of VEGF-induced tube formation, Inhibition of huANG-2 binding to Tie-2 (ELISA), Tie2 phosphorylation, and HUVEC proliferation of the bispecific, <VEGF-ANG-2> antibody molecules of Examples 10 to 14 can be determined analogously to the procedures described in Materials and Methods and Examples 4 to 9 above.

Example 16

In Vivo Efficacy of Bispecific Antibody <VEGF-ANG-2> Antibody in Comparison to <ANG-2> ANG2i-LC06, and the Combination of <ANG-2> ANG2i-LC06 and Bevacizumab in the Refractory Colo205 Xenograft Model in Scid Beige Mice (After Resistance to Bevacizumab Treatment)

Cell Lines and Culture Conditions:

Colo205 human colorectal cancer cells were originally obtained from ATCC and after expansion deposited in the Roche Penzberg internal cell bank. Tumor cell line was routinely cultured in RPMI 1640 medium (PAA, Laboratories, Austria) supplemented with 10% fetal bovine serum (PAA Laboratories, Austria) and 2 mM L-glutamine, at 37° C. in a water-saturated atmosphere at 5% $CO_2$. Passage 2-5 was used for transplantation.

Animals:

Female SCID beige mice; age 4-5 weeks at arrival (purchased from Charles River Germanyd), were maintained under specific-pathogen-free condition with daily cycles of 12 h light/12 h darkness according to committed guidelines (GV-Solas; Felasa; TierschG). Experimental study protocol was reviewed and approved by local government. After arrival animals were maintained in the quarantine part of the animal facility for one week to get accustomed to new environment and for observation. Continuous health monitoring was carried out on regular basis. Diet food (Provimi Kliba 3337) and water (acidified pH 2.5-3) were provided ad libitum. Age of mice at start of the study was about 10 weeks.

Tumor Cell Injection:

At the day of injection, tumor cells were harvested (trypsin-EDTA) from culture flasks (Greiner) and transferred into 50 ml culture medium, washed once and resuspended in PBS. After an additional washing step with PBS and filtration (cell strainer; Falcon ø 100 µm) the final cell titer was adjusted to $2.5 \times 10^7$/ml. Tumor cell suspension was carefully mixed with transfer pipette to avoid cell aggregation. After this, cell suspension was filled into a 1.0 ml tuberculin syringe (Braun Melsungen) using a wide needle (1.10×40 mm); for injection needle size was changed (0.45×25 mm) and for every injection a new needle was used. Anesthesia was performed using a Stephens inhalation unit for small animals with preincubation chamber (plexiglas), individual mouse nose-mask (silicon) and not flammable or explosive anesthesia compound Isoflurane (cp-pharma) in a closed circulation system. Two days before injection coat of the animals were shaved and for cell injection skin of anaesthetized animals was carefully lifted up with an anatomic forceps and 100 µl cell suspension (=$2.5 \times 10^6$ cells) was injected subcutaneously in the right flank of the animals.

Treatment of Animals

Pretreatment:

Animal treatment started 14 days after cell transplantation (study Ang2_PZ_Colo205_008) at a mean tumor volume of 100 $mm^3$ to 150 $mm^3$, respectively. Mice were treated once weekly with bevacizumab (10 mg/kg) for a time period of 5 weeks.

Secondary Treatment:

Thereafter mice were randomized for $2^{nd}$ treatment and divided to four groups with 10 mice in each group. Tumor volume at start of secondary treatment at day 51 was in the range from 336 to 341 $mm^3$. Mice were treated once weekly i.p. with the different compounds as indicated in following table.

| Group | No of animals | Compound | Dose (mg/kg) (nMol/kg) | Route/Mode of administration | No of treatments | Cumulative dose (mg/kg) |
|---|---|---|---|---|---|---|
| 11 | 10 | Bevacizumab | 10 mg/kg (68 nMol/kg) | i.p. once weekly | 11 | 110 |
| 12 | 10 | ANG2i-LC06 | 10 mg/kg (68 nMol/kg) | i.p. once weekly | 6 | 60 |
| 13 | 10 | ANG2i-LC06 + Bevacizumab | 10 mg/kg (68 nMol/kg) + 10 mg/kg (68 nMol/kg) | i.p. once weekly i.p. once weekly | 6 11 | 60 110 |
| 14 | 10 | TvAb-2441-bevacizumab-LC06 | 13 mg/kg (64 nMol/kg) | i.p. once weekly | 6 | 78 |

Monitoring:

Animals were controlled 2× per week for their health status. Body weights were documented 2× per week after cell injection. The tumor dimensions were measured by caliper beginning on the staging day and subsequently 2 times per week during the whole treatment period. Tumor volume was calculated according to NCI protocol (Tumor weight=½ab², where "a" and "b" are the long and the short diameters of the tumor, respectively). Termination criteria were the critical tumor mass (up to 1.7 g or Ø>1.5 cm), body weight loss more than 20% from baseline, tumor ulceration or poor general condition of the animals.

Results: Tumor Growth Inhibition Based on Medians (in Percent) at Day 91

|  | TGI |
| --- | --- |
| ANG2i-LC06 10 mg/kg (68 nMol/kg) i.p.; Bevacizumab 10 mg/kg (68 nMol/kg) i.p. | 45.3 |
| ANG2i-LC06 10 mg/kg i.p. (68 nMol/kg) | 44.4 |
| TvAb-2441-bevacizumab-LC06_13 mg/kg i.p. (64 nMol/kg) | 60.4 |

The results show that the bispecific <VEGF-ANG-2> antibody TvAb-2441-bevacizumab-LC06 showed a higher tumor growth inhibition (at lower doses) in the bevacizumab-resistant xenograft tumor model Colo205 in Scid beige mice compared to the treatment with monospecific antibody ANG2i-LC06 alone or the combination of ANG2i-LC06 and bevacizumab.

Example 17

In Vivo Inhibition of Tumor Angiogenesis in s.c Calu-3 NSCLC Xenograft

Detection Via Non-Invasive in Vivo Imaging of Angiogenesis Using Anti-CD31 Labeled with Cell Lines and Culture Conditions:

This human lung adenocarcinoma cancer cell line has been established from a human caucasian male with lung cancer. Cells were obtained from Roche, Kamakura and passaged in house for working cell bank. Tumor cells are routinely cultured in RPMI1640 medium (PAN Biotech, Germany) supplemented with 10% fetal bovine serum (PAN Biotech, Germany) and 2 mM L-glutamine (PAN Biotech, Germany) at 37° C. in a water-saturated atmosphere at 5% $CO_2$. Culture passage is performed with trypsin/EDTA 1× (PAN) splitting one time/week.

Animals:

Female BALB/c nude mice; age 4-5 weeks at arrival (purchased from Charles River Germany) were maintained under specific-pathogen-free condition with daily cycles of 12 h light/12 h darkness according to committed guidelines (GV-Solas; Felasa; TierschG). Experimental study protocol was reviewed and approved by local government. After arrival animals were maintained in the quarantine part of the animal facility for one week to get accustomed to the new environment and for observation. Continuous health monitoring was carried out on regular basis. Diet food (Provimi Kliba 3337) and water (acidified pH 2.5-3) were provided ad libitum. Age of mice at start of the study was about 10 weeks.

Tumor Cell Injection:

At the day of injection, tumor cells were harvested (trypsin-EDTA) from culture flasks (Greiner) and transferred into 50 ml culture medium, washed once and resuspended in PBS. After an additional washing step with PBS and filtration (cell strainer; Falcon ø 100 μm) the final cell titer was adjusted to $5.0 \times 10^7$/ml. Tumor cell suspension was carefully mixed with transfer pipette to avoid cell aggregation. After this, cell suspension was filled into a 1.0 ml tuberculin syringe (Braun Melsungen) using a wide needle (1.10×40 mm); for injection needle size was changed (0.45×25 mm) and for every injection a new needle was used. Anesthesia was performed using a Stephens inhalation unit for small animals with preincubation chamber (plexiglas), individual mouse nose-mask (silicon) and not flammable or explosive anesthesia compound Isoflurane (cp-pharma) in a closed circulation system. Two days before injection coat of the animals were shaved and for cell injection skin of anaesthetized animals was carefully lifted up with an anatomic forceps and 100 μl cell suspension (=$5.0 \times 10^6$ cells) was injected subcutaneously in the right flank of the animals.

Treatment of Animals

At study day 35, mice were randomized to statistically well distributed groups, depending on their body weight and tumor size. For the treatment with therapeutic antibodies, each group consisted of 10 mice and treatment with therapeutic antibodies was applied once weekly i.p. for a 6 week time period. (see FIG. 19)

Group 1: vehicle (Xolair) 10 mg/kg

Group 2: Bevacizumab 10 mg/kg

Group 3: Combination of monospecific <VEGF> bevacizumab 10 mg/kg plus monospecific <ANG-2> Ang2i-LC06 10 mg/kg (=bevacizumab/Ang2i-LC06)

Group 4: Bispecific <VEGF-ANG-2> antibody 2441-bevacizumab-scFv-LC06 13.3 mg/kg

Monitoring:

Animals were controlled 2× per week for their health status. Body weights were documented 2× per week after cell injection. The tumor dimensions were measured by caliper beginning on the staging day and subsequently 2 times per week during the whole treatment period. Tumor volume was calculated according to NCI protocol (Tumor weight=½ab², where "a" and "b" are the long and the short diameters of the tumor, respectively). Termination criteria were the critical tumor mass (up to 1.7 g or Ø>1.5 cm), body weight loss more than 20% from baseline, tumor ulceration or poor general condition of the animals.

Blood Vessel and Angiogenesis Monitoring with Labeled Anti-CD 31 Antibody

Figure 19:
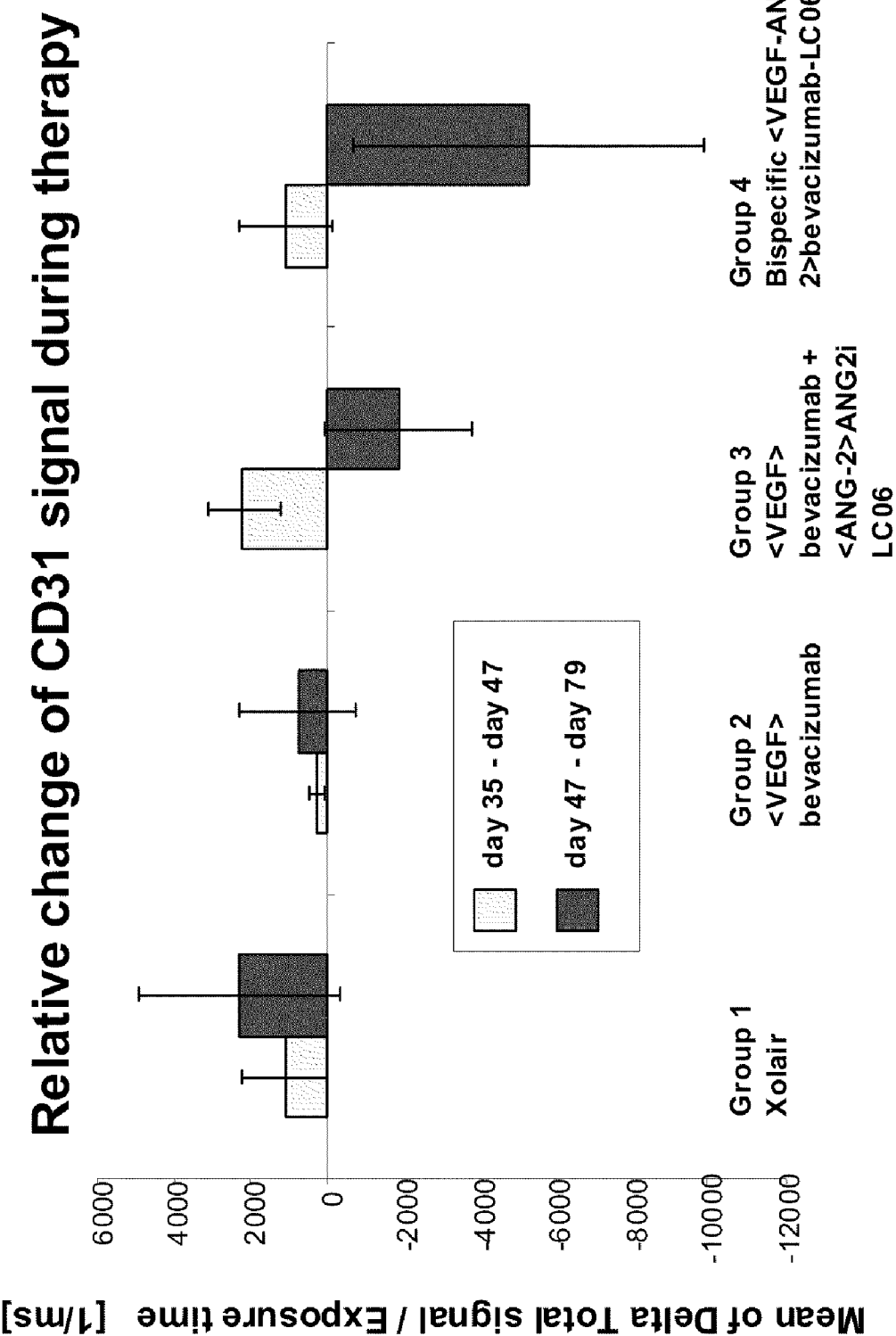

Preliminary studies revealed that anti-CD31 antibody as best agent for imaging tumor vasculature. This agent targets mouse endothelial CD31 receptors and visualizes single blood vessels with a low signal-to-background ratio. Therefore, imaging for anti-CD31 antibody represents a feasible way to image tumor vasculature. Three mice of each therapy group have been chosen and injected i.v. with 50 μg/mouse anti-CD3 antibody labeled covalently with the organic fluorophore Alexa610 at day 35, 49 and 79. Near-infrared imaging was carried out 24 hrs after each application of the labeled antibody under inhalation anesthesia. An increase or decrease of tumor vasculature was visualized by using the compare image tool of the MAESTRO system. Under treatment with the control mab Xolair and the therapeutic antibody bevacizumab, an increase of tumor blood vessels from day 35 to day 79 was observed. In contrast, the combined treatment with bevacizumab plus Ang2i-LC06 and 2441-bevacizumab-scFv-LC06 exhibited a decrease of tumor vasculature (FIG. 19).

Tumor regions were quantified by manually drawing measurement areas and signal intensities were evaluated in intensity values (total signal/exposure time). The average changes of CD31 signals from day 35 to 49 and from day 49 to 79 were plotted in FIG. 19. All treatment groups revealed an increase in tumor vasculature from day 35 to 49. While CD31 tumor signals steadily accelerated in group 1 (Xolair) and group 2 (bevacizumab), tumor vasculature significantly decreased in group 3 (Combination of bevacizumab plus <ANG-2> Ang2i-LC06) and group 4 (Bispecific <VEGF-ANG-2> antibody 2441-bevacizumab-scFv-LC06), with group 4 showing clearly the most pronounced antiangiogenic effect (FIG. 19).

Immediately after the last in vivo imaging studies, tumors were explantated (day 79), fixed in formalin and embedded in paraffin for ex vivo studies. Fluorescence microscopy showed numerous well defined capillaries in tumors treated with control mab Xolair. Several tumor blood vessels were observed in mice treated with bevacizumab. In contrast, treatment groups 3 and 4 had significantly fewer and less defined blood vessels in the tumors compared to treatment groups 1 and 2 whereas group 4 showed the most pronounced effect. Group 4 revealed lower microvessel density, capillaries were generally smaller and unstructured and they exhibited weaker anti-CD31 fluorescence signals as Group 1, 2 and 3. Histochemical HE-staining showed intratumoral necrotic regions for up to 90% of all regions in the treatment group with the bispecific antibody of group 4 which is clearly higher than for the other treatment groups (data not shown).

Example 18

In Vivo Efficacy of Bispecific Antibodies <VEGF-ANG-2> and Compared to the Parent Monospecific Antibodies (Alone or in Combination) in the Staged Subcutaneous Colo205 Xenograft Model in Scid Beige Mice Cell Lines and Culture Conditions:

Colo205 human colorectal cancer cells were originally obtained from ATCC and after expansion deposited in the Roche Penzberg internal cell bank. Tumor cell line was routinely cultured in RPMI 1640 medium (PAA, Laboratories, Austria) supplemented with 10% fetal bovine serum (PAA Laboratories, Austria) and 2 mM L-glutamine, at 37° C. in a water-saturated atmosphere at 5% $CO_2$. Passage 2-5 was used for transplantation.

Animals:

Female SCID beige mice; age 4-5 weeks at arrival (purchased from Charles River Germany) were maintained under specific-pathogen-free condition with daily cycles of 12 h light/12 h darkness according to committed guidelines (GV-Solas; Felasa; TierschG). Experimental study protocol was reviewed and approved by local government. After arrival, animals were maintained in the quarantine part of the animal facility for one week to get accustomed to the new environment and for observation. Continuous health monitoring was carried out on regular basis. Diet food (Provimi Kliba 3337) and water (acidified pH 2.5-3) were provided ad libitum. Age of mice at start of the study was about 10 weeks.

Tumor Cell Injection:

At day of injection Colo205 cells were centrifuged, washed once and resuspended in PBS. After an additional washing with PBS cell concentration and cell size were determined using a cell counter and analyzer system (Vi-CELL, Beckman Coulter). For injection of Colo205 cells, the final titer was adjusted to $5.0 \times 10E7$ cells/ml, viability ca. 90%. Subsequently 100 μl of this suspension corresponding to $2.5*10^6$ cells per animal was injected s.c. into the right flank of the mice.

Treatment of animals started at day of randomisation, 16 days after cell transplantation (study Ang2_PZ_Colo205_009)) at a mean tumor volume of 100 mm3, respectively.

Dose schedule of Study Ang2_PZ_Colo205_009:

| No of animals | Compound | Dose (mg/kg) | Route/Mode of administration |
|---|---|---|---|
| 10 | Xolair | 10 | i.p. once weekly |
| 10 | <VEGF> Bevacizumab | 10 | i.p. once weekly |
| 10 | <ANG-2> Ang2i-LC06 | 10 | i.p. once weekly |
| 10 | Ang2i-LC06 + Bevacizumab | 10 10 | i.p. once weekly i.p. once weekly |
| 10 | <VEGF-ANG-2> TvAb-2441-bevacizumab-LC06 | 13.3 | i.p. once weekly |
| 10 | <VEGF-ANG-2> Bevacizumab-LC06-CH1-CL | 20 | i.p. once weekly |
| 10 | <VEGF-ANG-2> scFAb-Bevacizumab-LC06-2620 | 16.6 | i.p. once weekly |

Monitoring:

Animals were controlled 2× per week for their health status. Body weights were documented 2× per week after cell injection. The tumor dimensions were measured by caliper beginning on the staging day and subsequently 2 times per week during the whole treatment period. Tumor volume was calculated according to NCI protocol (Tumor weight=½ab², where "a" and "b" are the long and the short diameters of the tumor, respectively).Termination criteria were the critical tumor mass (up to 1.7 g or Ø>1.5 cm), body weight loss more than 20% from baseline, tumor ulceration or poor general condition of the animals.

Results:

Tumor Growth Inhibition (TGI) Based on Medians (in Percent) at Day 61

| | TGI |
|---|---|
| <VEGF> Bevacizumab | 66 |
| <ANG-2> Ang2i-LC06 | 47 |
| Ang2i-LC06 + Bevacizumab | 78 |
| <VEGF-ANG-2> TvAb-2441-bevacizumab-LC06 | 87 |
| <VEGF-ANG-2> Bevacizumab-LC06-CH1-CL | 92 |
| <VEGF-ANG-2> scFAb-Bevacizumab-LC06-2620 | 86 |

The results show that all three bispecific <VEGF-ANG-2> bevacizumab-ANG2i-LC06 antibodies (all based on the bevacizumab sequences SEQ ID No: 7 and 8 and on ANG2i-LC06 sequences SEQ ID No: 52 and 53) showed a higher tumor growth inhibition in xenograft tumor model Colo205 in Scid beige mice compared to the treatment with monospecific antibodies ANG2i-LC06 and bevacizumab alone or the combination of ANG2i-LC06 and bevacizumab.

Example 19

Expression & Purification and Properties of Bispecific <VEGF-ANG-2> Antibody Molecules scFAb-Bevacizumab-LC10-2620, scFab-Bevacizumab-LC10-2640 and scFab-Bevacizumab-LC10-2641, Bevacizumab-LC10-KiH-C-scFab, Bevacizumab-LC10-C-Fab-6CSS, Bevacizumab-LC10-CH1-CL, Bevacizumab-LC10-VH-VL and Bevacizumab-LC10-VH-VL-SS, Bevacizumab-LC10-N-scFab and Bevacizumab-LC10-N-scFabSS By replacing the VH and VL domains of Ang2i-LC06 (SEQ ID No: 52 and 53) with the corresponding VH and VL domains of Ang2i-LC10 (SEQ ID No: 84 and 85) and using the (apart from such replacement) analogous procedures and sequences described in Example 10 to 14, the bispecific, <VEGF-ANG-2> antibody molecules scFab-bevacizumab-LC10-2620, scFab-bevacizumab-LC10-2640 and scFab-bevacizumab-LC10-2641, bevacizumab-LC10-KiH-C-scFab, bevacizumab-LC10-C-Fab-6CSS, bevacizumab-LC10-CH1-CL, bevacizumab-LC10-VH-VL and bevacizumab-LC10-VH-VL-SS, bevacizumab-LC10-N-scFab and bevacizumab-LC10-N-scFabSS, all based on <VEGF>bevacizumab and <ANG-2> Ang2i-LC10 are expressed and purified. Binding affinities and other in vitro properties are determined as described in the the Examples above.

Example 20

In Vivo Efficacy of Bispecific Antibody <VEGF-ANG-2> Molecules scFAb-Bevacizumab-LC10-2620, scFab-Bevacizumab-LC10-2640 and scFab-Bevacizumab-LC10-2641, Bevacizumab-LC10-KiH-C-scFab, Bevacizumab-LC10-C-Fab-6C SS, Bevacizumab-LC10-CH1-CL, Bevacizumab-LC10-VH-VL and Bevacizumab-LC10-VH-VL-SS, Bevacizumab-LC10-N-scFab and Bevacizumab-LC10-N-scFabSS In vivo efficacy of bispecific antibody <VEGF-ANG-2> molecules scFAb-bevacizumab-LC10-2620, scFab-bevacizumab-LC10-2640 and scFab-bevacizumab-LC10-2641, bevacizumab-LC10-KiH-C-scFab, bevacizumab-LC10-C-Fab-6CSS, bevacizumab-LC10-CH1-CL, bevacizumab-LC10-VH-VL and bevacizumab-LC10-VH-VL-SS, bevacizumab-LC10-N-scFab and bevacizumab-LC10-N-scFabSS is determined analogously to the corresponding Examples above.

The invention claimed is:

1. A bispecific antibody that binds specifically to human vascular endothelial growth factor (VEGF) and human angiopoietin-2 (ANG-2), said antibody comprising a first antigen-binding site that specifically binds to human VEGF and a second antigen-binding site that specifically binds to human ANG-2, wherein:
  i) said antigen-binding sites each comprise an antibody heavy chain variable domain and an antibody light chain variable domain;
  ii) said first antigen-binding site comprises in the heavy chain variable domain:
    a CDR3 region having an amino acid sequence selected from the group consisting of: SEQ ID NO: 1, SEQ ID NO: 9, SEQ ID NO: 17, and SEQ ID NO: 94;
    a CDR2 region having an amino acid sequence selected from the group consisting of: SEQ ID NO: 2, SEQ ID NO: 10, SEQ ID NO: 18, and SEQ ID NO: 95;
    and a CDR1 region having an amino acid sequence selected from the group consisting of: SEQ ID NO:3, SEQ ID NO: 11, SEQ ID NO: 19, and SEQ ID NO: 96, and
    in the light chain variable domain:
    a CDR3 region having an amino acid sequence selected from the group consisting of: SEQ ID NO: 4, SEQ ID NO: 12, SEQ ID NO: 20, and SEQ ID NO: 97,
    a CDR2 region having an amino acid sequence selected from the group consisting of: SEQ ID NO: 5, SEQ ID NO: 13, SEQ ID NO: 21, and SEQ ID NO: 98; and
    a CDR1 region having an amino acid sequence selected from the group consisting of: SEQ ID NO:6, SEQ ID NO: 14, SEQ ID NO: 22, and SEQ ID NO: 99; and
  iii) said second antigen-binding site comprises in the heavy chain variable domain:
    a CDR3 region having an amino acid sequence selected from the group consisting of: SEQ ID NO: 25, SEQ ID NO: 38, SEQ ID NO: 46, SEQ ID NO: 54, SEQ ID NO: 62, SEQ ID NO: 70, SEQ ID NO: 78, and SEQ ID NO: 86;
    a CDR2 region having an amino acid sequence selected from the group consisting of: SEQ ID NO: 26, SEQ ID NO: 39, SEQ ID NO: 47, SEQ ID NO: 55, SEQ ID NO: 63, SEQ ID NO: 71, SEQ ID NO: 79, and SEQ ID NO: 87; and
    a CDR1 region having an amino acid sequence selected from the group consisting of: SEQ ID NO:27, SEQ ID NO: 40, SEQ ID NO: 48, SEQ ID NO: 56, SEQ ID NO: 64, SEQ ID NO: 72, SEQ ID NO: 80, and SEQ ID NO: 88; and
    in the light chain variable domain:
    a CDR3 region having an amino acid sequence selected from the group consisting of: SEQ ID NO: 28, SEQ ID NO: 28 with the mutations T92L, H93Q and W94T, SEQ ID NO: 41, SEQ ID NO: 49, SEQ ID NO: 57, SEQ ID NO: 65, SEQ ID NO: 73, SEQ ID NO: 81, and SEQ ID NO: 89;
    a CDR2 region having an amino acid sequence selected from the group consisting of: SEQ ID NO:29, SEQ ID NO: 42, SEQ ID NO: 50, SEQ ID NO: 58, SEQ ID NO: 66, SEQ ID NO: 74, SEQ ID NO: 82 and SEQ ID NO: 90; and
    a CDR1 region having an amino acid sequence selected from the group consisting of: SEQ ID NO: 30, SEQ ID NO: 43, SEQ ID NO: 51, SEQ ID NO: 59, SEQ ID NO: 67, SEQ ID NO: 75, SEQ ID NO: 83, and SEQ ID NO: 91.

2. A bispecific antibody according to claim 1, characterized in that
  said first antigen-binding site comprises, in the heavy chain variable domain, a CDR3 region of SEQ ID NO: 1, a CDR2 region of SEQ ID NO: 2, and a CDR1 region of SEQ ID NO:3, and, in the light chain variable domain, a CDR3 region of SEQ ID NO: 4, a CDR2 region of SEQ ID NO:5, and a CDR1 region of SEQ ID NO:6; and
  said second antigen-binding site comprises, in the heavy chain variable domain, a CDR3 region of SEQ ID NO: 46, a CDR2 region of SEQ ID NO: 47, and a CDR1 region of SEQ ID NO: 48, and, in the light chain variable domain, a CDR3 region of SEQ ID NO: 49, a CDR2 region of SEQ ID NO: 50, and a CDR1 region of SEQ ID NO: 51.

3. A bispecific antibody according to claim 2, characterized in that said first antigen-binding site comprises, as the heavy chain variable domain, SEQ ID NO: 7, and, as the light chain variable domain, SEQ ID NO: 8, and
  said second antigen-binding site comprises, as the heavy chain variable domain, SEQ ID NO: 52, and, as the light chain variable domain, SEQ ID NO: 53.

4. A bispecific antibody according to claim 1, characterized in that said first antigen-binding site comprises, in the heavy chain variable domain, a CDR3 region of SEQ ID NO: 1, a CDR2 region of SEQ ID NO: 2, and a CDR1 region of SEQ ID NO:3, and, in the light chain variable domain, a CDR3 region of SEQ ID NO: 4, a CDR2 region of SEQ ID NO:5, and a CDR1 region of SEQ ID NO:6;
  said second antigen-binding site comprises, in the heavy chain variable domain, a CDR3 region of SEQ ID NO: 62, a CDR2 region of SEQ ID NO: 63, and a CDR1 region of SEQ ID NO: 64, and, in the light chain variable domain, a CDR3 region of SEQ ID NO: 65, a CDR2 region of SEQ ID NO: 66, and a CDR1 region of SEQ ID NO: 67.

5. A bispecific antibody according to claim 4, characterized in that said first antigen-binding site comprises, as the heavy chain variable domain, SEQ ID NO: 7, and, as the light chain variable domain, SEQ ID NO: 8; and
  said second antigen-binding site comprises, as the heavy chain variable domain, SEQ ID NO: 68, and, as the light chain variable domain, SEQ ID NO: 69.

6. A bispecific antibody according to claim 1, characterized in that said first antigen-binding site s comprises, in the heavy chain variable domain, a CDR3 region of SEQ ID NO: 1, a CDR2 region of SEQ ID NO: 2, and a CDR1 region of SEQ ID NO:3, and, in the light chain variable domain, a CDR3 region of SEQ ID NO: 4, a CDR2 region of SEQ ID NO:5, and a CDR1 region of SEQ ID NO:6;
  said second antigen-binding site comprises, in the heavy chain variable domain, a CDR3 region of SEQ ID NO: 78, a CDR2 region of SEQ ID NO: 79, and a CDR1 region of SEQ ID NO: 80, and, in the light chain variable domain, a CDR3 region of SEQ ID NO: 81, a CDR2 region of SEQ ID NO: 82, and a CDR1 region of SEQ ID NO: 83.

7. A bispecific antibody according to claim 6, characterized in that said first antigen-binding site comprises, as the heavy chain variable domain, SEQ ID NO: 7, and, as the light chain variable domain, SEQ ID NO: 8; and
  said second antigen-binding site comprises, as the heavy chain variable domain SEQ ID NO: 84, and, as the light chain variable domain, SEQ ID NO: 85.

8. A bispecific antibody according to claim 1, characterized in that the ratio of the binding affinities $K_D$ (antigen-binding site specific for VEGF)/ $K_D$ (antigen-binding site specific for ANG-2) is 1.0-10.0.

9. A bispecific antibody according to claim 1, characterized in that the second antigen-binding site that specifically binds to human ANG-2does not specifically bind to human Angiopoetin 1 (ANG-1).

10. A bispecific antibody according to claim claims 1, characterized in that said antibody is bivalent, trivalent or tetravalent.

11. A pharmaceutical composition comprising an antibody according to claim 1.

12. A nucleic acid encoding a bispecific antibody according to claim 1.

13. An expression vector which comprises the nucleic acid according claim 12 and is capable of expressing said nucleic acid in a prokaryotic or eukaryotic host cell.

14. A prokaryotic or eukaryotic host cell comprising a vector according to claim 13.

15. A method for the production of a bispecific antibody according to claim 1, comprising expressing a nucleic acid encoding such a bispecific antibody in a prokaryotic or eukaryotic host cell and recovering said bispecific antibody from said cell or the cell culture supernatant.

16. An antibody obtained by the recombinant method of claim 15.

17. A bispecific antibody according to claim 1 wherein:
(A) said first antigen-binding site comprises, in the heavy chain variable domain, a CDR3 region of SEQ ID NO: 9, a CDR2 region of SEQ ID NO: 10, and a CDR1 region of SEQ ID NO: 11, and, in the light chain variable domain, a CDR3 region of SEQ ID NO: 12, a CDR2 region of SEQ ID NO: 13, and a CDR1 region of SEQ ID NO: 14; and
(B) said second antigen-binding site comprises, in the heavy chain variable domain, a CDR3 region of SEQ ID NO: 78, a CDR2 region of SEQ ID NO: 79, and a CDR1 region of SEQ ID NO: 80, and, in the light chain variable domain, a CDR3 region of SEQ ID NO: 81, a CDR2 region of SEQ ID NO: 82, and a CDR1 region of SEQ ID NO: 83.

18. A bispecific antibody according to claim 17 wherein:
(A) said first antigen-binding site comprises, as the heavy chain variable domain, SEQ ID NO: 15, and, as the light chain variable domain, SEQ ID NO: 16; and
(B) said second antigen-binding site comprises, as the heavy chain variable domain, SEQ ID NO: 84, and, as the light chain variable domain, SEQ ID NO: 85.

* * * * *

UNITED STATES PATENT AND TRADEMARK OFFICE
CERTIFICATE OF CORRECTION

PATENT NO.      : 8,268,314 B2
APPLICATION NO. : 12/572289
DATED           : September 18, 2012
INVENTOR(S)     : Baehner et al.

It is certified that error appears in the above-identified patent and that said Letters Patent is hereby corrected as shown below:

Claim 10, column 213, line 9, delete "claim claims 1,"
and insert -- claim 1, --

Signed and Sealed this
Twenty-second Day of January, 2013

David J. Kappos
*Director of the United States Patent and Trademark Office*

```
                         SEQUENCE LISTING

<160> NUMBER OF SEQ ID NOS: 136

<210> SEQ ID NO 1
<211> LENGTH: 14
<212> TYPE: PRT
<213> ORGANISM: Artificial
<220> FEATURE:
<223> OTHER INFORMATION: heavy chain CDR3, <VEGF>bevacizumab

<400> SEQUENCE: 1

Tyr Pro His Tyr Tyr Gly Ser Ser His Trp Tyr Phe Asp Val
1               5                   10

<210> SEQ ID NO 2
<211> LENGTH: 17
<212> TYPE: PRT
<213> ORGANISM: Artificial
<220> FEATURE:
<223> OTHER INFORMATION: heavy chain CDR2, <VEGF>bevacizumab

<400> SEQUENCE: 2

Trp Ile Asn Thr Tyr Thr Gly Glu Pro Thr Tyr Ala Ala Asp Phe Lys
1               5                   10                  15
Arg

<210> SEQ ID NO 3
<211> LENGTH: 5
<212> TYPE: PRT
<213> ORGANISM: Artificial
<220> FEATURE:
<223> OTHER INFORMATION: heavy chain CDR1, <VEGF>bevacizumab

<400> SEQUENCE: 3

Asn Tyr Gly Met Asn
1               5

<210> SEQ ID NO 4
<211> LENGTH: 9
```

```
<212> TYPE: PRT
<213> ORGANISM: Artificial
<220> FEATURE:
<223> OTHER INFORMATION: light chain CDR3, <VEGF>bevacizumab

<400> SEQUENCE: 4

Gln Gln Tyr Ser Thr Val Pro Trp Thr
1               5

<210> SEQ ID NO 5
<211> LENGTH: 7
<212> TYPE: PRT
<213> ORGANISM: Artificial
<220> FEATURE:
<223> OTHER INFORMATION: light chain CDR2, <VEGF>bevacizumab

<400> SEQUENCE: 5

Phe Thr Ser Ser Leu His Ser
1               5

<210> SEQ ID NO 6
<211> LENGTH: 11
<212> TYPE: PRT
<213> ORGANISM: Artificial
<220> FEATURE:
<223> OTHER INFORMATION: light chain CDR1, <VEGF>bevacizumab

<400> SEQUENCE: 6

Ser Ala Ser Gln Asp Ile Ser Asn Tyr Leu Asn
1               5                   10

<210> SEQ ID NO 7
<211> LENGTH: 123
<212> TYPE: PRT
<213> ORGANISM: Artificial
<220> FEATURE:
<223> OTHER INFORMATION: heavy chain variable domain, <VEGF>bevacizumab

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 8
<211> LENGTH: 107
<212> TYPE: PRT
<213> ORGANISM: Artificial
<220> FEATURE:
<223> OTHER INFORMATION: heavy chain variable domain, <VEGF>bevacizumab

<400> SEQUENCE: 8
```

```
Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys
            100                 105
```

<210> SEQ ID NO 9
<211> LENGTH: 14
<212> TYPE: PRT
<213> ORGANISM: Artificial
<220> FEATURE:
<223> OTHER INFORMATION: heavy chain CDR3, <VEGF>ranibizumab

<400> SEQUENCE: 9

```
Tyr Pro Tyr Tyr Tyr Gly Thr Ser His Trp Tyr Phe Asp Val
1               5                   10
```

<210> SEQ ID NO 10
<211> LENGTH: 17
<212> TYPE: PRT
<213> ORGANISM: Artificial
<220> FEATURE:
<223> OTHER INFORMATION: heavy chain CDR2, <VEGF>ranibizumab

<400> SEQUENCE: 10

```
Trp Ile Asn Thr Tyr Thr Gly Glu Pro Thr Tyr Ala Ala Asp Phe Lys
1               5                   10                  15

Arg
```

<210> SEQ ID NO 11
<211> LENGTH: 5
<212> TYPE: PRT
<213> ORGANISM: Artificial
<220> FEATURE:
<223> OTHER INFORMATION: heavy chain CDR1, <VEGF>ranibizumab

<400> SEQUENCE: 11

```
His Tyr Gly Met Asn
1               5
```

<210> SEQ ID NO 12
<211> LENGTH: 9
<212> TYPE: PRT
<213> ORGANISM: Artificial
<220> FEATURE:
<223> OTHER INFORMATION: light chain CDR3, <VEGF>ranibizumab

<400> SEQUENCE: 12

```
Gln Gln Tyr Ser Thr Val Pro Trp Thr
1               5
```

<210> SEQ ID NO 13
<211> LENGTH: 7
<212> TYPE: PRT
<213> ORGANISM: Artificial

-continued

```
<220> FEATURE:
<223> OTHER INFORMATION: light chain CDR2, <VEGF>ranibizumab

<400> SEQUENCE: 13

Phe Thr Ser Ser Leu His Ser
1               5

<210> SEQ ID NO 14
<211> LENGTH: 11
<212> TYPE: PRT
<213> ORGANISM: Artificial
<220> FEATURE:
<223> OTHER INFORMATION: light chain CDR1, <VEGF>ranibizumab

<400> SEQUENCE: 14

Ser Ala Ser Gln Asp Ile Ser Asn Tyr Leu Asn
1               5                   10

<210> SEQ ID NO 15
<211> LENGTH: 123
<212> TYPE: PRT
<213> ORGANISM: Artificial
<220> FEATURE:
<223> OTHER INFORMATION: heavy chain variable domain, <VEGF>ranibizumab

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro Tyr Tyr Tyr Gly Thr Ser His Trp Tyr Phe Asp Val
            100                 105                 110

Trp Gly Gln Gly Thr Leu Val Thr Val Ser Ser
        115                 120

<210> SEQ ID NO 16
<211> LENGTH: 107
<212> TYPE: PRT
<213> ORGANISM: Artificial
<220> FEATURE:
<223> OTHER INFORMATION: light chain variable domain, <VEGF>ranibizumab

<400> SEQUENCE: 16

Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Ser Thr Val Pro Trp
             85                  90                  95
Thr Phe Gly Gln Gly Thr Lys Val Glu Ile Lys
            100                 105

<210> SEQ ID NO 17
<211> LENGTH: 11
<212> TYPE: PRT
<213> ORGANISM: Artificial
<220> FEATURE:
<223> OTHER INFORMATION: heavy chain CDR3, <VEGF>HuMab G6-31

<400> SEQUENCE: 17

Ser Ala Ser Gln Asp Ile Ser Asn Tyr Leu Asn
1               5                   10

<210> SEQ ID NO 18
<211> LENGTH: 17
<212> TYPE: PRT
<213> ORGANISM: Artificial
<220> FEATURE:
<223> OTHER INFORMATION: heavy chain CDR2, <VEGF>HuMab G6-31

<400> SEQUENCE: 18

Gly Ile Thr Pro Ala Gly Gly Tyr Thr Tyr Tyr Ala Asp Ser Val Lys
1               5                   10                  15
Gly

<210> SEQ ID NO 19
<211> LENGTH: 5
<212> TYPE: PRT
<213> ORGANISM: Artificial
<220> FEATURE:
<223> OTHER INFORMATION: heavy chain CDR1, <VEGF>HuMab G6-31

<400> SEQUENCE: 19

Asp Tyr Trp Ile His
1               5

<210> SEQ ID NO 20
<211> LENGTH: 9
<212> TYPE: PRT
<213> ORGANISM: Artificial
<220> FEATURE:
<223> OTHER INFORMATION: light chain CDR3, <VEGF>HuMab G6-31

<400> SEQUENCE: 20

Gln Gln Gly Tyr Gly Asn Pro Phe Thr
1               5

<210> SEQ ID NO 21
<211> LENGTH: 7
<212> TYPE: PRT
<213> ORGANISM: Artificial
<220> FEATURE:
<223> OTHER INFORMATION: light chain CDR2, <VEGF>HuMab G6-31

<400> SEQUENCE: 21

Ser Ala Ser Phe Leu Tyr Ser
1               5

<210> SEQ ID NO 22
<211> LENGTH: 11
<212> TYPE: PRT
<213> ORGANISM: Artificial
<220> FEATURE:
<223> OTHER INFORMATION: light chain CDR1, <VEGF>HuMab G6-31
```

-continued

<400> SEQUENCE: 22

Arg Ala Ser Gln Asp Val Ser Thr Ala Val Ala
1               5                   10

<210> SEQ ID NO 23
<211> LENGTH: 120
<212> TYPE: PRT
<213> ORGANISM: Artificial
<220> FEATURE:
<223> OTHER INFORMATION: heavy chain variable domain, <VEGF> HuMab G6-31

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
                20                  25                  30

Trp Ile His Trp Val Arg Gln Ala Pro Gly Lys Gly Leu Glu Trp Val
            35                  40                  45

Ala Gly Ile Thr Pro Ala Gly Gly Tyr Thr Tyr Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser
        115                 120

<210> SEQ ID NO 24
<211> LENGTH: 107
<212> TYPE: PRT
<213> ORGANISM: Artificial
<220> FEATURE:
<223> OTHER INFORMATION: light chain variable domain, <VEGF> HuMab G6-31

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Asn Pro Phe
                85                  90                  95

Thr Phe Gly Gln Gly Thr Lys Val Glu Ile Lys
            100                 105

<210> SEQ ID NO 25
<211> LENGTH: 13
<212> TYPE: PRT
<213> ORGANISM: Artificial
<220> FEATURE:
<223> OTHER INFORMATION: heavy chain CDR3, <ANG-2> Mab 536

<400> SEQUENCE: 25

Asp Leu Leu Asp Tyr Asp Ile Leu Thr Gly Tyr Gly Tyr
1               5                   10

<210> SEQ ID NO 26
<211> LENGTH: 17
<212> TYPE: PRT
<213> ORGANISM: Artificial
<220> FEATURE:
<223> OTHER INFORMATION: heavy chain CDR2, <ANG-2> Mab 536

<400> SEQUENCE: 26

Tyr Ile Ser Ser Ser Gly Ser Thr Ile Tyr Tyr Ala Asp Ser Val Lys
1               5                   10                  15

Gly

<210> SEQ ID NO 27
<211> LENGTH: 5
<212> TYPE: PRT
<213> ORGANISM: Artificial
<220> FEATURE:
<223> OTHER INFORMATION: heavy chain CDR1, <ANG-2> Mab 536

<400> SEQUENCE: 27

Ser Tyr Gly Met His
1               5

<210> SEQ ID NO 28
<211> LENGTH: 9
<212> TYPE: PRT
<213> ORGANISM: Artificial
<220> FEATURE:
<223> OTHER INFORMATION: light chain CDR3, <ANG-2> Mab 536

<400> SEQUENCE: 28

Met Gln Gly Thr His Trp Pro Pro Thr
1               5

<210> SEQ ID NO 29
<211> LENGTH: 7
<212> TYPE: PRT
<213> ORGANISM: Artificial
<220> FEATURE:
<223> OTHER INFORMATION: light chain CDR2, <ANG-2> Mab 536

<400> SEQUENCE: 29

Leu Gly Ser Asn Arg Ala Ser
1               5

<210> SEQ ID NO 30
<211> LENGTH: 16
<212> TYPE: PRT
<213> ORGANISM: Artificial
<220> FEATURE:
<223> OTHER INFORMATION: light chain CDR1, <ANG-2> Mab 536

<400> SEQUENCE: 30

Arg Ser Ser Gln Ser Leu Leu His Ser Asn Gly Tyr Asn Tyr Leu Asp
1               5                   10                  15

<210> SEQ ID NO 31
<211> LENGTH: 122
<212> TYPE: PRT
<213> ORGANISM: Artificial
<220> FEATURE:
<223> OTHER INFORMATION: heavy chain variable domain, <ANG-2> Mab 536

<400> SEQUENCE: 31

```
Glu Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ser Tyr Ile Ser Ser Ser Gly Ser Thr Ile Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Leu Asp Tyr Asp Ile Leu Thr Gly Tyr Gly Tyr Trp
            100                 105                 110

Gly Gln Gly Thr Leu Val Thr Val Ser Ser
            115                 120
```

<210> SEQ ID NO 32
<211> LENGTH: 112
<212> TYPE: PRT
<213> ORGANISM: Artificial
<220> FEATURE:
<223> OTHER INFORMATION: light chain variable domain, <ANG-2> Mab 536

<400> SEQUENCE: 32

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gln Gly Thr Lys Leu Glu Ile Lys
            100                 105                 110
```

<210> SEQ ID NO 33
<211> LENGTH: 20
<212> TYPE: PRT
<213> ORGANISM: Artificial
<220> FEATURE:
<223> OTHER INFORMATION: (G4S)4 linker

<400> SEQUENCE: 33

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 34
<211> LENGTH: 104
<212> TYPE: PRT
<213> ORGANISM: Homo sapiens

<400> SEQUENCE: 34

-continued

Pro Lys Ala Ala Pro Ser Val Thr Leu Phe Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 35
<211> LENGTH: 330
<212> TYPE: PRT
<213> ORGANISM: Homo sapiens

<400> SEQUENCE: 35

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 36
<211> LENGTH: 327
<212> TYPE: PRT
<213> ORGANISM: Homo sapiens

<400> SEQUENCE: 36

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320
```

```
Leu Ser Leu Ser Leu Gly Lys
            325

<210> SEQ ID NO 37
<211> LENGTH: 107
<212> TYPE: PRT
<213> ORGANISM: Homo sapiens

<400> SEQUENCE: 37

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 38
<211> LENGTH: 7
<212> TYPE: PRT
<213> ORGANISM: Artificial
<220> FEATURE:
<223> OTHER INFORMATION: heavy chain CDR3, <ANG-2> Ang2s_R3_LC03

<400> SEQUENCE: 38

Asp Leu Gly Tyr Asp Tyr Val
1               5

<210> SEQ ID NO 39
<211> LENGTH: 19
<212> TYPE: PRT
<213> ORGANISM: Artificial
<220> FEATURE:
<223> OTHER INFORMATION: heavy chain CDR2, <ANG-2> Ang2s_R3_LC03

<400> SEQUENCE: 39

Arg Ile Lys Ser Lys Thr Asp Gly Gly Thr Thr Asp Tyr Ala Ala Pro
1               5                   10                  15

Val Lys Gly

<210> SEQ ID NO 40
<211> LENGTH: 5
<212> TYPE: PRT
<213> ORGANISM: Artificial
<220> FEATURE:
<223> OTHER INFORMATION: heavy chain CDR1, <ANG-2> Ang2s_R3_LC03

<400> SEQUENCE: 40

Asn Ala Trp Met Ser
1               5

<210> SEQ ID NO 41
<211> LENGTH: 10
<212> TYPE: PRT
<213> ORGANISM: Artificial
<220> FEATURE:
<223> OTHER INFORMATION: light chain CDR3, <ANG-2> Ang2s_R3_LC03
```

<400> SEQUENCE: 41

Gln Gln Tyr Asp Asn Leu Pro Met Tyr Thr
1               5                   10

<210> SEQ ID NO 42
<211> LENGTH: 7
<212> TYPE: PRT
<213> ORGANISM: Artificial
<220> FEATURE:
<223> OTHER INFORMATION: light chain CDR2, <ANG-2> Ang2s_R3_LC03

<400> SEQUENCE: 42

His Ala Ser Asn Leu Glu Thr
1               5

<210> SEQ ID NO 43
<211> LENGTH: 11
<212> TYPE: PRT
<213> ORGANISM: Artificial
<220> FEATURE:
<223> OTHER INFORMATION: light chain CDR1, <ANG-2> Ang2s_R3_LC03

<400> SEQUENCE: 43

Gln Ala Ser Gln Asp Ile Ser Asn Arg Leu Asn
1               5                   10

<210> SEQ ID NO 44
<211> LENGTH: 118
<212> TYPE: PRT
<213> ORGANISM: Artificial
<220> FEATURE:
<223> OTHER INFORMATION: heavy chain variable domain, <ANG-2>
      Ang2s_R3_LC03

<400> SEQUENCE: 44

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Leu Gly Tyr Asp Tyr Val Trp Gly Gln Gly Thr
            100                 105                 110

Leu Val Thr Val Ser Ser
        115

<210> SEQ ID NO 45
<211> LENGTH: 110
<212> TYPE: PRT
<213> ORGANISM: Artificial
<220> FEATURE:
<223> OTHER INFORMATION: light chain variable domain, <ANG-2>
      Ang2s_R3_LC03

<400> SEQUENCE: 45

Asp Ile Gln Val Thr Gln Ser Pro Ser Ser Leu Ser Ala Ser Val Gly
1               5                   10                  15

```
Asp Arg Val Thr Ile Thr Cys Gln Ala Ser Gln Asp Ile Ser Asn Arg
            20                  25                  30
Leu Asn Trp Tyr Gln Gln Lys Pro Gly Lys Ala Pro Lys Leu Leu Ile
        35                  40                  45
Tyr His Ala Ser Asn Leu Glu Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln Tyr Asp Asn Leu Pro Met
                85                  90                  95
Tyr Thr Phe Gly Gln Gly Thr Lys Leu Glu Ile Lys Arg Thr
                100                 105                 110
```

```
<210> SEQ ID NO 46
<211> LENGTH: 20
<212> TYPE: PRT
<213> ORGANISM: Artificial
<220> FEATURE:
<223> OTHER INFORMATION: heavy chain CDR3, <ANG-2>Ang2i_LC06

<400> SEQUENCE: 46

Ser Pro Asn Pro Tyr Tyr Tyr Asp Ser Ser Gly Tyr Tyr Tyr Pro Gly
1               5                   10                  15
Ala Phe Asp Ile
            20

<210> SEQ ID NO 47
<211> LENGTH: 17
<212> TYPE: PRT
<213> ORGANISM: Artificial
<220> FEATURE:
<223> OTHER INFORMATION: heavy chain CDR2, <ANG-2>Ang2i_LC06

<400> SEQUENCE: 47

Trp Ile Asn Pro Asn Ser Gly Gly Thr Asn Tyr Ala Gln Lys Phe Gln
1               5                   10                  15
Gly

<210> SEQ ID NO 48
<211> LENGTH: 5
<212> TYPE: PRT
<213> ORGANISM: Artificial
<220> FEATURE:
<223> OTHER INFORMATION: heavy chain CDR1, <ANG-2>Ang2i_LC06

<400> SEQUENCE: 48

Gly Tyr Tyr Met His
1               5

<210> SEQ ID NO 49
<211> LENGTH: 11
<212> TYPE: PRT
<213> ORGANISM: Artificial
<220> FEATURE:
<223> OTHER INFORMATION: light chain CDR3, <ANG-2>Ang2i_LC06

<400> SEQUENCE: 49

Gln Val Trp Asp Ser Ser Ser Asp His Tyr Val
1               5                   10

<210> SEQ ID NO 50
<211> LENGTH: 7
<212> TYPE: PRT
```

```
<213> ORGANISM: Artificial
<220> FEATURE:
<223> OTHER INFORMATION: light chain CDR2, <ANG-2>Ang2i_LC06

<400> SEQUENCE: 50

Asp Asp Ser Asp Arg Pro Ser
1               5

<210> SEQ ID NO 51
<211> LENGTH: 11
<212> TYPE: PRT
<213> ORGANISM: Artificial
<220> FEATURE:
<223> OTHER INFORMATION: light chain CDR1, <ANG-2>Ang2i_LC06

<400> SEQUENCE: 51

Gly Gly Asn Asn Ile Gly Ser Lys Ser Val His
1               5                   10

<210> SEQ ID NO 52
<211> LENGTH: 129
<212> TYPE: PRT
<213> ORGANISM: Artificial
<220> FEATURE:
<223> OTHER INFORMATION: heavy chain variable domain, <ANG-2>Ang2i_LC06

<400> SEQUENCE: 52

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser

<210> SEQ ID NO 53
<211> LENGTH: 110
<212> TYPE: PRT
<213> ORGANISM: Artificial
<220> FEATURE:
<223> OTHER INFORMATION: light chain variable domain, <ANG-2>Ang2i_LC06

<400> SEQUENCE: 53

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60
```

```
Asn Ser Gly Asn Thr Ala Thr Leu Thr Ile Ser Arg Val Glu Ala Gly
 65                  70                  75                  80
Asp Glu Ala Asp Tyr Tyr Cys Gln Val Trp Asp Ser Ser Asp His
                 85                  90                  95
Tyr Val Phe Gly Thr Gly Thr Lys Val Thr Val Leu Gly Gln
                100                 105                 110

<210> SEQ ID NO 54
<211> LENGTH: 20
<212> TYPE: PRT
<213> ORGANISM: Artificial
<220> FEATURE:
<223> OTHER INFORMATION: heavy chain CDR3, <ANG-2>Ang2i_LC07

<400> SEQUENCE: 54

Ser Pro Asn Pro Tyr Tyr Tyr Asp Ser Ser Gly Tyr Tyr Tyr Pro Gly
1               5                   10                  15
Ala Phe Asp Ile
            20

<210> SEQ ID NO 55
<211> LENGTH: 17
<212> TYPE: PRT
<213> ORGANISM: Artificial
<220> FEATURE:
<223> OTHER INFORMATION: heavy chain CDR2, <ANG-2>Ang2i_LC07

<400> SEQUENCE: 55

Trp Ile Asn Pro Asn Ser Gly Gly Thr Asn Tyr Ala Gln Lys Phe Gln
1               5                   10                  15
Gly

<210> SEQ ID NO 56
<211> LENGTH: 5
<212> TYPE: PRT
<213> ORGANISM: Artificial
<220> FEATURE:
<223> OTHER INFORMATION: heavy chain CDR1, <ANG-2>Ang2i_LC07

<400> SEQUENCE: 56

Gly Tyr Tyr Met His
1               5

<210> SEQ ID NO 57
<211> LENGTH: 11
<212> TYPE: PRT
<213> ORGANISM: Artificial
<220> FEATURE:
<223> OTHER INFORMATION: light chain CDR3, <ANG-2>Ang2i_LC07

<400> SEQUENCE: 57

Gln Val Trp Asp Ser Asp Ser Asp Gln Gly Val
1               5                   10

<210> SEQ ID NO 58
<211> LENGTH: 7
<212> TYPE: PRT
<213> ORGANISM: Artificial
<220> FEATURE:
<223> OTHER INFORMATION: light chain CDR2, <ANG-2>Ang2i_LC07

<400> SEQUENCE: 58

Asp Asp Ser Glu Arg Pro Ser
1               5
```

```
<210> SEQ ID NO 59
<211> LENGTH: 11
<212> TYPE: PRT
<213> ORGANISM: Artificial
<220> FEATURE:
<223> OTHER INFORMATION: light chain CDR1, <ANG-2>Ang2i_LC07

<400> SEQUENCE: 59

Gly Gly Asn Phe Ile Gly Gly Lys Ser Val His
1               5                   10

<210> SEQ ID NO 60
<211> LENGTH: 129
<212> TYPE: PRT
<213> ORGANISM: Artificial
<220> FEATURE:
<223> OTHER INFORMATION: heavy chain variable domain, <ANG-2>Ang2i_LC07

<400> SEQUENCE: 60

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser

<210> SEQ ID NO 61
<211> LENGTH: 110
<212> TYPE: PRT
<213> ORGANISM: Artificial
<220> FEATURE:
<223> OTHER INFORMATION: light chain variable domain, <ANG-2>Ang2i_LC07

<400> SEQUENCE: 61

Gln Pro Val Leu Thr Gln Ser Pro Ser Val Ser Val Ala Pro Gly Glu
1               5                   10                  15

Thr Ala Arg Val Ala Cys Gly Gly Asn Phe Ile Gly Gly Lys Ser Val
            20                  25                  30

His Trp Tyr Gln Gln Lys Pro Gly Gln Ala Pro Val Leu Val Ile Tyr
        35                  40                  45

Asp Asp Ser Glu Arg Pro Ser Gly Ile Pro Glu Arg Ile Ser Gly Ser
    50                  55                  60

Asn Ser Gly Asn Thr Ala Thr Leu Ile Ile Thr Arg Ala Glu Ala Gly
65                  70                  75                  80

Asp Glu Ala Asp Tyr His Cys Gln Val Trp Asp Ser Asp Ser Asp Gln
                85                  90                  95

Gly Val Phe Gly Thr Gly Thr Lys Leu Thr Val Leu Gly Gln
            100                 105                 110
```

```
<210> SEQ ID NO 62
<211> LENGTH: 15
<212> TYPE: PRT
<213> ORGANISM: Artificial
<220> FEATURE:
<223> OTHER INFORMATION: heavy chain CDR3, <ANG-2>Ang2k_LC08

<400> SEQUENCE: 62

Pro Thr Leu Asp Ile Tyr Met Gly Tyr Tyr Tyr Gly Met Asp Val
1               5                   10                  15

<210> SEQ ID NO 63
<211> LENGTH: 17
<212> TYPE: PRT
<213> ORGANISM: Artificial
<220> FEATURE:
<223> OTHER INFORMATION: heavy chain CDR2, <ANG-2>Ang2k_LC08

<400> SEQUENCE: 63

Val Ile Ser Tyr Asp Gly Ser Asn Lys Tyr Tyr Ala Asp Ser Val Lys
1               5                   10                  15

Gly

<210> SEQ ID NO 64
<211> LENGTH: 5
<212> TYPE: PRT
<213> ORGANISM: Artificial
<220> FEATURE:
<223> OTHER INFORMATION: heavy chain CDR1, <ANG-2>Ang2k_LC08

<400> SEQUENCE: 64

Ser Tyr Gly Met His
1               5

<210> SEQ ID NO 65
<211> LENGTH: 11
<212> TYPE: PRT
<213> ORGANISM: Artificial
<220> FEATURE:
<223> OTHER INFORMATION: light chain CDR3, <ANG-2>Ang2k_LC08

<400> SEQUENCE: 65

Ala Ala Trp Asp Asp Ser Leu Asn Gly Pro Val
1               5                   10

<210> SEQ ID NO 66
<211> LENGTH: 7
<212> TYPE: PRT
<213> ORGANISM: Artificial
<220> FEATURE:
<223> OTHER INFORMATION: light chain CDR2, <ANG-2>Ang2k_LC08

<400> SEQUENCE: 66

Asn Asn Asp Gln Arg Pro Ser
1               5

<210> SEQ ID NO 67
<211> LENGTH: 13
<212> TYPE: PRT
<213> ORGANISM: Artificial
<220> FEATURE:
<223> OTHER INFORMATION: light chain CDR1, <ANG-2>Ang2k_LC08

<400> SEQUENCE: 67

Ser Gly Phe Ala Ser Asn Ile Gly Ser Asn Ser Val Asn
1               5                   10
```

```
<210> SEQ ID NO 68
<211> LENGTH: 124
<212> TYPE: PRT
<213> ORGANISM: Artificial
<220> FEATURE:
<223> OTHER INFORMATION: heavy chain variable domain, <ANG-2>
      Ang2k_LC08

<400> SEQUENCE: 68

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Thr Leu Asp Ile Tyr Met Gly Tyr Tyr Tyr Gly Met Asp
            100                 105                 110

Val Trp Gly Gln Gly Thr Thr Val Thr Val Ser Ser
        115                 120

<210> SEQ ID NO 69
<211> LENGTH: 112
<212> TYPE: PRT
<213> ORGANISM: Artificial
<220> FEATURE:
<223> OTHER INFORMATION: light chain variable domain, <ANG-2>
      Ang2k_LC08

<400> SEQUENCE: 69

Gln Pro Val Leu Thr Gln Pro Pro Ser Ala Ser Gly Ala Pro Gly Gln
1               5                   10                  15

Arg Val Thr Ile Ser Cys Ser Gly Phe Ala Ser Asn Ile Gly Ser Asn
            20                  25                  30

Ser Val Asn Trp Tyr Gln Gln Val Pro Gly Thr Ala Pro Lys Leu Leu
        35                  40                  45

Ile Tyr Asn Asn Asp Gln Arg Pro Ser Gly Val Pro Asp Arg Phe Ser
    50                  55                  60

Gly Ser Arg Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Gly Pro Val Phe Gly Gly Gly Thr Lys Leu Thr Val Leu Gly Gln
            100                 105                 110

<210> SEQ ID NO 70
<211> LENGTH: 7
<212> TYPE: PRT
<213> ORGANISM: Artificial
<220> FEATURE:
<223> OTHER INFORMATION: heavy chain CDR3, <ANG-2> Ang2s_LC09

<400> SEQUENCE: 70

Asp Leu Gly Tyr Asp Tyr Val
1               5
```

```
<210> SEQ ID NO 71
<211> LENGTH: 19
<212> TYPE: PRT
<213> ORGANISM: Artificial
<220> FEATURE:
<223> OTHER INFORMATION: heavy chain CDR2, <ANG-2> Ang2s_LC09

<400> SEQUENCE: 71

Arg Ile Lys Ser Lys Thr Asp Gly Gly Thr Thr Asp Tyr Ala Ala Pro
1               5                   10                  15

Val Lys Gly

<210> SEQ ID NO 72
<211> LENGTH: 5
<212> TYPE: PRT
<213> ORGANISM: Artificial
<220> FEATURE:
<223> OTHER INFORMATION: heavy chain CDR1, <ANG-2> Ang2s_LC09

<400> SEQUENCE: 72

Asn Ala Trp Met Ser
1               5

<210> SEQ ID NO 73
<211> LENGTH: 7
<212> TYPE: PRT
<213> ORGANISM: Artificial
<220> FEATURE:
<223> OTHER INFORMATION: light chain CDR3, <ANG-2> Ang2s_LC09

<400> SEQUENCE: 73

Met Gln Ala Leu Gln Ile Pro
1               5

<210> SEQ ID NO 74
<211> LENGTH: 7
<212> TYPE: PRT
<213> ORGANISM: Artificial
<220> FEATURE:
<223> OTHER INFORMATION: light chain CDR2, <ANG-2> Ang2s_LC09

<400> SEQUENCE: 74

Leu Gly Ser Asn Arg Ala Ser
1               5

<210> SEQ ID NO 75
<211> LENGTH: 16
<212> TYPE: PRT
<213> ORGANISM: Artificial
<220> FEATURE:
<223> OTHER INFORMATION: light chain CDR1, <ANG-2> Ang2s_LC09

<400> SEQUENCE: 75

Arg Ser Ser Gln Ser Leu Leu His Ser Asn Gly Tyr Asn Tyr Leu Asp
1               5                   10                  15

<210> SEQ ID NO 76
<211> LENGTH: 119
<212> TYPE: PRT
<213> ORGANISM: Artificial
<220> FEATURE:
<223> OTHER INFORMATION: heavy chain variable domain, <ANG-2>
      Ang2s_LC09

<400> SEQUENCE: 76

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
 50                  55                  60

Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Thr Thr Asp Leu Gly Tyr Asp Tyr Val Trp Gly Ser Pro Gly
            100                 105                 110

Thr Leu Val Thr Val Ser Ser
        115
```

<210> SEQ ID NO 77
<211> LENGTH: 109
<212> TYPE: PRT
<213> ORGANISM: Artificial
<220> FEATURE:
<223> OTHER INFORMATION: light chain variable domain, <ANG-2>
      Ang2s_LC09

<400> SEQUENCE: 77

```
Gln Ser Pro Leu Ser Leu Pro Val Thr Pro Gly Glu Pro Ala Ser Ile
 1               5                  10                  15

Ser Cys Arg Ser Ser Gln Ser Leu Leu His Ser Asn Gly Tyr Asn Tyr
            20                  25                  30

Leu Asp Trp Tyr Leu Gln Lys Pro Gly Gln Ser Pro Gln Leu Leu Ile
        35                  40                  45

Tyr Leu Gly Ser Asn Arg Ala Ser Gly Val Pro Asp Arg Phe Ser Gly
 50                  55                  60

Ser Gly Ser Gly Thr Asp Phe Thr Leu Lys Ile Ser Arg Val Glu Ala
 65                  70                  75                  80

Glu Asp Val Gly Val Tyr Tyr Cys Met Gln Ala Leu Gln Ile Pro Phe
                 85                  90                  95

Thr Phe Gly Pro Gly Thr Lys Val Thr Val Leu Arg Thr
            100                 105
```

<210> SEQ ID NO 78
<211> LENGTH: 20
<212> TYPE: PRT
<213> ORGANISM: Artificial
<220> FEATURE:
<223> OTHER INFORMATION: heavy chain CDR3, <ANG-2> Ang2i_LC10

<400> SEQUENCE: 78

```
Ser Pro Asn Pro Tyr Tyr Tyr Asp Ser Ser Gly Tyr Tyr Tyr Pro Gly
 1               5                  10                  15

Ala Phe Asp Ile
            20
```

<210> SEQ ID NO 79
<211> LENGTH: 17
<212> TYPE: PRT
<213> ORGANISM: Artificial
<220> FEATURE:
<223> OTHER INFORMATION: heavy chain CDR2, <ANG-2> Ang2i_LC10

<400> SEQUENCE: 79

```
Trp Ile Asn Pro Asn Ser Gly Gly Thr Asn Tyr Ala Gln Lys Phe Gln
```

<210> SEQ ID NO 80
<211> LENGTH: 5
<212> TYPE: PRT
<213> ORGANISM: Artificial
<220> FEATURE:
<223> OTHER INFORMATION: heavy chain CDR1, <ANG-2> Ang2i_LC10

<400> SEQUENCE: 80

Gly Tyr Tyr Met His
1               5

<210> SEQ ID NO 81
<211> LENGTH: 11
<212> TYPE: PRT
<213> ORGANISM: Artificial
<220> FEATURE:
<223> OTHER INFORMATION: light chain CDR3, <ANG-2> Ang2i_LC10

<400> SEQUENCE: 81

Gln Val Trp Asp Ser Ser Ser Asp His Trp Val
1               5                   10

<210> SEQ ID NO 82
<211> LENGTH: 7
<212> TYPE: PRT
<213> ORGANISM: Artificial
<220> FEATURE:
<223> OTHER INFORMATION: light chain CDR2, <ANG-2> Ang2i_LC10

<400> SEQUENCE: 82

Asp Asp Ser Asp Arg Pro Ser
1               5

<210> SEQ ID NO 83
<211> LENGTH: 11
<212> TYPE: PRT
<213> ORGANISM: Artificial
<220> FEATURE:
<223> OTHER INFORMATION: light chain CDR1, <ANG-2> Ang2i_LC10

<400> SEQUENCE: 83

Gly Gly Asn Asn Ile Gly Ser Lys Ser Val His
1               5                   10

<210> SEQ ID NO 84
<211> LENGTH: 129
<212> TYPE: PRT
<213> ORGANISM: Artificial
<220> FEATURE:
<223> OTHER INFORMATION: heavy chain variable domain, <ANG-2> Ang2i_LC10

<400> SEQUENCE: 84

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
           100                 105                 110

Pro Gly Ala Phe Asp Ile Trp Gly Gln Gly Thr Met Val Thr Val Ser
        115                 120                 125

Ser

<210> SEQ ID NO 85
<211> LENGTH: 105
<212> TYPE: PRT
<213> ORGANISM: Artificial
<220> FEATURE:
<223> OTHER INFORMATION: light chain variable domain, <ANG-2> Ang2i_LC10

<400> SEQUENCE: 85

Gln Pro Pro Ser Val Ser Val Ala Pro Gly Gln Thr Ala Arg Ile Thr
1               5                   10                  15

Cys Gly Gly Asn Asn Ile Gly Ser Lys Ser Val His Trp Tyr Gln Gln
            20                  25                  30

Lys Pro Gly Gln Ala Pro Val Leu Val Val Tyr Asp Asp Ser Asp Arg
        35                  40                  45

Pro Ser Gly Ile Pro Glu Arg Phe Ser Gly Ser Asn Ser Gly Asn Thr
    50                  55                  60

Ala Thr Leu Thr Ile Ser Arg Val Glu Ala Gly Asp Glu Ala Asp Tyr
65                  70                  75                  80

Tyr Cys Gln Val Trp Asp Ser Ser Asp His Trp Val Phe Gly Gly
                85                  90                  95

Gly Thr Lys Leu Thr Val Leu Gly Gln
            100                 105

<210> SEQ ID NO 86
<211> LENGTH: 15
<212> TYPE: PRT
<213> ORGANISM: Artificial
<220> FEATURE:
<223> OTHER INFORMATION: heavy chain CDR3, <ANG-2> Ang2k_LC11

<400> SEQUENCE: 86

Pro Thr Leu Asp Ile Tyr Met Gly Tyr Tyr Gly Met Asp Val
1               5                   10                  15

<210> SEQ ID NO 87
<211> LENGTH: 17
<212> TYPE: PRT
<213> ORGANISM: Artificial
<220> FEATURE:
<223> OTHER INFORMATION: heavy chain CDR2, <ANG-2> Ang2k_LC11

<400> SEQUENCE: 87

Val Ile Ser Tyr Asp Gly Ser Asn Lys Tyr Tyr Ala Asp Ser Val Lys
1               5                   10                  15

Gly

<210> SEQ ID NO 88
<211> LENGTH: 5
<212> TYPE: PRT
<213> ORGANISM: Artificial
<220> FEATURE:
<223> OTHER INFORMATION: heavy chain CDR1, <ANG-2> Ang2k_LC11

<400> SEQUENCE: 88

```
Ser Tyr Gly Met His
1               5
```

<210> SEQ ID NO 89
<211> LENGTH: 12
<212> TYPE: PRT
<213> ORGANISM: Artificial
<220> FEATURE:
<223> OTHER INFORMATION: light chain CDR3, <ANG-2> Ang2k_LC11

<400> SEQUENCE: 89

```
Gln Val Trp Asp Ser Ser Ser Asp His Pro Gly Val
1               5                   10
```

<210> SEQ ID NO 90
<211> LENGTH: 7
<212> TYPE: PRT
<213> ORGANISM: Artificial
<220> FEATURE:
<223> OTHER INFORMATION: light chain CDR2, <ANG-2> Ang2k_LC11

<400> SEQUENCE: 90

```
Asp Asp Ser Asp Arg Pro Ser
1               5
```

<210> SEQ ID NO 91
<211> LENGTH: 11
<212> TYPE: PRT
<213> ORGANISM: Artificial
<220> FEATURE:
<223> OTHER INFORMATION: light chain CDR1, <ANG-2> Ang2k_LC11

<400> SEQUENCE: 91

```
Gly Gly Asn Asn Ile Gly Ser Lys Ser Val His
1               5                   10
```

<210> SEQ ID NO 92
<211> LENGTH: 124
<212> TYPE: PRT
<213> ORGANISM: Artificial
<220> FEATURE:
<223> OTHER INFORMATION: heavy chain variable domain, <ANG-2> Ang2k_LC11

<400> SEQUENCE: 92

```
Gln Val Gln Leu Val Glu Ser Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Thr Leu Asp Ile Tyr Met Gly Tyr Tyr Tyr Gly Met Asp
            100                 105                 110

Val Trp Gly Gln Gly Thr Thr Val Thr Val Ser Ser
        115                 120
```

<210> SEQ ID NO 93
<211> LENGTH: 106

```
<212> TYPE: PRT
<213> ORGANISM: Artificial
<220> FEATURE:
<223> OTHER INFORMATION: light chain variable domain, <ANG-2> Ang2k_LC11
<220> FEATURE:
<221> NAME/KEY: misc_feature
<222> LOCATION: (98)..(98)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid

<400> SEQUENCE: 93

Gln Pro Pro Ser Val Ser Val Ala Pro Gly Gln Thr Ala Arg Ile Thr
1               5                   10                  15

Cys Gly Gly Asn Asn Ile Gly Ser Lys Ser Val His Trp Tyr Gln Gln
            20                  25                  30

Lys Pro Gly Gln Ala Pro Val Leu Val Val Tyr Asp Asp Ser Asp Arg
        35                  40                  45

Pro Ser Gly Ile Pro Glu Arg Phe Ser Gly Ser Asn Ser Gly Asn Thr
    50                  55                  60

Ala Thr Leu Thr Ile Ser Arg Val Glu Ala Gly Asp Glu Ala Asp Tyr
65                  70                  75                  80

Tyr Cys Gln Val Trp Asp Ser Ser Ser Asp His Pro Gly Val Phe Gly
                85                  90                  95

Gly Xaa Thr Lys Leu Xaa Val Leu Gly Gln
            100                 105

<210> SEQ ID NO 94
<211> LENGTH: 12
<212> TYPE: PRT
<213> ORGANISM: Artificial
<220> FEATURE:
<223> OTHER INFORMATION: heavy chain CDR3, <VEGF>B20-4.1

<400> SEQUENCE: 94

Trp Gly His Ser Thr Ser Pro Trp Ala Met Asp Tyr
1               5                   10

<210> SEQ ID NO 95
<211> LENGTH: 17
<212> TYPE: PRT
<213> ORGANISM: Artificial
<220> FEATURE:
<223> OTHER INFORMATION: heavy chain CDR2, <VEGF>B20-4.1

<400> SEQUENCE: 95

Ala Ile Trp Pro Phe Gly Gly Tyr Thr His Tyr Ala Asp Ser Val Lys
1               5                   10                  15

Gly

<210> SEQ ID NO 96
<211> LENGTH: 8
<212> TYPE: PRT
<213> ORGANISM: Artificial
<220> FEATURE:
<223> OTHER INFORMATION: heavy chain CDR1, <VEGF>B20-4.1

<400> SEQUENCE: 96

Phe Ser Ile Asn Gly Ser Trp Ile
1               5

<210> SEQ ID NO 97
<211> LENGTH: 9
```

```
<212> TYPE: PRT
<213> ORGANISM: Artificial
<220> FEATURE:
<223> OTHER INFORMATION: light chain CDR3, <VEGF>B20-4.1

<400> SEQUENCE: 97

Gln Gln Ser Asn Thr Ser Pro Leu Thr
1               5

<210> SEQ ID NO 98
<211> LENGTH: 8
<212> TYPE: PRT
<213> ORGANISM: Artificial
<220> FEATURE:
<223> OTHER INFORMATION: light chain CDR2, <VEGF>B20-4.1

<400> SEQUENCE: 98

Tyr Ala Ala Ser Asn Leu Ala Ser
1               5

<210> SEQ ID NO 99
<211> LENGTH: 11
<212> TYPE: PRT
<213> ORGANISM: Artificial
<220> FEATURE:
<223> OTHER INFORMATION: light chain CDR1, <VEGF>B20-4.1

<400> SEQUENCE: 99

Arg Ala Ser Gln Val Ile Arg Arg Ser Leu Ala
1               5                   10

<210> SEQ ID NO 100
<211> LENGTH: 117
<212> TYPE: PRT
<213> ORGANISM: Artificial
<220> FEATURE:
<223> OTHER INFORMATION: heavy chain variable domain, <VEGF>B20-4.1

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Asn Gly Ser
            20                  25                  30

Trp Ile Phe Trp Val Arg Gln Ala Pro Gly Lys Gly Leu Glu Trp Val
        35                  40                  45

Gly Ala Ile Trp Pro Phe Gly Gly Tyr Thr His Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Gly His Ser Thr Ser Pro Trp Ala Met Asp Tyr Trp Gly
            100                 105                 110

Gln Gly Thr Leu Val
        115

<210> SEQ ID NO 101
<211> LENGTH: 108
<212> TYPE: PRT
<213> ORGANISM: Artificial
<220> FEATURE:
<223> OTHER INFORMATION: light chain variable domain, <VEGF>B20-4.1

<400> SEQUENCE: 101
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Ile Arg Arg Ser
            20                  25                  30

Leu Ala Trp Tyr Gln Gln Lys Pro Gly Lys Ala Pro Lys Leu Leu Ile
            35                  40                  45

Tyr Ala Ala Ser Asn Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Thr Ser Pro Leu
                85                  90                  95

Thr Phe Gly Gln Gly Thr Lys Val Glu Ile Lys Arg
            100                 105

<210> SEQ ID NO 102
<211> LENGTH: 730
<212> TYPE: PRT
<213> ORGANISM: Artificial
<220> FEATURE:
<223> OTHER INFORMATION: bevacizumab heavy chain Ang2i_LC06 scFv fusion
      peptide of <VEGF-ANG-2> TvAb-2441-bevacizumab-LC06

<400> SEQUENCE: 102

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

```
Leu Met Ile Ser Arg Thr Pro Glu Val Thr Cys Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Ser Gly Gly Gly Ser Gly
    450                 455                 460

Gly Gly Gly Ser Gly Gly Gly Gly Ser Gln Val Gln Leu Val Glu Ser
465                 470                 475                 480

Gly Ala Glu Val Lys Lys Pro Gly Ala Ser Val Lys Val Ser Cys Lys
                485                 490                 495

Ala Ser Gly Tyr Thr Phe Thr Gly Tyr Tyr Met His Trp Val Arg Gln
            500                 505                 510

Ala Pro Gly Gln Cys Leu Glu Trp Met Gly Trp Ile Asn Pro Asn Ser
        515                 520                 525

Gly Gly Thr Asn Tyr Ala Gln Lys Phe Gln Gly Arg Val Thr Met Thr
    530                 535                 540

Arg Asp Thr Ser Ile Ser Thr Ala Tyr Met Glu Leu Ser Arg Leu Arg
545                 550                 555                 560

Ser Asp Asp Thr Ala Val Tyr Tyr Cys Ala Arg Ser Pro Asn Pro Tyr
                565                 570                 575

Tyr Tyr Asp Ser Ser Gly Tyr Tyr Pro Gly Ala Phe Asp Ile Trp
            580                 585                 590

Gly Gln Gly Thr Met Val Thr Val Ser Ser Gly Gly Gly Gly Ser Gly
        595                 600                 605

Gly Gly Gly Ser Gly Gly Gly Gly Ser Gly Gly Gly Gly Ser Gln Pro
    610                 615                 620

Gly Leu Thr Gln Pro Pro Ser Val Ser Val Ala Pro Gly Gln Thr Ala
625                 630                 635                 640

Arg Ile Thr Cys Gly Gly Asn Asn Ile Gly Ser Lys Ser Val His Trp
                645                 650                 655

Tyr Gln Gln Lys Pro Gly Gln Ala Pro Val Leu Val Val Tyr Asp Asp
            660                 665                 670

Ser Asp Arg Pro Ser Gly Ile Pro Glu Arg Phe Ser Gly Ser Asn Ser
        675                 680                 685
```

```
Gly Asn Thr Ala Thr Leu Thr Ile Ser Arg Val Glu Ala Gly Asp Glu
            690                 695                 700

Ala Asp Tyr Tyr Cys Gln Val Trp Asp Ser Ser Asp His Tyr Val
705                 710                 715                 720

Phe Gly Cys Gly Thr Lys Val Thr Val Leu
                725                 730

<210> SEQ ID NO 103
<211> LENGTH: 727
<212> TYPE: PRT
<213> ORGANISM: Artificial
<220> FEATURE:
<223> OTHER INFORMATION: bevacizumab heavy chain Ang2i_LC08 scFv fusion
      peptide of <VEGF-ANG-2> TvAb-2441-bevacizumab-LC08

<400> SEQUENCE: 103

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320
```

```
Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
            355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys Gly Gly Gly Gly Ser Gly Gly Gly Gly Ser Gly
            450                 455                 460

Gly Gly Ser Gly Gly Gly Gly Ser Gln Val Gln Leu Val Glu Ser
465                 470                 475                 480

Gly Gly Gly Val Val Gln Pro Gly Gly Ser Leu Arg Leu Ser Cys Ala
            485                 490                 495

Ala Ser Gly Phe Thr Phe Ser Ser Tyr Gly Met His Trp Val Arg Gln
            500                 505                 510

Ala Pro Gly Lys Cys Leu Glu Trp Val Ala Val Ile Ser Tyr Asp Gly
            515                 520                 525

Ser Asn Lys Tyr Tyr Ala Asp Ser Val Lys Gly Arg Phe Thr Ile Ser
            530                 535                 540

Arg Asp Asn Ser Lys Asn Thr Leu Tyr Leu Gln Met Asn Ser Leu Arg
545                 550                 555                 560

Ala Glu Asp Thr Ala Val Tyr Tyr Cys Ala Lys Pro Thr Leu Asp Ile
            565                 570                 575

Tyr Met Gly Tyr Tyr Gly Met Asp Val Trp Gly Gln Gly Thr Thr
            580                 585                 590

Val Thr Val Ser Ser Gly Gly Gly Gly Ser Gly Gly Gly Gly Ser Gly
            595                 600                 605

Gly Gly Ser Gly Gly Gly Gly Ser Gln Pro Val Leu Thr Gln Pro
            610                 615                 620

Pro Ser Ala Ser Gly Ala Pro Gly Gln Arg Val Thr Ile Ser Cys Ser
625                 630                 635                 640

Gly Phe Ala Ser Asn Ile Gly Ser Asn Ser Val Asn Trp Tyr Gln Gln
            645                 650                 655

Val Pro Gly Thr Ala Pro Lys Leu Leu Ile Tyr Asn Asn Asp Gln Arg
            660                 665                 670

Pro Ser Gly Val Pro Asp Arg Phe Ser Gly Ser Arg Ser Gly Thr Ser
            675                 680                 685

Ala Ser Leu Ala Ile Ser Gly Leu Gln Ser Glu Asp Glu Ala Asp Tyr
            690                 695                 700

Tyr Cys Ala Ala Trp Asp Asp Ser Leu Asn Gly Pro Val Phe Gly Cys
705                 710                 715                 720

Gly Thr Lys Leu Thr Val Leu
            725
```

<210> SEQ ID NO 104
<211> LENGTH: 214
<212> TYPE: PRT
<213> ORGANISM: Artificial
<220> FEATURE:
<223> OTHER INFORMATION: light chain of bevacizumab

<400> SEQUENCE: 104

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 105
<211> LENGTH: 191
<212> TYPE: PRT
<213> ORGANISM: Homo sapiens

<400> SEQUENCE: 105

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

```
Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Cys Asp Lys Pro Arg Arg
            180                 185                 190

<210> SEQ ID NO 106
<211> LENGTH: 504
<212> TYPE: PRT
<213> ORGANISM: Artificial
<220> FEATURE:
<223> OTHER INFORMATION: Human angiopoietin-2 (ANG-2) with leader and
      His-tag

<400> SEQUENCE: 106

Met Trp Gln Ile Val Phe Phe Thr Leu Ser Cys Asp Leu Val Leu Ala
1               5                   10                  15

Ala Ala Tyr Asn Asn Phe Arg Lys Ser Met Asp Ser Ile Gly Lys Lys
            20                  25                  30

Gln Tyr Gln Val Gln His Gly Ser Cys Ser Tyr Thr Phe Leu Leu Pro
        35                  40                  45

Glu Met Asp Asn Cys Arg Ser Ser Ser Pro Tyr Val Ser Asn Ala
    50                  55                  60

Val Gln Arg Asp Ala Pro Leu Glu Tyr Asp Asp Ser Val Gln Arg Leu
65                  70                  75                  80

Gln Val Leu Glu Asn Ile Met Glu Asn Asn Thr Gln Trp Leu Met Lys
            85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
            115                 120                 125

Thr Asn Leu Leu Asn Gln Thr Ala Glu Gln Thr Arg Lys Leu Thr Asp
            130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
            195                 200                 205

Ile Lys Glu Glu Lys Asp Gln Leu Gln Val Leu Val Ser Lys Gln Asn
            210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
            245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
            275                 280                 285
```

```
Lys Ser Gly His Thr Thr Asn Gly Ile Tyr Thr Leu Thr Phe Pro Asn
    290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
        355                 360                 365

Tyr Val Leu Lys Ile His Leu Lys Asp Trp Gly Asn Glu Ala Tyr
    370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
        435                 440                 445

Ala Cys Gly Pro Ser Asn Leu Asn Gly Met Tyr Tyr Pro Gln Arg Gln
450                 455                 460

Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

Ser Gly His His His His His His
            500

<210> SEQ ID NO 107
<211> LENGTH: 506
<212> TYPE: PRT
<213> ORGANISM: Artificial
<220> FEATURE:
<223> OTHER INFORMATION: Human angiopoietin-1 (ANG-1) with leader and
      His-tag

<400> SEQUENCE: 107

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140
```

```
Leu Thr Asp Val Glu Thr Gln Val Leu Asn Gln Thr Ser Arg Leu Glu
145                 150                 155                 160

Ile Gln Leu Leu Glu Asn Ser Leu Ser Thr Tyr Lys Leu Glu Lys Gln
            165                 170                 175

Leu Leu Gln Gln Thr Asn Glu Ile Leu Lys Ile His Glu Lys Asn Ser
            180                 185                 190

Leu Leu Glu His Lys Ile Leu Glu Met Glu Gly Lys His Lys Glu Glu
            195                 200                 205

Leu Asp Thr Leu Lys Glu Glu Lys Glu Asn Leu Gln Gly Leu Val Thr
            210                 215                 220

Arg Gln Thr Tyr Ile Ile Gln Glu Leu Glu Lys Gln Leu Asn Arg Ala
225                 230                 235                 240

Thr Thr Asn Asn Ser Val Leu Gln Lys Gln Gln Leu Glu Leu Met Asp
                245                 250                 255

Thr Val His Asn Leu Val Asn Leu Cys Thr Lys Glu Gly Val Leu Leu
                260                 265                 270

Lys Gly Gly Lys Arg Glu Glu Lys Pro Phe Arg Asp Cys Ala Asp
            275                 280                 285

Val Tyr Gln Ala Gly Phe Asn Lys Ser Gly Ile Tyr Thr Ile Tyr Ile
290                 295                 300

Asn Asn Met Pro Glu Pro Lys Lys Val Phe Cys Asn Met Asp Val Asn
305                 310                 315                 320

Gly Gly Gly Trp Thr Val Ile Gln His Arg Glu Asp Gly Ser Leu Asp
                325                 330                 335

Phe Gln Arg Gly Trp Lys Glu Tyr Lys Met Gly Phe Gly Asn Pro Ser
            340                 345                 350

Gly Glu Tyr Trp Leu Gly Asn Glu Phe Ile Phe Ala Ile Thr Ser Gln
            355                 360                 365

Arg Gln Tyr Met Leu Arg Ile Glu Leu Met Asp Trp Glu Gly Asn Arg
            370                 375                 380

Ala Tyr Ser Gln Tyr Asp Arg Phe His Ile Gly Asn Glu Lys Gln Asn
385                 390                 395                 400

Tyr Arg Leu Tyr Leu Lys Gly His Thr Gly Thr Ala Gly Lys Gln Ser
                405                 410                 415

Ser Leu Ile Leu His Gly Ala Asp Phe Ser Thr Lys Asp Ala Asp Asn
                420                 425                 430

Asp Asn Cys Met Cys Lys Cys Ala Leu Met Leu Thr Gly Gly Trp Trp
            435                 440                 445

Phe Asp Ala Cys Gly Pro Ser Asn Leu Asn Gly Met Phe Tyr Thr Ala
            450                 455                 460

Gly Gln Asn His Gly Lys Leu Asn Gly Ile Lys Trp His Tyr Phe Lys
465                 470                 475                 480

Gly Pro Ser Tyr Ser Leu Arg Ser Thr Thr Met Met Ile Arg Pro Leu
                485                 490                 495

Asp Phe Ser Gly His His His His His His
            500                 505

<210> SEQ ID NO 108
<211> LENGTH: 1124
<212> TYPE: PRT
<213> ORGANISM: Homo sapiens

<400> SEQUENCE: 108

Met Asp Ser Leu Ala Ser Leu Val Leu Cys Gly Val Ser Leu Leu Leu
1               5                   10                  15
```

-continued

```
Ser Gly Thr Val Glu Gly Ala Met Asp Leu Ile Leu Ile Asn Ser Leu
             20                  25                  30

Pro Leu Val Ser Asp Ala Glu Thr Ser Leu Thr Cys Ile Ala Ser Gly
         35                  40                  45

Trp Arg Pro His Glu Pro Ile Thr Ile Gly Arg Asp Phe Glu Ala Leu
 50                  55                  60

Met Asn Gln His Gln Asp Pro Leu Glu Val Thr Gln Asp Val Thr Arg
 65                  70                  75                  80

Glu Trp Ala Lys Lys Val Val Trp Lys Arg Glu Lys Ala Ser Lys Ile
                 85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Thr Pro Lys Ile
            340                 345                 350

Val Asp Leu Pro Asp His Ile Glu Val Asn Ser Gly Lys Phe Asn Pro
        355                 360                 365

Ile Cys Lys Ala Ser Gly Trp Pro Leu Pro Thr Asn Glu Glu Met Thr
    370                 375                 380

Leu Val Lys Pro Asp Gly Thr Val Leu His Pro Lys Asp Phe Asn His
385                 390                 395                 400

Thr Asp His Phe Ser Val Ala Ile Phe Thr Ile His Arg Ile Leu Pro
                405                 410                 415

Pro Asp Ser Gly Val Trp Val Cys Ser Val Asn Thr Val Ala Gly Met
            420                 425                 430

Val Glu Lys Pro Phe Asn Ile Ser Val Lys Val Leu Pro Lys Pro Leu
        435                 440                 445
```

```
Asn Ala Pro Asn Val Ile Asp Thr Gly His Asn Phe Ala Val Ile Asn
    450                 455                 460
Ile Ser Ser Glu Pro Tyr Phe Gly Asp Gly Pro Ile Lys Ser Lys Lys
465                 470                 475                 480
Leu Leu Tyr Lys Pro Val Asn His Tyr Glu Ala Trp Gln His Ile Gln
                485                 490                 495
Val Thr Asn Glu Ile Val Thr Leu Asn Tyr Leu Glu Pro Arg Thr Glu
            500                 505                 510
Tyr Glu Leu Cys Val Gln Leu Val Arg Arg Gly Glu Gly Gly Glu Gly
            515                 520                 525
His Pro Gly Pro Val Arg Arg Phe Thr Thr Ala Ser Ile Gly Leu Pro
        530                 535                 540
Pro Pro Arg Gly Leu Asn Leu Leu Pro Lys Ser Gln Thr Thr Leu Asn
545                 550                 555                 560
Leu Thr Trp Gln Pro Ile Phe Pro Ser Ser Glu Asp Asp Phe Tyr Val
                565                 570                 575
Glu Val Glu Arg Arg Ser Val Gln Lys Ser Asp Gln Gln Asn Ile Lys
            580                 585                 590
Val Pro Gly Asn Leu Thr Ser Val Leu Leu Asn Asn Leu His Pro Arg
        595                 600                 605
Glu Gln Tyr Val Val Arg Ala Arg Val Asn Thr Lys Ala Gln Gly Glu
610                 615                 620
Trp Ser Glu Asp Leu Thr Ala Trp Thr Leu Ser Asp Ile Leu Pro Pro
625                 630                 635                 640
Gln Pro Glu Asn Ile Lys Ile Ser Asn Ile Thr His Ser Ser Ala Val
                645                 650                 655
Ile Ser Trp Thr Ile Leu Asp Gly Tyr Ser Ile Ser Ser Ile Thr Ile
            660                 665                 670
Arg Tyr Lys Val Gln Gly Lys Asn Glu Asp Gln His Val Asp Val Lys
        675                 680                 685
Ile Lys Asn Ala Thr Ile Thr Gln Tyr Gln Leu Lys Gly Leu Glu Pro
        690                 695                 700
Glu Thr Ala Tyr Gln Val Asp Ile Phe Ala Glu Asn Asn Ile Gly Ser
705                 710                 715                 720
Ser Asn Pro Ala Phe Ser His Glu Leu Val Thr Leu Pro Glu Ser Gln
                725                 730                 735
Ala Pro Ala Asp Leu Gly Gly Gly Lys Met Leu Leu Ile Ala Ile Leu
            740                 745                 750
Gly Ser Ala Gly Met Thr Cys Leu Thr Val Leu Leu Ala Phe Leu Ile
        755                 760                 765
Ile Leu Gln Leu Lys Arg Ala Asn Val Gln Arg Arg Met Ala Gln Ala
    770                 775                 780
Phe Gln Asn Val Arg Glu Glu Pro Ala Val Gln Phe Asn Ser Gly Thr
785                 790                 795                 800
Leu Ala Leu Asn Arg Lys Val Lys Asn Asn Pro Asp Pro Thr Ile Tyr
                805                 810                 815
Pro Val Leu Asp Trp Asn Asp Ile Lys Phe Gln Asp Val Ile Gly Glu
            820                 825                 830
Gly Asn Phe Gly Gln Val Leu Lys Ala Arg Ile Lys Lys Asp Gly Leu
        835                 840                 845
Arg Met Asp Ala Ala Ile Lys Arg Met Lys Glu Tyr Ala Ser Lys Asp
850                 855                 860
Asp His Arg Asp Phe Ala Gly Glu Leu Glu Val Leu Cys Lys Leu Gly
```

```
                865                 870                 875                 880
His His Pro Asn Ile Ile Asn Leu Leu Gly Ala Cys Glu His Arg Gly
                    885                 890                 895

Tyr Leu Tyr Leu Ala Ile Glu Tyr Ala Pro His Gly Asn Leu Leu Asp
                900                 905                 910

Phe Leu Arg Lys Ser Arg Val Leu Glu Thr Asp Pro Ala Phe Ala Ile
            915                 920                 925

Ala Asn Ser Thr Ala Ser Thr Leu Ser Ser Gln Gln Leu Leu His Phe
        930                 935                 940

Ala Ala Asp Val Ala Arg Gly Met Asp Tyr Leu Ser Gln Lys Gln Phe
945                 950                 955                 960

Ile His Arg Asp Leu Ala Ala Arg Asn Ile Leu Val Gly Glu Asn Tyr
                965                 970                 975

Val Ala Lys Ile Ala Asp Phe Gly Leu Ser Arg Gly Gln Glu Val Tyr
            980                 985                 990

Val Lys Lys Thr Met Gly Arg Leu Pro Val Arg Trp Met Ala Ile Glu
        995                 1000                1005

Ser Leu Asn Tyr Ser Val Tyr Thr Thr Asn Ser Asp Val Trp Ser
    1010                1015                1020

Tyr Gly Val Leu Leu Trp Glu Ile Val Ser Leu Gly Gly Thr Pro
    1025                1030                1035

Tyr Cys Gly Met Thr Cys Ala Glu Leu Tyr Glu Lys Leu Pro Gln
    1040                1045                1050

Gly Tyr Arg Leu Glu Lys Pro Leu Asn Cys Asp Asp Glu Val Tyr
    1055                1060                1065

Asp Leu Met Arg Gln Cys Trp Arg Glu Lys Pro Tyr Glu Arg Pro
    1070                1075                1080

Ser Phe Ala Gln Ile Leu Val Ser Leu Asn Arg Met Leu Glu Glu
    1085                1090                1095

Arg Lys Thr Tyr Val Asn Thr Thr Leu Tyr Glu Lys Phe Thr Tyr
    1100                1105                1110

Ala Gly Ile Asp Cys Ser Ala Glu Glu Ala Ala
    1115                1120

<210> SEQ ID NO 109
<211> LENGTH: 946
<212> TYPE: PRT
<213> ORGANISM: Artificial
<220> FEATURE:
<223> OTHER INFORMATION: Heavy chain 1 of bispecific, tetravalent single
      chain Fab <VEGF-ANG-2> antibody molecule scFAb-bevacizumab-LC06-
      2620

<400> SEQUENCE: 109

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95
```

```
Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Gly Ser Gly Gly Gly Gly Ser Gln
    450                 455                 460

Pro Gly Leu Thr Gln Pro Pro Ser Val Ser Val Ala Pro Gly Gln Thr
465                 470                 475                 480

Ala Arg Ile Thr Cys Gly Gly Asn Asn Ile Gly Ser Lys Ser Val His
                485                 490                 495

Trp Tyr Gln Gln Lys Pro Gly Gln Ala Pro Val Leu Val Val Tyr Asp
            500                 505                 510

Asp Ser Asp Arg Pro Ser Gly Ile Pro Glu Arg Phe Ser Gly Ser Asn
        515                 520                 525
```

```
Ser Gly Asn Thr Ala Thr Leu Thr Ile Ser Arg Val Glu Ala Gly Asp
            530                 535                 540

Glu Ala Asp Tyr Tyr Cys Gln Val Trp Asp Ser Ser Ser Asp His Tyr
545                 550                 555                 560

Val Phe Gly Thr Gly Thr Lys Val Thr Val Leu Arg Thr Val Ala Ala
                565                 570                 575

Pro Ser Val Phe Ile Phe Pro Pro Ser Asp Glu Gln Leu Lys Ser Gly
                580                 585                 590

Thr Ala Ser Val Val Cys Leu Leu Asn Asn Phe Tyr Pro Arg Glu Ala
            595                 600                 605

Lys Val Gln Trp Lys Val Asp Asn Ala Leu Gln Ser Gly Asn Ser Gln
610                 615                 620

Glu Ser Val Thr Glu Gln Asp Ser Lys Asp Ser Thr Tyr Ser Leu Ser
625                 630                 635                 640

Ser Thr Leu Thr Leu Ser Lys Ala Asp Tyr Glu Lys His Lys Val Tyr
                645                 650                 655

Ala Cys Glu Val Thr His Gln Gly Leu Ser Ser Pro Val Thr Lys Ser
            660                 665                 670

Phe Asn Arg Gly Glu Cys Gly Gly Gly Gly Ser Gly Gly Gly Gly Ser
        675                 680                 685

Gly Gly Gly Gly Ser Gly Gly Gly Ser Gly Gly Gly Gly Ser Gly
690                 695                 700

Gly Gly Gly Ser Gly Gly Gln Val Gln Leu Val Glu Ser Gly Ala Glu
705                 710                 715                 720

Val Lys Lys Pro Gly Ala Ser Val Lys Val Ser Cys Lys Ala Ser Gly
                725                 730                 735

Tyr Thr Phe Thr Gly Tyr Tyr Met His Trp Val Arg Gln Ala Pro Gly
                740                 745                 750

Gln Gly Leu Glu Trp Met Gly Trp Ile Asn Pro Asn Ser Gly Gly Thr
            755                 760                 765

Asn Tyr Ala Gln Lys Phe Gln Gly Arg Val Thr Met Thr Arg Asp Thr
770                 775                 780

Ser Ile Ser Thr Ala Tyr Met Glu Leu Ser Arg Leu Arg Ser Asp Asp
785                 790                 795                 800

Thr Ala Val Tyr Tyr Cys Ala Arg Ser Pro Asn Pro Tyr Tyr Tyr Asp
                805                 810                 815

Ser Ser Gly Tyr Tyr Pro Gly Ala Phe Asp Ile Trp Gly Gln Gly
                820                 825                 830

Thr Met Val Thr Val Ser Ser Ala Ser Thr Lys Gly Pro Ser Val Phe
            835                 840                 845

Pro Leu Ala Pro Ser Ser Lys Ser Thr Ser Gly Gly Thr Ala Ala Leu
            850                 855                 860

Gly Cys Leu Val Lys Asp Tyr Phe Pro Glu Pro Val Thr Val Ser Trp
865                 870                 875                 880

Asn Ser Gly Ala Leu Thr Ser Gly Val His Thr Phe Pro Ala Val Leu
                885                 890                 895

Gln Ser Ser Gly Leu Tyr Ser Leu Ser Ser Val Val Thr Val Pro Ser
            900                 905                 910

Ser Ser Leu Gly Thr Gln Thr Tyr Ile Cys Asn Val Asn His Lys Pro
            915                 920                 925

Ser Asn Thr Lys Val Asp Lys Lys Val Glu Pro Lys Ser Cys Asp Lys
930                 935                 940

Thr His
```

<210> SEQ ID NO 110
<211> LENGTH: 214
<212> TYPE: PRT
<213> ORGANISM: Artificial
<220> FEATURE:
<223> OTHER INFORMATION: Light chain of bispecific, tetravalent single chain Fab <VEGF-ANG-2> antibody molecule scFab-bevacizumab-LC06-2620

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 111
<211> LENGTH: 956
<212> TYPE: PRT
<213> ORGANISM: Artificial
<220> FEATURE:
<223> OTHER INFORMATION: Heavy chain 1 of bispecific, tetravalent single chain Fab <VEGF-ANG-2> antibody molecule scFab-bevacizumab-Ang2i-LC06-2640

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

-continued

```
Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Gly Gly Gly Ser Gly Gly Gly Gly Ser Gly
450                 455                 460

Gly Gly Gly Ser Gly Gly Gly Gly Ser Gln Pro Gly Leu Thr Gln Pro
465                 470                 475                 480

Pro Ser Val Ser Val Ala Pro Gly Gln Thr Ala Arg Ile Thr Cys Gly
                485                 490                 495
```

```
Gly Asn Asn Ile Gly Ser Lys Ser Val His Trp Tyr Gln Gln Lys Pro
                500                 505                 510
Gly Gln Ala Pro Val Leu Val Val Tyr Asp Asp Ser Asp Arg Pro Ser
            515                 520                 525
Gly Ile Pro Glu Arg Phe Ser Gly Ser Asn Ser Gly Asn Thr Ala Thr
        530                 535                 540
Leu Thr Ile Ser Arg Val Glu Ala Gly Asp Glu Ala Asp Tyr Tyr Cys
545                 550                 555                 560
Gln Val Trp Asp Ser Ser Asp His Tyr Val Phe Gly Thr Gly Thr
                565                 570                 575
Lys Val Thr Val Leu Arg Thr Val Ala Ala Pro Ser Val Phe Ile Phe
                580                 585                 590
Pro Pro Ser Asp Glu Gln Leu Lys Ser Gly Thr Ala Ser Val Val Cys
            595                 600                 605
Leu Leu Asn Asn Phe Tyr Pro Arg Glu Ala Lys Val Gln Trp Lys Val
        610                 615                 620
Asp Asn Ala Leu Gln Ser Gly Asn Ser Gln Glu Ser Val Thr Glu Gln
625                 630                 635                 640
Asp Ser Lys Asp Ser Thr Tyr Ser Leu Ser Ser Thr Leu Thr Leu Ser
                645                 650                 655
Lys Ala Asp Tyr Glu Lys His Lys Val Tyr Ala Cys Glu Val Thr His
                660                 665                 670
Gln Gly Leu Ser Ser Pro Val Thr Lys Ser Phe Asn Arg Gly Glu Cys
            675                 680                 685
Gly Gly Gly Gly Ser Gly Gly Gly Gly Ser Gly Gly Gly Gly Ser Gly
        690                 695                 700
Gly Gly Gly Ser Gly Gly Gly Gly Ser Gly Gly Gly Gly Ser Gly Gly
705                 710                 715                 720
Gln Val Gln Leu Val Glu Ser Gly Ala Glu Val Lys Lys Pro Gly Ala
                725                 730                 735
Ser Val Lys Val Ser Cys Lys Ala Ser Gly Tyr Thr Phe Thr Gly Tyr
                740                 745                 750
Tyr Met His Trp Val Arg Gln Ala Pro Gly Gln Gly Leu Glu Trp Met
        755                 760                 765
Gly Trp Ile Asn Pro Asn Ser Gly Gly Thr Asn Tyr Ala Gln Lys Phe
        770                 775                 780
Gln Gly Arg Val Thr Met Thr Arg Asp Thr Ser Ile Ser Thr Ala Tyr
785                 790                 795                 800
Met Glu Leu Ser Arg Leu Arg Ser Asp Asp Thr Ala Val Tyr Tyr Cys
                805                 810                 815
Ala Arg Ser Pro Asn Pro Tyr Tyr Tyr Asp Ser Ser Gly Tyr Tyr Tyr
                820                 825                 830
Pro Gly Ala Phe Asp Ile Trp Gly Gln Gly Thr Met Val Thr Val Ser
            835                 840                 845
Ser Ala Ser Thr Lys Gly Pro Ser Val Phe Pro Leu Ala Pro Ser Ser
        850                 855                 860
Lys Ser Thr Ser Gly Gly Thr Ala Ala Leu Gly Cys Leu Val Lys Asp
865                 870                 875                 880
Tyr Phe Pro Glu Pro Val Thr Val Ser Trp Asn Ser Gly Ala Leu Thr
                885                 890                 895
Ser Gly Val His Thr Phe Pro Ala Val Leu Gln Ser Ser Gly Leu Tyr
                900                 905                 910
Ser Leu Ser Ser Val Val Thr Val Pro Ser Ser Ser Leu Gly Thr Gln
```

915                 920                 925
Thr Tyr Ile Cys Asn Val Asn His Lys Pro Ser Asn Thr Lys Val Asp
            930                 935                 940

Lys Lys Val Glu Pro Lys Ser Cys Asp Lys Thr His
945                 950                 955

<210> SEQ ID NO 112
<211> LENGTH: 214
<212> TYPE: PRT
<213> ORGANISM: Artificial
<220> FEATURE:
<223> OTHER INFORMATION: Light chain of bispecific, tetravalent single
      chain Fab <VEGF-ANG-2> antibody molecule scFab-bevacizumab-Ang2i-
      LC06-2640

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 113
<211> LENGTH: 956
<212> TYPE: PRT
<213> ORGANISM: Artificial
<220> FEATURE:
<223> OTHER INFORMATION: Heavy chain 1 of bispecific, tetravalent single
      chain Fab <VEGF-ANG-2> antibody molecule scFab-bevacizumab-Ang2i-
      LC06-2641

<400> SEQUENCE: 113

Glu Val Gln Leu Val Glu Ser Gly Gly Gly Leu Val Gln Pro Gly Gly
1               5                   10                  15

Ser Leu Arg Leu Ser Cys Ala Ser Gly Tyr Thr Phe Thr Asn Tyr
            20                  25                  30

```
Gly Met Asn Trp Val Arg Gln Ala Pro Gly Lys Gly Leu Glu Trp Val
         35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                 85                  90                  95

Ala Lys Tyr Pro His Tyr Tyr Gly Ser Ser His Trp Tyr Phe Asp Val
             100                 105                 110

Trp Gly Gln Gly Thr Leu Val Thr Val Ser Ser Ala Ser Thr Lys Gly
             115                 120                 125

Pro Ser Val Phe Pro Leu Ala Pro Ser Ser Lys Ser Thr Ser Gly Gly
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                 165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Gln Thr Tyr Ile Cys Asn Val
             195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                 245                 250                 255

Leu Met Ile Ser Arg Thr Pro Glu Val Thr Cys Val Val Val Asp Val
             260                 265                 270

Ser His Glu Asp Pro Glu Val Lys Phe Asn Trp Tyr Val Asp Gly Val
             275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                 325                 330                 335

Pro Ile Glu Lys Thr Ile Ser Lys Ala Lys Gly Gln Pro Arg Glu Pro
             340                 345                 350

Gln Val Tyr Thr Leu Pro Pro Ser Arg Asp Glu Leu Thr Lys Asn Gln
             355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                 405                 410                 415

Thr Val Asp Lys Ser Arg Trp Gln Gln Gly Asn Val Phe Ser Cys Ser
             420                 425                 430

Val Met His Glu Ala Leu His Asn His Tyr Thr Gln Lys Ser Leu Ser
             435                 440                 445

Leu Ser Pro Gly Lys Gly Gly Gly Ser Gly Gly Gly Gly Ser Gly
450                 455                 460
```

```
Gly Gly Gly Ser Gly Gly Gly Ser Gln Pro Gly Leu Thr Gln Pro
465                 470                 475                 480

Pro Ser Val Ser Val Ala Pro Gly Gln Thr Ala Arg Ile Thr Cys Gly
            485                 490                 495

Gly Asn Asn Ile Gly Ser Lys Ser Val His Trp Tyr Gln Gln Lys Pro
        500                 505                 510

Gly Gln Ala Pro Val Leu Val Val Tyr Asp Asp Ser Asp Arg Pro Ser
        515                 520                 525

Gly Ile Pro Glu Arg Phe Ser Gly Ser Asn Ser Gly Asn Thr Ala Thr
        530                 535                 540

Leu Thr Ile Ser Arg Val Glu Ala Gly Asp Glu Ala Asp Tyr Tyr Cys
545                 550                 555                 560

Gln Val Trp Asp Ser Ser Ser Asp His Tyr Val Phe Gly Cys Gly Thr
                565                 570                 575

Lys Val Thr Val Leu Arg Thr Val Ala Ala Pro Ser Val Phe Ile Phe
            580                 585                 590

Pro Pro Ser Asp Glu Gln Leu Lys Ser Gly Thr Ala Ser Val Val Cys
        595                 600                 605

Leu Leu Asn Asn Phe Tyr Pro Arg Glu Ala Lys Val Gln Trp Lys Val
        610                 615                 620

Asp Asn Ala Leu Gln Ser Gly Asn Ser Gln Glu Ser Val Thr Glu Gln
625                 630                 635                 640

Asp Ser Lys Asp Ser Thr Tyr Ser Leu Ser Ser Thr Leu Thr Leu Ser
                645                 650                 655

Lys Ala Asp Tyr Glu Lys His Lys Val Tyr Ala Cys Glu Val Thr His
                660                 665                 670

Gln Gly Leu Ser Ser Pro Val Thr Lys Ser Phe Asn Arg Gly Glu Cys
        675                 680                 685

Gly Gly Gly Gly Ser Gly Gly Gly Ser Gly Gly Gly Gly Ser Gly
        690                 695                 700

Gly Gly Ser Gly Gly Gly Ser Gly Gly Gly Ser Gly Gly
705                 710                 715                 720

Gln Val Gln Leu Val Glu Ser Gly Ala Glu Val Lys Lys Pro Gly Ala
                725                 730                 735

Ser Val Lys Val Ser Cys Lys Ala Ser Gly Tyr Thr Phe Thr Gly Tyr
            740                 745                 750

Tyr Met His Trp Val Arg Gln Ala Pro Gly Gln Cys Leu Glu Trp Met
        755                 760                 765

Gly Trp Ile Asn Pro Asn Ser Gly Gly Thr Asn Tyr Ala Gln Lys Phe
        770                 775                 780

Gln Gly Arg Val Thr Met Thr Arg Asp Thr Ser Ile Ser Thr Ala Tyr
785                 790                 795                 800

Met Glu Leu Ser Arg Leu Arg Ser Asp Asp Thr Ala Val Tyr Tyr Cys
                805                 810                 815

Ala Arg Ser Pro Asn Pro Tyr Tyr Tyr Asp Ser Ser Gly Tyr Tyr Tyr
            820                 825                 830

Pro Gly Ala Phe Asp Ile Trp Gly Gln Gly Thr Met Val Thr Val Ser
        835                 840                 845

Ser Ala Ser Thr Lys Gly Pro Ser Val Phe Pro Leu Ala Pro Ser Ser
        850                 855                 860

Lys Ser Thr Ser Gly Gly Thr Ala Ala Leu Gly Cys Leu Val Lys Asp
865                 870                 875                 880

Tyr Phe Pro Glu Pro Val Thr Val Ser Trp Asn Ser Gly Ala Leu Thr
```

```
                    885                 890                 895
Ser Gly Val His Thr Phe Pro Ala Val Leu Gln Ser Ser Gly Leu Tyr
                900                 905                 910

Ser Leu Ser Ser Val Val Thr Val Pro Ser Ser Ser Leu Gly Thr Gln
                915                 920                 925

Thr Tyr Ile Cys Asn Val Asn His Lys Pro Ser Asn Thr Lys Val Asp
                930                 935                 940

Lys Lys Val Glu Pro Lys Ser Cys Asp Lys Thr His
945                 950                 955

<210> SEQ ID NO 114
<211> LENGTH: 214
<212> TYPE: PRT
<213> ORGANISM: Artificial
<220> FEATURE:
<223> OTHER INFORMATION: Light chain of bispecific, tetravalent single
      chain Fab <VEGF-ANG-2> antibody molecule scFab-bevacizumab-Ang2i-
      LC06-2641

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
        50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 115
<211> LENGTH: 946
<212> TYPE: PRT
<213> ORGANISM: Artificial
<220> FEATURE:
<223> OTHER INFORMATION: Heavy chain 1 of bispecific, trivalent single
      chain Fab <VEGF-ANG-2> antibody molecule bevacizumab-LC06-KiH-C-
      scFab

<400> SEQUENCE: 115
```

-continued

```
Glu Val Gln Leu Val Glu Ser Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
        355                 360                 365

Val Ser Leu Trp Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430
```

```
Val Met His Glu Ala Leu His Asn His Tyr Thr Gln Lys Ser Leu Ser
            435                 440                 445

Leu Ser Pro Gly Lys Gly Gly Gly Ser Gly Gly Gly Gly Ser Gln
        450                 455                 460

Pro Gly Leu Thr Gln Pro Ser Val Ser Val Ala Pro Gly Gln Thr
465                 470                 475                 480

Ala Arg Ile Thr Cys Gly Gly Asn Asn Ile Gly Ser Lys Ser Val His
                485                 490                 495

Trp Tyr Gln Gln Lys Pro Gly Gln Ala Pro Val Leu Val Val Tyr Asp
            500                 505                 510

Asp Ser Asp Arg Pro Ser Gly Ile Pro Glu Arg Phe Ser Gly Ser Asn
            515                 520                 525

Ser Gly Asn Thr Ala Thr Leu Thr Ile Ser Arg Val Glu Ala Gly Asp
        530                 535                 540

Glu Ala Asp Tyr Tyr Cys Gln Val Trp Asp Ser Ser Ser Asp His Tyr
545                 550                 555                 560

Val Phe Gly Thr Gly Thr Lys Val Thr Val Leu Arg Thr Val Ala Ala
                565                 570                 575

Pro Ser Val Phe Ile Phe Pro Pro Ser Asp Glu Gln Leu Lys Ser Gly
            580                 585                 590

Thr Ala Ser Val Val Cys Leu Leu Asn Asn Phe Tyr Pro Arg Glu Ala
            595                 600                 605

Lys Val Gln Trp Lys Val Asp Asn Ala Leu Gln Ser Gly Asn Ser Gln
        610                 615                 620

Glu Ser Val Thr Glu Gln Asp Ser Lys Asp Ser Thr Tyr Ser Leu Ser
625                 630                 635                 640

Ser Thr Leu Thr Leu Ser Lys Ala Asp Tyr Glu Lys His Lys Val Tyr
                645                 650                 655

Ala Cys Glu Val Thr His Gln Gly Leu Ser Ser Pro Val Thr Lys Ser
            660                 665                 670

Phe Asn Arg Gly Glu Cys Gly Gly Gly Gly Ser Gly Gly Gly Gly Ser
        675                 680                 685

Gly Gly Gly Ser Gly Gly Gly Ser Gly Gly Gly Gly Ser Gly
        690                 695                 700

Gly Gly Gly Ser Gly Gly Gln Val Gln Leu Val Glu Ser Gly Ala Glu
705                 710                 715                 720

Val Lys Lys Pro Gly Ala Ser Val Lys Val Ser Cys Lys Ala Ser Gly
                725                 730                 735

Tyr Thr Phe Thr Gly Tyr Tyr Met His Trp Val Arg Gln Ala Pro Gly
            740                 745                 750

Gln Gly Leu Glu Trp Met Gly Trp Ile Asn Pro Asn Ser Gly Gly Thr
            755                 760                 765

Asn Tyr Ala Gln Lys Phe Gln Gly Arg Val Thr Met Thr Arg Asp Thr
        770                 775                 780

Ser Ile Ser Thr Ala Tyr Met Glu Leu Ser Arg Leu Arg Ser Asp Asp
785                 790                 795                 800

Thr Ala Val Tyr Tyr Cys Ala Arg Ser Pro Asn Pro Tyr Tyr Tyr Asp
                805                 810                 815

Ser Ser Gly Tyr Tyr Pro Gly Ala Phe Asp Ile Trp Gly Gln Gly
            820                 825                 830

Thr Met Val Thr Val Ser Ser Ala Ser Thr Lys Gly Pro Ser Val Phe
            835                 840                 845

Pro Leu Ala Pro Ser Ser Lys Ser Thr Ser Gly Gly Thr Ala Ala Leu
```

```
                    850                 855                 860

Gly Cys Leu Val Lys Asp Tyr Phe Pro Glu Pro Val Thr Val Ser Trp
865                 870                 875                 880

Asn Ser Gly Ala Leu Thr Ser Gly Val His Thr Phe Pro Ala Val Leu
                    885                 890                 895

Gln Ser Ser Gly Leu Tyr Ser Leu Ser Ser Val Val Thr Val Pro Ser
                    900                 905                 910

Ser Ser Leu Gly Thr Gln Thr Tyr Ile Cys Asn Val Asn His Lys Pro
                915                 920                 925

Ser Asn Thr Lys Val Asp Lys Lys Val Glu Pro Lys Ser Cys Asp Lys
                930                 935                 940

Thr His
945

<210> SEQ ID NO 116
<211> LENGTH: 453
<212> TYPE: PRT
<213> ORGANISM: Artificial
<220> FEATURE:
<223> OTHER INFORMATION: Heavy chain 2 of bispecific, trivalent single
      chain Fab <VEGF-ANG-2> antibody molecule bevacizumab-LC06-KiH-C-
      scFab

<400> SEQUENCE: 116

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
                20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255
```

-continued

```
Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 117
<211> LENGTH: 214
<212> TYPE: PRT
<213> ORGANISM: Artificial
<220> FEATURE:
<223> OTHER INFORMATION: Light chain of bispecific, trivalent single
      chain Fab <VEGF-ANG-2> antibody molecule bevacizumab-LC06-KiH-C-
      scFab

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 118
<211> LENGTH: 698
<212> TYPE: PRT
<213> ORGANISM: Artificial
<220> FEATURE:
<223> OTHER INFORMATION: Heavy chain 1 of bispecific, trivalent
      <VEGF-ANG-2> antibody molecule bevacizumab-LC06-C-Fab-6CSS

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300
```

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
            325                 330                 335

Pro Ile Glu Lys Thr Ile Ser Lys Ala Lys Gly Gln Pro Arg Glu Pro
            340                 345                 350

Gln Val Tyr Thr Leu Pro Pro Cys Arg Asp Glu Leu Thr Lys Asn Gln
            355                 360                 365

Val Ser Leu Trp Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
            435                 440                 445

Leu Ser Pro Gly Lys Gly Gly Gly Ser Gly Gly Gly Ser Gly
450                 455                 460

Gly Gly Ser Gly Gly Gly Ser Gly Gly Gly Ser Gly
465                 470                 475                 480

Gly Gly Ser Gln Pro Gly Leu Thr Gln Pro Pro Ser Val Ser Val Ala
            485                 490                 495

Pro Gly Gln Thr Ala Arg Ile Thr Cys Gly Gly Asn Asn Ile Gly Ser
            500                 505                 510

Lys Ser Val His Trp Tyr Gln Gln Lys Pro Gly Gln Ala Pro Val Leu
            515                 520                 525

Val Val Tyr Asp Asp Ser Asp Arg Pro Ser Gly Ile Pro Glu Arg Phe
530                 535                 540

Ser Gly Ser Asn Ser Gly Asn Thr Ala Thr Leu Thr Ile Ser Arg Val
545                 550                 555                 560

Glu Ala Gly Asp Glu Ala Asp Tyr Tyr Cys Gln Val Trp Asp Ser Ser
            565                 570                 575

Ser Asp His Tyr Val Phe Gly Cys Gly Thr Lys Val Thr Val Leu Arg
            580                 585                 590

Thr Val Ala Ala Pro Ser Val Phe Ile Phe Pro Pro Ser Asp Glu Gln
            595                 600                 605

Leu Lys Ser Gly Thr Ala Ser Val Val Cys Leu Leu Asn Asn Phe Tyr
610                 615                 620

Pro Arg Glu Ala Lys Val Gln Trp Lys Val Asp Asn Ala Leu Gln Ser
625                 630                 635                 640

Gly Asn Ser Gln Glu Ser Val Thr Glu Gln Asp Ser Lys Asp Ser Thr
            645                 650                 655

Tyr Ser Leu Ser Ser Thr Leu Thr Leu Ser Lys Ala Asp Tyr Glu Lys
            660                 665                 670

His Lys Val Tyr Ala Cys Glu Val Thr His Gln Gly Leu Ser Ser Pro
            675                 680                 685

Val Thr Lys Ser Phe Asn Arg Gly Glu Cys
            690                 695

<210> SEQ ID NO 119
<211> LENGTH: 719
<212> TYPE: PRT

<213> ORGANISM: Artificial
<220> FEATURE:
<223> OTHER INFORMATION: Heavy chain 2 of bispecific, trivalent
      <VEGF-ANG-2> antibody molecule bevacizumab-LC06-C-Fab-6CSS

<400> SEQUENCE: 119

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
    370                 375                 380

Val Glu Trp Glu Ser Asn Gly Gln Pro Glu Asn Asn Tyr Lys Thr Thr
```

```
                385                 390                 395                 400
Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
                435                 440                 445

Leu Ser Pro Gly Lys Gly Gly Gly Gly Ser Gly Gly Gly Gly Ser Gly
            450                 455                 460

Gly Gly Ser Gly Gly Gly Gly Ser Gly Gly Gly Gly Ser Gly Gly
465                 470                 475                 480

Gly Gly Ser Gln Val Gln Leu Val Glu Ser Gly Ala Glu Val Lys Lys
                485                 490                 495

Pro Gly Ala Ser Val Lys Val Ser Cys Lys Ala Ser Gly Tyr Thr Phe
                500                 505                 510

Thr Gly Tyr Tyr Met His Trp Val Arg Gln Ala Pro Gly Gln Cys Leu
            515                 520                 525

Glu Trp Met Gly Trp Ile Asn Pro Asn Ser Gly Gly Thr Asn Tyr Ala
            530                 535                 540

Gln Lys Phe Gln Gly Arg Val Thr Met Thr Arg Asp Thr Ser Ile Ser
545                 550                 555                 560

Thr Ala Tyr Met Glu Leu Ser Arg Leu Arg Ser Asp Asp Thr Ala Val
                565                 570                 575

Tyr Tyr Cys Ala Arg Ser Pro Asn Pro Tyr Tyr Tyr Asp Ser Ser Gly
                580                 585                 590

Tyr Tyr Tyr Pro Gly Ala Phe Asp Ile Trp Gly Gln Gly Thr Met Val
            595                 600                 605

Thr Val Ser Ser Ala Ser Thr Lys Gly Pro Ser Val Phe Pro Leu Ala
610                 615                 620

Pro Ser Ser Lys Ser Thr Ser Gly Gly Thr Ala Ala Leu Gly Cys Leu
625                 630                 635                 640

Val Lys Asp Tyr Phe Pro Glu Pro Val Thr Val Ser Trp Asn Ser Gly
                645                 650                 655

Ala Leu Thr Ser Gly Val His Thr Phe Pro Ala Val Leu Gln Ser Ser
            660                 665                 670

Gly Leu Tyr Ser Leu Ser Ser Val Val Thr Val Pro Ser Ser Ser Leu
            675                 680                 685

Gly Thr Gln Thr Tyr Ile Cys Asn Val Asn His Lys Pro Ser Asn Thr
            690                 695                 700

Lys Val Asp Lys Lys Val Glu Pro Lys Ser Cys Asp Lys Thr His
705                 710                 715

<210> SEQ ID NO 120
<211> LENGTH: 214
<212> TYPE: PRT
<213> ORGANISM: Artificial
<220> FEATURE:
<223> OTHER INFORMATION: Light chain of bispecific, trivalent
      <VEGF-ANG-2> antibody molecule bevacizumab-LC06-C-Fab-6CSS

<400> SEQUENCE: 120

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
                20                  25                  30

Leu Asn Trp Tyr Gln Gln Lys Pro Gly Lys Ala Pro Lys Val Leu Ile
```

```
                35                  40                  45
Tyr Phe Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 121
<211> LENGTH: 459
<212> TYPE: PRT
<213> ORGANISM: Artificial
<220> FEATURE:
<223> OTHER INFORMATION: Heavy chain 1 of bispecific, bivalent domain
      exchanged <VEGF-ANG-2> antibody molecule bevacizumab-LC06-CH1-CL

<400> SEQUENCE: 121

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
```

```
                    180                 185                 190
Ser Leu Ser Ser Val Val Thr Val Pro Ser Ser Leu Gly Thr Gln
            195                 200                 205

Thr Tyr Ile Cys Asn Val Asn His Lys Pro Ser Asn Thr Lys Val Asp
        210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Cys Arg Asp
        355                 360                 365

Glu Leu Thr Lys Asn Gln Val Ser Leu Trp Cys Leu Val Lys Gly Phe
    370                 375                 380

Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
            420                 425                 430

Asn Val Phe Ser Cys Ser Val Met His Glu Ala Leu His Asn His Tyr
        435                 440                 445

Thr Gln Lys Ser Leu Ser Leu Ser Pro Gly Lys
    450                 455

<210> SEQ ID NO 122
<211> LENGTH: 457
<212> TYPE: PRT
<213> ORGANISM: Artificial
<220> FEATURE:
<223> OTHER INFORMATION: Heavy chain 2 of bispecific, bivalent domain
      exchanged <VEGF-ANG-2> antibody molecule bevacizumab-LC06-CH1-CL

<400> SEQUENCE: 122

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Asp Phe Thr His Tyr
            20                  25                  30

Gly Met Asn Trp Val Arg Gln Ala Pro Gly Lys Cys Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
```

```
                85                  90                  95
Ala Lys Tyr Pro Tyr Tyr Gly Thr Ser His Trp Tyr Phe Asp Val
            100                 105                 110

Trp Gly Gln Gly Thr Leu Val Thr Val Ser Ser Ala Ser Val Ala Ala
        115                 120                 125

Pro Ser Val Phe Ile Phe Pro Pro Ser Asp Glu Gln Leu Lys Ser Gly
        130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
        210                 215                 220

Phe Asn Arg Gly Glu Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
        290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Cys Thr Leu Pro Pro Ser Arg Asp Glu Leu
        355                 360                 365

Thr Lys Asn Gln Val Ser Leu Ser Cys Ala Val Lys Gly Phe Tyr Pro
        370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Val Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 123
<211> LENGTH: 215
<212> TYPE: PRT
<213> ORGANISM: Artificial
<220> FEATURE:
<223> OTHER INFORMATION: Light chain 1 of bispecific, bivalent domain
      exchanged <VEGF-ANG-2> antibody molecule bevacizumab-LC06-CH1-CL
```

<400> SEQUENCE: 123

```
Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Thr Gly Thr Lys Val Thr Leu Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 124
<211> LENGTH: 212
<212> TYPE: PRT
<213> ORGANISM: Artificial
<220> FEATURE:
<223> OTHER INFORMATION: Light chain 2 of bispecific, bivalent domain exchanged <VEGF-ANG-2> antibody molecule bevacizumab-LC06-CH1-CL

<400> SEQUENCE: 124

```
Asp Ile Gln Leu Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Cys Gly Thr Lys Val Glu Ile Lys Ser Ser Ala Ser Thr
                100                 105                 110

Lys Gly Pro Ser Val Phe Pro Leu Ala Pro Ser Ser Lys Ser Thr Ser
            115                 120                 125

Gly Gly Thr Ala Ala Leu Gly Cys Leu Val Lys Asp Tyr Phe Pro Glu
```

```
                130               135               140
Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
                180                 185                 190

Asn Val Asn His Lys Pro Ser Asn Thr Lys Val Asp Lys Lys Val Glu
                195                 200                 205

Pro Lys Ser Cys
            210

<210> SEQ ID NO 125
<211> LENGTH: 459
<212> TYPE: PRT
<213> ORGANISM: Artificial
<220> FEATURE:
<223> OTHER INFORMATION: Heavy chain 1 of bispecific, bivalent domain
      exchanged <VEGF-ANG-2> antibody molecule bevacizumab-LC06-VH-VL

<400> SEQUENCE: 125

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
                35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
                100                 105                 110

Pro Gly Ala Phe Asp Ile Trp Gly Gln Gly Thr Met Val Thr Val Ser
                115                 120                 125

Ser Ala Ser Thr Lys Gly Pro Ser Val Phe Pro Leu Ala Pro Ser Ser
            130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
                180                 185                 190

Ser Leu Ser Ser Val Val Thr Val Pro Ser Ser Ser Leu Gly Thr Gln
                195                 200                 205

Thr Tyr Ile Cys Asn Val Asn His Lys Pro Ser Asn Thr Lys Val Asp
            210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
                260                 265                 270

Cys Val Val Val Asp Val Ser His Glu Asp Pro Glu Val Lys Phe Asn
```

```
                275                 280                 285
Trp Tyr Val Asp Gly Val Glu Val His Asn Ala Lys Thr Lys Pro Arg
290                 295                 300
Glu Glu Gln Tyr Asn Ser Thr Tyr Arg Val Val Ser Val Leu Thr Val
305                 310                 315                 320
Leu His Gln Asp Trp Leu Asn Gly Lys Glu Tyr Lys Cys Lys Val Ser
                325                 330                 335
Asn Lys Ala Leu Pro Ala Pro Ile Glu Lys Thr Ile Ser Lys Ala Lys
                340                 345                 350
Gly Gln Pro Arg Glu Pro Gln Val Tyr Thr Leu Pro Pro Cys Arg Asp
                355                 360                 365
Glu Leu Thr Lys Asn Gln Val Ser Leu Trp Cys Leu Val Lys Gly Phe
                370                 375                 380
Tyr Pro Ser Asp Ile Ala Val Glu Trp Glu Ser Asn Gly Gln Pro Glu
385                 390                 395                 400
Asn Asn Tyr Lys Thr Thr Pro Pro Val Leu Asp Ser Asp Gly Ser Phe
                405                 410                 415
Phe Leu Tyr Ser Lys Leu Thr Val Asp Lys Ser Arg Trp Gln Gln Gly
                420                 425                 430
Asn Val Phe Ser Cys Ser Val Met His Glu Ala Leu His Asn His Tyr
                435                 440                 445
Thr Gln Lys Ser Leu Ser Leu Ser Pro Gly Lys
                450                 455

<210> SEQ ID NO 126
<211> LENGTH: 439
<212> TYPE: PRT
<213> ORGANISM: Artificial
<220> FEATURE:
<223> OTHER INFORMATION: Heavy chain 2 of bispecific, bivalent domain
      exchanged <VEGF-ANG-2> antibody molecule bevacizumab-LC06-VH-VL

<400> SEQUENCE: 126

Asp Ile Gln Met Thr Gln Ser Pro Ser Ser Leu Ser Ala Ser Val Gly
1               5                   10                  15
Asp Arg Val Thr Ile Thr Cys Ser Ala Ser Gln Asp Ile Ser Asn Tyr
                20                  25                  30
Leu Asn Trp Tyr Gln Gln Lys Pro Gly Lys Ala Pro Lys Val Leu Ile
            35                  40                  45
Tyr Phe Thr Ser Ser Leu His Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Tyr Ser Thr Val Pro Trp
                85                  90                  95
Thr Phe Gly Gln Gly Thr Lys Val Glu Ile Lys Ser Ser Ala Ser Thr
                100                 105                 110
Lys Gly Pro Ser Val Phe Pro Leu Ala Pro Ser Ser Lys Ser Thr Ser
            115                 120                 125
Gly Gly Thr Ala Ala Leu Gly Cys Leu Val Lys Asp Tyr Phe Pro Glu
        130                 135                 140
Pro Val Thr Val Ser Trp Asn Ser Gly Ala Leu Thr Ser Gly Val His
145                 150                 155                 160
Thr Phe Pro Ala Val Leu Gln Ser Ser Gly Leu Tyr Ser Leu Ser Ser
                165                 170                 175
Val Val Thr Val Pro Ser Ser Ser Leu Gly Thr Gln Thr Tyr Ile Cys
```

```
                    180                 185                 190
Asn Val Asn His Lys Pro Ser Asn Thr Lys Val Asp Lys Lys Val Glu
                195                 200                 205
Pro Lys Ser Cys Asp Lys Thr His Thr Cys Pro Pro Cys Pro Ala Pro
            210                 215                 220
Glu Leu Leu Gly Gly Pro Ser Val Phe Leu Phe Pro Pro Lys Pro Lys
225                 230                 235                 240
Asp Thr Leu Met Ile Ser Arg Thr Pro Glu Val Thr Cys Val Val Val
                245                 250                 255
Asp Val Ser His Glu Asp Pro Glu Val Lys Phe Asn Trp Tyr Val Asp
            260                 265                 270
Gly Val Glu Val His Asn Ala Lys Thr Lys Pro Arg Glu Glu Gln Tyr
        275                 280                 285
Asn Ser Thr Tyr Arg Val Val Ser Val Leu Thr Val Leu His Gln Asp
        290                 295                 300
Trp Leu Asn Gly Lys Glu Tyr Lys Cys Lys Val Ser Asn Lys Ala Leu
305                 310                 315                 320
Pro Ala Pro Ile Glu Lys Thr Ile Ser Lys Ala Lys Gly Gln Pro Arg
                325                 330                 335
Glu Pro Gln Val Cys Thr Leu Pro Pro Ser Arg Asp Glu Leu Thr Lys
            340                 345                 350
Asn Gln Val Ser Leu Ser Cys Ala Val Lys Gly Phe Tyr Pro Ser Asp
        355                 360                 365
Ile Ala Val Glu Trp Glu Ser Asn Gly Gln Pro Glu Asn Asn Tyr Lys
        370                 375                 380
Thr Thr Pro Pro Val Leu Asp Ser Asp Gly Ser Phe Phe Leu Val Ser
385                 390                 395                 400
Lys Leu Thr Val Asp Lys Ser Arg Trp Gln Gln Gly Asn Val Phe Ser
                405                 410                 415
Cys Ser Val Met His Glu Ala Leu His Asn His Tyr Thr Gln Lys Ser
            420                 425                 430
Leu Ser Leu Ser Pro Gly Lys
        435

<210> SEQ ID NO 127
<211> LENGTH: 215
<212> TYPE: PRT
<213> ORGANISM: Artificial
<220> FEATURE:
<223> OTHER INFORMATION: Light chain 1 of bispecific, bivalent domain
      exchanged <VEGF-ANG-2> antibody molecule bevacizumab-LC06-VH-VL

<400> SEQUENCE: 127

Gln Pro Gly Leu Thr Gln Pro Pro Ser Val Ser Val Ala Pro Gly Gln
1               5                   10                  15
Thr Ala Arg Ile Thr Cys Gly Gly Asn Asn Ile Gly Ser Lys Ser Val
                20                  25                  30
His Trp Tyr Gln Gln Lys Pro Gly Gln Ala Pro Val Leu Val Val Tyr
            35                  40                  45
Asp Asp Ser Asp Arg Pro Ser Gly Ile Pro Glu Arg Phe Ser Gly Ser
        50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asp Ser Ser Ser Asp His
                85                  90                  95
Tyr Val Phe Gly Thr Gly Thr Lys Val Thr Val Leu Arg Thr Val Ala
```

```
            100                 105                 110
Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 128
<211> LENGTH: 230
<212> TYPE: PRT
<213> ORGANISM: Artificial
<220> FEATURE:
<223> OTHER INFORMATION: Light chain 2 of bispecific, bivalent domain
      exchanged <VEGF-ANG-2> antibody molecule bevacizumab-LC06-VH-VL

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Gly Ser Ser His Trp Tyr Phe Asp Val
            100                 105                 110

Trp Gly Gln Gly Thr Leu Val Thr Val Ser Ser Ala Ser Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly Glu Cys
225                 230
```

-continued

```
<210> SEQ ID NO 129
<211> LENGTH: 459
<212> TYPE: PRT
<213> ORGANISM: Artificial
<220> FEATURE:
<223> OTHER INFORMATION: Heavy chain 1 of bispecific, bivalent domain
      exchanged <VEGF-ANG-2> antibody molecule bevacizumab-LC06-VH-VL-SS

<400> SEQUENCE: 129

Gln Val Gln Leu Val Glu Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Cys Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Tyr Asp Ser Ser Gly Tyr Tyr Tyr
            100                 105                 110

Pro Gly Ala Phe Asp Ile Trp Gly Gln Gly Thr Met Val Thr Val Ser
        115                 120                 125

Ser Ala Ser Thr Lys Gly Pro Ser Val Phe Pro Leu Ala Pro Ser Ser
    130                 135                 140

Lys Ser Thr Ser Gly Gly Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Gln
        195                 200                 205

Thr Tyr Ile Cys Asn Val Asn His Lys Pro Ser Asn Thr Lys Val Asp
    210                 215                 220

Lys Lys Val Glu Pro Lys Ser Cys Asp Lys Thr His Thr Cys Pro Pro
225                 230                 235                 240

Cys Pro Ala Pro Glu Leu Leu Gly Gly Pro Ser Val Phe Leu Phe Pro
                245                 250                 255

Pro Lys Pro Lys Asp Thr Leu Met Ile Ser Arg Thr Pro Glu Val Thr
            260                 265                 270

Cys Val Val Val Asp Val Ser His Glu Asp Pro Glu Val Lys Phe Asn
        275                 280                 285

Trp Tyr Val Asp Gly Val Glu Val His Asn Ala Lys Thr Lys Pro Arg
    290                 295                 300

Glu Glu Gln Tyr Asn Ser Thr Tyr Arg Val Val Ser Val Leu Thr Val
305                 310                 315                 320

Leu His Gln Asp Trp Leu Asn Gly Lys Glu Tyr Lys Cys Lys Val Ser
                325                 330                 335

Asn Lys Ala Leu Pro Ala Pro Ile Glu Lys Thr Ile Ser Lys Ala Lys
            340                 345                 350

Gly Gln Pro Arg Glu Pro Gln Val Tyr Thr Leu Pro Pro Cys Arg Asp
        355                 360                 365

Glu Leu Thr Lys Asn Gln Val Ser Leu Trp Cys Leu Val Lys Gly Phe
```

```
                    370                 375                 380
Tyr Pro Ser Asp Ile Ala Val Glu Trp Glu Ser Asn Gly Gln Pro Glu
385                 390                 395                 400

Asn Asn Tyr Lys Thr Thr Pro Pro Val Leu Asp Ser Asp Gly Ser Phe
                405                 410                 415

Phe Leu Tyr Ser Lys Leu Thr Val Asp Lys Ser Arg Trp Gln Gln Gly
                420                 425                 430

Asn Val Phe Ser Cys Ser Val Met His Glu Ala Leu His Asn His Tyr
                435                 440                 445

Thr Gln Lys Ser Leu Ser Leu Ser Pro Gly Lys
                450                 455

<210> SEQ ID NO 130
<211> LENGTH: 439
<212> TYPE: PRT
<213> ORGANISM: Artificial
<220> FEATURE:
<223> OTHER INFORMATION: Heavy chain 2 of bispecific, bivalent domain
      exchanged <VEGF-ANG-2> antibody molecule bevacizumab-LC06-VH-VL-SS

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Asp Lys Thr His Thr Cys Pro Pro Cys Pro Ala Pro
    210                 215                 220

Glu Leu Leu Gly Gly Pro Ser Val Phe Leu Phe Pro Pro Lys Pro Lys
225                 230                 235                 240

Asp Thr Leu Met Ile Ser Arg Thr Pro Glu Val Thr Cys Val Val Val
                245                 250                 255

Asp Val Ser His Glu Asp Pro Glu Val Lys Phe Asn Trp Tyr Val Asp
            260                 265                 270

Gly Val Glu Val His Asn Ala Lys Thr Lys Pro Arg Glu Glu Gln Tyr
```

Asn Ser Thr Tyr Arg Val Val Ser Val Leu Thr Val Leu His Gln Asp
            275                 280                 285
290                                 295                 300

Trp Leu Asn Gly Lys Glu Tyr Lys Cys Lys Val Ser Asn Lys Ala Leu
305                 310                 315                 320

Pro Ala Pro Ile Glu Lys Thr Ile Ser Lys Ala Lys Gly Gln Pro Arg
                325                 330                 335

Glu Pro Gln Val Cys Thr Leu Pro Pro Ser Arg Asp Glu Leu Thr Lys
            340                 345                 350

Asn Gln Val Ser Leu Ser Cys Ala Val Lys Gly Phe Tyr Pro Ser Asp
            355                 360                 365

Ile Ala Val Glu Trp Glu Ser Asn Gly Gln Pro Glu Asn Asn Tyr Lys
        370                 375                 380

Thr Thr Pro Pro Val Leu Asp Ser Asp Gly Ser Phe Phe Leu Val Ser
385                 390                 395                 400

Lys Leu Thr Val Asp Lys Ser Arg Trp Gln Gln Gly Asn Val Phe Ser
                405                 410                 415

Cys Ser Val Met His Glu Ala Leu His Asn His Tyr Thr Gln Lys Ser
            420                 425                 430

Leu Ser Leu Ser Pro Gly Lys
        435

<210> SEQ ID NO 131
<211> LENGTH: 215
<212> TYPE: PRT
<213> ORGANISM: Artificial
<220> FEATURE:
<223> OTHER INFORMATION: Light chain 1 of bispecific, bivalent domain
      exchanged <VEGF-ANG-2> antibody molecule bevacizumab-
      LC06-VH-VL-SS

<400> SEQUENCE: 131

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Cys Gly Thr Lys Val Thr Val Leu Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

```
Tyr Ala Cys Glu Val Thr His Gln Gly Leu Ser Ser Pro Val Thr Lys
        195                 200                 205

Ser Phe Asn Arg Gly Glu Cys
    210                 215
```

<210> SEQ ID NO 132
<211> LENGTH: 230
<212> TYPE: PRT
<213> ORGANISM: Artificial
<220> FEATURE:
<223> OTHER INFORMATION: Light chain 2 of bispecific, bivalent domain
      exchanged <VEGF-ANG-2> antibody molecule bevacizumab-
      LC06-VH-VL-SS

<400> SEQUENCE: 132

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Val Ala Ala
        115                 120                 125

Pro Ser Val Phe Ile Phe Pro Pro Ser Asp Glu Gln Leu Lys Ser Gly
    130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
    210                 215                 220

Phe Asn Arg Gly Glu Cys
225                 230
```

<210> SEQ ID NO 133
<211> LENGTH: 706
<212> TYPE: PRT
<213> ORGANISM: Artificial
<220> FEATURE:
<223> OTHER INFORMATION: Heavy chain 1 of bispecific, bivalent ScFab-Fc
      fusion <VEGF-ANG-2> antibody molecule bevacizumab-LC06-N-scFab

<400> SEQUENCE: 133

```
Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30
```

-continued

```
His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Ser Ser Ser Asp His
                 85                  90                  95

Tyr Val Phe Gly Thr Gly Thr Lys Val Thr Val Leu Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys Gly Gly Gly Ser Gly Gly Gly Gly
210                 215                 220

Ser Gly Gly Gly Gly Ser Gly Gly Gly Gly Ser Gly Gly Gly Gly Ser
225                 230                 235                 240

Gly Gly Gly Gly Ser Gly Gly Gln Val Gln Leu Val Glu Ser Gly Ala
                245                 250                 255

Glu Val Lys Lys Pro Gly Ala Ser Val Lys Val Ser Cys Lys Ala Ser
            260                 265                 270

Gly Tyr Thr Phe Thr Gly Tyr Tyr Met His Trp Val Arg Gln Ala Pro
            275                 280                 285

Gly Gln Gly Leu Glu Trp Met Gly Trp Ile Asn Pro Asn Ser Gly Gly
290                 295                 300

Thr Asn Tyr Ala Gln Lys Phe Gln Gly Arg Val Thr Met Thr Arg Asp
305                 310                 315                 320

Thr Ser Ile Ser Thr Ala Tyr Met Glu Leu Ser Arg Leu Arg Ser Asp
                325                 330                 335

Asp Thr Ala Val Tyr Tyr Cys Ala Arg Ser Pro Asn Pro Tyr Tyr Tyr
            340                 345                 350

Asp Ser Ser Gly Tyr Tyr Pro Gly Ala Phe Asp Ile Trp Gly Gln
            355                 360                 365

Gly Thr Met Val Thr Val Ser Ser Ala Ser Thr Lys Gly Pro Ser Val
370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
            435                 440                 445

Ser Ser Ser Leu Gly Thr Gln Thr Tyr Ile Cys Asn Val Asn His Lys
450                 455                 460
```

```
Pro Ser Asn Thr Lys Val Asp Lys Lys Val Glu Pro Lys Ser Cys Asp
465                 470                 475                 480

Lys Thr His Thr Cys Pro Pro Cys Pro Ala Pro Glu Leu Leu Gly Gly
            485                 490                 495

Pro Ser Val Phe Leu Phe Pro Pro Lys Pro Lys Asp Thr Leu Met Ile
        500                 505                 510

Ser Arg Thr Pro Glu Val Thr Cys Val Val Val Asp Val Ser His Glu
    515                 520                 525

Asp Pro Glu Val Lys Phe Asn Trp Tyr Val Asp Gly Val Glu Val His
530                 535                 540

Asn Ala Lys Thr Lys Pro Arg Glu Glu Gln Tyr Asn Ser Thr Tyr Arg
545                 550                 555                 560

Val Val Ser Val Leu Thr Val Leu His Gln Asp Trp Leu Asn Gly Lys
                565                 570                 575

Glu Tyr Lys Cys Lys Val Ser Asn Lys Ala Leu Pro Ala Pro Ile Glu
            580                 585                 590

Lys Thr Ile Ser Lys Ala Lys Gly Gln Pro Arg Glu Pro Gln Val Tyr
        595                 600                 605

Thr Leu Pro Pro Cys Arg Asp Glu Leu Thr Lys Asn Gln Val Ser Leu
    610                 615                 620

Trp Cys Leu Val Lys Gly Phe Tyr Pro Ser Asp Ile Ala Val Glu Trp
625                 630                 635                 640

Glu Ser Asn Gly Gln Pro Glu Asn Asn Tyr Lys Thr Thr Pro Pro Val
                645                 650                 655

Leu Asp Ser Asp Gly Ser Phe Phe Leu Tyr Ser Lys Leu Thr Val Asp
            660                 665                 670

Lys Ser Arg Trp Gln Gln Gly Asn Val Phe Ser Cys Ser Val Met His
        675                 680                 685

Glu Ala Leu His Asn His Tyr Thr Gln Lys Ser Leu Ser Leu Ser Pro
    690                 695                 700

Gly Lys
705

<210> SEQ ID NO 134
<211> LENGTH: 699
<212> TYPE: PRT
<213> ORGANISM: Artificial
<220> FEATURE:
<223> OTHER INFORMATION: Heavy chain 2 of bispecific, bivalent ScFab-Fc
      fusion <VEGF-ANG-2> antibody molecule bevacizumab-LC06-N-scFab

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110
```

-continued

```
Pro Ser Val Phe Ile Phe Pro Pro Ser Asp Glu Gln Leu Lys Ser Gly
    115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Gly Gly Gly Ser Gly Gly Gly Gly Ser
    210                 215                 220
Gly Gly Gly Gly Ser Gly Gly Gly Ser Gly Gly Gly Ser Gly
225                 230                 235                 240
Gly Gly Gly Ser Gly Gly Glu Val Gln Leu Val Glu Ser Gly Gly Gly
                245                 250                 255
Leu Val Gln Pro Gly Gly Ser Leu Arg Leu Ser Cys Ala Ala Ser Gly
            260                 265                 270
Tyr Thr Phe Thr Asn Tyr Gly Met Asn Trp Val Arg Gln Ala Pro Gly
        275                 280                 285
Lys Gly Leu Glu Trp Val Gly Trp Ile Asn Thr Tyr Thr Gly Glu Pro
    290                 295                 300
Thr Tyr Ala Ala Asp Phe Lys Arg Arg Phe Thr Phe Ser Leu Asp Thr
305                 310                 315                 320
Ser Lys Ser Thr Ala Tyr Leu Gln Met Asn Ser Leu Arg Ala Glu Asp
                325                 330                 335
Thr Ala Val Tyr Tyr Cys Ala Lys Tyr Pro His Tyr Tyr Gly Ser Ser
            340                 345                 350
His Trp Tyr Phe Asp Val Trp Gly Gln Gly Thr Leu Val Thr Val Ser
        355                 360                 365
Ser Ala Ser Thr Lys Gly Pro Ser Val Phe Pro Leu Ala Pro Ser Ser
    370                 375                 380
Lys Ser Thr Ser Gly Gly Thr Ala Ala Leu Gly Cys Leu Val Lys Asp
385                 390                 395                 400
Tyr Phe Pro Glu Pro Val Thr Val Ser Trp Asn Ser Gly Ala Leu Thr
                405                 410                 415
Ser Gly Val His Thr Phe Pro Ala Val Leu Gln Ser Ser Gly Leu Tyr
            420                 425                 430
Ser Leu Ser Ser Val Val Thr Val Pro Ser Ser Ser Leu Gly Thr Gln
        435                 440                 445
Thr Tyr Ile Cys Asn Val Asn His Lys Pro Ser Asn Thr Lys Val Asp
    450                 455                 460
Lys Lys Val Glu Pro Lys Ser Cys Asp Lys Thr His Thr Cys Pro Pro
465                 470                 475                 480
Cys Pro Ala Pro Glu Leu Leu Gly Gly Pro Ser Val Phe Leu Phe Pro
                485                 490                 495
Pro Lys Pro Lys Asp Thr Leu Met Ile Ser Arg Thr Pro Glu Val Thr
            500                 505                 510
Cys Val Val Val Asp Val Ser His Glu Asp Pro Glu Val Lys Phe Asn
        515                 520                 525
Trp Tyr Val Asp Gly Val Glu Val His Asn Ala Lys Thr Lys Pro Arg
    530                 535                 540
```

Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
            580                 585                 590

Gly Gln Pro Arg Glu Pro Gln Val Cys Thr Leu Pro Pro Ser Arg Asp
        595                 600                 605

Glu Leu Thr Lys Asn Gln Val Ser Leu Ser Cys Ala Val Lys Gly Phe
    610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Val Ser Lys Leu Thr Val Asp Lys Ser Arg Trp Gln Gln Gly
            660                 665                 670

Asn Val Phe Ser Cys Ser Val Met His Glu Ala Leu His Asn His Tyr
        675                 680                 685

Thr Gln Lys Ser Leu Ser Leu Ser Pro Gly Lys
    690                 695

<210> SEQ ID NO 135
<211> LENGTH: 706
<212> TYPE: PRT
<213> ORGANISM: Artificial
<220> FEATURE:
<223> OTHER INFORMATION: Heavy chain 1 of bispecific, bivalent ScFab-Fc
      fusion <VEGF-ANG-2> antibody molecule bevacizumab-LC06-N-scFabSS

<400> SEQUENCE: 135

Gln Pro Gly Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Tyr Val Phe Gly Cys Gly Thr Lys Val Thr Val Leu Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

-continued

Ser Phe Asn Arg Gly Glu Cys Gly Gly Gly Ser Gly Gly Gly
210                 215                 220

Ser Gly Gly Gly Ser Gly Gly Gly Ser Gly Gly Gly Ser
225             230              235              240

Gly Gly Gly Gly Ser Gly Gly Gln Val Gln Leu Val Glu Ser Gly Ala
            245                 250                 255

Glu Val Lys Lys Pro Gly Ala Ser Val Lys Val Ser Cys Lys Ala Ser
        260                 265                 270

Gly Tyr Thr Phe Thr Gly Tyr Tyr Met His Trp Val Arg Gln Ala Pro
        275                 280                 285

Gly Gln Cys Leu Glu Trp Met Gly Trp Ile Asn Pro Asn Ser Gly Gly
        290                 295                 300

Thr Asn Tyr Ala Gln Lys Phe Gln Gly Arg Val Thr Met Thr Arg Asp
305                 310                 315                 320

Thr Ser Ile Ser Thr Ala Tyr Met Glu Leu Ser Arg Leu Arg Ser Asp
                325                 330                 335

Asp Thr Ala Val Tyr Tyr Cys Ala Arg Ser Pro Asn Pro Tyr Tyr Tyr
            340                 345                 350

Asp Ser Ser Gly Tyr Tyr Pro Gly Ala Phe Asp Ile Trp Gly Gln
        355                 360                 365

Gly Thr Met Val Thr Val Ser Ser Ala Ser Thr Lys Gly Pro Ser Val
370                 375                 380

Phe Pro Leu Ala Pro Ser Ser Lys Ser Thr Ser Gly Gly Thr Ala Ala
385                 390                 395                 400

Leu Gly Cys Leu Val Lys Asp Tyr Phe Pro Glu Pro Val Thr Val Ser
                405                 410                 415

Trp Asn Ser Gly Ala Leu Thr Ser Gly Val His Thr Phe Pro Ala Val
            420                 425                 430

Leu Gln Ser Ser Gly Leu Tyr Ser Leu Ser Ser Val Val Thr Val Pro
        435                 440                 445

Ser Ser Ser Leu Gly Thr Gln Thr Tyr Ile Cys Asn Val Asn His Lys
    450                 455                 460

Pro Ser Asn Thr Lys Val Asp Lys Lys Val Glu Pro Lys Ser Cys Asp
465                 470                 475                 480

Lys Thr His Thr Cys Pro Pro Cys Pro Ala Pro Glu Leu Leu Gly Gly
                485                 490                 495

Pro Ser Val Phe Leu Phe Pro Pro Lys Pro Lys Asp Thr Leu Met Ile
            500                 505                 510

Ser Arg Thr Pro Glu Val Thr Cys Val Val Val Asp Val Ser His Glu
        515                 520                 525

Asp Pro Glu Val Lys Phe Asn Trp Tyr Val Asp Gly Val Glu Val His
    530                 535                 540

Asn Ala Lys Thr Lys Pro Arg Glu Glu Gln Tyr Asn Ser Thr Tyr Arg
545                 550                 555                 560

Val Val Ser Val Leu Thr Val Leu His Gln Asp Trp Leu Asn Gly Lys
                565                 570                 575

Glu Tyr Lys Cys Lys Val Ser Asn Lys Ala Leu Pro Ala Pro Ile Glu
            580                 585                 590

Lys Thr Ile Ser Lys Ala Lys Gly Gln Pro Arg Glu Pro Gln Val Tyr
        595                 600                 605

Thr Leu Pro Pro Cys Arg Asp Glu Leu Thr Lys Asn Gln Val Ser Leu
    610                 615                 620

Trp Cys Leu Val Lys Gly Phe Tyr Pro Ser Asp Ile Ala Val Glu Trp
625                 630                 635                 640

-continued

Glu Ser Asn Gly Gln Pro Glu Asn Asn Tyr Lys Thr Thr Pro Pro Val
                645                 650                 655

Leu Asp Ser Asp Gly Ser Phe Phe Leu Tyr Ser Lys Leu Thr Val Asp
            660                 665                 670

Lys Ser Arg Trp Gln Gln Gly Asn Val Phe Ser Cys Ser Val Met His
        675                 680                 685

Glu Ala Leu His Asn His Tyr Thr Gln Lys Ser Leu Ser Leu Ser Pro
    690                 695                 700

Gly Lys
705

<210> SEQ ID NO 136
<211> LENGTH: 699
<212> TYPE: PRT
<213> ORGANISM: Artificial
<220> FEATURE:
<223> OTHER INFORMATION: Heavy chain 2 of bispecific, bivalent ScFab-Fc
      fusion <VEGF-ANG-2> antibody molecule bevacizumab-LC06-N-scFabSS

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Cys Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser
    210                 215                 220

Gly Gly Gly Gly Ser Gly Gly Gly Ser Gly Gly Gly Ser Gly
225                 230                 235                 240

Gly Gly Gly Ser Gly Gly Glu Val Gln Leu Val Glu Ser Gly Gly
                245                 250                 255

Leu Val Gln Pro Gly Gly Ser Leu Arg Leu Ser Cys Ala Ala Ser Gly
            260                 265                 270

Tyr Thr Phe Thr Asn Tyr Gly Met Asn Trp Val Arg Gln Ala Pro Gly
        275                 280                 285

-continued

```
Lys Cys Leu Glu Trp Val Gly Trp Ile Asn Thr Tyr Thr Gly Glu Pro
290                 295                 300

Thr Tyr Ala Ala Asp Phe Lys Arg Arg Phe Thr Phe Ser Leu Asp Thr
305                 310                 315                 320

Ser Lys Ser Thr Ala Tyr Leu Gln Met Asn Ser Leu Arg Ala Glu Asp
                325                 330                 335

Thr Ala Val Tyr Tyr Cys Ala Lys Tyr Pro His Tyr Tyr Gly Ser Ser
                340                 345                 350

His Trp Tyr Phe Asp Val Trp Gly Gln Gly Thr Leu Val Thr Val Ser
                355                 360                 365

Ser Ala Ser Thr Lys Gly Pro Ser Val Phe Pro Leu Ala Pro Ser Ser
370                 375                 380

Lys Ser Thr Ser Gly Gly Thr Ala Ala Leu Gly Cys Leu Val Lys Asp
385                 390                 395                 400

Tyr Phe Pro Glu Pro Val Thr Val Ser Trp Asn Ser Gly Ala Leu Thr
                405                 410                 415

Ser Gly Val His Thr Phe Pro Ala Val Leu Gln Ser Ser Gly Leu Tyr
                420                 425                 430

Ser Leu Ser Ser Val Val Thr Val Pro Ser Ser Ser Leu Gly Thr Gln
                435                 440                 445

Thr Tyr Ile Cys Asn Val Asn His Lys Pro Ser Asn Thr Lys Val Asp
                450                 455                 460

Lys Lys Val Glu Pro Lys Ser Cys Asp Lys Thr His Thr Cys Pro Pro
465                 470                 475                 480

Cys Pro Ala Pro Glu Leu Leu Gly Gly Pro Ser Val Phe Leu Phe Pro
                485                 490                 495

Pro Lys Pro Lys Asp Thr Leu Met Ile Ser Arg Thr Pro Glu Val Thr
                500                 505                 510

Cys Val Val Val Asp Val Ser His Glu Asp Pro Glu Val Lys Phe Asn
                515                 520                 525

Trp Tyr Val Asp Gly Val Glu Val His Asn Ala Lys Thr Lys Pro Arg
                530                 535                 540

Glu Glu Gln Tyr Asn Ser Thr Tyr Arg Val Val Ser Val Leu Thr Val
545                 550                 555                 560

Leu His Gln Asp Trp Leu Asn Gly Lys Glu Tyr Lys Cys Lys Val Ser
                565                 570                 575

Asn Lys Ala Leu Pro Ala Pro Ile Glu Lys Thr Ile Ser Lys Ala Lys
                580                 585                 590

Gly Gln Pro Arg Glu Pro Gln Val Cys Thr Leu Pro Pro Ser Arg Asp
                595                 600                 605

Glu Leu Thr Lys Asn Gln Val Ser Leu Ser Cys Ala Val Lys Gly Phe
610                 615                 620

Tyr Pro Ser Asp Ile Ala Val Glu Trp Glu Ser Asn Gly Gln Pro Glu
625                 630                 635                 640

Asn Asn Tyr Lys Thr Thr Pro Pro Val Leu Asp Ser Asp Gly Ser Phe
                645                 650                 655

Phe Leu Val Ser Lys Leu Thr Val Asp Lys Ser Arg Trp Gln Gln Gly
                660                 665                 670

Asn Val Phe Ser Cys Ser Val Met His Glu Ala Leu His Asn His Tyr
                675                 680                 685

Thr Gln Lys Ser Leu Ser Leu Ser Pro Gly Lys
                690                 695
```